US012703738B2

(12) United States Patent
Igawa et al.

(10) Patent No.: US 12,703,738 B2
(45) Date of Patent: Aug. 11, 2026

(54) ANTIBODY CONSTANT REGION VARIANT

(71) Applicant: Chugai Seiyaku Kabushiki Kaisha, Tokyo (JP)

(72) Inventors: Tomoyuki Igawa, Shizuoka (JP); Taichi Kuramochi, Shizuoka (JP); Atsuhiko Maeda, Shizuoka (JP); Hirotake Shiraiwa, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 628 days.

(21) Appl. No.: 17/530,542

(22) Filed: Nov. 19, 2021

(65) Prior Publication Data

US 2022/0064264 A1 Mar. 3, 2022

Related U.S. Application Data

(62) Division of application No. 16/298,032, filed on Mar. 11, 2019, now abandoned, which is a division of application No. 14/680,250, filed on Apr. 7, 2015, now Pat. No. 10,253,091, which is a division of application No. 13/257,145, filed as application No. PCT/JP2010/054767 on Mar. 19, 2010, now abandoned.

(30) Foreign Application Priority Data

Mar. 19, 2009 (JP) ................................ 2009-068631
Sep. 16, 2009 (JP) ................................ 2009-213901

(51) Int. Cl.
*C07K 16/00* (2006.01)
*C07K 16/28* (2006.01)

(52) U.S. Cl.
CPC .......... *C07K 16/00* (2013.01); *C07K 16/2866* (2013.01); *C07K 16/2875* (2013.01); *C07K 2317/515* (2013.01); *C07K 2317/52* (2013.01); *C07K 2317/522* (2013.01); *C07K 2317/524* (2013.01); *C07K 2317/526* (2013.01); *C07K 2317/528* (2013.01); *C07K 2317/53* (2013.01); *C07K 2317/71* (2013.01); *C07K 2317/72* (2013.01); *C07K 2317/76* (2013.01); *C07K 2317/92* (2013.01); *C07K 2317/94* (2013.01)

(58) Field of Classification Search
CPC ........................ C07K 2317/52; C07K 2317/72
USPC ...................................................... 530/387.3
See application file for complete search history.

(56) References Cited

U.S. PATENT DOCUMENTS 4,676,980 A 6/1987 Segal et al.
4,737,456 A 4/1988 Weng et al.
4,816,567 A 3/1989 Cabilly et al.
5,126,250 A 6/1992 McDonough et al.
5,208,020 A 5/1993 Chari et al.
5,322,678 A 6/1994 Morgan et al.
5,416,064 A 5/1995 Chari et al.
5,455,030 A 10/1995 Ladner et al.
5,468,634 A 11/1995 Liu
5,500,362 A 3/1996 Robinson et al.
5,571,894 A 11/1996 Wells et al.
5,587,458 A 12/1996 King et al.
5,624,821 A 4/1997 Winter et al.
5,635,483 A 6/1997 Pettit et al.
5,639,641 A 6/1997 Pedersen et al.
5,648,237 A 7/1997 Carter
5,648,260 A 7/1997 Winter et al.
5,670,373 A 9/1997 Kishimoto
5,712,374 A 1/1998 Kuntsmann et al.
5,714,586 A 2/1998 Kunstmann et al.
5,731,168 A 3/1998 Carter et al.
5,739,116 A 4/1998 Hamann et al.
5,750,373 A 5/1998 Garrard et al.
5,767,285 A 6/1998 Hammann et al.
5,770,429 A 6/1998 Lonberg et al.
5,770,701 A 6/1998 McGahren et al.
5,770,710 A 6/1998 McGahren et al.
5,773,001 A 6/1998 Hamann et al.
5,780,588 A 7/1998 Pettit et al.
5,789,199 A 8/1998 Joly et al.
5,795,965 A 8/1998 Tsuchiya et al.
5,817,790 A 10/1998 Tsuchiya et al.
5,821,337 A 10/1998 Carter et al.
5,840,523 A 11/1998 Simmons et al.
5,859,205 A 1/1999 Adair et al.
5,869,046 A 2/1999 Presta et al.
5,877,296 A 3/1999 Hamann et al.
5,888,510 A 3/1999 Kishimoto et al.
5,945,311 A 8/1999 Lindhofer et al.
5,959,177 A 9/1999 Hein et al.
5,990,286 A 11/1999 Khawli et al.

(Continued)

FOREIGN PATENT DOCUMENTS

AR 068564 11/2009
AU 2007255753 12/2007

(Continued)

OTHER PUBLICATIONS

Salfeld (Nature Biotech. 25(12): 1369-1372 (2007)).*

(Continued)

*Primary Examiner* — Lynn A Bristol
(74) *Attorney, Agent, or Firm* — Fish & Richardson P.C.

(57) ABSTRACT

Disclosed are IgG2 constant regions and human κ chain constant regions with altered amino acid sequences, antibodies comprising these constant regions, and pharmaceutical compositions comprising the antibodies.

6 Claims, 21 Drawing Sheets

Specification includes a Sequence Listing.

(56) References Cited

U.S. PATENT DOCUMENTS 6,018,032 A 1/2000 Koike et al.
6,040,498 A 3/2000 Stomp et al.
6,075,181 A 6/2000 Kucherlapati et al.
6,126,980 A 10/2000 Smith et al.
6,129,914 A 10/2000 Weiner
6,150,584 A 11/2000 Kucherlapati et al.
6,171,586 B1 1/2001 Lam et al.
6,194,551 B1 2/2001 Idusogie et al.
6,248,516 B1 6/2001 Winter et al.
6,267,958 B1 7/2001 Andya et al.
6,309,636 B1 10/2001 do Couto et al.
6,329,511 B1 12/2001 Vasquez et al.
6,417,429 B1 7/2002 Hein et al.
6,420,548 B1 7/2002 Vezina et al.
6,485,943 B2 11/2002 Stevens et al.
6,602,684 B1 8/2003 Umana et al.
6,677,436 B1 1/2004 Sato et al.
6,723,319 B1 4/2004 Ito et al.
6,737,056 B1 5/2004 Presta
6,884,879 B1 4/2005 Baca et al.
6,913,747 B1 7/2005 Co et al.
7,052,873 B2 5/2006 Tsuchiya
7,122,637 B2 10/2006 Presta
7,125,978 B1 10/2006 Vezina et al.
7,217,797 B2 5/2007 Hinton et al.
7,276,585 B2 10/2007 Lazar et al.
7,479,543 B2 1/2009 Tsuchiya et al.
7,482,440 B2 1/2009 Maeda et al.
7,615,213 B2 11/2009 Kasaian et al.
8,076,458 B2 12/2011 Ohta et al.
8,562,991 B2 10/2013 Igawa et al.
8,575,317 B2 11/2013 Kuramochi et al.
8,592,562 B2 11/2013 Kannan et al.
8,637,641 B2 1/2014 Dahiyat et al.
9,096,651 B2 8/2015 Igawa et al.
9,228,017 B2 1/2016 Igawa et al.
9,340,615 B2 5/2016 Maeda et al.
9,399,680 B2 7/2016 Kuramochi et al.
9,670,269 B2 6/2017 Igawa et al.
9,688,762 B2 6/2017 Igawa et al.
9,828,429 B2 11/2017 Igawa et al.
10,011,858 B2 7/2018 Igawa et al.
10,066,018 B2 9/2018 Igawa et al.
10,150,808 B2 12/2018 Kuramochi et al.
10,253,091 B2 * 4/2019 Igawa ................ C07K 16/2866
10,435,458 B2 * 10/2019 Kuramochi ............. A61P 37/00
10,604,561 B2 3/2020 Sampei et al.
10,662,245 B2 5/2020 Igawa et al.
10,774,148 B2 9/2020 Kakehi et al.
10,844,113 B2 11/2020 Sampei et al.
10,934,344 B2 * 3/2021 Igawa ..................... A61P 37/00
11,046,784 B2 6/2021 Igawa et al.
11,124,576 B2 9/2021 Igawa et al.
11,142,587 B2 10/2021 Igawa et al.
11,168,344 B2 11/2021 Igawa et al.
11,248,053 B2 2/2022 Igawa et al.
11,332,533 B2 5/2022 Igawa et al.
11,649,262 B2 5/2023 Tanaka et al.
12,116,414 B2 10/2024 Igawa et al.
12,122,840 B2 10/2024 Igawa et al.
2001/0001663 A1 5/2001 Kishimoto et al.
2001/0036923 A1 11/2001 Chari et al.
2002/0142374 A1 10/2002 Gallo et al.
2002/0147326 A1 10/2002 Chaiklin et al.
2002/0164328 A1 11/2002 Shinkawa et al.
2002/0164339 A1 11/2002 Do Couto et al.
2002/0164668 A1 11/2002 Durham et al.
2002/0187150 A1 12/2002 Mihara et al.
2002/0199213 A1 12/2002 Tomizuka et al.
2003/0115614 A1 6/2003 Kanda et al.
2003/0125520 A1 7/2003 Maeda et al.
2003/0144486 A1 7/2003 Rodman
2003/0157108 A1 8/2003 Presta
2003/0166871 A1 9/2003 Barbas et al.
2003/0187225 A1 10/2003 Penichet et al.
2003/0190311 A1 10/2003 Dall'Acqua et al.
2003/0215838 A1 11/2003 Sprecher et al.
2003/0224397 A1 12/2003 Lowman et al.
2003/0224487 A1 12/2003 Sprecher et al.
2004/0071706 A1 4/2004 Ito et al.
2004/0081651 A1 4/2004 Karpusas et al.
2004/0093621 A1 5/2004 Shitara et al.
2004/0109865 A1 6/2004 Niwa et al.
2004/0110282 A1 6/2004 Kanda et al.
2004/0110704 A1 6/2004 Yamane et al.
2004/0127688 A1 7/2004 Winter
2004/0132140 A1 7/2004 Satoh et al.
2004/0223970 A1 11/2004 Afar et al.
2004/0236080 A1 11/2004 Aburatani et al.
2005/0014934 A1 1/2005 Hinton et al.
2005/0079574 A1 4/2005 Bond
2005/0095243 A1 5/2005 Chan et al.
2005/0119455 A1 6/2005 Fuh et al.
2005/0123546 A1 6/2005 Umana et al.
2005/0130224 A1 6/2005 Saito et al.
2005/0142133 A1 6/2005 Lazar et al.
2005/0142635 A1 6/2005 Tsuchiya et al.
2005/0158825 A1 7/2005 Power et al.
2005/0164352 A1 7/2005 Lauder et al.
2005/0191293 A1 9/2005 Deshpande et al.
2005/0233382 A1 10/2005 Presta
2005/0238649 A1 10/2005 Doronina et al.
2005/0244403 A1 11/2005 Lazar et al.
2005/0260186 A1 11/2005 Bookbinder et al.
2005/0261229 A1 11/2005 Gillies et al.
2005/0266000 A1 12/2005 Bond et al.
2005/0276802 A1 12/2005 Adams et al.
2006/0019342 A1 1/2006 Dall Acqua et al.
2006/0024298 A1 2/2006 Lazar et al.
2006/0025576 A1 2/2006 Miller et al.
2006/0057149 A1 3/2006 Johnson et al.
2006/0063228 A1 3/2006 Kasaian et al.
2006/0074225 A1 4/2006 Chamberlain
2006/0104968 A1 5/2006 Bookbinder et al.
2006/0121022 A1 6/2006 Koga et al.
2006/0134105 A1 6/2006 Lazar et al.
2006/0134709 A1 6/2006 Stavenhagen et al.
2006/0134805 A1 6/2006 Berg et al.
2006/0141456 A1 6/2006 Edwards et al.
2006/0160184 A1 7/2006 Hoogenboom et al.
2006/0182743 A1 8/2006 Bilsborough
2006/0194280 A1 8/2006 Dillon et al.
2006/0194291 A1 8/2006 Presta
2006/0204493 A1 9/2006 Huang et al.
2006/0240012 A1 10/2006 Sugimura et al.
2006/0275282 A1 12/2006 Moore et al.
2006/0292147 A1 12/2006 Yoshizaki et al.
2007/0036785 A1 2/2007 Kishimoto et al.
2007/0036799 A1 2/2007 Stavenhagen et al.
2007/0041978 A1 2/2007 Hattori et al.
2007/0054354 A1 3/2007 Humphreys et al.
2007/0059312 A1 3/2007 Baca et al.
2007/0061900 A1 3/2007 Murphy et al.
2007/0092940 A1 4/2007 Eigenbrot et al.
2007/0110757 A1 5/2007 Wei et al.
2007/0117126 A1 5/2007 Sidhu et al.
2007/0134234 A1 6/2007 Smith et al.
2007/0148163 A1 6/2007 Takahashi et al.
2007/0148164 A1 6/2007 Farrington et al.
2007/0148167 A1 6/2007 Strohl
2007/0160598 A1 7/2007 Dennis et al.
2007/0160611 A1 7/2007 Yao et al.
2007/0212357 A1 9/2007 Pons et al.
2007/0224174 A1 9/2007 Kang et al.
2007/0237764 A1 10/2007 Birtalan et al.
2007/0280945 A1 12/2007 Stevens et al.
2007/0292936 A1 12/2007 Barthelemy et al.
2008/0063635 A1 3/2008 Takahashi et al.
2008/0069820 A1 3/2008 Fuh et al.
2008/0075712 A1 3/2008 Hattori et al.
2008/0125579 A1 5/2008 Owens et al.
2008/0166756 A1 7/2008 Tsuchiya et al.
2008/0219971 A1 9/2008 Smith et al.
2009/0002360 A1 1/2009 Chen et al.

(56) References Cited

U.S. PATENT DOCUMENTS

2009/0117097 A1 5/2009 Igawa et al.
2009/0202556 A1 8/2009 Ohta et al.
2009/0208416 A1 8/2009 Moretta et al.
2009/0221803 A1 9/2009 Dall'Acqua et al.
2009/0263392 A1 10/2009 Igawa et al.
2009/0291076 A1 11/2009 Morichika et al.
2009/0324589 A1 12/2009 Igawa et al.
2010/0003254 A1 1/2010 Hattori et al.
2010/0004429 A1 1/2010 Kai et al.
2010/0008907 A1 1/2010 Nishimoto et al.
2010/0015133 A1 1/2010 Igawa et al.
2010/0055092 A1 3/2010 Hasegawa et al.
2010/0239577 A1 9/2010 Igawa et al.
2010/0247523 A1 9/2010 Kano et al.
2010/0285030 A1 11/2010 Bowdish et al.
2010/0286374 A1 11/2010 Kannan et al.
2010/0291072 A1 11/2010 Lowman et al.
2010/0297697 A1 11/2010 Ambrosius et al.
2010/0298542 A1 11/2010 Igawa et al.
2010/0310556 A1 12/2010 Higuchi et al.
2010/0316636 A1 12/2010 Radin et al.
2010/0331527 A1 12/2010 Davis et al.
2011/0044984 A1 2/2011 Kittazawa et al.
2011/0076275 A1 3/2011 Igawa et al.
2011/0098450 A1 4/2011 Igawa et al.
2011/0111406 A1 5/2011 Igawa et al.
2011/0129459 A1 6/2011 Kuramochi et al.
2011/0229459 A1 9/2011 Kuramochi et al.
2011/0236374 A1 9/2011 Shitara et al.
2011/0245473 A1 10/2011 Igawa et al.
2011/0287009 A1 11/2011 Scheer et al.
2012/0009188 A1 1/2012 Behrens
2012/0010387 A1 1/2012 Niwa et al.
2012/0028304 A1 2/2012 Dahiyat et al.
2012/0065379 A1 3/2012 Igawa et al.
2012/0071634 A1 3/2012 Igawa et al.
2012/0121587 A1 5/2012 Maeda et al.
2012/0149876 A1 6/2012 Von Kreudenstein
2012/0238729 A1 9/2012 Kuramochi et al.
2012/0253016 A1 10/2012 Igawa et al.
2012/0301460 A1 11/2012 Bao et al.
2013/0011866 A1 1/2013 Igawa et al.
2013/0018174 A1 1/2013 Igawa et al.
2013/0030156 A1 1/2013 Apostolou et al.
2013/0039913 A1 2/2013 Labrijn et al.
2013/0052196 A1 2/2013 Apostolou et al.
2013/0085199 A1 4/2013 Tamori et al.
2013/0101581 A1 4/2013 Kuramochi et al.
2013/0115208 A1 5/2013 Ho et al.
2013/0195849 A1 8/2013 Spreter et al.
2013/0317203 A1 11/2013 Igawa et al.
2014/0039165 A1 2/2014 Kuramochi et al.
2014/0051833 A1 2/2014 Fischer et al.
2014/0112883 A1 4/2014 Ponath et al.
2014/0154270 A1 6/2014 Wang et al.
2014/0303356 A1 10/2014 Gramer et al.
2014/0377253 A1 12/2014 Harding et al.
2015/0118184 A1 4/2015 Kawai
2015/0166666 A1 6/2015 Igawa et al.
2015/0175704 A1 6/2015 Kuramochi et al.
2015/0274809 A1 10/2015 Igawa et al.
2015/0284465 A1 10/2015 Igawa et al.
2015/0297820 A1 10/2015 Kawai
2015/0315278 A1 11/2015 Igawa et al.
2016/0024147 A1 1/2016 Tustian et al.
2016/0039912 A1 2/2016 Mimoto et al.
2016/0159915 A1 6/2016 Igawa et al.
2016/0229915 A1 8/2016 Igawa et al.
2017/0275332 A1 9/2017 Igawa et al.
2018/0057607 A1 3/2018 Kakehi et al.
2018/0142027 A1 5/2018 Igawa et al.
2018/0148509 A1 5/2018 Kakehi et al.
2018/0162902 A1 6/2018 Igawa et al.
2019/0062368 A1 2/2019 Igawa et al.
2019/0085085 A1 3/2019 Igawa et al.
2019/0211081 A1 7/2019 Igawa et al.
2019/0330268 A1 10/2019 Tanaka et al.
2019/0352334 A1 11/2019 Igawa et al.
2020/0002429 A1 1/2020 Kuramochi et al.
2020/0207805 A1 7/2020 Igawa et al.
2020/0231688 A1 7/2020 Igawa et al.
2021/0017256 A1 1/2021 Fink et al.
2021/0017286 A1 1/2021 Kakehi et al.
2021/0040147 A1 2/2021 Igawa et al.
2021/0095008 A1 4/2021 Sampei et al.
2021/0206862 A1 7/2021 Igawa et al.
2021/0292360 A1 9/2021 Igawa et al.
2021/0324109 A1 10/2021 Igawa et al.
2022/0010030 A1 1/2022 Igawa et al.
2022/0041741 A1 2/2022 Igawa et al.
2022/0135618 A1 5/2022 Igawa et al.
2022/0251225 A1 8/2022 Igawa et al.
2022/0267822 A1 8/2022 Igawa et al.
2022/0306755 A1 9/2022 Igawa et al.
2022/0389054 A1 12/2022 Igawa et al.
2022/0389105 A1 12/2022 Igawa et al.
2023/0020377 A1 1/2023 Katada et al.
2023/0159648 A1 5/2023 Igawa et al.
2023/0183363 A1 6/2023 Kuramochi et al.
2023/0227498 A1 7/2023 Igawa et al.
2024/0010738 A1 1/2024 Igawa et al.
2024/0083939 A1 3/2024 Igawa et al.
2024/0150477 A1 5/2024 Kakehi et al.
2024/0190948 A1 6/2024 Fink et al.
2024/0190976 A1 6/2024 Igawa et al.
2024/0239906 A1 7/2024 Igawa et al.
2024/0294653 A1 9/2024 Kuramochi et al.
2024/0301075 A1 9/2024 Igawa et al.
2024/0391952 A1 11/2024 Igawa et al.
2024/0417480 A1 12/2024 Kakehi et al.

FOREIGN PATENT DOCUMENTS

AU 2008332271 6/2009
AU 2009290162 4/2010
BR PI0821145-0 6/2015
BR PI0821110-8 7/2015
CA 1 332 367 10/1994
CA 2 203 182 5/1996
CA 2 443 294 10/2002
CA 2 523 577 11/2004
CA 2 531 482 1/2005
CA 2 549 467 7/2005
CA 2 560 953 9/2005
CA 2 625 773 4/2007
CA 2 626 688 4/2007
CA 2 647 846 10/2007
CA 2 648 644 10/2007
CA 2 700 394 4/2009
CA 2 700 498 4/2009
CA 2 700 986 4/2009
CA 2 708 065 6/2009
CA 2 708 532 6/2009
CN 101198698 6/2008
CN 101849006 9/2010
CN 102946906 10/2011
CN 102471378 5/2012
CN 102782131 11/2012
CN 103476793 12/2013
CN 101874042 9/2018
EA 009026 10/2007
EP 0 329 185 8/1989
EP 0 361 902 4/1990
EP 0 404 097 12/1990
EP 0 425 235 5/1991
EP 0 628 639 12/1994
EP 0 637 593 2/1995
EP 0 783 893 7/1997
EP 0 791 359 8/1997
EP 0 811 691 12/1997
EP 0 983 767 3/2000
EP 1 004 315 5/2000
EP 1 069 185 1/2001
EP 1 074 268 2/2001

(56) References Cited

FOREIGN PATENT DOCUMENTS

| | | |
|---|---|---|
| EP | 1 188 830 | 3/2002 |
| EP | 1 334 731 | 8/2003 |
| EP | 1 374 900 | 1/2004 |
| EP | 1 382 969 | 1/2004 |
| EP | 1 510 943 | 3/2005 |
| EP | 1 690 550 | 8/2006 |
| EP | 1 701 979 | 9/2006 |
| EP | 1 707 215 | 10/2006 |
| EP | 1 728 801 | 12/2006 |
| EP | 1 733 740 | 12/2006 |
| EP | 1 752 471 | 2/2007 |
| EP | 1 772 465 | 4/2007 |
| EP | 1 773 391 | 4/2007 |
| EP | 1 847 602 | 10/2007 |
| EP | 1 870 458 | 12/2007 |
| EP | 1 870 459 | 12/2007 |
| EP | 1 900 814 | 3/2008 |
| EP | 1 941 907 | 7/2008 |
| EP | 1 941 908 | 7/2008 |
| EP | 1 967 207 | 9/2008 |
| EP | 1 967 209 | 9/2008 |
| EP | 1 990 060 | 11/2008 |
| EP | 2 006 381 | 12/2008 |
| EP | 2 009 101 | 12/2008 |
| EP | 2 031 064 | 3/2009 |
| EP | 2 047 863 | 4/2009 |
| EP | 2 107 115 | 10/2009 |
| EP | 2 123 302 | 11/2009 |
| EP | 2 174 667 | 4/2010 |
| EP | 2 194 066 | 6/2010 |
| EP | 2 196 220 | 6/2010 |
| EP | 2 196 541 | 6/2010 |
| EP | 2 202 245 | 6/2010 |
| EP | 2 206 775 | 7/2010 |
| EP | 2 228 392 | 9/2010 |
| EP | 2 236 604 | 10/2010 |
| EP | 2 241 332 | 10/2010 |
| EP | 2 275 443 | 1/2011 |
| EP | 2 305 306 | 4/2011 |
| EP | 2 330 193 | 8/2011 |
| EP | 2 354 161 | 8/2011 |
| EP | 2 409 991 | 1/2012 |
| EP | 2 522 724 | 11/2012 |
| EP | 2 543 727 | 1/2013 |
| EP | 2 578 233 | 4/2013 |
| EP | 2 644 698 | 10/2013 |
| EP | 2 905 290 | 8/2015 |
| EP | 2 914 634 | 9/2015 |
| EP | 3 059 246 | 8/2016 |
| JP | 2-028200 | 1/1990 |
| JP | 2-163096 | 6/1990 |
| JP | H03-500644 | 2/1991 |
| JP | 07-67688 | 3/1995 |
| JP | 08-500979 | 2/1996 |
| JP | 09-506001 | 6/1997 |
| JP | 11-500915 | 1/1999 |
| JP | 11-500916 | 1/1999 |
| JP | 2002-514406 | 5/2002 |
| JP | 2004-86862 | 3/2004 |
| JP | 2004-511426 | 4/2004 |
| JP | 2004-321100 | 11/2004 |
| JP | 2005-501514 | 1/2005 |
| JP | 2005-101105 | 3/2005 |
| JP | 2005-532805 | 11/2005 |
| JP | 2005-535341 | 11/2005 |
| JP | 2005-378266 | 12/2005 |
| JP | 2005-537009 | 12/2005 |
| JP | 2008-512995 | 5/2008 |
| JP | 2008-523140 | 7/2008 |
| JP | 2008-538920 | 11/2008 |
| JP | 2009-500458 | 1/2009 |
| JP | 2010-522701 | 7/2010 |
| JP | 2011-508604 | 3/2011 |
| JP | 2012-510281 | 5/2012 |
| JP | 2012-515160 | 7/2012 |
| JP | 2012-522527 | 9/2012 |
| JP | 2012-531439 | 12/2012 |
| JP | 5144499 | 2/2013 |
| JP | 2013-515509 | 5/2013 |
| JP | 2013-529084 | 7/2013 |
| JP | 2013-529190 | 7/2013 |
| JP | 2013-165716 | 8/2013 |
| JP | 2013-541594 | 11/2013 |
| JP | 5334319 | 11/2013 |
| JP | 5484060 | 5/2014 |
| JP | 2015-510764 | 4/2015 |
| JP | 5717624 | 5/2015 |
| JP | 2015-130883 | 7/2015 |
| JP | 5787446 | 9/2015 |
| JP | 2016-69329 | 5/2016 |
| JP | 6534615 | 6/2019 |
| KR | 2006/0010765 | 2/2006 |
| KR | 2007/0035482 | 3/2007 |
| KR | 2010/0074221 | 7/2010 |
| KR | 2010/0097721 | 9/2010 |
| KR | 2012/0123055 | 11/2012 |
| KR | 10/1643005 | 7/2016 |
| RU | 94028282 | 7/1996 |
| RU | 2195960 | 1/2003 |
| RU | 2232773 | 7/2004 |
| RU | 2266298 | 12/2005 |
| TW | 200722517 | 6/2007 |
| TW | 200810778 | 3/2008 |
| TW | 200932266 | 8/2009 |
| WO | WO 89/01343 | 2/1989 |
| WO | WO 91/01335 | 2/1991 |
| WO | WO 92/19759 | 11/1992 |
| WO | WO 93/01161 | 1/1993 |
| WO | WO 93/08829 | 5/1993 |
| WO | WO 93/16185 | 8/1993 |
| WO | WO 94/05690 | 3/1994 |
| WO | WO 94/10354 | 5/1994 |
| WO | WO 94/11026 | 5/1994 |
| WO | WO 94/12215 | 6/1994 |
| WO | WO 94/29351 | 12/1994 |
| WO | WO 95/09873 | 4/1995 |
| WO | WO 95/14710 | 6/1995 |
| WO | WO 95/33844 | 12/1995 |
| WO | WO 96/11020 | 4/1996 |
| WO | WO 96/12503 | 5/1996 |
| WO | WO 96/23071 | 8/1996 |
| WO | WO 96/27011 | 9/1996 |
| WO | WO 97/09351 | 3/1997 |
| WO | WO 97/10354 | 3/1997 |
| WO | WO 97/30087 | 8/1997 |
| WO | WO 98/03546 | 1/1998 |
| WO | WO 98/42377 | 10/1998 |
| WO | WO 98/50431 | 11/1998 |
| WO | WO 98/58964 | 12/1998 |
| WO | WO 99/03495 | 1/1999 |
| WO | WO 99/08707 | 2/1999 |
| WO | WO 99/18212 | 4/1999 |
| WO | WO 99/22764 | 5/1999 |
| WO | WO 99/47170 | 9/1999 |
| WO | WO 99/51642 | 10/1999 |
| WO | WO 99/51743 | 10/1999 |
| WO | WO 99/58572 | 11/1999 |
| WO | WO 00/34317 | 6/2000 |
| WO | WO 00/42072 | 7/2000 |
| WO | WO 00/61739 | 10/2000 |
| WO | WO 00/75314 | 12/2000 |
| WO | WO 01/29246 | 4/2001 |
| WO | WO 01/30854 | 5/2001 |
| WO | WO 01/82899 | 11/2001 |
| WO | WO 02/31140 | 4/2002 |
| WO | WO 02/34292 | 5/2002 |
| WO | WO 02/060919 | 8/2002 |
| WO | WO 02/072605 | 9/2002 |
| WO | WO 02/080969 | 10/2002 |
| WO | WO 03/000883 | 1/2003 |
| WO | WO 03/011878 | 2/2003 |
| WO | WO 03/012069 | 2/2003 |
| WO | WO 03/020949 | 3/2003 |
| WO | WO 03/057881 | 7/2003 |

(56) References Cited

FOREIGN PATENT DOCUMENTS

WO WO 03/060090 7/2003
WO WO 03/074679 9/2003
WO WO 03/084570 10/2003
WO WO 03/085107 10/2003
WO WO 03/085119 10/2003
WO WO 03/105757 12/2003
WO WO 2004/008147 1/2004
WO WO 2004/016740 2/2004
WO WO 2004/020579 3/2004
WO WO 2004/035752 4/2004
WO WO 2004/056312 7/2004
WO WO 2004/068931 8/2004
WO WO 2004/085476 10/2004
WO WO 2004/091543 10/2004
WO WO 2004/092219 10/2004
WO WO 2004/096273 11/2004
WO WO 2004/113387 12/2004
WO WO 2005/005604 1/2005
WO WO 2005/035586 4/2005
WO WO 2005/035753 4/2005
WO WO 2005/035754 4/2005
WO WO 2005/035756 4/2005
WO WO 2005/035778 4/2005
WO WO 2005/037315 4/2005
WO WO 2005/037867 4/2005
WO WO 2005/047327 5/2005
WO WO 2005/053742 6/2005
WO WO 2005/056606 6/2005
WO WO 2005/059106 6/2005
WO WO 2005/061000 7/2005
WO WO 2005/062916 7/2005
WO WO 2005/067620 7/2005
WO WO 2005/080429 9/2005
WO WO 2005/090405 9/2005
WO WO 2005/092925 10/2005
WO WO 2005/100402 10/2005
WO WO 2005/112564 12/2005
WO WO 2005/113606 A2 12/2005
WO WO 2005/121180 12/2005
WO WO 2005/123126 12/2005
WO WO 2005/123780 12/2005
WO WO 2006/004663 1/2006
WO WO 2006/019447 2/2006
WO WO 2006/023144 3/2006
WO WO 2006/029879 3/2006
WO WO 2006/030200 3/2006
WO WO 2006/030220 3/2006
WO WO 2006/031370 3/2006
WO WO 2006/033386 3/2006
WO WO 2006/044908 4/2006
WO WO 2006/047340 5/2006
WO WO 2006/047350 5/2006
WO WO 2006/050166 5/2006
WO WO 2006/050491 5/2006
WO WO 2006/053301 5/2006
WO WO 2006/065208 6/2006
WO WO 2006/067913 6/2006
WO WO 2006/070286 7/2006
WO WO 2006/071877 7/2006
WO WO 2006/075668 7/2006
WO WO 2006/088855 8/2006
WO WO 2006/106903 10/2006
WO WO 2006/106905 10/2006
WO WO 2006/109592 10/2006
WO WO 2006/113767 10/2006
WO WO 2006/116260 11/2006
WO WO 2006/118959 11/2006
WO WO 2006/119062 11/2006
WO WO 2006/119115 11/2006
WO WO 2006/121852 11/2006
WO WO 2007/009065 1/2007
WO WO 2007/024535 3/2007
WO WO 2007/043641 4/2007
WO WO 2007/046489 4/2007
WO WO 2007/058194 5/2007
WO WO 2007/060411 5/2007
WO WO 2007/061029 5/2007
WO WO 2007/074880 7/2007
WO WO 2007/086490 8/2007
WO WO 2007/108559 9/2007
WO WO 2007/108756 9/2007
WO WO 2007/114319 10/2007
WO WO 2007/114325 10/2007
WO WO 2007/133816 11/2007
WO WO 2007/137984 12/2007
WO WO 2007/142325 12/2007
WO WO 2007/143168 12/2007
WO WO 2008/022152 2/2008
WO WO 2008/043822 4/2008
WO WO 2008/077546 7/2008
WO WO 2008/090901 7/2008
WO WO 2008/090960 7/2008
WO WO 2008/092117 7/2008
WO WO 2008/103432 8/2008
WO WO 2008/119353 10/2008
WO WO 2008/132453 11/2008
WO WO 2008/145141 12/2008
WO WO 2008/145142 12/2008
WO WO 2009/011941 1/2009
WO WO 2009/014263 1/2009
WO WO 2009/036209 3/2009
WO WO 2009/041062 4/2009
WO WO 2009/041613 4/2009
WO WO 2009/041621 4/2009
WO WO 2009/041643 4/2009
WO WO 2009/041734 4/2009
WO WO 2009/044774 4/2009
WO WO 2009/052439 4/2009
WO WO 2009/053368 4/2009
WO WO 2009/058492 5/2009
WO WO 2009/063965 5/2009
WO WO 2009/072598 6/2009
WO WO 2009/072604 6/2009
WO WO 2009/079649 6/2009
WO WO 2009/086320 7/2009
WO WO 2009/089004 7/2009
WO WO 2009/100309 8/2009
WO WO 2009/125825 10/2009
WO WO 2009/139822 11/2009
WO WO 2009/148148 12/2009
WO WO 2010/035769 4/2010
WO WO 2010/043977 4/2010
WO WO 2010/045193 4/2010
WO WO 2010/063746 6/2010
WO WO 2010/064090 6/2010
WO WO 2010/064456 6/2010
WO WO 2010/064697 6/2010
WO WO 2010/065078 6/2010
WO WO 2010/080065 7/2010
WO WO 2010/106180 9/2010
WO WO 2010/107109 9/2010
WO WO 2010/107110 9/2010
WO WO 2010/115589 10/2010
WO WO 2010/131733 11/2010
WO WO 2010/151792 12/2010
WO WO 2011/037158 3/2011
WO WO 2011/078332 6/2011
WO WO 2011/090754 7/2011
WO WO 2011/090762 7/2011
WO WO 2011/091078 7/2011
WO WO 2011/091177 7/2011
WO WO 2011/091181 7/2011
WO WO 2011/108502 9/2011
WO WO 2011/108714 9/2011
WO WO 2011/111007 9/2011
WO WO 2011/122011 10/2011
WO WO 2011/125674 10/2011
WO WO 2011/131746 10/2011
WO WO 2011/133886 10/2011
WO WO 2011/143545 11/2011
WO WO 2011/149046 12/2011
WO WO 2012/016227 2/2012
WO WO 2012/020096 2/2012
WO WO 2012/064627 5/2012

(56) References Cited

FOREIGN PATENT DOCUMENTS

WO WO 2012/067176 5/2012
WO WO 2012/073985 6/2012
WO WO 2012/073992 6/2012
WO WO 2012/082073 6/2012
WO WO 2012/132067 10/2012
WO WO 2012/145238 10/2012
WO 201302219 1/2013
WO WO 2013/046704 4/2013
WO WO 2013/047752 4/2013
WO WO 2013/060867 5/2013
WO WO 2013/089647 6/2013
WO WO 2013/124450 8/2013
WO WO 2013/136186 9/2013
WO WO 2013/151764 10/2013
WO WO 2013/157954 10/2013
WO WO 2013/173348 11/2013
WO WO 2013/180200 12/2013
WO WO 2013/180201 12/2013
WO WO 2014/025546 2/2014
WO WO 2014/028354 2/2014
WO WO 2014/054804 4/2014
WO WO 2014/067011 5/2014
WO WO 2014/145159 9/2014
WO WO 2015/046467 4/2015
WO WO 2015/063339 5/2015
WO WO 2015/089492 6/2015
WO WO 2015/122995 8/2015
WO WO 2015/123362 8/2015
WO WO 2016/012800 1/2016
WO WO 2016/098357 6/2016
WO WO 2016/125495 8/2016
WO WO 2016/136933 9/2016
WO WO 2016/148653 9/2016
WO WO 2016/159213 10/2016
WO WO 2017/115773 7/2017
WO WO 2017/212291 12/2017
WO WO 2018/052375 3/2018
WO WO 2019/177543 9/2019
WO WO 2021/131021 7/2021
WO WO 2022/270611 12/2022
WO WO 2022/270612 12/2022

OTHER PUBLICATIONS

Dall'Acqua (J. Immunol. 177:1129-1138 (2006)).*
U.S. Appl. No. 18/176,201, Igawa et al., filed Feb. 28, 2023.
U.S. Appl. No. 18/193,697, Igawa et al., filed Mar. 31, 2023.
U.S. Appl. No. 18/453,418, Sampei et al., filed Aug. 22, 2023.
U.S. Appl. No. 18/464,407, Igawa et al., filed Sep. 11, 2023.
U.S. Appl. No. 18/470,185, Katada et al., filed Sep. 19, 2023.
U.S. Appl. No. 18/505,180, Igawa et al., filed Nov. 9, 2023.
Badri et al., "Optimization of radiation dosing schedules for proneural glioblastoma," J Math Biol, Apr. 2016, 72(5):1301-1336.
Baylot et al., Chapter 13 "TCTP Has a Crucial Role in the Different Stages of Prostate Cancer Malignant Progression," Results Probl Cell Differ, 2017, 64:255-261.
Keskin et al., "A new, structurally nonredundant, diverse data set of protein-protein interfaces and its implications," Protein Sci, Apr. 2004, 13(4):1043-1055.
Kuznetsova, "Brackets in Text of Legal Document as Linguo-Cognitive Phenomenon," Bulletin MGOU, Chapter: Russian Philology, 2015, 3:37-43 (with English translation).
Muller et al., "Spliceosomal Peptide P140 for Immunotherapy of Systemic Lupus Erythematosus," Arthritis Rheum, Dec. 2008, 58(12):3873-3883.
U.S. Appl. No. 17/848,983, Katada et al., filed Jun. 24, 2022.
U.S. Appl. No. 17/975,865, Kuramochi et al., filed Oct. 28, 2022.
U.S. Appl. No. 18/096,066, Igawa et al., filed Jan. 12, 2023.
U.S. Appl. No. 17/788,998, Katada et al., filed Jun. 24, 2022.
U.S. Appl. No. 17/821,494, Igawa et al., filed Aug. 23, 2022.
U.S. Appl. No. 18/330,420, Kakehi et al., filed Jun. 7, 2023.
Bournazos et al., "The role of IgG Fc receptors in antibody-dependent enhancement," Nat Rev Immunol, Oct. 2020, 20(10):633-664.
Chapter 3.316.2.1 "Affinity," Comprehensive Biomaterials, 2011, p. 278.
Dondelinger et al., "Understanding the Significance and Implications of Antibody Numbering and Antigen-Binding Surface/Residue Definition," Front Immunol, Oct. 16, 2018, 9:2278, 15 pages. doi: 10.3389/fimmu.2018.02278.
Lee et al., "IgG Fc domains that bind C1q but not effector Fcγ receptors delineate the importance of complement-mediated effector functions," Nat Immunol, Aug. 2017, 18(8):889-898. doi: 10.1038/ni.3770. Epub Jun. 12, 2017.
Roitt et al., "Antibody Structure and Function," Immunology, 1998, pp. 80-81.
U.S. Appl. No. 17/720,937, Igawa et al., filed Apr. 14, 2022.
U.S. Appl. No. 17/829,641, Igawa et al., filed Jun. 1, 2022.
Ausubel et al., Current Protocols in Molecular Biology, John Wiley & Sons Inc., Dec. 4, 2003, 4648 pages.
USPTO Restriction Requirement in U.S. Appl. No. 16/298,032, dated Oct. 8, 2020, 9 pages.
USPTO Non-Final Office Action in U.S. Appl. No. 16/298,032, dated May 26, 2021, 17 pages.
U.S. Appl. No. 15/263,617, Igawa et al., filed Sep. 13, 2016.
U.S. Appl. No. 15/490,936, Igawa et al., filed Apr. 19, 2017.
U.S. Appl. No. 15/562,186, Igawa et al., filed Sep. 27, 2017.
U.S. Appl. No. 15/614,842, Igawa et al., filed Jun. 6, 2017.
U.S. Appl. No. 15/725,692, Igawa et al., filed Oct. 5, 2017.
U.S. Appl. No. 15/782,256, Igawa et al., filed Oct. 12, 2017.
U.S. Appl. No. 15/875,847, Igawa et al., filed Jan. 19, 2018.
U.S. Appl. No. 16/041,976, Igawa et al., filed Jul. 23, 2018.
U.S. Appl. No. 16/061,454, Tanaka et al., filed Jun. 12, 2018.
U.S. Appl. No. 16/155,673, Igawa et al., filed Oct. 9, 2018.
U.S. Appl. No. 16/333,736, Sampei et al., filed Mar. 15, 2019.
U.S. Appl. No. 16/435,979, Sampei et al., filed Jun. 10, 2019.
U.S. Appl. No. 16/448,088, Igawa et al., filed Jun. 21, 2019.
U.S. Appl. No. 16/560,143, Kuramochi et al., filed Sep. 4, 2019.
U.S. Appl. No. 16/815,089, Igawa et al., filed Mar. 11, 2020.
U.S. Appl. No. 16/838,415, Igawa et al., filed Apr. 2, 2020.
U.S. Appl. No. 16/983,115, Kakehi et al., filed Aug. 3, 2020.
U.S. Appl. No. 17/076,938, Igawa et al., filed Oct. 22, 2020.
U.S. Appl. No. 17/097,298, Igawa et al., filed Nov. 13, 2020.
Abe et al., "Purification of monoclonal antibodies with light-chain heterogeneity produced by mouse hybridomas raised with NS-1 myelomas: application of hydrophobic interaction high-performance liquid chromatography," J Biochem Biophys Methods, 1993, 27:215-227.
Abe et al., "Novel Protein A Resin: Synthetic Polymer Matrix Design Impact on Antibody Binding Capacity," JSR Technical Review No. 119, 2012, pp. 1-5, retrieved from the Internet on Feb. 17, 2017: <URL:http://www.jsr.co.jp/pdf/rd/tec119-1.pdf> (with English translation).
Actemra (tocilizumab), Highlights of Prescribing Information, as revised in Aug. 2017, 1 page.
Adams et al., "Humanization of a recombinant monoclonal antibody to produce a therapeutic HER dimerization inhibitor, pertuzumab," Cancer Immunol Immunother, 2006, 55:717-727.
Adlersberg et al., "The Immunoglobulin Hinge (Interdomain) Region," Ric Clin Lab, Jul.-Sep. 1976, 6(3):191-205.
Akira et al., "Interleukin-6 in Biology and Medicine," Adv Immunol, Dec. 31, 1993; 54:1-78.
Algonomics—Tripole® applications, Feb. 21, 2009, 2 pages, retrieved from the Internet on Feb. 2, 20129: http://web.archive.org/web20090221052902/http://www.algonomics.com/proteinengineering/tripole_applications.php.
Allard et al., "Antigen binding properties of highly purified bispecific antibodies," Mol Immunol, Oct. 1992, 29(10):1219-1227.
Allen et al., "Interchain disulfide bonding in human IgG2 antibodies probed by site-directed mutagenesis," Biochemistry, 2009, 48(17):3755-3766.
Allen et al., "Novel mechanism for gonadotropin-releasing hormone neuronal migration involving Gas6/Ark signaling to p38 mitogen-activated protein kinase," Mol Cell Biol, 2002, 22(2):599-613.

(56) References Cited

OTHER PUBLICATIONS

Almagro et al., "Humanization of antibodies," Front Biosci, 2008, 13:1619-1633.
Amersham Biosciences, "Affinity Chromatography: Principles and Methods," Edition AD, 2002, pp. 16-18, 137.
Amersham Biosciences, "Protein Purification Handbook, " Edition AC, 2001, 98 pages.
Ando et al., "Tocilizumab, a Proposed Therapy for the Cachexia of Interleukin6-Expressing Lung Cancer," PLOS One, Jul. 10, 2014, 9(7):e102436. doi: 10.1371/journal.pone.0102436. eCollection 2014.
Annual Report 2012 (Integrated Edition Including CSR Report), Mar. 27, 2013, 154 pages.
Interleukin 6, Wikipedia, Feb. 22, 2019, XP055598802, 20 pages, retrieved from the Internet on Jun. 24, 2019: URL:https://en.wikipedia.org/wiki/Inteleukin_6).
Araki et al., "Clinical improvement in a patient with neuromyelitis optica following therapy with the anti-IL-6 receptor monoclonal antibody tocilizumab," Mod Rheumatol, Jul. 2013, 23(4):827-831. doi: 10. 1007/s10165-012-0715-9. Epub Jul. 11, 2012.
Aricha et al., "Blocking of IL-6 suppresses experimental autoimmune myasthenia gravis," J Autoimmun, Mar. 2011, 36(2):135-141. doi: 10.1016/j.jaut.2010.12.001. Epub Dec. 30, 2010.
Armour et al., "Recombinant human IgG molecules lacking Fcgamma receptor I binding and monocyte triggering activities," Eur J Immunol, 1999, 29(8):2613-2624.
Arndt et al., "Factors influencing the dimer to monomer transition of an antibody single-chain Fv fragment," Biochemistry, Sep. 15, 1998, 37(37):12918-12926.
Aslan et al., "Engineering a novel, stable dimeric streptavidin with lower isoelectric point," J Biotechnol, 2007, 128(2):213-225.
Atwell et al., "Stable heterodimers from remodeling the domain interface of a homodimer using a phage display library," J Mol Biol, 1997, 270:26-35.
Baerga-Ortiz et al., "Two different proteins that compete for binding to thrombin have opposite kinetic and thermodynamic profiles," Protein Sci, 2004, 13(1):166-176.
Baker et al., "Conversion of a T cell antagonist into an agonist by repairing a defect in the TCR/peptide/MHC interface: implications for TCR signaling," Immunity, 2000, 13:475-484.
Barrabes et al., "Effect of sialic acid content on glycoprotein pI analyzed by two-dimensional electrophoresis," Electrophoresis, Sep. 2010, 31(17):2903-2912. doi: 10.1002/elps.200900764.
Bartelds et al., "Clinical response to adalimumab: relationship to anti-adalimumab antibodies and serum adalimumab concentrations in rheumatoid arthritis," Ann Rheum Dis, 2007, 66(7):921-926.
Batra et al., "Pharmacokinetics and biodistribution of genetically engineered antibodies," Curr Opin Biotechnol, Dec. 2002, 13(6):603-608.
Bayry et al., "Immuno affinity purification of foot and mouth disease virus type specific antibodies using recombinant protein adsorbed to polystyrene wells," J Virol Methods, 1999, 81:21-30.
Beiboer et al., "Guided Selection of a Pan Carcinoma Specific Antibody Reveals Similar Binding Characteristics yet Structural Divergence Between the Original Murine Antibody and its Human Equivalent," J Mol Biol, Feb. 25, 2000, 296(3):833-849.
Bellosta et al., "Signaling through the ARK tyrosine kinase receptor protects from apoptosis in the absence of growth stimulation," Oncogene, 1997, 15(20):2387-2397.
Bender et al., "Immunogenicity, efficacy and adverse events of adalimumab in RA patients," Rheumatol Int, 2007, 27(3):269-274.
Bendig, "Humanization of rodent monoclonal antibodies by CDR grafting," Methods: A Comparison to Methods in Enzymology, 1995, 8:83-93.
Berglund et al., "The epitope space of the human proteome," Protein Sci, Apr. 2008, 17(4):606-613.
Besada, "Potential patient benefit of a subcutaneous formulation of a tocilizumab for the treatment of rheumatoid arthritis: a critical review," Patient Prefer and Adherence, Aug. 1, 2014, 8:1051-1059. doi: 10.2147/PPA. S34958. eCollection 2014.
Bian et al., "Discovery of promiscuous HLA-II-restricted T cell epitopes with TEPITOPE," Methods, Dec. 2004, 34(4):468-475.
Bilsborough, "IL-31 is associated with cutaneous lymphocyte antigen-positive skin homing T cells in patients with atopic dermatitis," J Allergy Clin Immunol, 2006, 117(2):418-425.
Binz et al., "Engineering novel binding proteins from nonimmunoglobulin domains," Nat Biotechnol, 2005, 23:1257-1268.
Bowie et al., "Deciphering the message in protein sequences: tolerance to amino acid substitutions," Science, 1990, 247:1306-1310.
Branden et al., "Recognition of Foreign Molecules by the Immune System," Introduction to Protein Structure, $2^{nd}$ ed., Garland Publishing, 1999, pp. 299-323.
Brenner et al., "Errors in genome annotation," Trends in Genetics, Apr. 1999, 15:132-133.
Brown et al., "Tolerance of single, but not multiple, amino acid replacements in antibody $V_H$ CDR 2: a means of minimizing B cell wastage from somatic hypermutation?," J Immunol, 1996, 156(9):3285-3291.
Budagian et al., "A promiscuous liaison between IL-15 receptor and Axl receptor tyrosine kinase in cell death control," EMBO J, 2005, 24(24):4260-4270.
Burges et al., "Effective relief of malignant ascites in patients with advanced ovarian cancer by a trifunctional anti-EpCAM x anti-CD3 antibody: a phase I/II study," Clin Cancer Res, 2007, 13(13):3899-3905.
Burgess et al., "Possible dissociation of the heparin-binding and mitogenic activities of heparin-binding (acidic fibroblast) growth factor-1 from its receptor-binding activities by site-directed mutagenesis of a single lysine residue," J Cell Biol, 1990, 111:2129-2138.
CALBIOCHEM® Buffers, "A guide for the preparation and use of buffers in biological systems," by Chandra Mohan, Ph.D., EMD Biosciences, Inc., an Affiliate of Merck KGaA, Darmstadt, Germany, Copyright © 2003, 37 pages.
Canfield et al., "The Binding Affinity of Human IgG for its High Affinity Fc Receptor Is Determined by Multiple Amino Acids in the $C_H2$ Domain and Is Modulated by the Hinge Region," J Exp Med, Jun. 1, 1991, 173(6):1483-1491.
Carter, "Bispecific human IgG by design," J Immunol Methods, 2001, 248:7-15.
Casset et al., "A peptide mimetic of an anti-CD4 monoclonal antibody by rational design," Biochem Biophys Res Commun, Jul. 18, 2003, 307:198-205.
Chamow et al., "A humanized, bispecific immunoadhesin-antibody that retargets $CD3^+$ effectors to kill HIV-1-infected cells," J Immunol, 1994, 153(9):4268-4280.
Chappel et al., "Identification of a secondary Fc gamma RI binding site within a genetically engineered human IgG antibody," J Biol Chem, Nov. 25, 1993, 268(33):25124-25131.
Chappel et al., "Identification of the Fc gamma receptor class I binding site in human IgG through the use of recombinant IgG1/IgG2 hybrid and point-mutated antibodies," Proc Natl Acad Sci USA, Oct. 15, 1991, 88(20):9036-9040.
Chatellier et al., "Functional mapping of conserved residues located at the $V_L$ and $V_H$ domain interface of a Fab," J Mol Biol, Nov. 22, 1996, 264(1):1-6.
Chattopadhyay et al., "Interleukin-31 and Oncostatin-M Mediate Distinct Signaling Reactions and Response Patterns in Lung Epithelial Cells," J Biol Chem, Feb. 2, 2007, 282(5):3014-3026. doi:10.1074/jbc.M609655200.
Chau et al., "HuM291(Nuvion), a humanized Fc receptor-nonbinding antibody against CD3, anergizes peripheral blood T cells as partial agonist of the T cell receptor," Transplantation, 2001, 71(7):941-950.
Chen et al., "Defective secretion of an immunoglobulin caused by mutations in the heavy chain complementarity determining region 2," J Exp Med, 1994, 180(2):577-586.
Chen et al., "Generation and analysis of random point mutations in an antibody CDR2 sequence: many mutated antibodies lose their ability to bind antigen," J Exp Med, 1992, 176(3):855-866.
Chen et al., "Selection and analysis of an optimized anti-VEGF antibody: crystal structure of an affinity-matured Fab in complex with antigen," J Mol Biol, Nov. 5, 1999, 293(4):865-881.

(56) References Cited

OTHER PUBLICATIONS

Chien et al., "Significant structural and functional change of an antigen-binding site by a distant amino acid substitution: proposal of a structural mechanism," Proc Natl Acad Sci USA, 1989, 86(14):5532-5536.
Chihara et al., "Interleukin 6 signaling promotes anti-aquaporin 4 autoantibody production from plasmablasts in neuromyelitis optica," Proc Natl Acad Sci USA, Mar. 1, 2011, 108(9):3701-3706.
Chirino et al., "Minimizing the immunogenicity of protein therapeutics," Drug Discov Today, 2004, 9(2):82-90.
Choi et al., "Engineering of Immunoglobulin Fc Heterodimers Using Yeast Surface-Displayed Combinatorial Fc Library Screening," PLoS One, Dec. 16, 2015, 10(12):e0145349. doi: 10.1371/journal.pone.0145349. eCollection 2015.
Choi et al., "Crystal structures of immunoglobulin Fc heterodimers reveal the molecular basis for heterodimer formation," Mol Immunol, Jun. 2015, 65(2):377-383. doi: 10.1016/j.molimm.2015.02.017. Epub Mar. 2, 2015.
Chu et al., "Accumulation of succinimide in a recombinant monoclonal antibody in mildly acidic buffers under elevated temperatures," Pharm Res, 2007, 24(6):1145-1156.
Chung et al., "Expression of the proto-oncogene Ax1 in renal cell carcinoma," DNA Cell Biol, 2003, 22(8):533-540.
Cole et al., "Human IgG2 variants of chimeric anti-CD3 are nonmitogenic to T cells," J Immunol, 1997, 159(7):3613-3621.
Coloma et al., "Position effects of variable region carbohydrate on the affinity and in vivo behavior of an anti-(1→6) dextran antibody," J Immunol, Feb. 15, 1999, 162(4):2162-2170.
Comper et al., "Charge selectivity in kidney ultrafiltration," Kidney Int, 1995, 47:1242-1251.
Cordoba et al., "Non-enzymatic hinge region fragmentation of antibodies in solution," J Chromatogr B Analyt Technol Biomed Life Sci, 2005, 818(2):115-121.
Costa et al., "Efficacy of tocilizumab in a patient with refractory psoriatic arthritis," Clin Rheumatol, Sep. 2014, 33(9):1355-1357.
Couto et al., "Anti-BA46 Monoclonal Antibody Mc3: Humanization Using a Novel Positional Consensus and in Vivo and in Vitro Characterization," Cancer Research, 1995, 55:1717-1722.
Craven et al., "Receptor tyrosine kinases expressed in metastatic colon cancer," Int J Cancer, 1995, 60(6):791-797.
Cruse et al., Chapter 3 "Antigens and Immunogens," Atlas of Immunology, CRC Press LLC, 2004, p. 109.
Dall'Acqua et al., "Antibody humanization by framework shuffling," Methods, 2005, 36(1):43-60.
Dall'Acqua et al., "Increasing the affinity of a human IgG1 for the neonatal Fc receptor: biological consequences," J Immunol, Nov. 1, 2002, 169(9):5171-5180.
Dall'Acqua et al., "Modulation of the effector functions of a human IgG1 through engineering of its hinge region," J Immunol, 2006, 177(2):1129-1138.
Dall'Acqua et al., Properties of Human IgG1s Engineered for Enhanced Binding to the Neonatal Fc Receptor (FcRn), J Biol Chem Aug. 18, 2006, 281(33):23514-23524. Epub Jun. 21, 2006.
Dall'Acqua et al., "Contribution of Domain Interface Residues to the Stability of Antibody $C_H3$ Domain Homodimers," Biochemistry, Jun. 30, 1998, 37(26):9266-9273. doi: 10.1021/bi980270i. PMID: 9649307.
Damschroder et al., "Framework shuffling of antibodies to reduce immunogenicity and manipulate functional and biophysical properties," Mol Immunol, 2007, 44(11):3049-3060.
Datta-Mannan et al., "Monoclonal antibody clearance. Impact of modulating the interaction of IgG with the neonatal Fc receptor," J Biol Chem, 2007, 282(3):1709-1717.
Davies et al., "Affinity improvement of single antibody VH domains: residues in all three hypervariable regions affect antigen binding," Immunotechnology, 1996, 2(3):169-179.
Davies et al., "Antibody VH domains as small recognition units," Biotechnology (NY), May 1995, 13(5):475-479.
De Groot et al., "De-immunization of therapeutic proteins by T-cell epitope modification," Dev Biol (Basel), 2005, 122:171-194.
De Pascalis et al., "Grafting of 'abbreviated' complementarity-determining regions containing specificity-determining residues essential for ligand contact to engineer a less immunogenic humanized monoclonal antibody," J Immunol, 2002, 169(6):3076-3084.
Decision of the EPO Opposition Division for EP 2 006 381 on Jul. 25, 2018, 17 pages.
Declaration of Christian Beil, signed Jun. 18, 2020, 6 pages, (submitted by the opponent in EPO opposition of EP 3 050 963).
Deen et al., "Structural determinants of glomerular permeability," Am J Physiol Renal Physiol, 2001, 281:F579-F596.
Del Rio et al., "An Engineered Penicillin Acylase with Altered Surface Charge Is More Stable in Alkaline pH," Ann NY Acad Sci, 1996, 799:61-64.
Decision of the EPO Opposition Division in EP 2 275 443, dated Apr. 26, 2018, 29 pages (submitted on May 24, 2019 by the patentee during EPO opposition procedure for EP 2 202 245).
Declaration of Taichi Kuramochi, signed May 23, 2019, 11 pages (submitted on May 24, 2019 by the patentee during EPO opposition procedure for EP 2 202 245).
Declaration of Dr. Anette Henriksen, signed Apr. 17, 2019, 4 pages (submitted by the opponent during EPO opposition procedure for EP 2 006 381).
Deng et al., "An Agonist Murine Monoclonal Antibody to the Human c-Mp1 Receptor Stimulates Megakaryocytopoiesis," Blood, 1998, 92:1981-1988.
Dhiman et al., "Gene expression microarrays: a 21st century tool for directed vaccine design," Vaccine, Oct. 12, 2001, 20(1-2):22-30.
Diaz et al., "Effects of engineering charged amino acids in the $C_H3$ domains on antibody heavy chain dimerization," Philippine Science Letters, 2011, 4(1):48-55.
Dillon et al., "Interleukin 31, a cytokine produced by activated T cells, induces dermatitis in mice," Nat Immunol, 2004, 5(7):752-760.
Dillon et al., "Structural and functional characterization of disulfide isoforms of the human IgG2 subclass," J Biol Chem, 2008, 283(23):16206-16215.
Diveu et al., "GPL, a novel cytokine receptor related to GP130 and leukemia inhibitory factor receptor," J Biol Chem, 2003, 278(50):49850-49859.
Do et al., "A rapid method for determining dynamic binding capacity of resins for the purification of proteins," Protein Expr Purif, Aug. 2008, 60(2):147-150. doi: 10.1016/j.pep.2008.04.009. Epub May 3, 2008.
Dufner et al., "Harnessing phage and ribosome display for antibody optimization," Trends Biotechnol, Nov. 2006, 24(11):523-529.
Dumont et al., "Monomeric Fc fusions: impact on pharmacokinetic and biological activity of protein therapeutics," BioDrugs, 2006, 20(3):151-60.
Ejima et al., "Effects of Acid Exposure on the Conformation, Stability, and Aggregation of Monoclonal Antibodies," Proteins, Mar. 1, 2007, 66(4):954-962.
Elliott et al., "Activation of the erythropoietin (EPO) receptor by bivalent anti-EPO receptor antibodies," J Biol Chem, Oct. 4, 1996, 271(40):24691-24697.
EPO Register Extract EP 1915397, 4 pages (document submitted in EPO opposition and posted by EPO on Feb. 2, 2018).
Ewert et al., "Stability improvement of antibodies for extracellular and intracellular applications: CDR grafting to stable frameworks and structure-based framework engineering," Methods, 2004, 34:184-199.
Feige et al., "How antibodies fold," Trends Biochem Sci, Apr. 2010, 35(4):189-198. doi: 10.1016/j.tibs.2009.11.005. Epub Dec. 21, 2009.
Fridell et al., "GAS6 induces Ax1-mediated chemotaxis of vascular smooth muscle cells," J Biol Chem, 1998, 273(12):7123-7126.
Fujii, "Antibody affinity maturation by random mutagenesis," Methods Mol Biol, 2004, 248:345-359.
Furuya et al., "Interleukin-6 as a Potential Therapeutic Target for Pulmonary Arterial Hypertension," Int J Rheumatol, Aug. 2010, 2010:720305:1-8. doi: 10.1155/2010/720305. Epub Aug. 2, 2010.
GE Healthcare Life Sciences, Dynamic binding capacity study on MabSelect SuRe™ LX for capturing high-titer monoclonal antibodies, Application Note 28-9875-25-AA, 2011, retrieved from the

(56) References Cited

OTHER PUBLICATIONS

Internet on Feb. 1, 20177: http://www.processdevelopmentforum.com/images/articles/28-9875-25_AA_AN_DBC_study_on_MabSelect_SuRe_LX_final.pdf>.
Gen Bank Accession No. AAG00910.2, "recombinant IgG2 heavy chain, partial [*Homo sapiens*]," May 14, 2001, 1 page.
Geneseq Accession No. AEM45140, "Light chain constant region of therapeutic human IgG antibody," Feb. 22, 2007, 1 page.
Geneseq Accession No. ARZ17615, "Human antibody IgG2 heavy chain constant region SEQ ID No. 36," Aug. 21, 2008, 1 page.
Gershoni et al., "Epitope Mapping," BioDrugs, May 2007, 21(3):145-156.
Gerstner et al., "Sequence plasticity in the antigen-binding site of a therapeutic anti-HER2 antibody," J Mol Biol, 2002, 321(5):851-862.
Gessner et al., "The IgG Fc receptor family," Ann Hematol, 1998, 76(6):231-248.
Ghetie et al., "FcRn: the MHC class I-related receptor that is more than an IgG transporter," Immunol Today, 1997, 18:592-598.
Ghetie et al., "Increasing the serum persistence of an IgG fragment by random mutagenesis," Nat Biotechnol, 1997, 15:637-640.
Ghetie et al., "Multiple roles for the major histocompatibility complex class I-related receptor FcRn," Annu Rev Immunol, 2000, 18:739-766.
Gobburu et al., "Pharmacokinetics/dynamics of 5c8, a monoclonal antibody to CD154 (CD40 ligand) suppression of an immune response in monkeys," J Pharmacol Exp Ther, 1998, 286:925-930.
Goode et al., "The glomerular basement membrane charge-selectivity barrier: an oversimplified concept?," Nephrol Dial Transplant, 1996, 11:1714-1716.
Goruppi et al., "Requirement of phosphatidylinositol 3-kinase-dependent pathway and Src for Gas6-Ax1 mitogenic and survival activities in NIH 3T3 fibroblasts," Mol Cell Biol, 1997, 17(8):4442-4453.
Goulet et al., "Kinetic mechanism of controlled Fab-arm exchange for the formation of bispecific immunoglobulin G1 antibodies," J Biol Chem, Jan. 12, 2018, 293(2):651-661. doi:10.1074/jbc.RA117.000303. Epub Nov. 17, 2017.
Gramer et al., "Production of stable bispecific IgG1 by controlled Fab-arm exchange: scalability from bench to large-scale manufacturing by application of standard approaches," mAbs, Nov.-Dec. 2013, 5(6):962-973. doi: 10.4161/mabs.26233. Epub Aug. 22, 2013.
Granted claims of EP 2 275 443, 1 page (submitted on May 24, 2019 by the patentee during EPO opposition procedure for EP 2 202 245).
Graves et al., "Molecular modeling and preclinical evaluation of the humanized NR-LU-13 antibody," Clin Cancer Res, 1999, 5:899-908.
Greenwood et al., "Structural motifs involved in human IgG antibody effector functions," Eur J Immunol, May 1993, 23(5):1098-1104.
Griffin et al., "Analysis of heavy and light chain sequences of conventional camelid antibodies from Camelus dromedarius and Camelus bactrianus species," J Immunol Methods, Mar. 2014, 405:35-46. doi: 10.1016/j.jim.2014.01.003. Epub Jan. 18, 2014.
Golay et al., "Mechanism of action of therapeutic monoclonal antibodies: Promises and pitfalls of in vitro and in vivo assays," Archived of Biochemistry and Biophysics, Feb. 2012, 526:146-153.
Gunasekaran et al., "Enhancing antibody Fc heterodimer formation through electrostatic steering effects: applications to bispecific molecules and monovalent IgG," J Biol Chem, 2010, 285(25):19637-19646.
Gunawardane et al., "Agonistic Human Antibodies Binding to Lecithin-Cholesterol Acyltransferase Modulate High Density Lipoprotein Metabolism," J Biol Chem, Feb. 5, 2016, 291(6):2799-2811. doi: 10.1074/ibc.MIIS.672790. Epub Dec. 7, 2015.
Gupta et al., "Affinity chromatography and co-chromatography of bispecific monoclonal antibody immunoconjugates," J Biochem Biophys Methods, 2002, 51:203-216.
Gussow et al., "Humanization of monoclonal antibodies," Methods Enzymol, 1991, 203:99-121.
Guyre et al., "Increased potency of Fc-receptor-targeted antigens," Cancer Immunol Immunother, 1997, 45(3-4):146-148.
Haagen et al., "Unprimed CD4+ and CD8+ T cells can be rapidly activated by a CD3 x CD19 bispecific antibody to proliferate and become cytotoxic," Cancer Immunol Immunother, Dec. 1994, 39(6):391-396.
Hafizi et al., "Interaction of Ax1 receptor tyrosine kinase with C1-TEN, a novel Cl domain-containing protein with homology to tensin," Biochem Biophys Res Commun, 2002, 299(5):793-800.
Hafizi et al., "Signalling and functional diversity within the Ax1 subfamily of receptor tyrosine kinases," Cytokine Growth Factor Rev, 2006, 17(4):295-304.
Hamers-Casterman et al., "Naturally occurring antibodies devoid of light chains," Nature, Jun. 3, 1993, 363(6428):446-448.
Hanes et al., "Picomolar affinity antibodies from a fully synthetic naive library selected and evolved by ribosome display," Nat Biotechnol, 2000, 18(12):1287-1292.
Hanson et al., "Catalytic antibodies and their applications," Curr Opin Biotechnol, 2005, 16:631-636.
Hashizume et al., "Tocilizumab, a humanized anti-interleukin-6 receptor antibody, improved anemia in monkey arthritis by suppressing IL-6-induced hepcidin production," Rheumatol Int, May 2010, 30(7):917-923. doi: 10.1007/s00296-009-1075-4. Epub Jul. 29, 2009.
Hattori, "Introduction of ART-Ig and application to hemophilia A treatment," Chugai Pharmaceutical Co., Ltd, Research Division, Dec. 2012, 18:42-57 (with English translation).
He et al., "Humanization and pharmacokinetics of a monoclonal antibody with specificity for both E- and P-selectin," J Immunol, 1998, 160:1029-1035.
Helguera et al., "Antibody-Cytokine Fusion Proteins for the Therapy of Cancer," Methods Mol Med, 2005, 109:347-374. doi: 10.1385/1-59259-862-5:347. PMID: 15585931.
Hinton et al., "An engineered human IgG1 antibody with longer serum half-life," J Immunol, Jan. 1, 2006, 176:346-356.
Hinton et al., "Engineered human IgG antibodies with longer serum half-lives in primates," J Biol Chem, Feb. 20, 2004, 279(8):6213-6216. Epub Dec. 29, 2003.
Hirano et al., "Complementary DNA for a novel human interleukin (BSF-2) that induces B lymphocytes to produce immunoglobulin," Nature, Nov. 1986, 324:73-76.
Hirata et al., "Characterization of IL-6 Receptor Expression by Monoclonal and Polyclonal Antibodies," J Immunol, Nov. 1, 1989, 143(9):2900-2906.
Hird et al., "Tumour localisation with a radioactively labelled reshaped human monoclonal antibody," Br J Cancer, Nov. 1991, 64(5):911-914.
Holland et al., "Multiple roles for the receptor tyrosine kinase ax1 in tumor formation," Cancer Res, Oct. 15, 2005, 65(20):9294-9303.
Holm et al., "Functional mapping and single chain construction of the anti-cytokeratin 8 monoclonal antibody TS1," Mol Immunol, Feb. 2007, 44(6):1075-1084.
Holt et al., "Domain antibodies: proteins for therapy," Trends Biotechnol, 2003, 21(11):484-490.
Hombach et al., "A CD16/CD30 bispecific monoclonal antibody induces lysis of Hodgkin's cells by unstimulated natural killer cells in vitro and in vivo," Int J Cancer, 1993, 55:830-836.
Honda et al., "Marginal zone B cells exacerbate endotoxic shock via interleukin-6 secretion induced by Fca/mR-coupled TLR4 signalling," Nat Commun, May 5, 2016, 7:11498. doi: 0.1038/ncomms11498.
Hong et al., "Enhanced cellular uptake and transport of polyclonal immunoglobulin G and fab after their cationization," J Drug Target, 2000, 8(2):67-77.
Hotzel et al., "A strategy for risk mitigation of antibodies with fast clearance," mAbs, Nov.-Dec. 2012, 4(6):753-760. doi: 10.4161/mabs.22189.
Huang et al., "A Monoclonal Anti-Human IL-6 Receptor Antibody Inhibits the Proliferation of Human Myeloma Cells," Hybridoma, Oct. 1993, 12(5):621-630.
Hugo et al., "Functional aspects of co-variant surface charges in an antibody fragment," Protein Sci, Nov. 2002, 11(11):2697-2705. doi: 10.1110/ps.0209302. PMID: 12381851; PMCID: PMC2373727.

(56) References Cited

OTHER PUBLICATIONS

Huizinga et al., "Sarilumab, a fully human monoclonal antibody against IL-6Rα in patients with rheumatoid arthritis and an inadequate response to methotrexate: efficacy and safety results from the randomised SARIL-RA-MOBILITY Part A trial," Ann Rheum Dis, Sep. 2014, 73(9):1626-1634. doi: 10.1136/annrheumdis-2013-204405. Epub Dec. 2, 2013.
Hwang et al., "Use of human germline genes in a CDR homology-based approach to antibody humanization," Methods, 2005, 36(1):35-42.
Igawa et al., "Antibody recycling by engineered pH-dependent antigen binding improves the duration of antigen neutralization," Nat Biotechnol, 2010, 28(11):1203-1207.
Igawa et al., "Engineering the variable region of therapeutic IgG antibodies," mAbs, 2011, 3(3):243-252.
Igawa et al., "Reduced elimination of IgG antibodies by engineering the variable region," Protein Eng Des Sel, 2010, 23(5):385-392.
Igawa et al., "$V_H/V_L$ interface engineering to promote selective expression and inhibit conformational isomerization of thrombopoietin receptor agonist single-chain diabody," Protein Eng Des Sel, Aug. 2010, 23(8):667-677. doi: 10.1093/protein/gzq034. Epub Jun. 24, 2010.
Igawa et al., "pH-dependent antigen-binding antibodies as a novel therapeutic modality," Biochim Biophys Acta, Nov. 2014, 1844(11):1943-1950. doi: 10.1016/j.bbapap.2014.08.003. Epub Aug. 12, 2014.
Iijima et al., "Tocilizumab improves systemic rheumatoid vasculitis with necrotizing crescentic glomerulonephritis," Mod Rheumatol, Jan. 2015, 25(1):138-142. doi: 0.3109/14397595.2013.874748. Epub Feb. 18, 2014.
IMGT Scientific charts depicting the correspondence between Eu and Kabat numberings for the human IgG constant region, created May 17, 2001 and last updated Aug. 13, 2014, 2 pages.
Ito et al., "Expression of receptor-type tyrosine kinase, Ax1, and its ligand, Gas6, in pediatric thyroid carcinomas around Chernobyl," Thyroid, 2002, 12(11):971-975.
Ito et al., "The His-probe method: effects of histidine residues introduced into the complementarity-determining regions of antibodies on antigen-antibody interactions at different pH values," FEBS Lett, 1992, 309:85-88.
Jackman et al., "Development of a two-part strategy to identify a therapeutic human bispecific antibody that inhibits IgE receptor signaling," J Biol Chem, Jul. 2, 2010, 285(27):20850-20859. doi: 10.1074/jbc.M110.113910. Epub May 5, 2010.
Jain et al., "Engineering antibodies for clinical applications," Trends Biotechnol, 2007, 25(7):307-316.
Janeway et al., Chapter 3 "Antigen Recognition by B-cell and T-cell Receptors," Immunobiology, $5^{th}$ ed., 2001, pp. 93-122.
Janeway et al., Chapter 4 "The Generation of Lymphocyte Antigen Receptors," Immunobiology, $5^{th}$ ed., 2001, pp. 123-154.
Jefferis et al., "Recognition sites on human IgG for Fc gamma receptors: the role of glycosylation," Immunol Lett, 1995, 44(2-3):111-117.
Jendeberg et al., "Engineering of $Fc_1$ and $Fc_3$ from human immunoglobulin G to analyse subclass specificity for staphylococcal protein A," J Immunol Methods, 1997, 201(1):25-34.
Johnson et al., "Cation exchange-HPLC and mass spectrometry reveal C-terminal amidation of an IgG1 heavy chain," Anal Biochem, 2007, 360(1):75-83.
Johnson et al., "Kabat database and its applications: 30 years after the first variability plot," Nucleic Acids Res, Jan. 1, 2000, 28(1):214-218.
Jones et al., "Identification and removal of a promiscuous CD4+ T cell epitope from the C1 domain of factor VIII," Thromb Haemost, 2005, 3(5):991-1000.
Ju et al., "Conversion of the interleukin 1 receptor antagonist into an agonist by site-specific mutagenesis," Proc Natl Acad Sci USA, 1991, 88:2658-2662.
Jung et al., "The importance of framework residues H6, H7 and H10 in antibody heavy chains: experimental evidence for a new structural subclassification of antibody $V_H$ domains," J Mol Biol, Jun. 8, 2001, 309(3):701-716.
Kabat et al., Sequences of Proteins of Immunological Interest, National Institutes of Health, Publ'n No. 91-3242, $5^{th}$ ed., 1991, vol. 1, pp. 647-660.
Kabat et al., Sequence of Proteins of Immunological Interest, National Institutes of Health, Publ'n No. 91-3242, $5^{th}$ ed., 1991, pp. 690, 693.
Kai et al., "Switching constant domains enhances agonist activities of antibodies to a thrombopoietin receptor," Nat Biotechnol, Feb. 2008, 26(2):209-211. Epub Dec. 23, 2007.
Kashmiri et al., "Generation, characterization, and in vivo studies of humanized anticarcinoma antibody CC49," 1995, Hybridoma, 14:461-473.
Katayose et al., "MUC1-specific targeting immunotherapy with bispecific antibodies: inhibition of xenografted human bile duct carcinoma growth," Cancer Res, 1996, 56(18):4205-4212.
Kenanova et al., "Tailoring the pharmacokinetics and positron emission tomography imaging properties of anti-carcinoembryonic antigen single-chain Fv-Fc antibody fragments," Cancer Res, Jan. 15, 2005, 65(2):622-631.
Khalifa et al., "Effects on interaction kinetics of mutations at the VH-VL interface of Fabs depend on the structural context," J Mol Recognit, May-Jun. 2000, 13(3):127-139.
Khawli et al., "Improved tumor localization and radioimaging with chemically modified monoclonal antibodies," Cancer Biother Radiopharm, 1996, 11:203-215.
Kim et al., "Antibody Engineering for the Development of Therapeutic Antibodies," Mol Cells, 2005, 20:17-29.
Kim et al., "Chemical modification to reduce renal uptake of disulfide-bonded variable region fragment of anti-tac monoclonal antibody labeled with 99mTc," Bioconjugate Chem, 1999, 10:447-453.
Kim et al., "Lowering of pI by acylation improves the renal uptake of $^{99m}$Tc-labeled anti-Tac dsFv: effect of different acylating reagents," Nucl Med Biol, 2002, 29:795-801.
Kim et al., "Mapping the site on human IgG for binding of the MHC class I-related receptor, FcRn," Eur J Immunol, Sep. 1999, 29(9):2819-2825.
Kipriyanov et al., "Bispecific tandem diabody for tumor therapy with improved antigen binding and pharmacokinetics," J Mol Biol, Oct. 15, 1999, 293(1):41-56.
Kipriyanov et al., "Effect of domain order on the activity of bacterially produced bispecific single-chain Fv antibodies," J Mol Biol, Jun. 27, 2003, 330(1):99-111.
Kishimoto, "Interleukin-6 and its Receptor in Autoimmunity," J Autoimmun, Apr. 1992, 5 Suppl A:123-132.
Klein et al., "Progress in overcoming the chain association issue in bispecific heterodimeric IgG antibodies," mAbs, Nov.-Dec. 2012, 4(6):653-663. doi: 10.4161/mabs.21379. Epub Aug. 27, 2012.
Klimka et al., "Human anti-CD30 recombinant antibodies by guided phage antibody selection using cell panning," Br J Cancer, Jul. 2000, 83(2):252-260.
Kobayashi et al., "A monoclonal antibody specific for a distinct region of hen egg-white lysozyme," Mol Immunol, 1982, 19:619-630.
Kobayashi et al., "The pharmacokinetic characteristics of glycolated humanized anti-Tac Fabs are determined by their isoelectric points," Cancer Res, 1999, 59:422-430.
Komissarov et al., "Site-specific mutagenesis of a recombinant anti-single-stranded DNA Fab—Role of heavy chain complementarity-determining region 3 residues in antigen interaction," J Biol Chem, 1997, 272(43):26864-26870.
Kondo et al., "A case of overlap syndrome successfully treated with tocilizumab: a hopeful treatment strategy for refractory dermatomyositis?," Rheumatology (Oxford), Oct. 2014, 53(10):1907-1908. doi: 10.1093/rheumatology/keu234. Epub May 23, 2014.
Kontermann, "Recombinant bispecific antibodies for cancer therapy," Acta Pharmacol Sin, Jan. 2005, 26(1):1-9.
Korn et al., "Recombinant bispecific antibodies for the targeting of adenoviruses to CEA-expressing tumour cells: a comparative analy-

(56) References Cited

OTHER PUBLICATIONS sis of bacterially expressed single-chain diabody and tandem scFv," J Gene Med, Jun. 2004, 6(6):642-651.
Kranenborg et al., "Development and characterization of anti-renal cell carcinoma x antichelate bispecific monoclonal antibodies for two-phase targeting of renal cell carcinoma," Cancer Res, 1995, 55:5864s-5867s.
Krauss et al., "Impact of antibody framework residue $V_H$-71 on the stability of a humanised anti-MUC1 scFv and derived immunoenzyme," Br J Cancer, 2004, 90:1863-1870.
Kreutz et al., "Efficient bispecific monoclonal antibody purification using gradient thiophilic affinity chromatography," J Chromatogr B, 1998, 714:161-170.
Krieckaert et al., "Immunogenicity of biologic therapies—we need tolerance," Nat Rev Rheumatol, Oct. 2010, 6(10):558-559. doi: 10.1038/nrrheum.2010.153.
Kufer et al., "A revival of bispecific antibodies," Trends Biotechnol, 2004, 22(5):238-244.
Kumar et al., "The second PDZ domain of INAD is a type I domain involved in binding to eye protein kinase C. Mutational analysis and naturally occurring variants," J Biol Chem, Jul. 6, 2001, 276(27):24971-24977. Epub May 7, 2001.
Kurfis et al., "Role of Arg182 in the second extracellular loop of angiotensin II receptor AT2 in ligand binding," Biochem Biophys Res Commun, 1999, 263:816-819.
Labrijn et al., "Therapeutic IgG4 antibodies engage in Fab-arm exchange with endogenous human IgG4 in vivo," Nat Biotechnol, 2009, 27:767-771.
Labrijn et al., "Controlled Fab-arm exchange for the generation of stable bispecific IgG1," Nat Protoc, Oct. 2014, 9(10):2450-2463. doi: 10.1038/nprot.2014.169. Epub Sep. 25, 2014.
Labrijn et al., "Efficient generation of stable bispecific IgG1 by controlled Fab-arm exchange," Pro Natl Acad Sci USA, Mar. 26, 2013, 110(13):5145-5150. doi: 10.1073/pnas.1220145110. Epub Mar. 11, 2013.
Labrijn et al., "Species-specific determinants in the IgG CH3 domain enable Fab-arm exchange by affecting the noncovalent CH3-CH3 interaction strength," J Immunol, Sep. 15, 2011, 187(6):3238-3246. doi: 10.4049/jimmunol.1003336. Epub Aug. 12, 2011.
Lansdorp et al., "Purification and analysis of bispecific tetrameric antibody complexes," Mol Immunol, 1990, 27:659-666.
Lay et al., "Sulfasalazine suppresses drug resistance and invasiveness of lung adenocarcinoma cells expressing AXL," Cancer Res, 2007, 67(8):3878-3887.
Lazar et al., "Transforming growth factor alpha: mutation of aspartic acid 47 and leucine 48 results in different biological activities," Mol Cell Biol, 1988, 8:1247-1252.
Le Gall et al., "Effect of linker sequences between the antibody variable domains on the formation, stability and biological activity of a bispecific tandem diabody," Protein Eng Des Sel, Apr. 2004, 17(4):357-366. Epub May 4, 2004.
Lebegue et al., "Production and characterization of hybrid monoclonal antibodies with IgG1/IgG3 double isotype," C R Acad Sci III, 1990, 310(9):377-382.
Leong et al., "Adapting pharmacokinetic properties of a humanized anti-interleukin-8 antibody for therapeutic applications using site-specific pegylation," Cytokine, 2001, 16(3):106-119.
Levin et al., "Optimizing the affinity and specificity of proteins with molecular display," Mol Biosyst, 2006, 2(1):49-57. Epub Nov. 8, 2005.
Li et al., "Construction and characterization of a humanized anti-human CD3 monoclonal antibody 12F6 with effective immunoregulation functions," Immunology, Dec. 2005, 116(4):487-498.
Lin et al., "Preclinical pharmacokinetics, interspecies scaling, and tissue distribution of a humanized monoclonal antibody against vascular endothelial growth factor," J Pharmacol Exp Ther, 1999, 288(1):371-378.
Lindhofer et al., "Preferential Species-Restricted Heavy/Light Chain Pairing in Rat/Mouse Quadromas," J Immunol, 1995, 155:219-225.
Liu et al., "Functional interactions between arginine-133 and aspartate-88 in the human reduced folate carrier: evidence for a charge-pair association," Biochem J, Sep. 2001, 358(Pt. 2):511-516.
Liu et al., "Heterogeneity of monoclonal antibodies," J Pharm Sci, 2008, 97(7):2426-2447.
Lloyd et al., "The production of a bispecific anti-CEA, anti-hapten (4-amino-phthalate) hybrid-hybridoma," J Natl Med Assoc, Oct. 1991, 83(10):901-904.
Lobo et al., "Antibody pharmacokinetics and pharmacodynamics," J Pharm Sci, 2004, 93:2645-2668.
Lotz et al., "B Cell Stimulating Factor 2/Interleukin 6 is a Costimulant for Human Thymocytes and T Lymphocytes," J Exp Med, Mar. 1, 1988, 167(3):1253-1258.
Lund et al., "Multiple Interactions of IgG with Its Core Oligosaccharide Can Modulate Recognition by Complement and Human Fcγ Receptor I and Influence the Synthesis of Its Oligosaccharide Chains," The Journal of Immunology, 1996, 157:4963-4969.
Lund et al., "Expression and characterization of truncated forms of humanized L243 IgG1—Architectural features can influence synthesis of its oligosaccharide chains and affect superoxide production triggered through human Fcγ receptor I," Eur J Biochem, Dec. 2000, 267(24):7246-7256.
MacCallum et al., "Antibody-antigen interactions: contact analysis and binding site topography," J Mol Biol, 1996, 262:732-745.
Maeda et al., "pH-dependent receptor/ligand dissociation as a determining factor for intracellular sorting of ligands for epidermal growth factor receptors in rat hepatocytes," J Control Release, 2002, 82(1):71-82.
Maini et al., "Double-blind randomized controlled clinical trial of the interleukin-6 receptor antagonist, tocilizumab, in European patients with rheumatoid arthritis who had an incomplete response to methotrexate," Arthritis Rheum, 2006, 54(9):2817-2829.
Maity et al., "Equilibrium unfolding of dimeric and engineered monomeric forms of λ Cro (F58W) repressor and the effect of added salts: evidence for the formation of folded monomer induced by sodium perchlorate," Arch Biochem Biophys, Feb. 1, 2005, 434(1):93-107.
Male et al., "Antibodies," Immunology, published by Elsevier Ltd., $7^{th}$ ed., 2006, pp. 59-86.
Manz et al., "Biomolecules," Bioanalytical Chemistry, World Scientific Publishing Co., 2003, p. 7.
Manzke et al., "Single-step purification of bispecific monoclonal antibodies for immunotherapeutic use by hydrophobic interaction chromatography," J Immunol Methods, 1997, 208:65-73.
Marchalonis et al., "Antigenic mapping of a human lambda light chain: correlation with three dimensional structure," J Protein Chem, Apr. 1992, 11(2):129-137.
Mariuzza et al., "The structural basis of antigen-antibody recognition," Annu Rev Biophys Chem, 1987, 16:139-159.
Marks et al., "By-passing immunization: building high affinity human antibodies by chain shuffling," Biotechnology (NY), 1992, 10(7):779-783.
Marshall et al., "Rational design and engineering of therapeutic proteins," Drug Discov Today, Mar. 1, 2003, 8(5):212-221.
Marti et al., "Inverse electrostatic effect: electrostatic repulsion in the unfolded state stabilizes a leucine zipper," Biochemistry, 2004, 43(39):12436-12447.
Martin et al., "Crystal structure at 2.8 Å of an FcRn/heterodimeric Fc complex: mechanism of pH-dependent binding," Mol Cell, 2001, 7:867-877.
Martinez et al., "Disulfide connectivity of human immunoglobulin G2 structural isoforms," Jul. 15, 2008, 47(28):7496-7508. doi: 10.1021/bi800576c. Epub Jun. 13, 2008.
Marvin et al., "Recombinant approaches to IgG-like bispecific antibodies," Acta Pharmacol Sin, 2005, 26:649-658.
Marvin et al., "Redesigning an antibody fragment for faster association with its antigen," Biochemistry, 2003, 42:7077-7083.
Maxfield et al., "Endocytic recycling," Nat Rev Mol Cell Biol, 2004, 5(2):121-132.
Maynard et al., "Antibody engineering," Annu Rev Biomed Eng, 2000, 2:339-376.

(56) References Cited

OTHER PUBLICATIONS

McCloskey et al., "GAS6 mediates adhesion of cells expressing the receptor tyrosine kinase Ax1," J Biol Chem, 1997, 272(37):23285-23291.
Mcphee et al., "Engineering human immunodeficiency virus 1 protease heterodimers as macromolecular inhibitors of viral maturation," Proc Natl Acad Sci USA, Oct. 15, 1996, 93(21):11477-11481.
Medesan et al., "Delineation of the amino acid residues involved in transcytosis and catabolism of mouse IgG1," J Immunol, Mar. 1, 1997, 158(5):2211-2217.
Merchant et al., "An efficient route to human bispecific IgG," Nat Biotechnol, 1998, 16:677-681.
Meric et al., "Expression profile of tyrosine kinases in breast cancer," Clin Cancer Res, 2002, 8(2):361-367.
Michaelsen et al., "A mutant human IgG molecule with only one C1q binding site can activate complement and induce lysis of target cells," Eur J Immunol, Jan. 2006, 36(1):129-138.
Mihara et al., "Tocilizumab inhibits signal transduction mediated by both mIL-6R and sIL-6R, but not by the receptors of other members of IL-6 cytokine family," Int Immunopharmacol, 2005, 5(12):1731-1740.
Mihara et al., "Anti-interleukin 6 receptor antibody inhibits murine AA-amyloidosis," J Rheumatol, Jun. 2004, 31(6):1132-1138.
Morell et al., "Metabolic properties of IgG subclasses in man," J Clin Invest, 1970, 49(4):673-680.
Mori et al., "Novel models of cancer-related anemia in mice inoculated with IL-6-producing tumor cells," Biomed Res, Feb. 2009, 30(1):47-51.
Morimoto et al., "Single-step purification of F(ab')$_2$ fragments of mouse monoclonal antibodies (immunoglobulins G1) by hydrophobic interaction high performance liquid chromatography using TSKgel Phenyl-5PW," J Biochem Biophys Methods, 1992, 24:107-117.
Motozawa et al., "Unique circumferential peripheral keratitis in relapsing polychondritis," Medicine (Baltimore), Oct. 2017, 96(41):e7951. doi: 10.1097/MD.0000000000007951.
Murata et al., "Anti-Digoxin Fab Variants Generated by Phage Display," Mol Biotechnol, Jun. 2013, 54(2):269-277. doi: 10.1007/s12033-012-9564-1.
Murtaugh et al., "A combinatorial histidine scanning library approach to engineer highly pH-dependent protein switches," Protein Sci, 2011, 20(9):1619-1631. doi: 10.1002/pro 696.
Nakano et al., "Prevention of growth arrest-induced cell death of vascular smooth muscle cells by a product of growth arrest-specific gene, gas6," FEBS Lett, 1996, 387(1):78-80.
Nakano et al., "Vascular smooth muscle cell-derived, Gla-containing growth-potentiating factor for Ca$^{2+}$-mobilizing growth factors," J Biol Chem, 1995, 270(11):5702-5705.
Narazaki et al., "Therapeutic effect of tocilizumab on two patients with polymyositis," Rheumatology (Oxford), Jul. 2011, 50(7):1344-1346. doi: 10.1093/rheumatology/ker152. Epub Apr. 22, 2011.
Narhi et al., "Asn to Lys mutations at three sites which are N-glycosylated in the mammalian protein decrease the aggregation of *Escherichia coli*-derived erythropoietin," Protein Eng, Feb. 2001, 14(2):135-140.
Neis et al., "Enhanced expression levels of IL-31 correlate with IL-4 and IL-13 in atopic and allergic contact dermatitis," J Allergy Clin Immunol, 2006, 118(4):930-937.
Nemoto et al., "Overexpression of protein tyrosine kinases in human esophageal cancer," Pathobiology, 1997, 65(4):195-203.
Nesterova et al., "Glypican-3 as a novel target for an antibody-drug conjugate," AACR Abstract No. 656, Los Angeles, CA, Apr. 4-18, 2007.
Neubauer et al., "Expression of ax1, a transforming receptor tyrosine kinase, in normal and malignant hematopoiesis," Blood, 1994, 84(6):1931-1941.
Newman et al., "Modification of the Fc Region of a Primatized IgG Antibody to Human CD4 Retains Its Ability to Modulate CD4 Receptors but Does Not Deplete CD4 T Cells in Chimpanzees," Clin Immunol, Feb. 2001, 98(2):164-174.
Nieba et al., "Disrupting the hydrophobic patches at the antibody variable/constant domain interface: improved in vivo folding and physical characterization of an engineered scFv fragment," Protein Eng, Apr. 1997, 10(4):435-444.
Nishimoto et al., "Humanized anti-interleukin-6 receptor antibody treatment of multicentric Castleman disease," Blood, 2005, 106(8):2627-2632.
Nishimoto et al., "Interleukin 6: from bench to bedside," Nat Clin Pract Rheumatol, 2006, 2(11):619-626.
Nohaile et al., "Altering dimerization specificity by changes in surface electrostatics," Proc Natl Acad Sci USA, Mar. 13, 2001, 98(6):3109-3114.
Novick et al., "Monoclonal Antibodies to the Soluble Human IL-6 Receptor: Affinity Purification, ELISA, and Inhibition of Ligand Binding," Hybridoma, Feb. 1991, 10(1):137-146.
O'Bryan et al., "ax1, a transforming gene isolated from primary human myeloid leukemia cells, encodes a novel receptor tyrosine kinase," Mol Cell Biol, 1991, 11(10):5016-5031.
O'Shea et al., "Peptide 'Velcro': design of a heterodimeric coiled coil," Curr Biol, Oct. 1, 1993, 3(10):658-667.
Ohno et al., "Antigen-binding specificities of antibodies are primarily determined by seven residues of $V_H$," Proc Natl Acad Sci USA, 1985, 82(9):2945-2949.
Ohsugi et al., "Current Antibody Drugs—Developments/Manufacturing Technology/Scope of Patents—Success Story of Pre-market Approved Pipeline," Pharm Stage, 2007, 7(5):13-18 (with English translation).
Okabe, "Proprietary Innovative Antibody Engineering Technologies in Chugai Pharmaceutical," Chugai Pharmaceutical Co., Ltd., Dec. 18, 2012, 78 pages.
Okiyama et al., "Therapeutic Effects of Interleukin-6 Blockade in a Murine Model of Polymyositis That Does Not Require Interleukin-17A," Arthritis Rheum, Aug. 2009, 60(8):2505-12.
Onda et al., "Lowering the Isoelectric Point of the Fv Portion of Recombinant Immunotoxins Leads to Decreased Nonspecific Animal Toxicity without Affecting Antitumor Activity," Cancer Res, 2001, 61:5070-5077.
Ono et al., "The humanized anti-HM1.24 antibody effectively kills multiple myeloma cells by human effector cell-mediated cytotoxicity," Mol Immunol, 1999, 36(6):387-395.
Otomo et al., "Structure of the heterodimeric complex between CAD domains of CAD and ICAD," Nat Struct Biol, Aug. 2000, 7(8):658-662. doi: 10.1038/77957. PMID: 10932250.
Ozhegov et al., Tolkovyi Slovar Russkogo iazyka, 2004, p. 292 (with an English translation of the relevant passage defining "control").
Pabst et al., "Engineering of novel Staphylococcal Protein A ligands to enable milder elution pH and high dynamic binding capacity," J Chromatogr A, Oct. 3, 2014, 1362:180-185. doi: 10.1016/j.chroma.2014.08.046. Epub Aug. 19, 2014.
Pabst et al., "Evaluation of recent Protein A stationary phase innovations for capture of biotherapeutics," J Chromatogr A, Jun. 15, 2018, 1554:45-60. doi: 10.1016/j.chroma.2018.03.060. Epub Apr. 7, 2018.
Padlan et al., "Identification of specificity-determining residues in antibodies," FASEB J, 1995, 9:133-139.
Padlan et al., "Structure of an antibody-antigen complex: crystal structure of the HyHEL-10 Fab-lysozyme complex," Proc Natl Acad Sci USA, 1989, 86:5938-5942.
Padlan et al., "X-ray crystallography of antibodies," Adv Protein Chem, 1996, 49:57-133.
Pakula et al., "Genetic Analysis of Protein Stability and Function," Annu Rev Genet, 1989, 23:289-310.
Pan et al., "Blocking neuropilin-1 function has an additive effect with anti-VEGF to inhibit tumor growth," Cancer Cell, Jan. 2007, 11(1):53-67.
Pardridge et al., "Enhanced cellular uptake and in vivo biodistribution of a monoclonal antibody following cationization," J Pharm Sci, Aug. 1995, 84(8):943-948.
Pardridge et al., "Enhanced endocytosis in cultured human breast carcinoma cells and in vivo biodistribution in rats of a humanized monoclonal antibody after cationization of the protein," J Pharmacol Exp Ther, 1998, 286(1):548-554.

(56) References Cited

OTHER PUBLICATIONS

Paul, "Structure and function of immunoglobulins," Fundamental Immunology, 3rd ed., 1993, pp. 292-295.
Pavlaki et al., "Matrix metalloproteinase inhibitors (MMPIs): the beginning of phase I or the termination of phase III clinical trials," Cancer Metastasis Rev, 2003, 22(2-3):177-203.
Pavlinkova et al., "Charge-modified single chain antibody constructs of monoclonal antibody CC49: Generation, characterization, pharmacokinetics, and biodistribution analysis," Nucl Med Biol, 1999, 26:27-34.
Pavlou et al., "The therapeutic antibodies market to 2008," Eur J Pharm Biopharm, 2005, 59:389-396.
Pejchal et al., "A Conformational Switch in Human Immunodeficiency Virus gp41 Revealed by the Structures of Overlapping Epitopes Recognized by Neutralizing Antibodies," J Virol, Sep. 2009, 83(17):8451-8462. doi: 10.1128/ JVI.00685-09. Epub Jun. 10, 2009.
Peters et al., "Engineering an improved IgG4 molecule with reduced disulfide bond heterogeneity and increased Fab domain thermal stability," J Biol Chem, Jul. 13, 2012, 287(29):24525-24533. doi: 10.1074/jbc.M112.369744. Epub May 18, 2012.
Petkova et al., "Enhanced half-life of genetically engineered human IgGI antibodies in a humanized FcRn mouse model: potential application in humorally mediated autoimmune disease," Int Immunol, Dec. 2006, 18(12):1759-1769. Epub Oct. 31, 2006.
Pini et al., "Design and use of a phage display library—Human antibodies with subnanomolar affinity against a marker of angiogenesis eluted from a two-dimensional gel," J Biol Chem, 1998, 273(34):21769-21776.
Poduslo et al., "Polyamine modification increases the permeability of proteins at the blood-nerve and blood-brain barriers," J Neurochem, 1996, 66:1599-1609.
Pokkuluri et al., "A domain flip as a result of a single amino-acid substitution," Structure, Aug. 15, 1998, 6(8):1067-1073.
Pons et al., "Energetic analysis of an antigen/antibody interface: alanine scanning mutagenesis and double mutant cycles on the HyHEL-10/lysozyme interaction," Protein Sci, 1999, 8(5):958-968.
Presta et al., "Molecular engineering and design of therapeutic antibodies," Curr Opin Immunol, 2008, 20(4):460-470. doi: 10.1016/ j.coi.2008.06.012.
Presta, "Engineering of therapeutic antibodies to minimize immunogenicity and optimize function," Adv Drug Deliv Rev, 2006, 58(5-6):640-656.
Queen et al., "A humanized antibody that binds to the interleukin 2 receptor," Proc Natl Acad Sci USA, 1989, 86(24):10029-10033.
R&D Systems, "Anti-human IL-31 RA Antibody," Catalog #AF2769, Oct. 2008, 1 page.
R&D Systems, "Biotinylated Anti-human IL-31 RA Antibody," Catalog #BAF2769, Nov. 2005, 1 page.
Raap et al., "Correlation of IL-31 serum levels with severity of atopic dermatitis," J Allergy Clin Immunol, 2008, 122(2):421-423.
Rader et al., "A phage display approach for rapid antibody humanization: designed combinatorial V gene libraries," Proc Natl Acad Sci USA, Jul. 21, 1998, 95(15):8910-8915.
Raffen et al., "Reengineering immunoglobulin domain interactions by introduction of charged residues," Protein Eng, Apr. 1998, 11:303-309.
Raghavan et al., "Fc Receptors and Their Interactions with Immunoglobulins," Annu Rev Cell Dev Biol, Nov. 1996, 12:181-220.
Rajpal et al., A general method for greatly improving the affinity of antibodies by using combinatorial libraries, Proc Natl Acad Sci USA, 2005, 102:8466-8471.
Raposo et al., "Epitope-specific antibody response is controlled by immunoglobulin $V_H$ polymorphisms," J Exp Med, Mar. 10, 2014, 211(3):405-411. doi: 10.1084/jem.20130968. Epub Feb. 17, 2014.
Rathanaswami et al., "Demonstration of an in vivo generated sub-picomolar affinity fully human monoclonal antibody to interleukin-8," Biochem Biophys Res Commun, 2005, 334:1004-1013.
Reddy et al., "Elimination of Fc receptor-dependent effector functions of a modified IgG4 monoclonal antibody to human CD4," J Immunol, 2000, 164(4):1925-1933.
Reference table: IMGT exon, EU and Kabat numbering of residues within the human 1gG1 sequence; retrieved from http://www.imgt.org/IMGTScientificChart/Numbering/Hu_1GHGnber.html on Jun. 1, 2020, 4 pages (cited by the opponents in the EPO opposition procedure for EP 3 050 963).
Reichert et al., "Development trends for monoclonal antibody cancer therapeutics," Nat Rev Drug Discov, 2007, 6(5):349-356.
Reichert et al., "Monoclonal antibody successes in the clinic," Nat Biotechnol, 2005, 23:1073-1078.
Reichert, "Antibodies to watch in 2014," mAbs, Jul./Aug. 2014, 6(4):799-802.
Reimann et al., "A humanized form of a CD4-specific monoclonal antibody exhibits decreased antigenicity and prolonged plasma half-life in rhesus monkeys while retaining its unique biological and antiviral properties," AIDS Res Hum Retroviruses, Jul. 20, 1997, 13(11):933-943.
Reist et al., "Human IgG2 constant region enhances in vivo stability of anti-tenascin antibody 81C6 compared with its murine parent," Clin Cancer Res, Oct. 1998, 4(10):2495-2502.
Ridgway et al., "'Knobs-into-holes' engineering of antibody $C_H3$ domains for heavy chain heterodimerization," Protein Eng, 1996, 9:617-621.
Rispens et al., "Mechanism of Immunoglobulin G4 Fab-arm Exchange," J Am Chem Soc, Jul. 6, 2011, 133(26):10302-10311. doi: 10.1021/ ja203638y. Epub Jun. 15, 2011.
Rispens et al., "Dynamics of inter-heavy chain interactions in human immunoglobulin G (IgG) subclasses studied by kinetic Fab arm exchange," J Biol Chem, Feb. 28, 2014, 289(9):6098-6109. doi: 10.1074/jbc.M113.541813. Epub Jan. 14, 2014.
Roguska et al., "Humanization of murine monoclonal antibodies through variable domain resurfacing," Proc Natl Acad Sci USA, 1994, 91:969-973.
Roitt et al., Immunology, M., Mir, 5th ed., 2000, pp. 110, 150, and 537-539 (with what are believed to be the corresponding p. from an English version of Immunology).
Roitt et al., Chapter 3 "Antibodies," Immunology, M., Mir, 5th ed., 2000, pp. 97-113 (with what are believed to be the corresponding pages from an English version of Immunology).
Roopenian et al., "FcRn: the neonatal Fc receptor comes of age," Nat Rev Immunol, Sep. 2007, 7(9):715-725. Epub Aug. 17, 2007.
Rothe et al., "Ribosome display for improved biotherapeutic molecules," Expert Opin Biol Ther, 2006, 6(2):177-187.
Rudikoff et al., "Single amino acid substitution altering antigen-binding specificity," Proc Natl Acad Sci USA, 1982, 79(6):1979-1983.
Ruf et al., "Pharmacokinetics and in vivo stability of intraperitoneally administered therapeutic antibody catumaxomab," J Clin Oncol, 2008, 26 (May 20 suppl), abstr 14006.
Ryman et al., "Pharmacokinetics of Monoclonal Antibodies," CPT Pharmacometrics Syst Pharmacol, Sep. 2017, 6(9):576-588. doi: 10.1002/psp4.12224. Epub Jul. 29, 2017.
Sainaghi et al., "Gas6 induces proliferation in prostate carcinoma cell lines expressing the Ax1 receptor," J Cell Physiol, 2005, 204(1):36-44.
Salfeld et al., "Isotype selection in antibody engineering," Nat Biotechnol, 2007, 25(12):1369-1372.
Sal-Man et al., "Arginine mutations within a transmembrane domain of Tar, an *Escherichia coli* aspartate receptor, can drive homodimer dissociation and heterodimer association in vivo," Biochem J, 2005, 385:29-36.
Sampei et al., "Identification and multidimensional optimization of an asymmetric bispecific IgG antibody mimicking the function of factor VIII cofactor activity," PLoS One, 2013, 8(2):e57479. doi: 10.1371/journal.pone.0057479. Epub Feb. 28, 2013.
Sampei et al., "Non-antigen-contacting region of an asymmetric bispecific antibody to factors IXa/X significantly affects factor VIII-mimetic activity," mAbs, 2015, 7(1):120-128. doi: 10.4161/ 19420862.2015.989028.

(56) References Cited

OTHER PUBLICATIONS

Sarkar et al., "Rational cytokine design for increased lifetime and enhanced potency using pH-activated 'histidine switching'," Nat Biotechnol, Sep. 2002, 20(9):908-913. Epub Aug. 5, 2002.
Sarmay et al., "Mapping and comparison of the interaction sites on the Fc region of IgG responsible for triggering antibody dependent cellular cytotoxicity (ADCC) through different types of human Fc gamma receptor," Mol Immunol, 1992, 29(5):633-639.
Sato et al., "Reshaping a human antibody to inhibit the interleukin 6-dependent tumor cell growth," Cancer Res, 1993, 53(4):851-856.
Sawabu et al., "Growth arrest-specific gene 6 and Axl signaling enhances gastric cancer cell survival via Akt pathway," Mol Carcinog, 2007, 46(2):155-164.
Schaefer et al., "Immunoglobulin domain crossover as a generic approach for the production of bispecific IgG antibodies," Proc Natl Acad Sci USA, Jul. 5, 2011, 108(27):11187-11192. doi: 10.1073/pnas. 1019002108. Epub Jun. 20, 2011.
Schaeffer et al., "The Rat Glomerular Filtration Barrier Does Not Show Negative Charge Selectivity," Microcirculation, 2002, 9:329-342.
Schmitz et al., "Phage display: a molecular tool for the generation of antibodies—a review," Placenta, 2000, 21 Suppl A:S106-12.
Schuurman et al., "Normal human immunoglobulin G4 is bispecific: it has two different antigen-combining sites," Immunology, Aug. 1999, 97(4):693-698.
Schuurman et al., "The inter-heavy chain disulfide bonds of IgG4 are in equilibrium with intra-chain disulfide bonds," Mol Immunol, Jan. 2001, 38(1):1-8.
Sebba et al., "Tocilizumab: the first interleukin-6-receptor inhibitor," Am J Health Syst Pharm, Aug. 1, 2008, 65(15):1413-1418. doi: 10.2146/ajhp070449.
Segal et al., "Bispecific antibodies in cancer therapy," Curr Opin Immunol, 1999, 11:558-562.
Sequence alignments and modification scheme, 3 pages (document filed during Oral Proceedings and mentioned in minutes of the Oral Proceedings posted by EPO on Jul. 25, 2018).
Serada et al., "IL-6 blockade inhibits the induction of myelin antigen-specific Th17 cells and Th1 cells in experimental autoimmune encephalomyelitis," Proc Natl Acad Sci USA, Jul. 1, 2008, 105(26):9041-9046. doi: 10.1073/pnas.0802218105. Epub Jun. 24, 2008.
Sharifi et al., "Improving monoclonal antibody pharmacokinetics via chemical modification," Q J Nucl Med, Dec. 1998, 42(4):242-249.
Shaul, "Exploring the charge space of protein-protein association: a proteomic study," Proteins, 2005, 60:341-352.
Shieh et al., "Expression of axl in lung adenocarcinoma and correlation with tumor progression," Neoplasia, 2005, 7(12):1058-1064.
Shields et al., "High resolution mapping of the binding site on human IgG1 for FcγRI, FcγRII, FcγRIII, and FcRn and design of IgG1 variants with improved binding to the FcγR," J Biol Chem, 2001, 276:6591-6604. Epub Nov. 28, 2000.
Shima et al., "Tocilizumab, a humanized anti-interleukin-6 receptor antibody, ameliorated clinical symptoms and MRI findings of a patient with ankylosing spondylitis," Mod Rheumatol, Aug. 2011, 21(4):436-439. doi: 10.1007/s10165-011-0416-9. Epub Feb. 9, 2011.
Shimizu et al., "Successful treatment with tocilizumab for refractory scleritis associated with relapsing polychondritis," Scand J Rheumatol, Sep. 2017, 46(5):418-419. doi: 10.1080/03009742.2016.1275774. Epub Jan. 25, 2017.
Shire et al., "Challenges in the development of high protein concentration formulations," J Pharm Sci, 2004, 93(6):1390-1402.
Silpa-Archa et al., "Outcome of tocilizumab treatment in refractory ocular inflammatory diseases," Acta Ophthalmol, Sep. 2016, 94(6): e400-406. doi: 10.1111/aos. 13015. Epub Mar. 24, 2016.
Singer et al., Genes & Genomes, 1998, 1:63-64 (with English translation).
Singer et al., "Structure of Proteins," Genes & Genomes, 1991, pp. 59-71.
Sinha et al., "Electrostatics in protein binding and function," Curr Protein Pept Sci, 2002, 3(6):601-614.
Smans et al., "Bispecific antibody-mediated lysis of primary cultures of ovarian carcinoma cells using multiple target antigens," Int J Cancer, 1999, 83:270-277.
Smith et al., "The challenges of genome sequence annotation or 'the devil is in the details'," Nature Biotechnology, Nov. 1997, 15:1222-1223.
Smolen et al., "Interleukin-6: a new therapeutic target," Arthritis Res Ther, 2006, 8 Suppl 2:S5. Epub Jul. 28, 2006.
Sonkoly et al., "IL-31: a new link between T cells and pruritus in atopic skin inflammation," J Allergy Clin Immunol, 2006, 117:411-417.
Spiess et al., "Bispecific antibodies with natural architecture produced by co-culture of bacteria expressing two distinct half-antibodies," Nat Biotechnol, Aug. 2013, 31(8):753-758. doi: 10.1038/nbt.2621. Epub Jul. 7, 2013.
Staerz et al., "Hybrid hybridoma producing a bispecific monoclonal antibody that can focus effector T-cell activity," Proc Natl Acad Sci USA, 1986, 83:1453-1457.
Stenhoff et al., "Vitamin K-dependent Gas6 activates ERK kinase and stimulates growth of cardiac fibroblasts," Biochem Biophys Res Commun, 2004, 319(3):871-878.
Stancovski et al., "Mechanistic Aspects of the Opposing Effects of Monoclonal Antibodies to the ERBB2 Receptor on Tumor Growth," Proc Natl Acad. Sci USA, 1991, 88: 8691-8695.
Strand et al., "Biologic therapies in rheumatology: lessons learned, future directions," Nat Rev Drug Discov, 2007, 6(1):75-92.
Summary of information about antibodies in examples of patent, 3 pages (document submitted in EPO opposition and posted by EPO on Apr. 13, 2018).
Sun et al., "Coexpression of Gas6/Axl in human ovarian cancers," Oncology, 2004, 66(6):450-457.
Supplemental Material to RAPOSO et al., "Epitope-specific antibody response is controlled by immunoglobulin VH polymorphisms," J Exp Med, Mar. 10, 2014, 211(3):405-411. doi: 10.1084/jem.20130968. Epub Feb. 17, 2014, 4 pages (submitted on May 24, 2019 by the patentee during EPO opposition procedure for EP 2 202 245).
Suresh et al., "Bispecific monoclonal antibodies from hybrid hybridomas," Methods Enzymol, 1986, 121:210-228.
Suzuki et al., "Anti-murine IL-6 receptor antibody inhibits IL-6 effects in vivo," Immunol Lett, Sep. 1991, 30(1):17-21.
Tabrizi et al., "Elimination mechanisms of therapeutic monoclonal antibodies," Drug Discov Today, Jan. 2006, 11(1-2):81-88.
Taga et al., "Interleukin-6 Triggers the Association of Its Receptor with a Possible Signal Transducer, gp130," Cell, Aug. 11, 1989, 58(3): 573-581.
Taga et al., "Receptors for B Cell Stimulatory Factor 2," J Exp Med, Oct. 1, 1987, 166(4):967-981.
Takkinen et al., "Affinity and Specificity Maturation by CDR Walking," Antibody Engineering, Springer Lab Manuals, 2001, pp. 540-545.
Tan et al., "Contributions of a highly conserved $V_H/V_L$ hydrogen bonding interaction to scFv folding stability and refolding efficiency," Biophys J, Sep. 1998, 75(3):1473-1482.
Tan et al., "Engineering the isoelectric point of a renal cell carcinoma targeting antibody greatly enhances scFv solubility," Immunotechnology, 1998, 4(2):107-114.
Tarditi et al., "Selective high-performance liquid chromatographic purification of bispecific monoclonal antibodies," J Chromatogr, 1992, 599:13-20.
Teeling et al., "The biological activity of human CD20 monoclonal antibodies is linked to unique epitopes on CD20," J Immunol, 2006, 177(1):362-371.
Ten Kate et al., "Effect of isoelectric point on biodistribution and inflammation: imaging with indium-111-labelled IgG," Eur J Nucl Med, 1990, 17:305-309.
Thies et al., "The alternatively folded state of the antibody $C_H3$ domain," J Mol Biol, Jun. 2, 20012, 309(5):1077-1085.
Tsubaki et al., "C-terminal modification of monoclonal antibody drugs: amidated species as a general product-related substance," Int J Biol Macromol, 52:139-147. doi: 10.1016/j.ijbiomac.2012.09.016. Epub Sep. 25, 2012.

(56) References Cited

OTHER PUBLICATIONS

Tsuchiya, "Therapeutic Antibody," Chugai Pharmaceutical Co., Ltd., Fuji-Gotemba Laboratories, Sep. 22, 2006, p. 21 (with English translation).
Tsurushita et al., "Design of humanized antibodies: From anti-Tac to Zenapax," Methods, 2005, 36:69-83.
Vaisitti et al., "Cationization of monoclonal antibodies: another step towards the 'magic bullet'?," J Biol Regul Homeost Agents, 2005, 19(3-4):105-112.
Vaccaro et al., "Divergent activities of an engineered antibody in murine and human systems have implications for therapeutic antibodies," Proc Natl Acad Sci USA, Dec. 5, 2006, 103(49):18709-18714. Epub Nov. 20, 2006.
Vajdos et al., "Comprehensive functional maps of the antigen-binding site of an anti-ErbB2 antibody obtained with shotgun scanning mutagenesis," J Mol Biol, 2002, 320(2):415-428.
Vajkoczy et al., "Dominant-negative inhibition of the Ax1 receptor tyrosine kinase suppresses brain tumor cell growth and invasion and prolongs survival," Proc Natl Acad Sci USA, 2006, 103(15):5799-5804.
Van Den Abbeele et al., "Antigen-Binding Site Protection During Radiolabeling Leads to a Higher Immunoreactive Fraction," J Nucl Med, Jan. 1991, 32(1):116-122.
Van Der Neut Kolfschoten et al., "Anti-inflammatory activity of human IgG4 antibodies by dynamic Fab arm exchange," Science, Sep. 14, 2007, 317(5844):1554-1557.
Van Loghem et al., "Staphylococcal protein A and human IgG subclasses and allotypes," Scand J Immunol, 1982, 15(3):275-278.
Van Walle et al., "Immunogenicity screening in protein drug development," Expert Opin Biol Ther, 2007, 7(3):405-418.
Vargas-Madrazo et al., "An improved model of association for VH-VL immunoglobulin domains: asymmetries between VH and VL in the packing of some interface residues," J Mol Recognit, May-Jun. 2003, 16(3):113-120.
Varnum et al., "Ax1 receptor tyrosine kinase stimulated by the vitamin K-dependent protein encoded by growth-arrest-specific gene 6," Nature, 1995, 373(6515):623-626.
Verhoeyen et al., "Construction of a reshaped HMFG1 antibody and comparison of its fine specificity with that of the parent mouse antibody," Immunology, Mar. 1993, 78(3):364-370.
Verhoeyen et al., Chapter 5 "Monoclonal Antibodies in Clinical Oncology," 1991, Edited by AA Epenetos, Chapman and Hall, pp. 37-43.
Wally et al., "Identification of a novel substitution in the constant region of a gene coding for an amyloidogenic kappa1 light chain," Biochim Biophys Acta, May 31, 1999, 1454(1):49-56.
Wang et al., "Conserved amino acid networks involved in antibody variable domain interactions," Proteins, Jul. 2009, 76(1):99-114. doi: 10.1002/prot.22319.
Wang et al., "Polyethylene Glycol-modified Chimeric Toxin Composed of Transforming Growth Factor alpha and Pseudomonas Exotoxin," Cancer Res, Oct. 1, 1993, 53:4588-4594.
Ward et al., "Binding activities of a repertoire of single immunoglobulin variable domains secreted from *Escherichia coli*," Nature, 1989, 341:544-546.
Ward et al., "Effects of engineering complementary charged residues into the hydrophobic subunit interface of tyrosyl-tRNA synthetase. Appendix: Kinetic analysis of dimeric enzymes that reversibly dissociate into inactive subunits," Biochemistry, Jun. 30, 1987, 26(13):4131-4138.
Warnaar et al., "Purification of bispecific F(ab')$_2$ from murine trinoma OC/TR with specificity for CD3 and ovarian cancer," Hybridoma, 1994, 13:519-526.
Wenig et al., "Structure of the streptococcal endopeptidase IdeS, a cysteine proteinase with strict specificity for IgG," Proc Nat Acad Sci USA, Oct. 28, 2004, 101:17371-17376.
Wiens et al., "Mutation of a single conserved residue in $V_H$ complementarity-determining region 2 results in a severe Ig secretion defect," J Immunol, 2001, 167(4):2179-2186.
Wiens et al., "Somatic mutation in $V_H$ complementarity-determining region 2 and framework region 2: differential effects on antigen binding and Ig secretion," J Immunol, 1997, 159(3):1293-1302.
Winkler et al., "Changing the antigen binding specificity by single point mutations of an anti-p24 (HIV-1) antibody," J Immunol, 2000, 165:4505-4514.
Worn et al., "Stability engineering of antibody single-chain Fv fragments," J Mol Biol, Feb. 2, 2001, 305(5):989-1010.
Written Submissions by Opponent 1 (Alexion Pharmaceuticals, Inc.) in EPO opposition of EP 2 006 381, dated Apr. 13, 2018, 19 pages.
Written Submissions by Opponent 2 (Novo Nordisk A/S) in EPO opposition of EP 2 006 381, dated Apr. 13, 2018, 14 pages.
Written Submissions by Opponent 3 (name Unknown) in EPO opposition of EP 2 006 381, dated Apr. 13, 2018, 16 pages.
Wu et al., "Development of motavizumab, an ultra-potent antibody for the prevention of respiratory syncytial virus infection in the upper and lower respiratory tract," J Mol Biol, 2007, 368(3):652-665.
Wu et al., "Humanization of a murine monoclonal antibody by simultaneous optimization of framework and CDR residues," J Mol Biol, 1999, 294(1):151-162.
Wu et al., "Multimerization of a chimeric anti-CD20 single-chain Fv-Fc fusion protein is mediated through variable domain exchange," Protein Eng, Dec. 2001, 14(12):1025-1033.
Wu et al., "Ultra-potent Antibodies Against Respiratory Syncytial Virus: Effects of Binding Kinetics and Binding Valence on Viral Neutralization," J Mol Biol, Jul. 1, 2005, 350(1):126-144.
Wypych et al., "Human IgG2 antibodies display disulfide-mediated structural isoforms," J Biol Chem, Jun. 6, 2008, 283(23):16194-16205. Epub Mar. 13, 2008.
Xiang et al., "Study of B72.3 combining sites by molecular modeling and site-directed mutagenesis," Protein Eng, 2000, 13(5):339-344.
Yagi et al., "Interleukin-31 stimulates production of inflammatory mediators from human colonic subepithelial myofibroblasts," Int J Mol Med, 2007, 19(6):941-946.
Yamagata et al., "Synaptic adhesion molecules," Curr Opin Cell Biol, 2003, 15(5):621-632.
Yamasaki et al., "Cloning and Expression of the Human Interleukin-6 (BSF-2/IFNβ 2) Receptor," Science, Aug. 12, 1988, 241(4867):825-828.
Yamasaki et al., "Pharmacokinetic analysis of in vivo disposition of succinylated proteins targeted to liver nonparenchymal cells via scavenger receptors: importance of molecular size and negative charge density for in vivo recognition by receptors," J Pharmacol Exp Ther, 2002, 301:467-477.
Yang et al., "CDR walking mutagenesis for the affinity maturation of a potent human anti-HIV-1 antibody into the picomolar range," J Mol Biol, 1995, 254(3):392-403.
Yang et al., "Tailoring structure-function and pharmacokinetic properties of single-chain Fv proteins by site-specific PEGylation," Protein Eng, 2003, 16:761-770.
Yarilin, Fundamentals of Immunology M:Medicina, 1999, pp. 169-172, 354-358, 21 pages (with English translation).
Yarilin, Fundamentals of Immunology M:Medicina, 1999, pp. 172-174, 8 pages (with English translation).
Zhu et al., "MHC class I-related neonatal Fc receptor for IgG is functionally expressed in monocytes, intestinal macrophages, and dendritic cells," J Immunol, 2001, 166(5):3266-3276.
Zhu et al., "Remodeling domain interfaces to enhance heterodimer formation," Protein Sci, Apr. 1997, 6(4):781-788.
Zuckier et al., "Chimeric human-mouse IgG antibodies with shuffled constant region exons demonstrate that multiple domains contribute to in vivo half-life," Cancer Res, 1998, 58:3905-3908.
Zwick et al., "The long third complementarity-determining region of the heavy chain is important in the activity of the broadly neutralizing anti-human immunodeficiency virus type 1 antibody 2F5," J Virol, 2004, 78(6):3155-3161.
International Search Report for App. Ser. No. PCT/JP2008/067483, mailed Oct. 21, 2008, 2 pages.

(56) References Cited

OTHER PUBLICATIONS

International Preliminary Report on Patentability for App. Ser. No. PCT/JP2008/067483, mailed Apr. 7, 2010, 13 pages.
International Search Report for App. Ser. No. PCT/JP2009/066590, mailed Oct. 20, 2009, 2 pages.
International Preliminary Report on Patentability for PCT App. Ser. No. PCT/JP2008/067499, dated Apr. 7, 2010, 6 pages.
USPTO Restriction Requirement in U.S. Appl. No. 12/680,112, dated Oct. 7, 2011, 6 pages.
Fish & Richardson P.C., Amendment and Response to Species Election Requirement dated Oct. 7, 2011 in U.S. Appl. No. 12/680,112, filed on Dec. 6, 2011, 15 pages.
USPTO Non Final Office Action in U.S. Appl. No. 12/680,112, dated Feb. 29, 2012, 8 pages.
Fish & Richardson P.C., Amendment in Reply to Action of Feb. 29, 2012 in U.S. Appl. No. 12/680,112, filed Aug. 27, 2012, 12 pages.
USPTO Restriction Requirement in U.S. Appl. No. 12/680,112, dated Sep. 19, 2012, 6 pages.
Fish & Richardson P.C., Amendment and Reply to Restriction Requirement dated Sep. 19, 2012 in U.S. Appl. No. 12/680,112, filed on Oct. 17, 2012, 13 pages.
USPTO Non Final Office Action in U.S. Appl. No. 12/680,112, dated Feb. 4, 2013, 9 pages.
USPTO Restriction Requirement in U.S. Appl. No. 12/680,082, dated Jun. 6, 2012, 12 pages.
Fish & Richardson P.C., Fourth Preliminary Amendment and Response to Restriction Requirement dated Jun. 6, 2012 in U.S. Appl. No. 12/680,082, filed Jun. 29, 2012, 13 pages.
USPTO Restriction Requirement in U.S. Appl. No. 12/680,082, dated Sep. 14, 2012, 6 pages.
Fish & Richardson P.C., Amendment and Response to Election Requirement dated Sep. 14, 2012 in U.S. Appl. No. 12/680,082, filed Nov. 8, 2012, 14 pages.
USPTO Non-Final Office Action in U.S. Appl. No. 12/680,082, dated Feb. 14, 2013, 12 pages.
Fish & Richardson P.C., Amendment in Reply to Non-Final Office Action dated Feb. 14, 2013 in U.S. Appl. No. 12/680,082, filed Aug. 12, 2013, 17 pages.
USPTO Final Office Action in U.S. Appl. No. 12/680,082, dated Oct. 22, 2013, 12 pages.
Fish & Richardson P.C., Amendment in Reply to Final Office Action dated Oct. 22, 2013 in U.S. Appl. No. 12/680,082, filed Feb. 21, 2014, 14 pages.
USPTO Interview Summary in U.S. Appl. No. 12/680,082, dated Feb. 25, 2014, 3 pages.
USPTO Non-Final Office Action in U.S. Appl. No. 12/680,082, dated Feb. 5, 2015, 9 pages.
USPTO Restriction Requirement in U.S. Appl. No. 13/257,112, dated Oct. 15, 2013, 10 pages.
Fish & Richardson P.C., Amendment and Response to Election Requirement dated Oct. 15, 2013 in U.S. Appl. No. 13/257,112, filed Nov. 15, 2013, 6 pages.
USPTO Non-Final Office Action in U.S. Appl. No. 13/257,112, dated Jan. 30, 2014, 18 pages.
Fish & Richardson P.C., Amendment and Reply to Non-Final Office Action dated Jan. 30, 2014 in U.S. Appl. No. 13/257,112, filed Jul. 1, 2014, 12 pages.
USPTO Final Office Action in U.S. Appl. No. 13/257,112, dated Sep. 5, 2014, 16 pages.
Fish & Richardson P.C., Amendment and Reply to Final Office Action dated Sep. 5, 2014 in U.S. Appl. No. 13/257,112, filed Feb. 5, 2015, 6 pages.
International Search Report for App. Ser. No. PCT/JP2010/054769, mailed Apr. 20, 2010, 4 pages.
International Preliminary Report on Patentability for App. Ser. No. PCT/JP2010/054769, dated Oct. 18, 2011, 6 pages.
USPTO Restriction Requirement in U.S. Appl. No. 13/257,145, dated Mar. 20, 2013, 11 pages.
Fish & Richardson P.C., Preliminary Amendment and Response to Restriction Requirement dated Mar. 20, 2013 in U.S. Appl. No. 13/257,145, filed Apr. 22, 2013, 7 pages.
USPTO Non-Final Office Action in U.S. Appl. No. 13/257,145, dated Jul. 2, 2013, 20 pages.
Fish & Richardson P.C., Amendment in Reply to Office Action dated Jul. 2, 2013 in U.S. Appl. No. 13/257,145, filed Dec. 2, 2013, 12 pages.
USPTO Final Office Action in U.S. Appl. No. 13/257,145, dated Feb. 6, 2014, 12 pages.
Fish & Richardson P.C., Amendment in Reply to Office Action dated Feb. 6, 2014 in U.S. Appl. No. 13/257,145, filed May 6, 2014, 10 pages.
USPTO Notice of Allowance in U.S. Appl. No. 13/257,145, dated Oct. 1, 2014, 9 pages.
USPTO Notice of Allowance in U.S. Appl. No. 13/257,145, dated Jan. 9, 2015, 7 pages.
USPTO Notice of Allowance in U.S. Appl. No. 13/257,145, dated Mar. 11, 2015, 7 pages.
USPTO Advisory Action in U.S. Appl. No. 13/257,145, dated May 14, 2014, 6 pages.
International Search Report for App. Ser. No. PCT/JP2010/054767, mailed Jun. 15, 2010, 7 pages.
International Preliminary Report on Patentability for App. Ser. No. PCT/JP2010/054767, dated Oct. 18, 2011, 12 pages.
Non-Final Office Action in U.S. Appl. No. 14/680,250, dated Feb. 1, 2016, 10 pages.
Final Office Action in U.S. Appl. No. 14/680,250, dated Jun. 21, 2016, 21 pages.
USPTO Non-Final Office Action in U.S. Appl. No. 14/680,250, dated Feb. 1, 2017, 22 pages.
USPTO Interview Summary in U.S. Appl. No. 14/680,250, dated Aug. 2, 2017, 4 pages.
USPTO Final Office Action in U.S. Appl. No. 14/680,250, dated Sep. 19, 2017, 24 pages.
USPTO Notice of Allowance and Examiner-Initiated Interview Summary in U.S. Appl. No. 14/680,250, dated Nov. 23, 2018, 25 pages.
USPTO Applicant-Initiated Interview Summary in U.S. Appl. No. 14/680,250, dated Nov. 30, 2018, 7 pages.
International Search Report for App. Ser. No. PCT/JP2008/067534, mailed Oct. 21, 2008, 4 pages.
International Preliminary Report on Patentability for App. Ser. No. PCT/JP2008/067534, dated Apr. 7, 2010, 7 pages.
International Search Report for App. Ser. No. PCT/JP2009/057309, mailed Jul. 7, 2009, 8 pages.
International Preliminary Report on Patentability for App. Ser. No. PCT/JP2009/057309, mailed Nov. 30, 2010, 7 pages.
European Search Report for App. Ser. No. EP 09 72 9337, dated Nov. 3, 2011, 3 pages.
USPTO Restriction Requirement in U.S. Appl. No. 12/295,039, dated Oct. 12, 2010, 9 pages.
Fish & Richardson P.C., Response to Restriction Requirement dated Oct. 12, 2010 in U.S. Appl. No. 12/295,039, filed Apr. 11, 2011, 9 pages.
USPTO Non-Final Office Action in U.S. Appl. No. 12/295,039, dated Jun. 28, 2011, 9 pages.
Fish & Richardson P.C., Amendment in Reply to Action dated Jun. 28, 2011 in U.S. Appl. No. 12/295,039, filed Dec. 27, 2011, 14 pages.
USPTO Final Office Action in U.S. Appl. No. 12/295,039, dated Apr. 12, 2012, 8 pages.
Fish & Richardson P.C., Amendment in Reply to Action dated Apr. 12, 2012 in U.S. Appl. No. 12/295,039, filed Sep. 11, 2012, 12 pages.
International Preliminary Report on Patentability for App. Ser. No. PCT/JP2007/057036, dated Oct. 21, 2008, 6 pages.
International Search Report for App. Ser. No. PCT/JP2007/057036, dated May 1, 2007, 2 pages.
European Search Report for App. Ser. No. 07 74 0494, dated Sep. 3, 2009, 3 pages.
International Preliminary Report on Patentability for App. Ser. No. PCT/JP2007/057058, dated Oct. 21, 2008, 11 pages.

(56) References Cited

OTHER PUBLICATIONS

International Search Report App. Ser. No. PCT/JP2007/057058, mailed May 7, 2001, 2 pages.
USPTO Restriction Requirement in U.S. Appl. No. 12/295,075, dated Feb. 22, 2011, 9 pages.
Fish & Richardson P.C., Response to Restriction Requirement dated Feb. 22, 2011 in U.S. Appl. No. 12/295,075, filed Aug. 18, 2011, 2 pages.
USPTO Non-Final Office Action in U.S. Appl. No. 12/295,075, dated Nov. 4, 2011, 14 pages.
Fish & Richardson P.C., Amendment in Reply to Action dated Nov. 4, 2011 in U.S. Appl. No. 12/295,075, filed May 3, 2012, 12 pages.
USPTO Final Office Action in U.S. Appl. No. 12/295,075, dated Jul. 19, 2012, 12 pages.
Fish & Richardson P.C., Amendment in Reply to Action dated Jul. 19, 2012 in U.S. Appl. No. 12/295,075, filed Jan. 17, 2013, 113 pages.
USPTO Non-Final Office Action in U.S. Appl. No. 12/295,075, dated Jun. 7, 2013, 17 pages.
Fish & Richardson P.C., Amendment in Reply to Action dated Jun. 7, 2013, in U.S. Appl. No. 12/295,075, filed Nov. 6, 2013, 16 pages.
USPTO Final Office Action in U.S. Appl. No. 12/295,075, dated Jan. 27, 2014, 15 pages.
USPTO Restriction Requirement in U.S. Appl. No. 11/910,128, dated Jun. 9, 2011, 10 pages.
Fish & Richardson P.C., Response to Restriction Requirement dated Jun. 9, 2011 in U.S. Appl. No. 11/910,128, filed Dec. 2, 2011, 1 page.
USPTO Non-Final Office Action in U.S. Appl. No. 11/910,128, dated Apr. 25, 2012, 21 pages.
Fish & Richardson P.C., Amendment in Reply to Office Action dated Apr. 25, 2012 in U.S. Appl. No. 11/910,128, filed Oct. 25, 2012, 32 pages.
Fish & Richardson P.C., Supplemental Amendment in U.S. Appl. No. 11/910,128, filed Nov. 14, 2012, 20 pages.
USPTO Final Office Action in U.S. Appl. No. 11/910,128, dated Sep. 10, 2013, 12 pages.
USPTO Non-Final Office Action in U.S. Appl. No. 11/910,128, dated Nov. 28, 2016, 17 pages.
International Preliminary Report on Patentability for App. Ser. No. PCT/JP2009/066590, dated May 10, 2011, 6 pages.
International Preliminary Report on Patentability for App. Ser. No. PCT/JP2009/070376, dated Jul. 5, 2011, 11 pages.
USPTO Non-Final Office Action U.S. Appl. No. 12/680,087, dated Oct. 27, 2011, 6 pages.
Fish & Richardson P.C., Amendment and Reply to Action dated Oct. 27, 2011 in U.S. Appl. No. 12/680,087, filed Jan. 26, 2012, 6 pages.
USPTO Notice of Allowance in U.S. Appl. No. 12/680,087, dated Feb. 24, 2012, 5 pages.
USPTO Notice of Allowance in U.S. Appl. No. 12/680,087, dated Jun. 25, 2012, 11 pages.
USPTO Notice of Allowance in U.S. Appl. No. 12/680,087, dated Nov. 26, 2012, 7 pages.
USPTO Notice of Allowance in U.S. Appl. No. 12/680,087, dated Apr. 15, 2013, 9 pages.
USPTO Notice of Allowance in U.S. Appl. No. 12/680,087, dated Aug. 2, 2013, 8 pages.
USPTO Restriction Requirement in U.S. Appl. No. 12/936,587, dated Dec. 6, 2011, 5 pages.
Fish & Richardson P.C., Third Preliminary Amendment and Response to Restriction Requirement dated Dec. 6, 2011 in U.S. Appl. No. 12/936,587, filed Jun. 5, 2012, 7 pages.
USPTO Restriction Requirement in U.S. Appl. No. 12/936,587, dated Jun. 25, 2012, 5 pages.
Fish & Richardson P.C., Response to Species Election Requirement dated Jun. 25, 2012 in U.S. Appl. No. 12/936,587, filed Jul. 25, 2012, 1 page.
USPTO Non-Final Office Action in U.S. Appl. No. 12/936,587, dated Nov. 7, 2012, 13 pages.
International Preliminary Report on Patentability for App. Ser. No. PCT/JP2010/058166, dated Dec. 16, 2011, 15 pages.
International Search Report for App. Ser. No. PCT/JP2010/066490, mailed Nov. 9, 2010, 5 pages.
International Preliminary Report on Patentability for App. Ser. No. PCT/JP2010/066490, dated Apr. 11, 2012, 6 pages.
USPTO Restriction Requirement in U.S. Appl. No. 12/745,781, dated Sep. 4, 2012, 10 pages.
Fish & Richardson P.C., Response to Restriction Requirement dated Sep. 4, 2012 in U.S. Appl. No. 12/745,781, filed Sep. 21, 2012, 176 pages.
USPTO Non-Final Office Action in U.S. Appl. No. 12/745,781, dated Oct. 18, 2012, 21 pages.
Fish & Richardson P.C., Amendment in Reply to Office Action dated Oct. 18, 2012 in U.S. Appl. No. 12/745,781, filed Apr. 17, 2013, 23 pages.
USPTO Final Office Action in U.S. Appl. No. 12/745,781, dated May 21, 2013, 16 pages.
Fish & Richardson P.C., Amendment in Reply to Office Action dated May 21, 2013 in U.S. Appl. No. 12/745,781, filed Oct. 18, 2013, 13 pages.
USPTO Restriction Requirement in U.S. Appl. No. 12/679,922, dated Oct. 2, 2012, 9 pages.
Fish & Richardson P.C., Response to Restriction Requirement dated Oct. 2, 2012 in U.S. Appl. No. 12/679,922, filed Nov. 1, 2012, 2 pages.
USPTO Non-Final Office Action in U.S. Appl. No. 12/679,922, dated Jan. 3, 2013, 25 pages.
Fish & Richardson P.C., Amendment in Reply to Action dated Jan. 3, 2013 in U.S. Appl. No. 12/679,922, filed Jul. 2, 2013, 18 pages.
USPTO Final Office Action in U.S. Appl. No. 12/679,922, dated Aug. 2, 2013, 12 pages.
International Preliminary Report on Patentability for App. Ser. No. PCT/JP2010/073361, dated Aug. 14, 2012, 7 pages.
USPTO Non-Final Office Action in U.S. Appl. No. 13/595,139, dated Nov. 14, 2012, 10 pages.
International Search Report for App. Ser. No. PCT/JP2011/055101, mailed May 10, 2011, 4 pages.
International Preliminary Report on Patentability for App. Ser. No. PCT/JP2011/055101, dated Oct. 2, 2012, 6 pages.
USPTO Restriction Requirement in U.S. Appl. No. 13/497,269, dated Dec. 6, 2012, 9 pages.
Fish & Richardson P.C., Response to Restriction Requirement dated Dec. 6, 2012 in U.S. Appl. No. 13/497,269, filed May 1, 2013, 2 pages.
USPTO Non-Final Office Action in U.S. Appl. No. 13/497,269, dated Aug. 15, 2013, 13 pages.
Fish & Richardson P.C., Reply to Non-Final Action dated Aug. 15, 2013 in U.S. Appl. No. 13/497,269, filed Nov. 15, 2013, 13 pages.
USPTO Final Office Action in U.S. Appl. No. 13/497,269, dated Mar. 14, 2014, 10 pages.
Fish & Richardson P.C., Reply to Final Office Action dated Mar. 14, 2014 in U.S. Appl. No. 13/497,269, filed Sep. 10, 2014, 12 pages.
USPTO Non-Final Office Action in U.S. Appl. No. 13/497,269, dated Dec. 20, 2016, 27 pages.
USPTO Restriction Requirement in U.S. Appl. No. 12/809,138, dated Dec. 13, 2012, 8 pages.
Fish & Richardson P.C., Response to Restriction Requirement dated Dec. 13, 2012 in U.S. Appl. No. 12/809,138, filed Apr. 5, 2013, 2 pages.
USPTO Notice of Allowance in U.S. Appl. No. 12/809,138, dated Aug. 23, 2013, 9 pages.
USPTO Restriction Requirement in U.S. Appl. No. 13/320,317, dated Dec. 18, 2012, 13 pages.
Fish & Richardson P.C., Response to Restriction Requirement dated Dec. 18, 2012 in U.S. Appl. No. 13/320,317, filed Jan. 18, 2013, 3 pages.
USPTO Non-Final Office Action in U.S. Appl. No. 13/320,317, dated December Apr. 25, 2013, 25 pages.
Fish & Richardson P.C., Reply to Office Action dated Apr. 25, 2013 in U.S. Appl. No. 13/320,317, filed Oct. 25, 2013, 26 pages.
USPTO Restriction Requirement in U.S. Appl. No. 13/524,528, dated Mar. 21, 2013, 7 pages.

(56) References Cited

OTHER PUBLICATIONS

Fish & Richardson P.C., Reply to Restriction Requirement dated Mar. 21, 2013 in U.S. Appl. No. 13/524,528, filed Sep. 13, 2013, 1 page.
USPTO Non-Final Office Action in U.S. Appl. No. 13/524,528, dated Sep. 30, 2013, 9 pages.
USPTO Restriction Requirement in U.S. Appl. No. 13/582,073, dated Feb. 6, 2014, 9 pages.
Fish & Richardson P.C., Response to Restriction Requirement dated Feb. 6, 2014 in U.S. Appl. No. 13/582,073, filed Apr. 7, 2014, 1 page.
USPTO Non-Final Office Action in U.S. Appl. No. 13/582,073, dated Jul. 18, 2014, 10 pages.
Fish & Richardson P.C., Amendment in Reply to Action dated Jul. 18, 2014 in U.S. Appl. No. 13/582,073, filed Jan. 20, 2015, 32 pages.
USPTO Final Office Action in U.S. Appl. No. 13/582,073, dated May 24, 2017, 19 pages.
USPTO Non-Final Office Action in U.S. Appl. No. 13/582,073, dated May 4, 2018, 16 pages.
U.S. Appl. No. 13/518,861, Igawa et al., filed Oct. 4, 2012 (abandoned).
U.S. Appl. No. 15/617,008, Igawa et al., filed Jun. 8, 2017 (abandoned).
U.S. Appl. No. 15/875,847, Igawa et al., filed Jan. 19, 2018 (abandoned).
U.S. Appl. No. 16/155,673, Igawa et al., filed Oct. 9, 2018 (abandoned).
U.S. Appl. No. 16/448,088, Igawa et al., filed Jun. 21, 2019 (abandoned).
U.S. Appl. No. 16/815,089, Igawa et al., filed Mar. 11, 2020 (abandoned).
U.S. Appl. No. 17/076,938, Igawa et al., filed Oct. 22, 2020 (abandoned).
U.S. Appl. No. 17/336,538, Igawa et al., Jun. 2, 2021 (abandoned).
U.S. Appl. No. 17/574,614, Igawa et al., filed Jan. 13, 2022.
U.S. Appl. No. 17/578,524, Igawa et al., filed Jan. 19, 2022.
U.S. Appl. No. 17/483,898, Igawa et al., filed Sep. 24, 2021.
U.S. Appl. No. 17/520,368, Igawa et al., filed Nov. 5, 2021.
U.S. Appl. No. 17/359,867, Igawa et al., filed Jun. 28, 2021.
U.S. Appl. No. 13/524,528, Igawa et al., filed Jun. 15, 2012 (abandoned).
U.S. Appl. No. 16/838,415, Igawa et al., filed April, 2, 2020 (abandoned).
U.S. Appl. No. 17/509,128, Igawa et al., filed Oct. 25, 2021.
U.S. Appl. No. 12/680,112, Igawa et al., filed Jun. 23, 2010 (abandoned).
U.S. Appl. No. 13/959,489, Igawa et al., filed Aug. 5, 2013 (abandoned).
U.S. Appl. No. 15/263,617, Igawa et al., filed Sep. 13, 2016 (abandoned).
U.S. Appl. No. 16/041,976, Igawa et al., filed Jul. 23, 2018 (abandoned).
U.S. Appl. No. 12/745,781, Kuramochi et al., filed Sep. 13, 2010 (abandoned).
U.S. Appl. No. 14/340,883, Kuramochi et al., filed Jul. 25, 2014 (abandoned).
U.S. Appl. No. 13/257,145, Igawa et al., filed Nov. 22, 2011 (abandoned).
U.S. Appl. No. 16/298,032, Igawa et al., Mar. 11, 2019 (abandoned).
U.S. Appl. No. 16/980,611, Fink, filed Sep. 14, 2020.
U.S. Appl. No. 17/066,092, Sampei et al., filed Oct. 8, 2020.
U.S. Appl. No. 16/298,032, Igawa et al., filed Mar. 11, 2019.
U.S. Appl. No. 17/336,538, Igawa et al., filed Jun. 2, 2021.
Aalberse et al., "IgG4 breaking the rules," Immunology, Jan. 2002, 105(1):9-19.
Annex from opponent 2's submission of Jun. 7, 2018, 13 pages (document cited by the opponent during the EPO opposition proceedings of EP 2 202 245 on May 19, 2021).
Antibodies in Example 29 of EP 2 202 245, 2 pages (document cited by the opponent during the EPO opposition proceedings of EP 2 202 245 on May 19, 2020).
Arduin et al., "Highly reduced binding to high and low affinity mouse Fc gamma receptors by L234A/L235A and N297A Fc mutations engineered into mouse IgG2a," Mol Immunol, Feb. 2015, 63(2):456-463.
Baca et al., "Antibody Humanization Using Monovalent Phage Display," J Biol Chem, Apr. 18, 1997, 272(16):10678-10684.
Barba-Spaeth et al., "Structural basis of potent Zika-dengue virus antibody cross-neutralization," Nature, Aug. 4, 2016, 536(7614):48-53.
Boerner et al., Production of antigen-specific human monoclonal antibodies from in vitro-primed human splenocytes, J Immunol, Jul. 1, 1991, 147(1):86-95.
Brooks et al., "Structure and Expression of Human IgG FcRII(CD32)—Functional Heterogeneity is Encoded by the Alternatively Spliced Products of Multiple Genes," J Exp Med, Oct. 1, 1989, 170(4):1369-1385.
Bruggemann et al., "Comparison of the Effector Functions of Human Immunoglobulins Using a Matched Set of Chimeric Antibodies," J Exp Med, Nov. 1, 1987, 166(5):1351-1361.
Capel et al., "Heterogeneity of Human IgG Fc Receptors," Immunomethods, Feb. 1994, 4(1):25-34.
Carter et al., "Humanization of an anti-p185$^{HER2}$ antibody for human cancer therapy," Proc Natl Acad Sci USA, May 15, 1992, 89(10):4285-4289.
Chan et al., "Therapeutic antibodies as a treatment option for dengue fever," Expert Rev Anti Infect Ther, Nov. 2013, 11(11):1147-1157. doi: 10.1586/14787210.2013.839941. Epub Oct. 4, 2013 (Abstract Only).
Chari et al., "Immunoconjugates Containing Novel Maytansinoids: Promising Anticancer Drugs," Cancer Res, Jan. 1, 1992, 52(1):127-131.
Chothia et al., "Canonical Structures for the Hypervariable Regions of Immunoglobulins," J Mol Biol, 1987, 196(4):901-917.
Chowdhury, Chapter 14 "Engineering scFvs for Improved Stability," Methods Mol Biol, 2003, 207:179-96.
Chugai NMO Clinical Trial Webinar, Sakura Star Study, dated Dec. 12, 2014, downloaded on Sep. 5, 2019 from https://s3.amazonaws.com/gjcf-wp-uploads/wpcontent/uploads/2016/05/16162202/12_12_14_Chugai_Webinar_PPT_Complete_Deck_FINAL.pdf, 18 pages.
Chugai Pharmaceutical, A phase I, multiple-dose study of SA237, Study JapicCTI-No. 121786; submitted to Clinicaltrials.jp on Jan. 31, 2014; downloaded from Clinicaltrials.jp archive on Sep. 5, 2019 as https://www.clinicaltrials.jp/ctiuser/trial/Show.jsp, 5 pages.
Chugai Pharmaceutical, A phase I, multiple-dose study of SA237, Study JapicCTI-No. 121786; submitted to Clinicaltrials.jp on Mar. 19, 2012; downloaded from Clinicaltrials.jp archive on Sep. 5, 2019 as https://www.clinicaltrials.jp/ctiuser/trial/Show.jsp, 5 pages.
Chugai Pharmaceutical, A phase I, multiple-dose study of SA237, Study JapicCTI-No. 121786; submitted to Clinicaltrials.jp on Jun. 19, 2012; downloaded from Clinicaltrials.jp archive on Sep. 5, 2019 as https://www.clinicaltrials.jp/ctiuser/trial/Show.jsp, 5 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 1; submitted to ClinicalTrials.gov on Jan. 6, 2014; downloaded from ClinicalTrials.gov archive on Sep. 4, 2019 as https://clinicaltrials.gov/ct2/history/NCT02028884?V_1=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 2; submitted to ClinicalTrials.gov on Feb. 25, 2014; downloaded from ClinicalTrials.gov archive on Sep. 4, 2019 as https://clinicaltrials.gov/ct2/history/NCT02028884?V_2=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 3; submitted to ClinicalTrials.gov on Sep.

(56) References Cited

OTHER PUBLICATIONS 4, 2015; downloaded from ClinicalTrials.gov archive on Sep. 4, 2019 as https://clinicaltrials.gov/ct2/history/NCT02028884?V_3=View#StudyPageTop, 6 pages.
Chugai Pharmaceutical, Efficacy and Safety Study of Satralizumab (SA237) as Add-on Therapy to Treat Participants With Neuromyelitis Optica (NMO) and NMO Spectrum Disorder (NMOSD), Study NCT02028884, version 4; submitted to ClinicalTrials.gov on Dec. 8, 2015; downloaded from ClinicalTrials.gov archive on Sep. 4, 2019 as https://clinicaltrials.gov/ct2/history/NCT02028884?V_4=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 1; submitted to ClinicalTrials.gov on Feb. 25, 2014; downloaded from ClinicalTrials.gov archive on Sep. 4, 2019 as https://clinicaltrials.gov/ct2/history/NCT02073279?V_1=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 10; submitted to ClinicalTrials.gov on Jul. 7, 2015; downloaded from ClinicalTrials.gov archive on Sep. 5, 2019 as https://clinicaltrials.gov/ct2/history/NCT02073279?V_10=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 11; submitted to ClinicalTrials.gov on Aug. 3, 2015; downloaded from ClinicalTrials.gov archive on Sep. 5, 2019 as https://clinicaltrials.gov/ct2/history/NCT02073279?V_11=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 12; submitted to ClinicalTrials.gov on Sep. 3, 2015; downloaded from ClinicalTrials.gov archive on Sep. 5, 2019 as https://clinicaltrials.gov/ct2/history/NCT02073279?V_12=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 13; submitted to ClinicalTrials.gov on Oct. 5, 2015; downloaded from ClinicalTrials.gov archive on Sep. 5, 2019 as https://clinicaltrials.gov/ct2/history/NCT02073279?V_13=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 14; submitted to ClinicalTrials.gov on Dec. 8, 2015; downloaded from ClinicalTrials.gov archive on Sep. 5, 2019 as https://clinicaltrials.gov/ct2/history/NCT02073279?V_14=View#StudyPageTop, 10 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 2; submitted to ClinicalTrials.gov on Jul. 22, 2014; downloaded from ClinicalTrials.gov archive on Sep. 5, 2019 as https://clinicaltrials.gov/ct2/history/NCT02073279?V_2=View#StudyPageTop, 6 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 3; submitted to ClinicalTrials.gov on Dec. 15, 2014; downloaded from ClinicalTrials.gov archive on Sep. 5, 2019 as https://clinicaltrials.gov/ct2/history/NCT02073279?V_3=View#StudyPageTop, 7 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 4; submitted to ClinicalTrials.gov on Feb. 5, 2015; downloaded from ClinicalTrials.gov archive on Sep. 5, 2019 as https://clinicaltrials.gov/ct2/history/NCT02073279?V_4=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 5; submitted to ClinicalTrials.gov on Feb. 6, 2015; downloaded from ClinicalTrials.gov archive on Sep. 5, 2019 as https://clinicaltrials.gov/ct2/history/NCT02073279?V_5=View#StudyPageTop, 8 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 6; submitted to ClinicalTrials.gov on Mar. 4, 2015; downloaded from ClinicalTrials.gov archive on Sep. 5, 2019 as https://clinicaltrials.gov/ct2/history/NCT02073279?V_6=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 7; submitted to ClinicalTrials.gov on Apr. 1, 2015; downloaded from ClinicalTrials.gov archive on Sep. 5, 2019 as https://clinicaltrials.gov/ct2/history/NCT02073279?V_7=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 8; submitted to ClinicalTrials.gov on May 7, 2015; downloaded from ClinicalTrials.gov archive on Sep. 5, 2019 as https://clinicaltrials.gov/ct2/history/NCT02073279?V_8=View#StudyPageTop, 9 pages.
Chugai Pharmaceutical, Efficacy and Safety Study of Satralizumab (SA237) as Monotherapy to Treat Participants With Neuromyelitis Optica (NMO) and Neuromyelitis Optica Spectrum Disorder (NMOSD), Study NCT02073279, version 9; submitted to ClinicalTrials.gov on Jun. 5, 2015; downloaded from ClinicalTrials.gov archive on Sep. 5, 2019 as https://clinicaltrials.gov/ct2/history/NCT02073279?V_9=View#StudyPageTop, 9 pages.
Clackson et al., "Making antibody fragments using phage display libraries," Nature, Aug. 15, 1991, 352(6336):624-628.
Clynes et al., "Fc receptors are required in passive and active immunity to melanoma," Proc Natl Acad Sci USA, Jan. 20, 1998, 95(2):652-656.
Cragg et al., "Complement-mediated lysis by anti-CD20 mAb correlates with segregation into lipid rafts," Blood, Feb. 1, 2003, 101(3):1045-1052. Epub Sep. 19, 2002.
Cragg et al., "Antibody specificity controls in vivo effector mechanisms of anti-CD20 reagents," Blood, Apr. 1, 2004, 103(7):2738-2743. Epub Oct. 9, 2003.
Daeron et al., "Fc receptor biology," Annu Rev Immunol, 1997, 15:203-234.
Datta-Mannan et al., "FcRn affinity-pharmacokinetic relationship of five human IgG4 antibodies engineered for improved in vitro FcRn binding properties in cynomolgus monkeys," Drug Metab Dispos, Aug. 2012, 40(8):1545-1555.
De Alwis et al., "Identification of human neutralizing antibodies that bind to complex epitopes on dengue virions," Proc Natl Acad Sci USA, May 8, 2012, 109(19):7439-7444.
Dejnirattisai et al., "Dengue virus sero-cross-reactivity drives antibody-dependent enhancement of infection with zika virus," Nat Immunol, Sep. 2016, 17(9):1102-1108.
Deng et al., "Pharmacokinetics of Humanized Monoclonal Anti-Tumor Necrosis Factor-α Antibody and Its Neonatal Fc Receptor Variants in Mice and Cynomolgus Monkeys," Drug Metab Dispos, Apr. 2010, 38(4):600-605. doi: 10.1124/dmd.109.031310. Epub Jan. 13, 2010.
Derer et al., "A Complement-Optimized EGFR Antibody Improves Cytotoxic Functions of Polymorphonuclear Cells against Tumor Cells," J Immunol, Nov. 15, 2015, 195(10):5077-5087.
Dubowchik et al., "Doxorubicin Immunoconjugates Containing Bivalent, Lysosomally-Cleavable Dipeptide Linkages," Bioorg Med Chem Lett, Jun. 3, 2002, 12(11):1529-1532.

(56) References Cited

OTHER PUBLICATIONS

Duncan et al., "The binding cite for C1q on IgG," Nature, Apr. 21, 1988, 332(6166):738-740.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Germany; submitted to clinicaltrialsregister.eu on Dec. 20, 2013; downloaded from clinicaltrialsregister.eu archive on Sep. 5, 2019 as https://www.clinicaltrialsregister.eu/ctrsearch/trial/2013-003752-21/DE, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Hungary; submitted to clinicaltrialsregister.eu on Feb. 25, 2015; downloaded from clinicaltrialsregister.eu archive on Sep. 5, 2019 as https://www.clinicaltrialsregister.eu/ctrsearch/trial/2013-003752-21/HU, 6 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Italy; submitted to clinicaltrialsregister.eu on Feb. 6, 2014; downloaded from clinicaltrialsregister.eu archive on Sep. 5, 2019 as https://www.clinicaltrialsregister.eu/ctrsearch/trial/2013-003752-21/IT, 5 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Poland; submitted to clinicaltrialsregister.eu on Oct. 15, 2013; downloaded from clinicaltrialsregister.eu archive on Sep. 5, 2019 as https://www.clinicaltrialsregister.eu/ctrsearch/trial/2013-003752-21/PL, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in Spain; submitted to clinicaltrialsregister.eu on Mar. 11, 2015; downloaded from clinicaltrialsregister.eu archive on Sep. 5, 2019 as https://www.clinicaltrialsregister.eu/ctrsearch/trial/2013-003752-21/ES, 7 pages.

F. Hoffmann-La Roche Ltd., A multicenter, randomized, addition to baseline treatment, double-blind, placebo-controlled, Phase 3 study to evaluate the efficacy and safety of Satralizumab (SA237) in patients with neuromyelitis optica (NMO) and NMO spectrum disorder (NMOSD), Study EudraCT 2013-003752-21 in the United Kingdom; submitted to clinicaltrialsregister.eu on Oct. 15, 2013; downloaded from clinicaltrialsregister.eu archive on Sep. 5, 2019 as https://www.clinicaltrialsregister.eu/ctrsearch/trial/2013-003752-21/GB, 6 pages.

F. Hoffmann-La Roche Ltd., A Multicenter, Randomized, Double-blind, Placebo controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Croatia; submitted to clinicaltrialsregister.eu on Dec. 15, 2016; downloaded from clinicaltrialsregister.eu archive on Sep. 5, 2019 as https://www.clinicaltrialsregister.eu/ctr-search/trial/2015-005431-41/HR, 6 pages.

F. Hoffmann-La Roche Ltd., A Multicenter, Randomized, Double-blind, Placebo controlled, Phase 3 Study to Evaluate the Efficacy and Safety of Satralizumab (SA237) as Monotherapy in Patients With Neuromyelitis Optica (NMO) and Neuromyelitis Optica Spectrum Disorder(NMOSD), Study EudraCT 2015-005431-41 in Poland; submitted to clinicaltrialsregister.eu on Apr. 7, 2016; downloaded from clinicaltrialsregister.eu archive on Sep. 5, 2019 as https://www.clinicaltrialsregister.eu/ctrsearch/trial/2015-005431-41/PL, 6 pages.

Fellouse et al., "Synthetic antibodies from a four-amino-acid code: A dominant role for tyrosine in antigen recognition," Proc Natl Acad Sci USA, Aug. 24, 2004, 101(34):12467-12472. Epub Aug. 11, 2004.

Fernandez et al., "Anti-Dengue E-dimer epitope human antibodies have therapeutic activity against Zika virus infection," Nat Immunol, Nov. 2017, 18(11):1261-1269.

Flatman et al., "Process analytics for purification of monoclonal antibodies," J Chromatogr B Analyt Technol Biomed Life Sci, Mar. 15, 2007, 848(1):79-87. Epub Dec. 11, 2006.

Gazzano-Santoro et al., "A non-radioactive complement-dependent cytotoxicity assay for anti-CD20 monoclonal antibody," J Immunol Methods, Mar. 28, 1997, 202(2):163-171.

Gerngross, "Advances in the production of human therapeutic proteins in yeasts and filamentous fungi," Nat Biotechnol, Nov. 2004, 22(11):1409-1414.

Golay et al., "Design and Validation of a Novel Generic Platform for the Production of Tetravalent IgG1-like Bispecific Antibodies," J Immunol, Apr. 1, 2016, 196 (7):3199-3211.

Graham et al., "Characteristics of a Human Cell Line Transformed by DNA from Human Adenovirus Type 5," J Gen Virol, Jul. 1977, 36(1):59-74.

Griffiths et al., Human anti-self antibodies with high specificity from phage display libraries, EMBO J, Feb. 1993, 12(2):725-734.

Gruber et al., "Efficient Tumor Cell Lysis Mediated by a Bispecific Single Chain Antibody Expressed in *Escherichia coli*," J Immunol, Jun. 1, 1994, 152(11):5368-5374.

Guyer et al., "Immunoglobulin Binding by Mouse Intestinal Epithelial Cell Receptors," J Immunol, Aug. 1976, 117(2):587-593.

Haas et al., "Fcγ receptors of phagocytes," J Lab Clin Med, Oct. 1995, 126(4):330-341.

Hashimoto-Gotoh et al., "An oligodeoxyribonucleotide-directed dual amber method for site-directed mutagenesis," Gene, Jan. 23, 1995, 152(2):271-275.

Hellstrom et al., "Antitumor effects of L6, an IgG2a antibody that reacts with most human carcinomas," Proc Natl Acad Sci USA, Sep. 1986, 83(18):7059-7063.

Hellstrom et al., "Strong antitumor activities of IgG3 antibodies to a human melanoma-associated ganglioside," Proc Natl Acad Sci USA, Mar. 1985, 82(5):1499-1502.

Hinman et al., "Preparation and Characterization of Monoclonal Antibody Conjugates of the Calicheamicins: A Novel and Potent Family of Antitumor Antibiotics," Cancer Res, Jul. 15, 1993, 53(14):3336-3342.

Ho et al., "In vitro antibody evolution targeting germline hot spots to increase activity of an anti-CD22 immunotoxin," J Biol Chem, Jan. 7, 2005, 280(1):607-617. doi: 10.1074/jbc.M409783200. Epub Oct. 18, 2004.

Holliger et al., "'Diabodies': Small bivalent and bispecific antibody fragments," Proc Natl Acad Sci USA, Jul. 15, 1993, 90(14):6444-6448.

Hoogenboom, Chapter 1 "Overview of Antibody Phage-Display Technology and Its Applications," Methods in Molecular Biology, 2001, 178:1-37.

Hoogenboom et al., "By-passing Immunisation—Human Antibodies from Synthetic Repertoires of Germline $V_H$ Gene Segments Rearranged in Vitro," J Mol Biol, Sep. 20, 1992, 227(2):381-388.

Hudson et al., "Engineered antibodies," Nat Med, Jan. 2003, 9(1):129-134.

Idusogie et al., "Mapping of the Clq Binding Site on Rituxan, a Chimeric Antibody with a Human IgG1 Fc," J Immunol, Apr. 15, 2000, 164(8):4178-4184.

Idusogie et al., "Engineered Antibodies with Increased Activity to Recruit Complement," J Immunol, Feb. 15, 2001, 166(4):2571-2575.

Jeffrey et al., "Dipeptide-based highly potent doxorubicin antibody conjugates," Bioorg Med Chem Lett, Jan. 15, 2006, 16(2):358-362. Epub Nov. 3, 2005.

Kam et al., "Carbon nanotubes as multifunctional biological transporters and near-infrared agents for selective cancer cell destruction," Proc Natl Acad Sci USA, Aug. 16, 2005, 102(33):11600-11605. Epub Aug. 8, 2005.

(56) References Cited

OTHER PUBLICATIONS

Kam et al., "Cross-reactive dengue human monoclonal antibody prevents severe pathologies and death from Zika virus infections," JCI Insight, Apr. 20, 2017, 2(8):e92428, 11 pages.
Kanda et al., "Comparison of Cell Lines for Stable Production of Fucose-Negative Antibodies With Enhanced ADCC," Biotechnol Bioeng, Jul. 5, 2006, 94(4):680-688.
Kashmiri et al., SDR grafting—a new approach to antibody humanization, Methods, May 2005, 36(1):25-34.
King et al., "Monoclonal Antibody Conjugates of Doxorubicin Prepared with Branched Peptide Linkers: Inhibition of Aggregation by Methoxytriethyleneglycol Chains," J Med Chem, Sep. 12, 2002, 45(19):4336-4343.
Kohler et al., "Continuous cultures of fused cells secreting antibody of predefined specificity," Nature, Aug. 7, 1975, 256(5517):495-497.
Kono et al., "FcγRIIB 11e232Thr transmembrane polymorphism associated with human systemic lupus erythematosus decreases affinity to lipid rafts and attenuates inhibitory effects on B cell receptor signaling," Hum Mol Genet, Oct. 1, 2005, 14(19):2881-2892. Epub Aug. 22, 2005.
Kostelny et al., "Formation of a bispecific antibody by the use of leucine zippers," J Immunol, Mar. 1, 1992, 148(5):1547-1553.
Kozbor, "A human hybrid myeloma for production of monoclonal antibodies," J Immunol, Dec. 1984, 133(6):3001-3005.
Kramer et al., "The gapped duplex DNA approach to oligonucleotide-directed mutation construction," Nucleic Acids Res, Dec. 21, 1984, 12(24):9441-9456.
Kramer et al., "Oligonucleotide-Directed Construction of Mutations via Gapped Duplex DNA," Methods Enzymol, 1987, 154:350-367.
Kratz et al., "Prodrugs of Anthracyclines in Cancer Chemotherapy," Curr Med Chem, 2006, 13(5):477-523.
Kunkel et al., "Rapid and efficient site-specific mutagenesis without phenotypic selection," Proc Natl Acad Sci USA, Jan. 1985, 82(2):488-492.
Kyogoju et al., "Fcγ Receptor Gene Polymorphisms in Japanese Patients With Systemic Lupus Erythematosus—Contribution of FCGR2B to Genetic Susceptibility," Arthritis Rheum, May 2002, 46(5):1242-1254.
Lazar et al., "Engineered antibody Fc variants with enhanced effector function," Proc Natl Acad Sci USA, Mar. 14, 2006, 103(11):4005-4010. Epub Mar. 6, 2006.
Lee et al., "High-affinity Human Antibodies from Phage-displayed Synthetic Fab Libraries with a Single Framework Scaffold," J Mol Biol, Jul. 23, 2004, 340(5):1073-1093.
Lee et al., "Bivalent antibody phage display mimics natural immunoglobulin," J Immunol Methods, Jan. 2004, 284(1-2):119-132.
Li et al., "Optimization of humanized IgGs in glycoengineered Pichia pastoris," Nat Biotechnol, Feb. 2006, 24(2):210-215. Epub Jan. 22, 2006.
Li et al., "Human antibodies for immunotherapy development generated via a human B cell hybridoma technology," Proc Natl Acad Sci USA, Mar. 7, 2006, 103(10):3557-3562. Epub Feb. 27, 2006.
Li et al., "A Novel Polymorphism in the Fcγ Receptor IIB (CD32B) Transmembrane Region Alters Receptor Signaling," Arthritis Rheum, Nov. 2003, 48(11):3242-3252.
Lode et al., "Targeted Therapy with a Novel Enediyene Antibiotic Calicheamicin $\Theta^I_1$ Effectively Suppresses Growth and Dissemination of Liver Metastases in a Syngeneic Model of Murine Neuroblastoma," Cancer Res, Jul. 15, 1998, 58(14):2925-2928.
Lonberg, "Fully human antibodies from transgenic mouse and phage display platforms," Curr Opin Immunol, Aug. 2008, 20(4):450-459. doi: 10.1016/j.coi.2008.06.004. Epub Jul. 21, 2008.
Lonberg, "Human antibodies from transgenic animals," Nat Biotechnol, Sep. 2005, 23(9):1117-1125.
Marks et al., "By-passing Immunization—Human Antibodies from V-gene Libraries Displayed on Phage," J Mol Biol, Dec. 5, 1991, 222(3):581-597.
Marks et al., Chapter 8 "Selection of Human Antibodies from Phage Display Libraries," Methods Mol Biol, 2004, 248:161-176.
Mather et al., "Establishment and Characterization of Two Distinct Mouse Testicular Epithelial Cell Lines," Biol Reprod, Aug. 1980, 23(1):243-252.
Mather et al., "Culture of Testicular Cells in Hormone-Supplemented Serum-Free Medium," Ann NY Acad Sci, 1982, 383:44-68.
Mazor et al., "Improving target cell specificity using a novel monovalent bispecific IgG design," mAbs, Mar./Apr. 2015, 7(2):377-389.
Mccafferty et al., "Phage antibodies: filamentous phage displaying antibody variables domains," Nature, Dec. 6, 1990, 348(6301):552-554.
Milstein et al., "Hybrid hybridomas and their use in immunohistochemistry," Nature, Oct. 6-12, 1983, 305(5934):537-540.
Moore et al., "Engineered Fc variant antibodies with enhanced ability to recruit complement and mediate effector functions," mAbs, Mar.-Apr. 2010, 2(2):181-189.
Morrison et al., "Chimeric human antibody molecules: Mouse antigen-binding domains with human constant region domains," Proc Natl Acad Sci USA, Nov. 1984, 81(21):6851-6855.
Muller et al., "The first constant domain ($C_H1$ and $C_L$) of an antibody used as heterodimerization domain for bispecific miniantibodies," FEBS Lett, Jan. 30, 1998, 422(2):259-64.
Munson et al., "Ligand: A Versatile Computerized Approach for Characterization of Ligand-Binding Systems," Anal Biochem, Sep. 1, 1980, 107(1):220-139.
Nagy et al., "Stability of cytotoxic luteinizing hormone-releasing hormone conjugate (AN-152) containing doxorubicin 14-O-hemiglutarate in mouse and human serum in vitro: Implications for the design of preclinical studies," Proc Natl Acad Sci USA, Jan. 18, 2000, 97(2):829-834.
Nishimoto et al., "Humanized anti-interleukin-6 receptor antibody treatment of multicentric Castleman disease," Blood, Oct. 15, 2005, 106:2627-2632.
Okazaki et al., "Fucose Depletion from Human IgG1 Oligosaccharide Enhances Binding Enthalpy and Association Rate Between IgG1 and FcγRIIIa," J Mol Biol, Mar. 5, 2004, 336(5):1239-1249.
Ory et al., "Sequences of Complementary DNAs That Encode the NA1 and NA2 Forms of Fc Receptor III on Human Neutrophils," J Clin Invest, Nov. 1989, 84(5):1688-1691.
Osbourn et al., "From rodent reagents to human therapeutics using antibody guided selection," Methods, May 2005, 36(1):61-68.
Pace et al., "How to measure and predict the molar absorption coefficient of a protein," Protein Sci, Nov. 1995, 4(11):2411-2423.
Padlan, "A Possible Procedure for Reducing the Immunogenicity of Antibody Variable Domains While Preserving Their Ligand-Binding Properties," Mol Immunol, Apr.-May 1991, 28(4-5):489-498.
Portolano et al., "Lack of Promiscuity in Autoantigen-Specific H and L Chain Combinations as Revealed by Human H and L Chain 'Roulette'," J Immunol, Feb. 1, 1993, 150(3):880-887.
Presta et al., "Humanization of an Anti-Vascular Endothelial Growth Factor Monoclonal Antibody for the Therapy of Solid Tumors and Other Disorders," Cancer Res, Oct. 15, 1997, 57(20):4593-4599.
Presta et al., "Humanization of an antibody directed against IgE," J Immunol, Sep. 1, 1993, 151(5):2623-2632.
Priyamvada et al., "Human antibody responses after dengue virus infection are highly cross-reactive to Zika virus," Proc Natl Acad Sci USA, Jul. 12, 2016, 113(28):7852-7857.
Ravetch et al., "Fc Receptors," Annu Rev Immunol, 1991, 9:457-492.
Riechmann et al., "Reshaping human antibodies for therapy," Nature, Mar. 24, 1988, 332(6162):323-327.
Ripka et al., "Microarray-Based Comparative Genomic Hybridization Using Sex-Matched Reference DNA Provides Greater Sensitivity for Detection of Sex Chromosome Imbalances than Array-Comparative Genomic Hybridization with Sex-Mismatched Reference DNA," Arch Biochem Biophys, Sep. 1986, 249(2):533-545.
Rosenburg et al., Chapter 11 "Antibodies from *Escherichia coli*," The Pharmacology of Monoclonal Antibodies, 1994, 113:269-315.

(56) References Cited

OTHER PUBLICATIONS

Rosok et al., "A Combinatorial Library Strategy for the Rapid Humanization of Anticarcinoma BR96 Fab," J Biol Chem, Sep. 13, 1996, 271(37):22611-22618.
Screenshots of Genetyx software, 3 pages (document cited by opponent during the opposition proceedings of EP 2 202 245 on May 22, 2020).
Screenshots of the web-based calculator, 9 pages (document cited by opponent during the EPO opposition proceedings of EP 2 202 245 on May 22, 2020).
Sections of the Genetyx manual pertaining to isoelectric point, 5 pages (document cited by opponent during the EPO opposition proceedings of EP 2 202 245 on May 22, 2020, with English translation).
Sidhu et al., "Phage-displayed Antibody Libraries of Synthetic Heavy Chain Complementarity Determining Regions," J Mol Biol, Apr. 23, 2004, 338(2):299-310.
Story et al., "A Major Histocompatibility Complex Class I-like Fc Receptor Cloned from Human Placenta: Possible Role in Transfer of Immunoglobulin G from Mother to Fetus," J Exp Med, Dec. 1, 1994, 180(6):2377-2381.
Strausberg et al., "Generation and initial analysis of more than 15,000 full-length human and mouse cDNA sequences," Proc Natl Acad Sci USA, Dec. 24, 2002, 99(26):16899-16903. Epub Dec. 11, 2002.
Tan et al., "A Non Mouse-Adapted Dengue Virus Strain as a New Model of Severe Dengue Infection in AG129 Mice," PLoS Negl Trop Dis, Apr. 27, 2010, 4(4):e672. doi: 10.1371/journal.pntd.0000672.
Tan, Book Reviews—Current Protocols in Immunology, eds. Coligan et al., 1991, 1 page.
Torgov et al., "Generation of an Intensely Potent Anthracycline by a Monoclonal Antibody—β-Galactosidase Conjugate," Bioconjug Chem, May-Jun. 2005, 16(3):717-721.
Traunecker et al., "Bispecific single chain molecules (Janusins) target cytotoxic lymphocytes on HIV infected cells," EMBO J, Dec. 1991, 10(12):3655-3659.
Tutt et al., Trispecific F(ab')3 derivatives that use cooperative signaling via the TCR/CD3 complex and CD2 to activate and redirect resting cytotoxic T cells, Trispecific J Immunol, Jul. 1, 1991, 147(1):60-69.
Urlaub et al., "Isolation of Chinese hamster cell mutants deficient in dihydrofolate reductase activity," Proc Natl Acad Sci USA, Jul. 1980, 77(7):4216-4220.
Van Dijk et al., "Human antibodies as next generation therapeutics," Curr Opin Chem Biol, Aug. 2001, 5(4):368-374.
Vincent et al., "Current strategies in antibody engineering: Fc engineering and pH-dependent antigen binding, bispecific antibodies and antibody drug conjugates," Biotechnol J, 2012, 7(12):1444-1450. doi: 10.1002/biot.201200250.
Vitetta et al., "Redesigning Nature's Poisons to Create Anti-Tumor Reagents," Science, Nov. 20, 1987, 238(4830):1098-1104.
Vollmers et al., "The 'early birds': natural IgM antibodies and immune surveillance," Histol Histopathol, Jul. 2005, 20(3):927-937. doi: 10.14670/HH-20.927.
Vollmers et al., "Death by Stress: Natural IgM-Induced Apoptosis," Methods Find Exp Clin Pharmacol, Apr. 2005, 27(3):185-191.
Warmerdam et al., "Molecular Basis for a Polymorphism of Human Fcγ Receptor II (CD32)," J Exp Med, Jul. 1, 1990, 172(1):19-25.
Winter et al., "Making Antibodies by Phage Display Technology," Annu Rev Immunol, 1994, 12:433-455.
Wright et al., "Effect of glycosylation on antibody function: implications for genetic engineering Trends," Biotechnol, Jan. 1997, 15(1):26-32.
Wu et al., "A novel polymorphism of FcgammaRIIIa (CD16) alters receptor function and predisposes to autoimmune disease," J Clin Invest, Sep. 1, 1997, 100(5):1059-1070.
Xu et al., "Plasmablasts Generated during Repeated Dengue Infection Are Virus Glycoprotein-Specific and Bind to Multiple Virus Serotypes," J Immunol, Dec. 15, 2012, 189(12):5877-5885.
Xu et al., "A potent neutralizing antibody with therapeutic potential against all four serotypes of dengue virus," NPJ Vaccines, Jan. 23, 2017, 2(2), 10 pages.
Yamane-Ohnuki et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnol Bioeng, Sep. 5, 2004, 87(5):614-622.
Yazaki et al., Chapter 15 "Expression of Recombinant Antibodies in Mammalian Cell Lines," Methods Mol Biol, 2004, 248:255-268.
Zalevsky et al., "Enhanced antibody half-life improves in vivo activity," Nat Biotechnol, Feb. 2010, 28(2):157-159. Epub Jan. 17, 2010.
Zheng et al., "Translational Pharmacokinetics and Pharmacodynamics of an FcRn-Variant Anti-CD4 Monoclonal Antibody From Preclinical Model to Phase I Study," Clin Pharmacol Ther, Feb. 2011, 89(2):283-290. doi: 10.1038/clpt.2010.311. Epub Dec. 29, 2010.
Zola, Chapter 6 "Using Monoclonal Antibodies: Soluble Antigens," Monoclonal Antibodies: A Manual of Techniques, 1987, pp. 147-158.
Zoller, "Oligonucleotide-Directed Mutagenesis of DNA Fragments Cloned into M13 Vectors," Methods Enzymol, 1983, 100:468-500.
Zust et al., "Type I Interferon Signals in Macrophages and Dendritic Cells Control Dengue Virus Infection: Implications for a New Mouse Model To Test Dengue Vaccines," Dengue Vaccines, J Virol, Jul. 2014, 88(13):7276-7285. doi: 10.1128/JVI.03827-13. Epub Apr. 16, 2014.
Fish & Richardson P.C., Amendment and Reply to Action of Feb. 1, 2016 in U.S. Appl. No. 14/680,250, filed May 2, 2016, 17 pages.
Fish & Richardson P.C., Amendment and Reply to Action of Jun. 21, 2016 in U.S. Appl. No. 14/680,250, filed Dec. 21, 2016, 34 pages.
Supplemental Reply to Office Action of Feb. 6, 2014 and Advisory Action of May 14, 2014 in U.S. Appl. No. 13/257,145 dated May 14, 2014, filed on Jun. 3, 2014, 8 pages.
USPTO Restriction Requirement in U.S. Appl. No. 16/298,932, dated Oct. 8, 2020, 9 pages.
Fish & Richardson P.C., Reply to Restriction Requirement in U.S. Appl. No. 16/298,032, filed Apr. 7, 2021, 2 pages.
USPTO Non-Final Office Action in U.S. Appl. No. 16/298,932, dated May 26, 2021, 17 pages.
U.S. Appl. No. 18/545,077, Fink et al., filed Dec. 19, 2023.
U.S. Appl. No. 18/411,372, Kakehi et al., filed Jan. 12, 2024 (abandoned).
U.S. Appl. No. 18/425,859, Igawa et al., filed Jan. 29, 2024.
U.S. Appl. No. 18/432,567, Igawa et al., filed Feb. 5, 2024.
U.S. Appl. No. 18/633,674, Igawa et al., filed Apr. 12, 2024.
U.S. Appl. No. 18/651,896, Igawa et al., filed May 1, 2024.
U.S. Appl. No. 18/661,829, Kuramochi et al., filed May 13, 2024.
U.S. Appl. No. 18/748,951, Igawa et al., filed Jun. 20, 2024.
U.S. Appl. No. 18/820,608, Kakehi et al., filed Aug. 30, 2024.
U.S. Appl. No. 18/883,787, Igawa et al., filed Sep. 12, 2024.
U.S. Appl. No. 18/411,372, Kakehi et al., filed Jan. 12, 2024.
Brusco et al., "Molecular characterization of immunoglobulin G4 gene isoallotypes," Eur J Immunogenet, Oct. 1998, 25(5):349-355.
Shah et al., "Observation of Heavy-Chain C-Terminal Des-GK Truncation in Recombinant and Human Endogenous IgG4," J Pharm Sci, Jul. 2023, 112(7):1845-1849.
Zuckier et al., "Chimeric Human-Mouse IgG Antibodies with Shuffled Constant Region Exons Demonstrate that Multiple Domains Contribute to in Vivo Half-Life," Cancer Res, Sep. 1, 1998, 58(17):3905-3908.
USPTO Advisory Action in U.S. Appl. No. 14/680,250, dated Apr. 20, 2018, 3 pages.
U.S. Appl. No. 18/956,095, Igawa et al., filed Nov. 22, 2024.
U.S. Appl. No. 18/975,370, Igawa et al., filed Dec. 10, 2024.

* cited by examiner

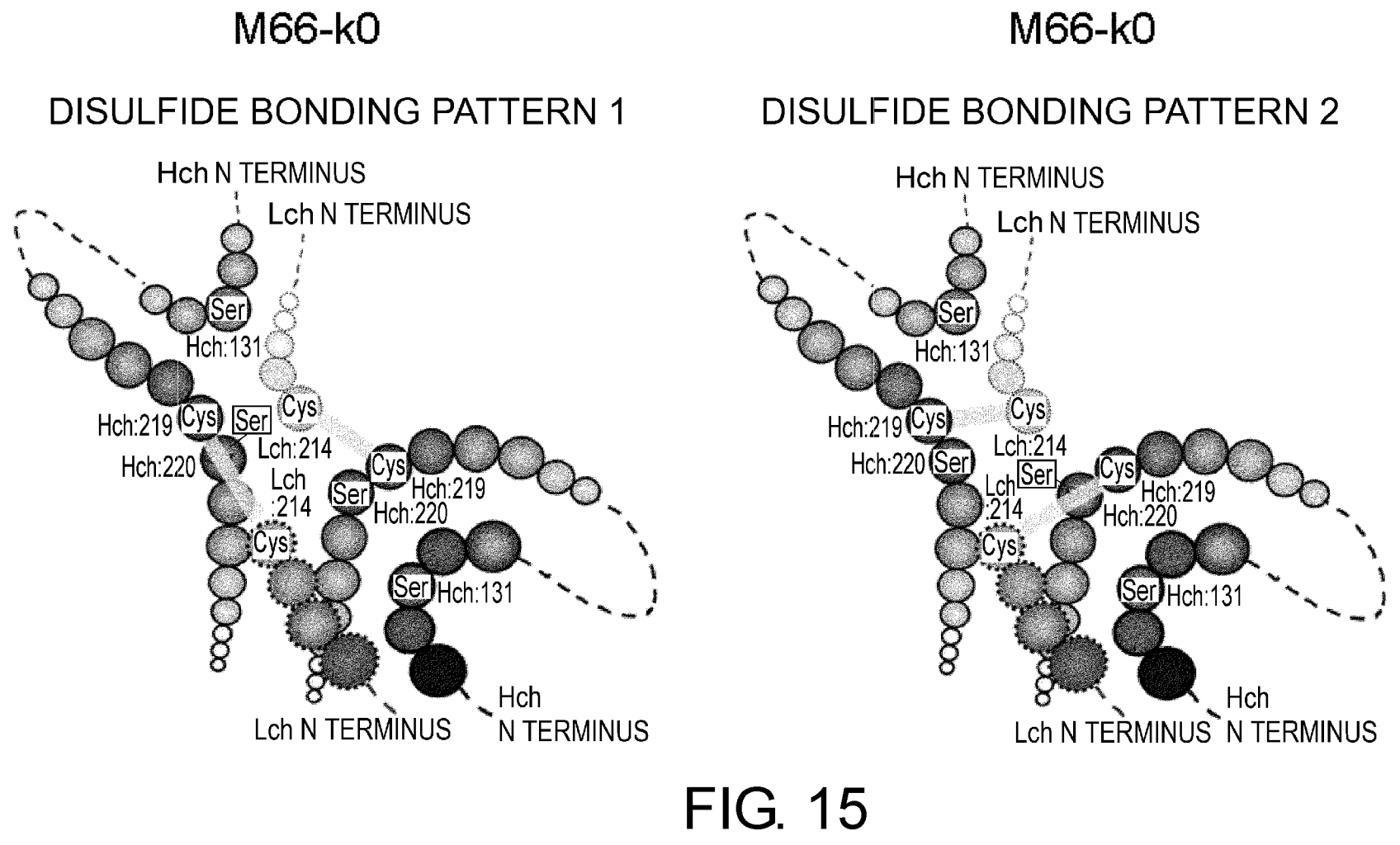

M66-k0

DISULFIDE BONDING PATTERN 1

Hch N TERMINUS
Lch N TERMINUS
Ser
Hch:131
Cys
Ser
Lch:214
Lch
:214
Cys
Hch:219
Hch:220
Cys
Ser
Hch:219
Hch:220
Ser
Hch:131
Hch
N TERMINUS
Lch N TERMINUS
Cys

M66-k0

DISULFIDE BONDING PATTERN 2

Hch N TERMINUS
Lch N TERMINUS
Ser
Hch:131
Cys
Lch:214
Ser
Lch
:214
Cys
Cys
Ser
Hch:219
Hch:220
Cys
Hch:219
Hch:220
Ser
Hch:131
Hch
N TERMINUS
Lch N TERMINUS

FIG. 15

SEQUENCE LISTING

<160> NUMBER OF SEQ ID NOS: 43

<210> SEQ ID NO 1
<211> LENGTH: 449
<212> TYPE: PRT
<213> ORGANISM: Artificial
<220> FEATURE:
<223> OTHER INFORMATION: An artificially synthesized peptide sequence

<400> SEQUENCE: 1

Gln Val Gln Leu Gln Glu Ser Gly Pro Gly Leu Val Arg Pro Ser Gln
1 5 10 15

Thr Leu Ser Leu Thr Cys Thr Val Ser Gly Tyr Ser Ile Thr Ser Asp
20 25 30

His Ala Trp Ser Trp Val Arg Gln Pro Pro Gly Arg Gly Leu Glu Trp
35 40 45

Ile Gly Tyr Ile Ser Tyr Ser Gly Ile Thr Thr Tyr Asn Pro Ser Leu
50 55 60

Lys Ser Arg Val Thr Met Leu Arg Asp Thr Ser Lys Asn Gln Phe Ser
65 70 75 80

Leu Arg Leu Ser Ser Val Thr Ala Ala Asp Thr Ala Val Tyr Tyr Cys
85 90 95

Ala Arg Ser Leu Ala Arg Thr Thr Ala Met Asp Tyr Trp Gly Gln Gly
100 105 110

Ser Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp
260 265 270

Pro Glu Val Lys Phe Asn Trp Tyr Val Asp Gly Val Glu Val His Asn
275 280 285

Ala Lys Thr Lys Pro Arg Glu Glu Gln Tyr Asn Ser Thr Tyr Arg Val
290 295 300

Val Ser Val Leu Thr Val Leu His Gln Asp Trp Leu Asn Gly Lys Glu
305 310 315 320

Tyr Lys Cys Lys Val Ser Asn Lys Ala Leu Pro Ala Pro Ile Glu Lys
325 330 335

Thr Ile Ser Lys Ala Lys Gly Gln Pro Arg Glu Pro Gln Val Tyr Thr
340 345 350

Leu Pro Pro Ser Arg Asp Glu Leu Thr Lys Asn Gln Val Ser Leu Thr

```
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 2
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 3
<211> LENGTH: 448
<212> TYPE: PRT
<213> ORGANISM: Artificial
<220> FEATURE:
<223> OTHER INFORMATION: An artificially synthesized peptide sequence
```

<400> SEQUENCE: 3

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 4
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 4

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
        435                 440                 445


<210> SEQ ID NO 5
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 5

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 6
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 6

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175
```

```
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445


<210> SEQ ID NO 7
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 7

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95
```

```
Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445
```

<210> SEQ ID NO 8
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 8

```
Gln Val Gln Leu Gln Glu Ser Gly Pro Gly Leu Val Arg Pro Ser Gln
1               5                   10                  15
```

```
Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430
```

```
His Tyr Thr Gln Lys Ser Leu Ser Leu Ser Pro Gly Lys
        435                 440                 445


<210> SEQ ID NO 9
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 9

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350
```

```
Arg Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445


<210> SEQ ID NO 10
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 10

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Ser Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270
```

```
Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440


<210> SEQ ID NO 11
<211> LENGTH: 451
<212> TYPE: PRT
<213> ORGANISM: Artificial
<220> FEATURE:
<223> OTHER INFORMATION: An artificially synthesized peptide sequence

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 12
<211> LENGTH: 214
<212> TYPE: PRT
<213> ORGANISM: Artificial
<220> FEATURE:
<223> OTHER INFORMATION: An artificially synthesized peptide sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 13
<211> LENGTH: 447
<212> TYPE: PRT
<213> ORGANISM: Artificial
<220> FEATURE:
<223> OTHER INFORMATION: An artificially synthesized peptide sequence

<400> SEQUENCE: 13

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Cys Cys
    210                 215                 220

Val Glu Cys Pro Pro Cys Pro Ala Pro Pro Val Ala Gly Pro Ser Val
225                 230                 235                 240
```

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 14
<211> LENGTH: 445
<212> TYPE: PRT
<213> ORGANISM: Artificial
<220> FEATURE:
<223> OTHER INFORMATION: An artificially synthesized peptide sequence

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Ile Met Asn Trp Val Arg Gln Ala Pro Gly Gln Gly Leu Glu Trp Met
        35                  40                  45

Gly Leu Ile Asn Pro Tyr Asn Gly Gly Thr Ser Tyr Asn Gln Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Asp Asp Gly Pro Tyr Thr Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
        195                 200                 205

Lys Pro Ser Asn Thr Lys Val Asp Lys Thr Val Glu Arg Lys Ser Cys
    210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Phe Arg Val Val Ser
    290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Pro
        435                 440                 445


<210> SEQ ID NO 15
<211> LENGTH: 452
<212> TYPE: PRT
<213> ORGANISM: Artificial
<220> FEATURE:
<223> OTHER INFORMATION: An artificially synthesized peptide sequence

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 16
<211> LENGTH: 215
<212> TYPE: PRT
<213> ORGANISM: Artificial
<220> FEATURE:
<223> OTHER INFORMATION: An artificially synthesized peptide sequence

<400> SEQUENCE: 16

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Gly Arg
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Phe Tyr Cys Gln Gln Tyr Gly Ser Ser Pro
                85                  90                  95

Arg Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 17
<211> LENGTH: 448
<212> TYPE: PRT
<213> ORGANISM: Artificial
<220> FEATURE:
<223> OTHER INFORMATION: An artificially synthesized peptide sequence

<400> SEQUENCE: 17

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125
```

```
Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Cys
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 18
<211> LENGTH: 446
<212> TYPE: PRT
<213> ORGANISM: Artificial
<220> FEATURE:
<223> OTHER INFORMATION: An artificially synthesized peptide sequence

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Gly Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Pro Gly Thr Thr Val Ile Met Ser Trp Phe Asp Pro Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Asn Phe Gly Thr Gln Thr Tyr Thr Cys Asn Val Asp
        195                 200                 205

His Lys Pro Ser Asn Thr Lys Val Asp Lys Thr Val Glu Arg Lys Ser
    210                 215                 220

Cys Val Glu Cys Pro Pro Cys Pro Ala Pro Pro Val Ala Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Phe Arg Val Val
    290                 295                 300

Ser Val Leu Thr Val Val His Gln Asp Trp Leu Asn Gly Lys Glu Tyr
305                 310                 315                 320

Lys Cys Lys Val Ser Asn Lys Gly Leu Pro Ala Pro Ile Glu Lys Thr
                325                 330                 335

Ile Ser Lys Thr Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Met Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro
        435                 440                 445
```

<210> SEQ ID NO 19
<211> LENGTH: 443
<212> TYPE: PRT

```
<213> ORGANISM: Artificial
<220> FEATURE:
<223> OTHER INFORMATION: An artificially synthesized peptide sequence

<400> SEQUENCE: 19

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
```

```
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440


<210> SEQ ID NO 20
<211> LENGTH: 443
<212> TYPE: PRT
<213> ORGANISM: Artificial
<220> FEATURE:
<223> OTHER INFORMATION: An artificially synthesized peptide sequence

<400> SEQUENCE: 20

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Ser Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
```

```
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro
        435                 440


<210> SEQ ID NO 21
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Cys
    210
```

<210> SEQ ID NO 22
<211> LENGTH: 213
<212> TYPE: PRT
<213> ORGANISM: Artificial
<220> FEATURE:
<223> OTHER INFORMATION: An artificially synthesized peptide sequence

<400> SEQUENCE: 22

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Asn Ala Lys Thr Leu Ala Lys Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Glu Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Glu Cys
    210
```

<210> SEQ ID NO 23
<211> LENGTH: 330
<212> TYPE: PRT
<213> ORGANISM: Homo sapiens

<400> SEQUENCE: 23

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 24
<211> LENGTH: 326
<212> TYPE: PRT
<213> ORGANISM: Homo sapiens

<400> SEQUENCE: 24

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
```

```
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 25
<211> LENGTH: 327
<212> TYPE: PRT
<213> ORGANISM: Homo sapiens

<400> SEQUENCE: 25

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 26
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 26

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 27
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 27

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

```
Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 28
<211> LENGTH: 326
<212> TYPE: PRT
<213> ORGANISM: Artificial
<220> FEATURE:
<223> OTHER INFORMATION: An artificially synthesized peptide sequence

<400> SEQUENCE: 28

Ala Ser Thr Lys Gly Pro Ser Val Phe Pro Leu Ala Pro Ser Ser Lys
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 29
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320
```

Ser Leu Ser Pro

<210> SEQ ID NO 30
<211> LENGTH: 324
<212> TYPE: PRT
<213> ORGANISM: Artificial
<220> FEATURE:
<223> OTHER INFORMATION: An artificially synthesized peptide sequence

<400> SEQUENCE: 30

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro

<210> SEQ ID NO 31
<211> LENGTH: 324
<212> TYPE: PRT
<213> ORGANISM: Artificial

<220> FEATURE:
<223> OTHER INFORMATION: An artificially synthesized peptide sequence

<400> SEQUENCE: 31

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro
```

<210> SEQ ID NO 32
<211> LENGTH: 107
<212> TYPE: PRT
<213> ORGANISM: Homo sapiens

<400> SEQUENCE: 32

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 33
<211> LENGTH: 106
<212> TYPE: PRT
<213> ORGANISM: Artificial
<220> FEATURE:
<223> OTHER INFORMATION: An artificially synthesized peptide sequence

<400> SEQUENCE: 33

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Cys
            100                 105


<210> SEQ ID NO 34
<211> LENGTH: 106
<212> TYPE: PRT
<213> ORGANISM: Artificial
<220> FEATURE:
<223> OTHER INFORMATION: An artificially synthesized peptide sequence

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Glu Cys
            100                 105
```

<210> SEQ ID NO 35
<211> LENGTH: 267
<212> TYPE: PRT
<213> ORGANISM: Homo sapiens

<400> SEQUENCE: 35

```
Ala Glu Ser His Leu Ser Leu Leu Tyr His Leu Thr Ala Val Ser Ser
1               5                   10                  15

Pro Ala Pro Gly Thr Pro Ala Phe Trp Val Ser Gly Trp Leu Gly Pro
            20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
    50                  55                  60

Thr Thr Asp Leu Arg Ile Lys Glu Lys Leu Phe Leu Glu Ala Phe Lys
65                  70                  75                  80

Ala Leu Gly Gly Lys Gly Pro Tyr Thr Leu Gln Gly Leu Leu Gly Cys
                85                  90                  95

Glu Leu Gly Pro Asp Asn Thr Ser Val Pro Thr Ala Lys Phe Ala Leu
            100                 105                 110

Asn Gly Glu Glu Phe Met Asn Phe Asp Leu Lys Gln Gly Thr Trp Gly
        115                 120                 125

Gly Asp Trp Pro Glu Ala Leu Ala Ile Ser Gln Arg Trp Gln Gln Gln
    130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
            180                 185                 190

Phe Ser Val Leu Thr Cys Ser Ala Phe Ser Phe Tyr Pro Pro Glu Leu
        195                 200                 205

Gln Leu Arg Phe Leu Arg Asn Gly Leu Ala Ala Gly Thr Gly Gln Gly
    210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
            260                 265
```

<210> SEQ ID NO 36
<211> LENGTH: 99
<212> TYPE: PRT
<213> ORGANISM: Homo sapiens

<400> SEQUENCE: 36

```
Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60
```

```
Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met


<210> SEQ ID NO 37
<211> LENGTH: 105
<212> TYPE: PRT
<213> ORGANISM: Homo sapiens

<400> SEQUENCE: 37

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105


<210> SEQ ID NO 38
<211> LENGTH: 104
<212> TYPE: PRT
<213> ORGANISM: Artificial
<220> FEATURE:
<223> OTHER INFORMATION: An artificially synthesized peptide sequence

<400> SEQUENCE: 38

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Cys Ser
            100


<210> SEQ ID NO 39
<211> LENGTH: 104
<212> TYPE: PRT
<213> ORGANISM: Artificial
<220> FEATURE:
<223> OTHER INFORMATION: An artificially synthesized peptide sequence

<400> SEQUENCE: 39

Gln Pro Lys Ala Ala Pro Ser Val Thr Leu Phe Pro Pro Ser Ser Glu
```

```
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Glu Cys Ser
            100


<210> SEQ ID NO 40
<211> LENGTH: 107
<212> TYPE: PRT
<213> ORGANISM: Mus spp.

<400> SEQUENCE: 40

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105


<210> SEQ ID NO 41
<211> LENGTH: 107
<212> TYPE: PRT
<213> ORGANISM: Rattus spp.

<400> SEQUENCE: 41

Arg Ala Asp Ala Ala Pro Thr Val Ser Ile Phe Pro Pro Ser Thr Glu
1               5                   10                  15

Gln Leu Ala Thr Gly Gly Ala Ser Val Val Cys Leu Met Asn Asn Phe
            20                  25                  30

Tyr Pro Arg Asp Ile Ser Val Lys Trp Lys Ile Asp Gly Thr Glu Arg
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Ala Asp Tyr Glu
65                  70                  75                  80

Ser His Asn Leu Tyr Thr Cys Glu Val Val His Lys Thr Ser Ser Ser
                85                  90                  95

Pro Val Val Lys Ser Phe Asn Arg Asn Glu Cys
            100                 105
```

```
<210> SEQ ID NO 42
<211> LENGTH: 104
<212> TYPE: PRT
<213> ORGANISM: Oryctolagus cuniculus

<400> SEQUENCE: 42

Arg Asp Pro Val Ala Pro Thr Val Leu Ile Phe Pro Pro Ala Ala Asp
1               5                   10                  15

Gln Val Ala Thr Gly Thr Val Thr Ile Val Cys Val Ala Asn Lys Tyr
            20                  25                  30

Phe Pro Asp Val Thr Val Thr Trp Glu Val Asp Gly Thr Thr Gln Thr
        35                  40                  45

Thr Gly Ile Glu Asn Ser Lys Thr Pro Gln Asn Ser Ala Asp Cys Thr
    50                  55                  60

Tyr Asn Leu Ser Ser Thr Leu Thr Leu Thr Ser Thr Gln Tyr Asn Ser
65                  70                  75                  80

His Lys Glu Tyr Thr Cys Lys Val Thr Gln Gly Thr Thr Ser Val Val
                85                  90                  95

Gln Ser Phe Asn Arg Gly Asp Cys
            100


<210> SEQ ID NO 43
<211> LENGTH: 106
<212> TYPE: PRT
<213> ORGANISM: Oryctolagus cuniculus

<400> SEQUENCE: 43

Arg Asp Pro Val Ala Pro Ser Val Leu Leu Phe Pro Pro Ser Lys Glu
1               5                   10                  15

Glu Leu Thr Thr Gly Thr Ala Thr Ile Val Cys Val Ala Asn Lys Phe
            20                  25                  30

Tyr Pro Ser Asp Ile Thr Val Thr Trp Lys Val Asp Gly Thr Thr Gln
        35                  40                  45

Gln Ser Gly Ile Glu Asn Ser Lys Thr Pro Gln Ser Pro Glu Asp Asn
    50                  55                  60

Thr Tyr Ser Leu Ser Ser Thr Leu Ser Leu Thr Ser Ala Gln Tyr Asn
65                  70                  75                  80

Ser His Ser Val Tyr Thr Cys Glu Val Val Gln Gly Ser Ala Ser Pro
                85                  90                  95

Ile Val Gln Ser Phe Asn Arg Gly Asp Cys
            100                 105
```

ANTIBODY CONSTANT REGION VARIANT

CROSS-REFERENCE TO RELATED APPLICATIONS

This application is a divisional application of U.S. application Ser. No. 16/298,032, filed Mar. 11, 2019 (abandoned), which is a divisional of U.S. application Ser. No. 14/680,250, filed Apr. 7, 2015 (U.S. Pat. No. 10,253,091), which is a divisional of U.S. application Ser. No. 13/257,145, having a 371 (c) date of Nov. 22, 2011 (abandoned), which is the National Stage of International Application No. PCT/JP2010/054767, filed Mar. 19, 2010, which claims priority to Japanese Application Nos. 2009-068631 and 2009-213901, filed Mar. 19, 2009, and Sep. 16, 2009, respectively. The entire content of parent application Ser. No. 16/298,032 is hereby incorporated by reference.

SEQUENCE LISTING

This application contains a Sequence Listing that has been submitted electronically as an ASCII text file named SequenceListing.txt. The ASCII text file, created on Nov. 18, 2021, is 116,171 bytes in size. The material in the ASCII text file is hereby incorporated by reference in its entirety.

TECHNICAL FIELD

The present invention relates to antibody constant regions with an altered amino acid sequence, and antibodies comprising these constant regions.

BACKGROUND

Antibodies are drawing attention as pharmaceuticals as they are highly stable in plasma (blood) and have few side effects. Of these, a number of IgG-type antibody pharmaceuticals are available on the market and many antibody pharmaceuticals are currently under development (Non-patent Documents 1 and 2).

Almost all antibody pharmaceuticals currently available on the market are of the IgG1 subclass. IgG1 type antibodies are expected to be useful as anti-cancer antibody pharmaceuticals since they can bind to Fcγ receptor and exert ADCC activity. However, when it comes to antibody pharmaceuticals intended for neutralizing biological activity of an antigen, the binding of the Fc domain to Fcγ receptor, which is important for effector functions such as ADCC, can cause unnecessary side effects, and thus it is preferable to eliminate such binding activity (Non-patent Document 3). Furthermore, since Fcγ receptor is expressed in antigen-presenting cells, molecules that bind to Fcγ receptor tend to be presented as antigens. It has been reported that immunogenicity is and can be enhanced by linking a protein or peptide to the Fc domain of IgG1 (Non-patent Document 4 and Patent Document 1). Interaction between the antibody Fc domain and Fcγ receptor is thought to be a cause of the serious side effects encountered in phase-I clinical trials of TGN1412 (Non-patent Document 5). Thus, binding to Fcγ receptor is considered unfavorable in antibody pharmaceuticals intended for neutralizing the biological activity of an antigen from the perspective of side effects and immunogenicity.

A method for impairing the binding to Fcγ receptor is to alter the subtype of the IgG antibody from IgG1 to IgG2 or IgG4; however, this method cannot completely inhibit the binding (Non-patent Document 6). One of the methods reported for completely inhibiting the binding to Fcγ receptor is to artificially alter the Fc domain. For example, the effector functions of anti-CD3 antibodies and anti-CD4 antibodies cause side effects. Thus, amino acids that are not present in the wild type sequence were introduced into the Fcγ-receptor-binding domain of Fc (Non-patent Documents 3 and 7), and clinical trials are currently being conducted to assess anti-CD3 antibodies and anti-CD4 antibodies that have a mutated Fc domain and do not bind to Fcγ receptor (Non-patent Documents 5 and 8). Alternatively, Fcγ receptor-nonbinding antibodies can be prepared by altering the FcγR-binding domain of IgG1 (positions 233, 234, 235, 236, 327, 330, and 331 in the EU numbering; hereinafter abbreviated as position X (EU numbering)) to an IgG2 or IgG4 sequence (Non-patent Document 9 and Patent Document 2). However, these molecules contain new non-native peptide sequences of nine to twelve amino acids, which may constitute a T-cell epitope peptide and thus pose an immunogenicity risk. There is no previous report on Fcγ receptor-nonbinding antibodies that have overcome these problems.

Furthermore, for heterogeneity of the C-terminal sequence of an antibody, deletion of C-terminal amino acid lysine residue, and amidation of the C-terminal amino group due to deletion of both of the two C-terminal amino acids, glycine and lysine, have been reported (Non-patent Document 12). It is preferable to eliminate such heterogeneity when developing antibodies into pharmaceuticals.

Furthermore, in general, it is necessary that subcutaneous formulations are high-concentration formulations. From the perspective of stability and such, the concentration limit of IgG-type antibody formulations is generally thought to be about 100 mg/ml (Non-patent Document 13). Thus, it was a challenge to secure stability at high concentrations. However, there has been no report published on the improvement of the stability of IgG at high concentrations by introducing amino acid substitutions into its constant region. Meanwhile, instead of increasing the antibody concentration, methods that reduce the antibody dose by improving antibody kinetics in blood can be thought. A method for prolonging the antibody half-life in plasma has been reported and it substitutes amino acids in the constant region (Non-patent Documents 14 and 15); however, introduction of non-native sequences into the constant region is unpreferable from the perspective of immunogenicity risk.

Furthermore, physicochemical properties of antibody proteins, in particular, homogeneity, are very crucial in the development of antibody pharmaceuticals. For the IgG2 subtype, heterogeneity caused by disulfide bonds in the hinge region has been reported (Non-patent Documents 10, 16, 17, and 18 and Patent Document 3). It is not easy to manufacture them as a pharmaceutical in a large scale while maintaining differences of objective substance/related substance-related heterogeneity between productions. Thus, single substances are desirable as much as possible for antibody molecules developed as pharmaceuticals. In the present invention, differences in heterogeneity among productions can be understood, for example, as differences in heterogeneity among production lots. Heterogeneity in the production lots can be evaluated quantitatively by determining the diversity of molecular weight and structure of the produced antibody molecules.

As described above, it is desirable that the constant region sequences of antibody pharmaceuticals that are intended for neutralizing an antigen meet all the requirements in terms of the stability, C-terminal heterogeneity, immunogenicity (antigenicity), blood pharmacokinetics, and heterogeneity of hinge region. In particular, constant regions that do not have the heterogeneity of hinge region, which are more superior in blood pharmacokinetics than the natural constant regions such as of IgG1, are expected to be very useful as a constant region of antibody pharmaceuticals. However, altered constant regions that meet all of the above requirements have not yet been reported. Thus, there is a demand for antibody constant regions that have overcome the problems described above.

Documents of related prior arts for the present invention are described below.

PRIOR ART DOCUMENTS

Non-Patent Documents

[Non-patent Document 1] Monoclonal antibody successes in the clinic, Janice M Reichert, Clark J Rosensweig, Laura B Faden & Matthew C Dewitz, Nature Biotechnology 23, 1073-1078 (2005)

[Non-patent Document 2] Pavlou A K, Belsey M J., The therapeutic antibodies market to 2008., Eur J Pharm Biopharm. 2005 April; 59(3): 389-96

[Non-patent Document 3] Reddy M P, Kinney C A, Chaikin M A, Payne A, Fishman-Lobell J, Tsui P, Dal Monte P R, Doyle M L, Brigham-Burke M R, Anderson D, Reff M, Newman R, Hanna N, Sweet R W, Truneh A. Elimination of Fc receptor-dependent effector functions of a modified IgG4 monoclonal antibody to human CD4. J Immunol. 2000 Feb. 15; 164(4): 1925-33

[Non-patent Document 4] Guyre P M, Graziano R F, Goldstein J, Wallace P K, Morganelli P M, Wardwell K, Howell A L. Increased potency of Fc-receptor-targeted antigens. Cancer Immunol Immunother. 1997 November-December; 45(3-4): 146-8

[Non-patent Document 5] Strand V, Kimberly R, Isaacs J D. Biologic therapies in rheumatology: lessons learned, future directions. Nat Rev Drug Discov. 2007 January; 6(1): 75-92

[Non-patent Document 6] Gessner J E, Heiken H, Tamm A, Schmidt R E. The IgG Fc receptor family. Ann Hematol. 1998 June; 76(6): 231-48

[Non-patent Document 7] Cole M S, Anasetti C, Tso J Y. Human IgG2 variants of chimeric anti-CD3 are nonmitogenic to T cells. J Immunol. 1997 Oct. 1; 159(7): 3613-21

[Non-patent Document 8] Chau L A, Tso J Y, Melrose J, Madrenas J. HuM291(Nuvion), a humanized Fc receptor-nonbinding antibody against CD3, anergizes peripheral blood T cells as partial agonist of the T cell receptor. Transplantation. 2001 Apr. 15; 71(7): 941-50

[Non-patent Document 9] Armour K L, Clark M R, Hadley A G, Williamson L M., Recombinant human IgG molecules lacking Fcgamma receptor I binding and monocyte triggering activities. Eur J Immunol. 1999 August; 29(8): 2613-24

[Non-patent Document 10] Chu G C, Chelius D, Xiao G, Khor H K, Coulibaly S, Bondarenko P V. Accumulation of Succinimide in a Recombinant Monoclonal Antibody in Mildly Acidic Buffers Under Elevated Temperatures. Pharm Res. 2007 Mar. 24; 24(6): 1145-56

[Non-patent Document 11]A.J. Cordoba, B.J. Shyong, D. Breen, R.J. Harris, Nonenzymatic hinge region fragmentation of antibodies in solution, J. Chromatogr., B, Anal. Technol. Biomed. Life Sci. (2005) 818: 115-121

[Non-patent Document 12] Johnson K A, Paisley-Flango K, Tangarone B S, Porter T J, Rouse J C. Cation exchange-HPLC and mass spectrometry reveal C-terminal amidation of an IgG1 heavy chain. Anal Biochem. 2007 Jan. 1; 360(1): 75-83

[Non-patent Document 13] Shire S J, Shahrokh Z, Liu J. Challenges in the development of high protein concentration formulations., J Pharm Sci. 2004 June; 93(6): 1390-402

[Non-patent Document 14] Hinton P R, Xiong J M, Johlfs M G, Tang M T, Keller S, Tsurushita N., An engineered human IgG1 antibody with longer serum half-life., J Immunol. 2006 Jan. 1; 176(1): 346-56

[Non-patent Document 15] Ghetie V, Popov S, Borvak J, Radu C, Matesoi D, Medesan C, Ober R J, Ward E S., Increasing the serum persistence of an IgG fragment by random mutagenesis., Nat Biotechnol. 1997 July; 15(7): 637-40

[Non-patent Document 16]
Wypych J, Li M, Guo A, Zhang Z, Martinez T, Allen M J, Fodor S, Kelner D N, Flynn G C, Liu YD, Bondarenko P V, Ricci M S, Dillon™, Balland A., Human IgG2 antibodies display disulfide-mediated structural isoforms., J Biol Chem. 2008 Jun. 6; 283(23): 16194-205

[Non-patent Document 17]
Dillon™, Ricci M S, Vezina C, Flynn G C, Liu Y D, Rehder D S, Plant M, Henkle B, Li Y, Deechongkit S, Varnum B, Wypych J, Balland A, Bondarenko P V., Structural and functional characterization of disulfide isoforms of the human IgG2 subclass., J Biol Chem. 2008 Jun. 6; 283 (23): 16206-15

[Non-patent Document 18]
Martinez T, Guo A, Allen M J, Han M, Pace D, Jones J, Gillespie R, Ketchem R R, Zhang Y, Balland A., Disulfide connectivity of human immunoglobulin G2 structural isoforms., Biochemistry. 2008 Jul. 15; 47(28): 7496-508

PATENT DOCUMENTS

[Patent Document 1] US 20050261229 A1
[Patent Document 2] WO 99/58572
[Patent Document 3] US 2006/0194280

SUMMARY

Problems to be Solved by the Invention

The present invention was achieved in view of the above circumstances. An objective of the present invention is to provide constant regions that can confer antibodies with properties preferable for pharmaceuticals by altering amino acids in the antibody constant regions, and antibodies comprising these constant regions and variable regions.

Means for Solving the Problems

The present inventors conducted dedicated studies to generate antibody constant regions that have been improved by altering their amino acid sequences, which have improved homogeneity (C-terminal and hinge region), immunogenicity, stability, and pharmacokinetics. As a result, the present inventors successfully produced antibody constant regions with improved heterogeneity, immunogenicity, and stability. The present inventors also successfully produced antibody constant regions with a reduced Fcγ receptor-binding activity by further altering amino acids in the constant regions described above. The resulting antibody constant regions are excellent constant regions that are superior to the native IgG1 constant region in pharmacokinetics and have an improved heterogeneity of hinge region.

The present invention relates to antibody constant regions that are superior in terms of safety, immunogenicity risk, physicochemical properties (stability and homogeneity), and more superior in terms of pharmacokinetics and heterogeneity of hinge region through improvement by amino acid alterations; antibodies comprising such antibody constant region; pharmaceutical compositions comprising such antibody; and methods for producing them. More specifically, the present invention provides:

[1] an antibody constant region comprising an amino acid sequence in which Cys at position 14 (position 131 in the EU numbering), Arg at position 16 (position 133 in the EU numbering), Cys at position 103 (position 220 in the EU numbering), Glu at position 20 (position 137 in the EU numbering), Ser at position 21 (position 138 in the EU numbering), His at position 147 (position 268 in the EU numbering), Arg at position 234 (position 355 in the EU numbering), and Gln at position 298 (position 419 in the EU numbering) in the amino acid sequence of SEQ ID NO: 24 (IgG2 constant region) are substituted with other amino acids;

[2] the antibody constant region of [1], wherein Ser is substituted for Cys at position 14, Lys is substituted for Arg at position 16, Ser is substituted for Cys at position 103, Gly is substituted for Glu at position 20, Gly is substituted for Ser at position 21, Gln is substituted for His at position 147, Gln is substituted for Arg at position 234, and Glu is substituted for Gln at position 298;

[3] the antibody constant region of [1] or [2], which comprises an amino acid sequence additionally having deletion of Gly at position 325 (position 446 in the EU numbering) and Lys at position 326 (position 447 in the EU numbering);

[4] an antibody constant region comprising an amino acid sequence in which Cys at position 14 (position 131 in the EU numbering), Arg at position 16 (position 133 in the EU numbering), Cys at position 103 (position 220 in the EU numbering), Glu at position 20 (position 137 in the EU numbering), Ser at position 21 (position 138 in the EU numbering), His at position 147 (position 268 in the EU numbering), Arg at position 234 (position 355 in the EU numbering), Gln at position 298 (position 419 in the EU numbering), Ala at position 209 (position 330 in the EU numbering), Pro at position 210 (position 331 in the EU numbering), and Thr at position 218 (position 339 in the EU numbering) in the amino acid sequence of SEQ ID NO: 24 (IgG2 constant region) are substituted with other amino acids;

[5] the antibody constant region of [4], wherein Ser is substituted for Cys at position 14, Lys is substituted for Arg at position 16, Ser is substituted for Cys at position 103, Gly is substituted for Glu at position 20, Gly is substituted for Ser at position 21, Gln is substituted for His at position 147, Gln is substituted for Arg at position 234, Glu is substituted for Gln at position 298, Ser is substituted for Ala at position 209, Ser is substituted for Pro at position 210, and Ala is substituted for Thr at position 218;

[6] the antibody constant region of [4] or [5], which also comprises an amino acid sequence in which Gly at position 325 (position 446 in the EU numbering) and Lys at position 326 (position 447 in the EU numbering) are deleted;

[7] an antibody comprising the constant region of any one of [1] to [6];

[8] a pharmaceutical composition comprising the antibody of [7];

[9] a human κ chain constant region comprising at least one Cys at positions 102 to 106;

[10] a human κ chain constant region which does not comprise Cys at position 107;

[11] a human κ chain constant region which comprises at least one Cys at positions 102 to 106 but does not comprise Cys at position 107;

[12] the human κ chain constant region of any one of [9] to [11], in which at least one amino acid at positions 1 to 106 in the amino acid sequence of SEQ ID NO: 32 is deleted;

[13] the human κ chain constant region of [12], in which at least one amino acid at positions 102 to 106 is deleted;

[14] the human κ chain constant region of [13], in which the amino acid at position 105 is deleted;

[15] the human κ chain constant region of [13], in which the amino acid at position 106 is deleted;

[16] the human κ chain constant region of [9], in which at least one amino acid at position 102 to 106 is substituted with Cys;

[17] the human κ chain constant region of any one of [9] to [11], in which at least one amino acid at positions 102 to 106 is substituted with Cys, and Cys at position 107 is deleted or substituted with another amino acid;

[18] an antibody comprising the human κ chain constant region of any one of [9] to [17];

[19] a pharmaceutical composition comprising the antibody of [18];

[20] an antibody comprising the heavy chain constant region of any one of [1] to [6] and the light chain constant region of any one of [9] to [17]; and

[21] a pharmaceutical composition comprising the antibody of [20].

Effects of the Invention

The present invention provides constant regions that can confer to antibodies properties desirable for pharmaceutical agents. By means of amino acid sequence alterations, the constant regions of the present invention can improve the following antibody properties to conditions favorable for pharmaceutical agents.

Decrease in Antibody Heterogeneity:

Polypeptides obtainable by expressing a DNA encoding a certain amino acid sequence should theoretically be homogeneous polypeptide molecules consisting of the same amino acid sequence. However, in practice, when a DNA encoding an antibody is expressed in suitable hosts, heterogeneous polypeptides with different structures may be formed due to various factors. In the production of antibodies, an antibody population comprising many heterogeneous polypeptides can be referred to as having high heterogeneity. The constant regions of the present invention have the causes of heterogeneity removed by amino acid sequence alteration. Therefore, constructing antibodies using the constant regions of the present invention enables production of antibodies with low heterogeneity. Specifically, by introducing alterations provided by the present invention into heavy chain constant regions of antibodies, the homogeneity of the antibodies can be maintained at a high level. Suppressing the antibody heterogeneity to a low level means ameliorating the heterogeneity and this is an important objective in maintaining the quality of pharmaceuticals. Therefore, the constant regions of the present invention contribute to the maintenance of the quality of antibody-containing pharmaceuticals.

Improvement of Pharmacokinetics:

In a preferred embodiment, the present invention contributes to improvement of antibody pharmacokinetics. Specifically, when specific amino acid residues are altered in an antibody constant region of the present invention, blood concentration of the antibody composed of this constant region is maintained for a longer time than an antibody without amino acid sequence alterations. Maintaining blood concentration for as long a time as possible means that, when an antibody is administered as a pharmaceutical, its therapeutic effect can be maintained for a long time with a smaller amount of antibody. Alternatively, the antibody can be administered with wider intervals and smaller number of administrations.

BRIEF DESCRIPTION OF THE DRAWINGS

FIG. 15 shows in diagrams two types of predicted disulfide bond patterns in the constant region M66-k0.

DETAILED DESCRIPTION

Figure 1:
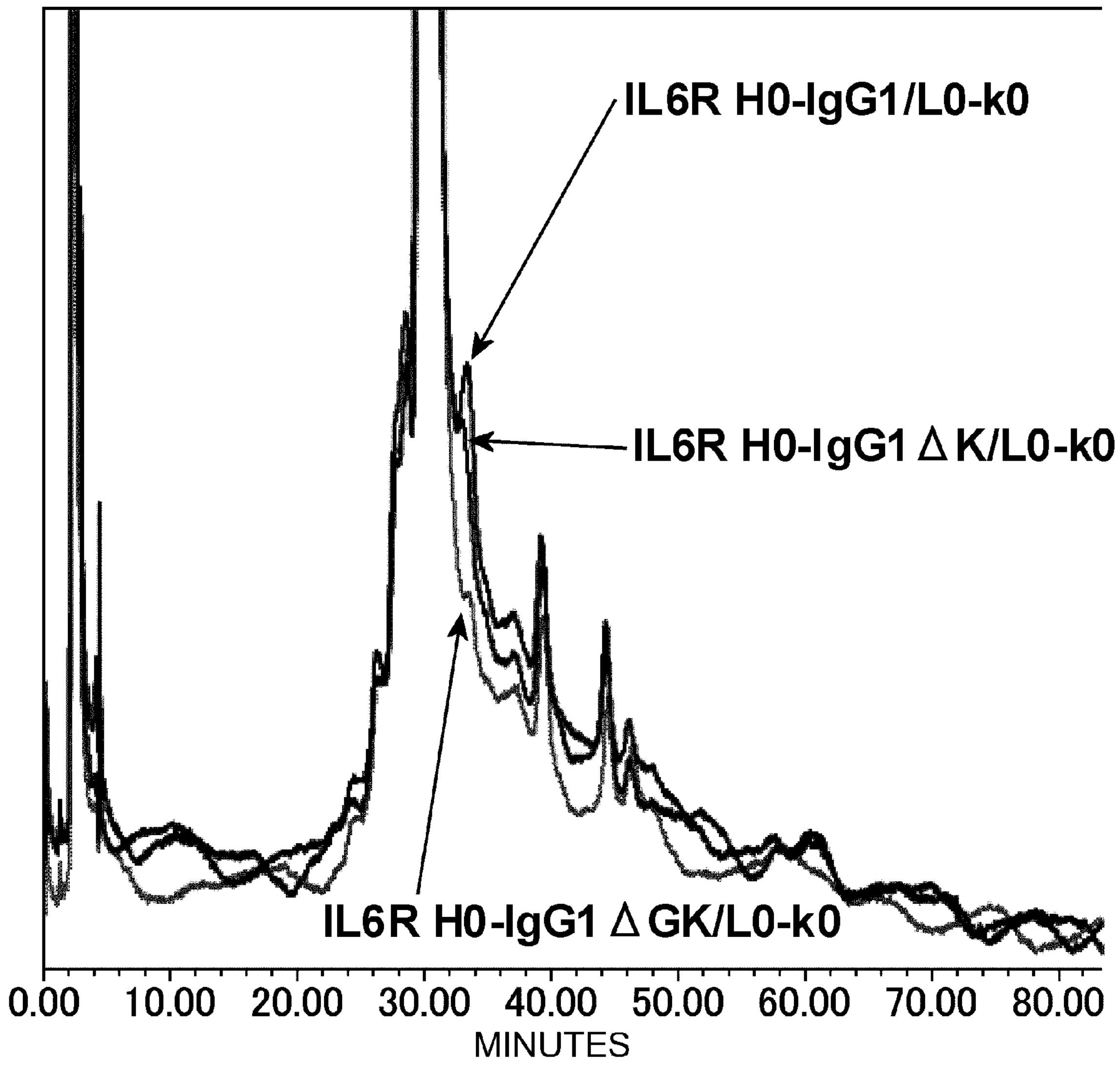
FIG. 1 shows in a graph the results of performing cation exchange chromatography on IL6R H0-IgG1/L0-k0, IL6R H0-IgG1AK/L0-k0, and IL6R H0-IgG1AGK/L0-k0 to evaluate the heterogeneity derived from the C terminus. In the figure, the vertical axis shows absorbance at 280 nm and the horizontal axis shows elution time (minutes).

The present invention provides antibody constant regions with an altered amino acid sequence, antibodies comprising such constant regions, pharmaceutical compositions comprising such antibodies, and methods for producing them.

The constant regions of antibody heavy chain include IgG1-, IgG2-, IgG3-, and IgG4-type constant regions. The heavy-chain constant region of the present invention is not particularly limited; however, it is preferably a human heavy-chain constant region. A human IgG2 constant region is particularly preferred in the present invention. The amino acid sequence of human IgG2 constant region is known in the art (SEQ ID NO: 24). A number of allotype sequences of human IgG2 constant regions due to gene polymorphisms are described in "Sequences of proteins of immunological interest", NIH Publication No. 91-3242. Any of such sequences may be used in the present invention.

Meanwhile, antibody light-chain constant regions include κ- and λ-chain type constant regions. The light-chain constant region of the present invention is not particularly limited; however, it is preferably a human light-chain constant region. A human κ chain constant region is preferred in the present invention. The amino acid sequence of human κ chain constant region is known (SEQ ID NO: 32). A number of allotype sequences of human κ and λ chain constant regions due to gene polymorphisms are described in "Sequences of proteins of immunological interest", NIH Publication No. 91-3242. Any of such sequences may be used in the present invention.

The antibody constant regions of the present invention with an amino acid alteration (substitution, deletion, addition and/or insertion) may additionally contain other amino acid alterations and modifications, as long as they comprise amino acid alternations of the present invention.

Specifically, constant regions with the following alterations are all included in the present invention.

An alteration of the present invention is introduced into the amino acid sequence of SEQ ID NO: 24 (human IgG2 constant region).

An alteration of the present invention is introduced into an altered amino acid sequence of SEQ ID NO: 24 (human IgG2 constant region).

An alteration of the present invention plus an additional alteration is introduced into the amino acid sequence of SEQ ID NO: 24 (human IgG2 constant region).

Furthermore, constant regions with the following alterations are also included in the present invention.

An alteration of the present invention is introduced into the amino acid sequence of SEQ ID NO: 32 (human κ chain constant region).

An alteration of the present invention is introduced into an altered amino acid sequence of SEQ ID NO: 32 (human κ chain constant region).

An alteration of the present invention plus an additional alteration is introduced into the amino acid sequence of SEQ ID NO: 32 (human κ chain constant region).

Furthermore, constant regions with the following alterations are also included in the present invention.

An alteration of the present invention is introduced into the amino acid sequence of SEQ ID NO: 37 (human λ chain constant region).

An alteration of the present invention is introduced into an altered amino acid sequence of SEQ ID NO: 37 (human λ chain constant region).

An alteration of the present invention plus an additional alteration is introduced into the amino acid sequence of SEQ ID NO: 37 (human λ chain constant region).

Furthermore, when sugar chains bind to the constant regions, they may have any structure. For example, the sugar chain bound at position 297 (EU numbering) may have any sugar chain structure (fucosylated sugar chains are preferred). Alternatively, it is acceptable that the constant regions have no sugar chain (for example, such constant regions can be produced in *E. coli*).

<Amino Acid-Altered IgG2 Constant Regions and Antibodies Comprising Such Constant Regions>

The present invention provides heavy-chain constant regions with improved stability, heterogeneity, immunogenicity, and/or pharmacokinetics. The present invention also provides antibodies comprising the heavy-chain constant region.

More specifically, the present invention provides heavy chain constant regions that comprise an amino acid sequence in which Cys at position 14 (position 131 (EU numbering)), Arg at position 16 (position 133 (EU numbering)), Cys at position 103 (position 220 (EU numbering)), Glu at position 20 (position 137 (EU numbering)), Ser at position 21 (position 138 (EU numbering)), His at position 147 (position 268 (EU numbering)), Arg at position 234 (position 355 (EU numbering)), and Gln at position 298 (position 419 (EU numbering)) in a heavy-chain constant region (IgG2 constant region) having the amino acid sequence of SEQ ID NO: 24 has been substituted with other amino acids, and antibodies comprising the heavy-chain constant regions.

Amino acids after substitution are not particularly limited; however, substitutions of Ser for Cys at position 14; Lys for Arg at position 16; Ser for Cys at position 103; Gly for Glu at position 20; Gly for Ser at position 21; Gln for His at position 147; Gln for Arg at position 234; and Glu for Gln at position 298 are preferred.

Such substitutions can improve antibody stability, immunogenicity, and/or pharmacokinetics. In particular, such substitutions enable one to provide excellent heavy-chain constant regions that are superior to IgG1 in pharmacokinetics, stability, and immunogenicity as well as to provide antibodies comprising such heavy-chain constant regions.

As long as heavy-chain constant regions of the present invention comprise at least the above-described amino acid substitution, they may comprise other amino acid alterations (substitutions, deletions, additions, insertions, and/or such) or modifications.

Furthermore, the present invention provides heavy-chain constant regions whose Fcγ receptor-binding activity has been reduced by additionally substituting amino acids in the above-described heavy-chain constant regions. The present invention also provides antibodies comprising the heavy-chain constant regions.

More specifically, the present invention provides heavy-chain constant regions having an amino acid sequence in which Cys at position 14 (position 131 (EU numbering)), Arg at position 16 (position 133 (EU numbering)), Cys at position 103 (position 220 (EU numbering)), Glu at position 20 (position 137 (EU numbering)), Ser at position 21 (position 138 (EU numbering)), His at position 147 (position 268 (EU numbering)), Arg at position 234 (position 355 (EU numbering)), Gln at position 298 (position 419 (EU numbering)), Ala at position 209 (position 330 (EU numbering)), Pro at position 210 (position 331 (EU numbering)), and Thr at position 218 (position 339 (EU numbering)) in a heavy-chain constant region (IgG2 constant region) comprising the amino acid sequence of SEQ ID NO: 24 have been substituted with other amino acids. The present invention also provides antibodies comprising such heavy-chain constant regions.

Amino acids after substitution are not particularly limited; however, substitutions of Ser for Cys at position 14; Lys for Arg at position 16; Ser for Cys at position 103; Gly for Glu at position 20; Gly for Ser at position 21; Gln for His at position 147; Gln for Arg at position 234; and Glu for Gln at position 298; Ser for Ala at position 209; Ser for Pro at position 210; and Ala for Thr at position 218 are preferred.

Such substitutions can improve antibody stability, heterogeneity, immunogenicity, safety, and/or pharmacokinetics.

As long as heavy-chain constant regions of the present invention comprise at least the above-described amino acid substitution, they may comprise other amino acid alterations (substitutions, deletions, additions, insertions, and/or such) or modifications.

Furthermore, the present invention provides heavy-chain constant regions comprising an amino acid sequence additionally having deletion of Gly and Lys at positions 325 and 326 (positions 446 and 447 (EU numbering)), respectively, in the above-described heavy-chain constant regions. The present invention also provides antibodies comprising the heavy-chain constant regions. The C-terminal heterogeneity can be improved by deleting these amino acids.

Specifically, such heavy-chain constant regions with altered amino acids include, for example, heavy-chain constant regions comprising the amino acid sequence of SEQ ID NO: 30 (M66) or 31 (M106).

Those described above are optimized heavy-chain constant regions with reduced Fcγ receptor-binding activity, reduced immunogenicity risk, reduced hinge-region heterogeneity, reduced C-terminal heterogeneity, and/or improved pharmacokinetics.

Furthermore, in the present invention, the heavy-chain constant regions of the present invention may comprise amino acid alterations to improve the stability under acidic conditions, in addition to the above-described amino acid alterations.

Specifically, the amino acid alterations to improve stability under acidic conditions include, for example, substitution of Met at position 276 (position 397 (EU numbering)) in the IgG2 constant region having the amino acid sequence of SEQ ID NO: 24 with another amino acid. The other amino acid is not particularly limited; however, Val is preferred. The substitution of Met at position 276 (position 397 (EU numbering)) in the amino acid sequence of SEQ ID NO: 24 with another amino acid can improve antibody stability under acidic conditions.

<κ Chain Constant Regions with Altered Amino Acids and Antibodies Comprising Such κ Chain Constant Regions>

Furthermore, the present invention provides light-chain constant regions that can be used to improve the heterogeneity of hinge region. The present invention also provides antibodies comprising such light-chain constant regions.

More specifically, the present invention provides human κ chain constant regions having at least one Cys at positions 102 to 106, and antibodies comprising the human κ chain constant regions. For example, "a human κ chain comprising the amino acid sequence of SEQ ID NO: 32 has at least one Cys at positions 102 to 106" means that there is at least one Cys in the region between Phe at position 102 and Glu at position 106.

The number of Cys present in the region of positions 102 to 106 in the human κ chain is not particularly limited; however, the number is five or less, preferably three or less, more preferably two or less, and still more preferably one.

The position of Cys is not particularly limited; however, Cys is preferably located at position 104, 105, or 106, more preferably at position 105 or 106, and particularly preferably at position 106.

The number of amino acids in the human κ chain constant region that has at least one Cys at positions 102 to 106 is not particularly limited; however, the number is preferably 102 to 107 amino acids, more preferably 105 or 106 amino acids, and still more preferably 106 amino acids.

Methods for producing a human κ chain constant region that has at least one Cys at positions 102 to 106 are not particularly limited, and include, for example, the methods described below. It is also possible to use a combination of the insertion, substitution, and deletion described below.

Insertion of at least one Cys at positions 102 to 106;

Substitution of Cys for at least one amino acid at positions 102 to 106;

Deletion of one to five amino acids at positions 1 to 106.

Furthermore, the present invention provides human κ chain constant regions that do not have Cys at position 107, and antibodies comprising such human κ chain constant regions. For example, "a human κ chain comprising the amino acid sequence of SEQ ID NO: 32 does not have Cys at position 107" means deletion of Cys at position 107, substitution of another amino acid for Cys at position 107, insertion of other amino acids, relocation of Cys from position 107 to a different position, etc. Preferred human κ chain constant regions include those having deletion of Cys at position 107, relocation of Cys from position 107 to a different position, or substitution of Cys at position 107 with another amino acid.

In a preferred embodiment, human κ chain constant regions of the present invention include those which have at least one Cys at positions 102 to 106 but do not have Cys at position 107.

Preferred human κ chain constant regions include, for example, those having deletion of at least one amino acid at positions 1 to 106. For example, in the human κ chain constant region having the amino acid sequence of SEQ ID NO: 32, deletion of Glu at position 106 leads to relocation of Cys from position 107 to 106, resulting in a human κ chain constant region having Cys at position 106 but not at position 107. The position of amino acid deletion is not particularly limited; however, a human κ chain constant region preferably comprises deletion of at least one amino acid at positions 102 to 106, more preferably deletion of the amino acid at position 105 or 106.

The number of deleted amino acids is not particularly limited; however, the number is typically one to five, preferably one to three, more preferably one or two, and still more preferably one.

Such preferred human κ chain constant regions include, for example, those having deletion of the amino acid at position 105 or 106.

In another preferred embodiment, the above-described human κ chain constant regions include those having substitution of Cys for at least one amino acid at positions 102 to 106 and additionally having deletion of Cys at position 107 or substitution of Cys at position 107 with another amino acid. The number of amino acids substituted with Cys is not particularly limited; however, the number is typically one to five, preferably one to three, more preferably one or two, and still more preferably one.

The position of substitution by Cys is not particularly limited; however, such preferred substitution positions include positions 105 and 106.

Such preferred human κ chain constant regions include, for example, those having substitution of Cys for Gly at position 105, and deletion of Cys at position 107 or substitution of another amino acid for Cys at position 107, and those having substitution of Cys for Glu at position 106, and deletion of Cys at position 107 or substitution of Cys at position 107 with another amino acid. Specific examples of the human κ chain constant regions of the present invention include those comprising the amino acid sequence of SEQ ID NO: 33 (k3) or 34 (k4).

The human κ chain constant regions of the present invention may comprise other amino acid alterations in addition to the above-described amino acid alterations. Such human κ chain constant regions additionally comprising other amino acid alterations and modifications are also included in the human κ chain constant regions of the present invention, as long as they comprise the above-described amino acid alteration.

The heterogeneity of hinge region can be reduced by using the human κ chain constant region of the present invention. In particular, the κ chain constant region of the present invention is efficient when used in combination with a heavy-chain constant region having Cys either at position 219 or 220 in the EU numbering (for example, heavy-chain constant regions having Cys only at position 219 in the EU numbering) such as a heavy-chain constant region comprising the amino acid sequence of SEQ ID NO: 30 (M66) or 31 (M106).

<λ Chain Constant Region with Altered Amino Acids and Antibodies Comprising the λ Chain Constant Regions>

Furthermore, the present invention provides light-chain constant regions that can be used to reduce the heterogeneity of hinge region. The present invention also provides antibodies comprising the above-described light-chain constant regions.

More specifically, the present invention provides human λ chain constant regions having at least one Cys at positions 99 to 103, and antibodies comprising such human λ chain constant regions. For example, "a human λ chain comprising the amino acid sequence of SEQ ID NO: 37 has at least one Cys at positions 99 to 103" means that there is at least one Cys in the region between Val at position 99 and Glu at position 103.

The number of Cys present in the region at positions 99 to 103 in the human λ chains is not particularly limited; however, the number is five or less, preferably three or less, more preferably two or one, and still more preferably one.

The position of Cys is not particularly limited; however, Cys is preferably located at position 101, 102, or 103, more preferably at position 102 or 103, and particularly preferably at position 103.

The number of amino acids in a human λ chain that has at least one Cys at positions 99 to 103 is not particularly limited; however, the number is preferably 100 to 103 amino acids, more preferably 102 or 103 amino acids, and still more preferably 103 amino acids.

Methods for producing a λ chain constant region that has at least one Cys at positions 99 to 103 are not particularly limited, and include, for example, the methods described below. It is also possible to use a combination of the insertion, substitution, and deletion described below.

Insertion of at least one Cys at positions 99 to 103;

Substitution of Cys at least one amino acid at positions 99 to 103;

Deletion of one to five amino acids at positions 1 to 103.

Furthermore, the present invention provides human λ chain constant regions that do not have Cys at position 104, and antibodies comprising such human λ chain constant regions. For example, "a human λ chain comprising the amino acid sequence of SEQ ID NO: 37 does not have Cys at position 104" means deletion of Cys at position 104, substitution of another amino acid for Cys at position 104, insertion of another amino acid, relocation of Cys from position 104 to another position; etc. Preferred human λ chain constant regions include those having deletion of Cys at position 104, relocation of Cys from position 104 to a different position, or substitution of another amino acid for Cys at position 104.

In a preferred embodiment, human λ chain constant region of the present invention include those that have at least one Cys at positions 99 to 103 but do not have Cys at position 104.

Such preferred human λ chain constant regions include, for example, those having deletion of at least one amino acid at positions 1 to 103. For example, in the human λ chain constant region comprising the amino acid sequence of SEQ ID NO: 37, the deletion of Glu at position 103 leads to relocation of Cys at position 104 to position 103, resulting in a human λ chain constant region having Cys at position 103 but not at position 104. The position of amino acid deletion is not particularly limited; however, a human κ chain constant region preferably comprises deletion of at least one amino acid at positions 99 to 103, more preferably deletion of the amino acid at position 102 or 103.

The number of deleted amino acids is not particularly limited; however, the number is typically one to five, preferably one to three, more preferably one or two, and still more preferably one.

Preferred examples of human λ chain constant regions include those having an amino acid deletion at position 102 or 103.

In another preferred embodiment, the above-described human λ chain constant regions include those having substitution of Cys for at least one amino acid at positions 99 to 103, and additionally having deletion of Cys at position 104 or substitution of Cys at position 104 with another amino acid. The number of amino acids substituted with Cys is not particularly limited; however, the number is typically one to five, preferably one to three, more preferably one or two, and still more preferably one.

The position of substitution with Cys is not particularly limited; however, such preferred substitution positions include 102 and 103.

Such preferred human λ chain constant regions include, for example, those having substitution of Cys for Thr at position 102, and deletion of Cys at position 104 or substitution of Cys at position 104 with another amino acid, and those having substitution of Cys for Glu at position 103, and deletion of Cys at position 104 or substitution of Cys at position 104 with another amino acid. Specifically, the human λ chain constant regions of the present invention include, for example, those comprising the amino acid sequence of SEQ ID NO: 38 or 39.

The human λ chain constant regions of the present invention may comprise other amino acid alterations in addition to the above-described amino acid alterations. The human λ chain constant regions additionally comprising other amino acid alterations and modifications are also included in the human λ chain constant regions of the present invention, as long as they comprise the above-described amino acid alteration.

The heterogeneity of hinge region can be reduced by using the human λ chain constant regions of the present invention. In particular, the human λ chain constant region of the present invention is efficient when used in combination with a heavy-chain constant region comprising Cys either at position 219 or 220 in the EU numbering (for example, heavy-chain constant regions comprising Cys only at position 219 in the EU numbering) such as a heavy-chain constant region comprising the amino acid sequence of SEQ ID NO: 30 (M66) or 31 (M106).

Without being restricted to a particular theory, the reason why the human κ or λ chain constant regions of the present invention reduces the heterogeneity of hinge region can be described below using κ chain as an example.

As shown in FIG. 15, cysteine at position 107 in the human κ chain constant region can form a disulfide bond with cysteine at position 219 (EU numbering) in both of the two H chains of an antibody. It is thought that the resulting two types of disulfide bonds cause heterogeneity in hinge region.

On the other hand, as in the human κ chain constant region of the present invention, by relocating cysteine to its N-terminal side, the distance between this cysteine and cysteine at position 219 (EU numbering) in one H chain becomes greater, and as a result cysteine in the κ chain constant region can only form a disulfide bond with cysteine at position 219 (EU numbering) in one of the two H chains. This causes reduction of heterogeneity in hinge region (see FIG. 16). Specifically, the heterogeneity of hinge region can be reduced by increasing the distance between cysteine in the human κ chain constant region and cysteine at position 219 (EU numbering) in one H chain. In the same manner, the heterogeneity of hinge region in a human λ chain constant region can also be reduced by increasing the distance from cysteine at position 219 (EU numbering) in one H chain.

<κ Chain Constant Regions Derived from Nonhuman Animals and Antibodies Comprising Such κ Chain Constant Regions>

The present invention can also be used to alter light-chain constant regions derived from nonhuman animals. Examples of light-chain constant regions derived from nonhuman animals include mouse antibody κ chain constant region (SEQ ID NO: 40), rat antibody κ chain constant region (SEQ ID NO: 41), and rabbit antibody κ chain constant regions (SEQ ID NOs: 42 and 43), but are not limited thereto.

Thus, the present invention provides mouse and rat antibody κ chain constant regions having at least one Cys at positions 102 to 106, and antibodies comprising such light-chain constant regions. For example, "there is at least one Cys at positions 102 to 106 in the mouse κ chain constant region comprising the amino acid sequence of SEQ ID NO: 40 or the rat κ chain constant region comprising the amino acid sequence of SEQ ID NO: 41" means that there is at least one Cys in the region between Phe at position 102 and Glu at position 106.

Furthermore, the present invention provides rabbit κ chain constant regions having at least one Cys at positions 99 to 103 in the rabbit antibody κ chain constant region (SEQ ID NO: 42), and antibodies comprising such rabbit κ chain constant regions. For example, "there is at least one Cys at positions 99 to 103 in the rabbit κ chain comprising the amino acid sequence of SEQ ID NO: 42" means that there is at least one Cys in the region between Phe at position 99 and Asp at position 103.

The present invention also provides rabbit κ chain constant regions having at least one Cys at positions 101 to 105 in the rabbit antibody κ chain constant region (SEQ ID NO: 43), and antibodies comprising the rabbit κ chain constant region. For example, "there is at least one Cys at positions 101 to 105 in the rabbit κ chain comprising the amino acid sequence of SEQ ID NO: 43" means that there is at least one Cys in the region between Phe at position 101 and Asp at position 105.

The number of Cys present in the region of positions 102 to 106 in a mouse κ chain constant region, positions 102 to 106 in a rat κ chain constant region, positions 99 to 103 in the rabbit κ chain constant region (SEQ ID NO: 42), or positions 101 to 105 in the rabbit κ chain constant region (SEQ ID NO: 43) is not particularly limited; however, the number is five or less, preferably three or less, more preferably two or less, and still more preferably one.

The position of Cys is not particularly limited; however,
in a mouse or rat κ chain constant region, the position is preferably 104, 105, or 106, more preferably 105 or 106, and particularly preferably 106;
in the rabbit κ chain constant region (SEQ ID NO: 42), the position is preferably 101, 102, or 103, more preferably 102 or 103, and particularly preferably 103; and
in the rabbit κ chain constant region (SEQ ID NO: 43), the position is preferably 103, 104, or 105, more preferably 104 or 105, and particularly preferably 105.

The number of amino acids in such κ chain constant region is not particularly limited; however,
in mouse or rat κ chain constant regions, the number is preferably 102 to 107 amino acids, more preferably 105 or 106 amino acids, and still more preferably 106 amino acids;
in the rabbit κ chain constant region (SEQ ID NO: 42), the number is preferably 99 to 104 amino acids, more preferably 102 or 103 amino acids, and still more preferably 103 amino acids; and
in the rabbit κ chain constant region (SEQ ID NO: 43), the number is preferably 101 to 106 amino acids, more preferably 104 or 105 amino acids, and still more preferably 105 amino acids.

Methods for producing a mouse or rat κ chain constant region that has at least one Cys at positions 102 to 106 are not particularly limited, and include, for example, the methods described below. It is also possible to use in combination the insertion, substitution, and deletion described below.

Insertion of at least one Cys at positions 102 to 106.

Substitution of Cys for at least one amino acid at positions 102 to 106.

Deletion of one to five amino acids at positions 1 to 106.

Meanwhile, methods for producing a mouse or rabbit κ chain constant region that has at least one Cys at positions 99 to 103 are not particularly limited, and include, for example, the methods described below. It is also possible to use in combination the insertion, substitution, and deletion described below.

Insertion of at least one Cys at positions 99 to 103.

Substitution of Cys for at least one amino acid at positions 99 to 103.

Deletion of one to five amino acids at positions 1 to 103.

Methods for producing a rabbit κ chain constant region that has at least one Cys at positions 101 to 105 are not particularly limited, and include, for example, the methods described below. It is also possible to use in combination the insertion, substitution, and deletion described below.

Insertion of at least one Cys at positions 101 to 105.

Substitution of Cys for at least one amino acid at positions 101 to 105.

Deletion of one to five amino acids at positions 1 to 105.

Furthermore, the present invention provides mouse and rat κ chain constant regions that do not have Cys at position 107, and antibodies comprising such κ chain constant regions. For example, "there is no Cys at position 107 in a mouse κ chain constant region comprising the amino acid sequence of SEQ ID NO: 40 or a rat κ chain constant region comprising the amino acid sequence of SEQ ID NO: 41" means deletion of Cys at position 107, substitution of Cys at position 107 with another amino acid, insertion of other amino acids, relocation of Cys from position 107 to a different position; etc. Preferred κ chain constant regions include those having deletion of Cys at position 107, relocation of Cys from position 107 to another position, or substitution of Cys at position 107 with another amino acid.

In a preferred embodiment, κ chain constant regions of the present invention include those which have at least one Cys at positions 102 to 106 but do not have Cys at position 107.

Such preferred κ chain constant regions include, for example, κ chain constant regions having deletion of at least one amino acid at positions 1 to 106. For example, in a κ chain constant region comprising the amino acid sequence of SEQ ID NO: 40 or 41, deletion of Glu at position 106 leads to relocation of Cys from position 107 to position 106, resulting in a κ chain constant region having Cys at position 106 but not at position 107. The position of amino acid deletion is not particularly limited; however, the κ chain constant region preferably comprises deletion of at least one amino acid at positions 102 to 106, more preferably deletion of the amino acid at position 105 or 106.

The number of deleted amino acids is not particularly limited; however, the number is typically one to five, preferably one to three, more preferably one or two, and still more preferably one.

Such preferred κ chain constant regions include, for example, those having deletion of the amino acid at position 105 or 106.

In another preferred embodiment, the above-described mouse and rat κ chain constant regions which do not have Cys at position 107 include those having substitution of Cys for at least one amino acid at positions 102 to 106, and additionally having deletion of Cys at position 107 or substitution of Cys at position 107 with another amino acid. The number of amino acids substituted with Cys is not particularly limited; however, the number is typically one to five, preferably one to three, more preferably one or two, and still more preferably one.

The position of Cys substitution is not particularly limited; however, such preferred substitution positions include positions 105 and 106.

Such preferred κ chain constant regions include, for example, those having substitution of Cys for Asn at position 105, and deletion of Cys at position 107 or substitution of Cys at position 107 with another amino acid, and those having substitution of Cys for Glu at position 106, and deletion of Cys at position 107 or substitution of Cys at position 107 with another amino acid.

The mouse or rat κ chain constant regions of the present invention may comprise other amino acid alterations in addition to the above-described amino acid alterations. Such κ chain constant regions comprising other amino acid alterations and modifications are also included in the κ chain constant regions of the present invention, as long as they comprise the above-described amino acid alteration.

Furthermore, the present invention provides rabbit κ chain constant regions which do not have Cys at position 104 in the rabbit κ chain constant region (SEQ ID NO: 42) and antibodies comprising such κ chain constant regions. For example, "there is no Cys as position 104 in the rabbit κ chain constant region comprising the amino acid sequence of SEQ ID NO: 42" means deletion of Cys at position 104, substitution of Cys at position 104 with another amino acid, insertion of other amino acids, relocation of Cys from position 104 to a different position; etc. Preferred κ chain constant regions include those having deletion of Cys at position 104, relocation of Cys from position 104 to a different position, or substitution of Cys at position 104 with another amino acid.

In a preferred embodiment of the present invention, κ chain constant regions include those which have at least one Cys at positions 99 to 103 but do not have Cys at position 104.

Such preferred κ chain constant regions include, for example, those having deletion of at least one amino acid at positions 1 to 103. For example, in a κ chain constant region comprising the amino acid sequence of SEQ ID NO: 42, deletion of Asp at position 103 leads to relocation of Cys from position 104 to position 103, resulting in a κ chain constant region having Cys at position 103 but not at position 104. The position of amino acid deletion is not particularly limited; however, a κ chain constant region preferably comprises deletion of at least one amino acid at positions 99 to 103, more preferably deletion of the amino acid at position 102 or 103.

The number of deleted amino acids is not particularly limited; however, the number is typically one to five, preferably one to three, more preferably one or two, and still more preferably one.

Such preferred κ chain constant regions include, for example, those having deletion of the amino acid at position 102 or 103.

In another preferred embodiment, the above-described rabbit κ chain constant regions which do not have Cys at position 104 include those having substitution of Cys for at least one amino acid at positions 99 to 103 and additionally having deletion of Cys at position 104 or substitution of Cys at position 104 with another amino acid. The number of amino acids substituted with Cys is not particularly limited; however, the number is typically one to five, preferably one to three, more preferably one or two, and still more preferably one.

The position of Cys substitution is not particularly limited; however, such preferred positions of substitution include positions 102 and 103.

Such preferred κ chain constant regions include, for example, those having substitution of Cys for Gly at position 102, and deletion of Cys at position 104 or substitution of Cys at position 104 with another amino acid, and those having substitution of Cys for Asp at position 103, and deletion of Cys at position 104 or substitution of Cys at position 104 with another amino acid.

The rabbit κ chain constant regions of the present invention may comprise other amino acid alterations in addition to the above-described amino acid alterations. κ chain constant regions comprising other amino acid alterations and modifications are also included in the κ chain constant regions of the present invention, as long as they comprise the above-described amino acid alterations.

Furthermore, the present invention provides rabbit κ chain constant regions which do not have Cys at position 106 in the rabbit κ chain constant region (SEQ ID NO: 43) and antibodies comprising such κ chain constant regions. For example, "there is no Cys at position 106 in the rabbit κ chain constant region comprising the amino acid sequence of SEQ ID NO: 43" means deletion of Cys at position 106, substitution of Cys at position 106 with another amino acid, insertion of other amino acids, relocation of Cys from position 106 to a different position; etc. Preferred κ chain constant regions include those having deletion of Cys at position 106, relocation of Cys from position 106 to a different position, or substitution of Cys at position 106 with another amino acid.

In a preferred embodiment, κ chain constant regions of the present invention include those which have at least one Cys at positions 101 to 105 but do not have Cys at position 106.

Such preferred κ chain constant regions include, for example, those having deletion of at least one amino acid at positions 1 to 105. For example, in a κ chain constant region comprising the amino acid sequence of SEQ ID NO: 43, deletion of Asp at position 105 leads to relocation of Cys from position 106 to 105, resulting in a κ chain constant region having Cys at position 105 but not at position 106. The position of amino acid deletion is not particularly limited; however, a human κ chain constant region preferably comprises deletion of at least one amino acid at positions 101 to 105, more preferably deletion of the amino acid at position 104 or 105.

The number of deleted amino acids is not particularly limited; however, the number is typically one to five, preferably one to three, more preferably one or two, and still more preferably one.

Such preferred κ chain constant regions include, for example, those having deletion of the amino acid at position 104 or 105.

In another preferred embodiment, the above-described rabbit κ chain constant regions which do not have Cys at position 106 include those which have substitution of Cys for at least one amino acid at positions 101 to 105, and additionally have deletion of Cys at position 106 or substitution of Cys at position 106 with another amino acid. The number of amino acids substituted with Cys is not particularly limited; however, the number is typically one to five, preferably one to three, more preferably one or two, and still more preferably one.

The position of Cys substitution is not particularly limited; however, such preferred positions of substitution include positions 104 and 105.

Such preferred κ chain constant regions include, for example, those having substitution of Cys for Gly at position 104, and deletion of Cys at position 106 or substitution of Cys at position 106 with another amino acid, and those having substitution of Cys for Asp at position 105, and deletion of Cys at position 106 or substitution of Cys at position 106 with another amino acid.

The rabbit κ chain constant regions of the present invention may comprise other amino acid alterations in addition to the above-described amino acid alterations. K chain constant regions comprising other amino acid alterations and modifications are also included in the κ chain constant regions of the present invention, as long as they comprise the above-described amino acid alterations.

Furthermore, the present invention provides antibodies comprising heavy-chain constant regions having the above-described amino acid alterations. The present invention also provides antibodies comprising light chain constant regions having the above-described amino acid alterations. The present invention also provides antibodies comprising heavy chain constant regions having the above-described amino acid alterations and light chain constant regions having the above-described amino acid alterations. Amino acid alterations in the antibodies of the present invention include all possible alterations specified by the description herein and combinations thereof.

The present invention also provides antibodies comprising light chains comprising light chain constant regions having the above-described amino acid alterations and heavy chain constant regions in which at least one Cys is substituted with another amino acid. Such heavy chain constant regions are not particularly limited; however, IgG2 heavy chain constant regions are preferred. When the heavy chain constant region is an IgG2 constant region, Cys to be substituted is not particularly limited; however, the constant region includes, for example, those having substitution of another amino acid for at least one of Cys at position 131 in the EU numbering (position 14 in SEQ ID NO: 24), Cys at position 219 in the EU numbering (position 102 in SEQ ID NO: 24), and Cys at position 220 in the EU numbering (position 103 in SEQ ID NO: 24). When two Cys are substituted with other amino acids, the combination is not particularly limited and includes the combination of substitutions at positions 131 and 219 (EU numbering) and the combination of substitutions at positions 131 and 220.

Furthermore, the present invention provides antibodies comprising light chains comprising light chain constant regions having the above-described amino acid alterations, and heavy chains comprising heavy chain constant regions which have Cys at position 219 in the EU numbering (position 102 in SEQ ID NO: 24) but not at position 220 in the EU numbering (position 103 in SEQ ID NO: 24). Such heavy chain constant regions are not particularly limited; however, they are preferably IgG2 constant regions, more preferably M66 and M106. The antibody constant regions may have one or more amino acid substitutions, deletions, additions, and/or insertions (for example, 20 amino acids or less, or 10 amino acids or less).

Variable regions that constitute the antibodies of the present invention may recognize any antigen. Preferred variable regions of the present invention include antibody variable regions having an antigen-neutralizing activity. The variable regions that constitute the antibodies of the present invention include, for example, antibody variable regions having an activity of neutralizing IL6 receptor, IL31 receptor, or RANKL.

The antibodies of the present invention are not particularly limited in type, origin, or such; any antibody may be used in the present invention as long as it has the above-described antibody constant region. The origin of antibodies is not particularly limited. The antibodies include human, mouse, rat, and rabbit antibodies. The antibodies of the present invention may be chimeric, humanized, fully humanized antibodies, or such. In a preferred embodiment, the antibodies of the present invention are humanized antibodies.

Antibody molecules of the present invention usually include heavy chains and light chains. Heavy chains may include variable regions in addition to constant regions. Variable regions may include variable portions derived not only from humans but also from nonhuman animal species. Furthermore, CDRs from variable portions derived from non-human species such as mice can be transplanted to humanize the variable portions. Antibody molecules composed of heavy chains and light chains may be oligomers. Specifically, they may be monomers, dimers, or larger oligomers.

Alternatively, the above-described antigen constant regions may be linked with various molecules such as bioactive peptides or antigen-binding peptides to be fusion proteins.

The antibodies of the present invention also include modification products of an antibody comprising any one of the constant regions described above.

Such antibody modification products include, for example, antibodies linked with various molecules such as polyethylene glycol (PEG) and cytotoxic substances. Such antibody modification products can be obtained by chemically modifying antibodies of the present invention. Methods for modifying antibodies are already established in this field.

The antibodies of the present invention may also be bispecific antibodies. “Bispecific antibody” refers to an antibody that has in a single molecule variable regions that recognize different epitopes. The epitopes may be present in a single molecule or in separate molecules.

The antibody constant regions described above can be used as a constant region in an antibody against an arbitrary antigen. The antigen is not particularly limited.

The antibodies of the present invention can also be obtained by methods known to one skilled in the art. Methods for substituting or deleting one or more amino acid residues with amino acids of interest include, for example, site-directed mutagenesis (Hashimoto-Gotoh, T., Mizuno, T., Ogasahara, Y., and Nakagawa, M. An oligodeoxyribonucleotide-directed dual amber method for site-directed mutagenesis. Gene (1995) 152: 271-275; Zoller, M. J., and Smith, M. Oligonucleotide-directed mutagenesis of DNA fragments cloned into M13 vectors. Methods Enzymol. (1983) 100: 468-500; Kramer, W., Drutsa, V., Jansen, H. W., Kramer, B., Pflugfelder, M., and Fritz, H. J. The gapped duplex DNA approach to oligonucleotide-directed mutation construction. Nucleic Acids Res. (1984) 12: 9441-9456; Kramer W., and Fritz H. J. Oligonucleotide-directed construction of mutations via gapped duplex DNA Methods. Enzymol. (1987) 154: 350-367; Kunkel, T. A. Rapid and efficient site-specific mutagenesis without phenotypic selection. Proc. Natl. Acad. Sci. USA (1985) 82: 488-492). These methods can be used to substitute target amino acids in the constant region of an antibody with amino acids of interest. Furthermore, one or more amino acid residues can be deleted.

In another embodiment to obtain antibodies, an antibody that binds to an antigen of interest is first prepared by methods known to those skilled in the art. When the prepared antibody is derived from a nonhuman animal, it can be humanized. The binding activity of the antibody can be determined by known methods. Next, one or more amino acid residues in the constant region of the antibody are deleted or substituted with amino acids of interest.

The present invention relates to methods for producing antibodies with altered amino acid residues in the heavy chain and/or light chain constant regions, which comprise the steps of:

(a) expressing a DNA encoding a heavy chain having deletion or substitution of one or more amino acid residues in a constant region with amino acids of interest, and/or a light chain having deletion or substitution of one or more amino acid residues in a constant region with amino acids of interest; and (b) collecting the expression product of (a).

Such alterations of amino acid residues in the heavy chain constant region include, but are not limited to, for example, those described below.

(1) In an IgG2 constant region (the amino acid sequence of SEQ ID NO: 24),

Ser is substituted for Cys at position 14 (position 131 (EU numbering));

Lys is substituted for Arg at position 16 (position 133 (EU numbering));

Ser is substituted for Cys at position 103 (position 220 (EU numbering));

Gly is substituted for Glu at position 20 (position 137 (EU numbering));

Gly is substituted for Ser at position 21 (position 138 (EU numbering));

Gln is substituted for His at position 147 (position 268 (EU numbering));

Gln is substituted for Arg at position 234 (position 355 (EU numbering)); and

Glu is substituted for Gln at position 298 (position 419 (EU numbering)).

Antibodies with improved stability, immunogenicity, and/or pharmacokinetics can be produced using such substitutions.

(2) In an IgG2 constant region (the amino acid sequence of SEQ ID NO: 24),

Ser is substituted for Cys at position 14 (position 131 (EU numbering));

Lys is substituted for Arg at position 16 (position 133 (EU numbering));

Ser is substituted for Cys at position 103 (position 220 (EU numbering));

Gly is substituted for Glu at position 20 (position 137 (EU numbering));

Gly is substituted for Ser at position 21 (position 138 (EU numbering));

Gln is substituted for His at position 147 (position 268 (EU numbering));

Gln is substituted for Arg at position 234 (position 355 (EU numbering));

Glu is substituted for Gln at position 298 (position 419 (EU numbering));

Ser is substituted for Ala at position 209 (position 330 (EU numbering));

Ser is substituted for Pro at position 210 (position 331 (EU numbering)); and

Ala is substituted for Thr at position 218 (position 339 (EU numbering)).

Antibodies with reduced Fcγ receptor-binding activity can be produced using such substitutions.

(3) In an IgG2 constant region (the amino acid sequence of SEQ ID NO: 24), Gly at position 325 (position 446 (EU numbering)) and Lys at position 326 (position 447 (EU numbering)) are deleted. Antibodies with reduced C-terminal heterogeneity can be produced using such deletions.

(4) In an IgG2 constant region (the amino acid sequence of SEQ ID NO: 24), Val is substituted for Met at position 276 (position 397 (EU numbering)). Antibodies with improved stability under acidic conditions can be produced using such substitutions.

Meanwhile, amino acid alterations of light chain constant regions include, for example, those described below; but are not limited thereto. The alterations described below can reduce the heterogeneity of hinge region.

(1) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), amino acids are substituted or deleted so that it has at least one Cys at positions 102 to 106.

(2) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), amino acids are substituted or deleted so that it does not have Cys at position 107.

(3) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), amino acids are substituted or deleted so that it has at least one Cys at positions 102 to 106 but does not have Cys at position 107.

(4) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), at least one amino acid at positions 1 to 106 is deleted.

(5) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), at least one amino acid at positions 102 to 106 is deleted.

(6) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), the amino acid at position 105 is deleted.

(7) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), the amino acid at position 106 is deleted.

(8) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), Cys is substituted for at least one amino acid at positions 102 to 106.

(9) In a human κ chain constant region (the amino acid sequence of SEQ ID NO: 32), mouse κ chain constant region (the amino acid sequence of SEQ ID NO: 40), or rat κ chain constant region (the amino acid sequence of SEQ ID NO: 41), Cys is substituted for at least one amino acid at positions 102 to 106, and Cys at position 107 is deleted or substituted with another amino acid.

(10) In a human κ chain constant region (the amino acid sequence of SEQ ID NO: 37) or rabbit κ chain constant region (the amino acid sequence of SEQ ID NO: 42), amino acids are substituted or deleted so that it has at least one Cys at positions 99 to 103.

(11) In a human λ chain constant region (the amino acid sequence of SEQ ID NO: 37) or rabbit κ chain constant region (the amino acid sequence of SEQ ID NO: 42), amino acids are substituted or deleted so that it does not have Cys at position 104.

(12) In a human λ chain constant region (the amino acid sequence of SEQ ID NO: 37) or rabbit κ chain constant region (the amino acid sequence of SEQ ID NO: 42), amino acids are substituted or deleted so that it has at least one Cys at positions 99 to 103 but does not have Cys at position 104.

(13) In a human λ chain constant region (the amino acid sequence of SEQ ID NO: 37) or rabbit κ chain constant region (the amino acid sequence of SEQ ID NO: 42), at least one amino acid at positions 1 to 103 is deleted.

(14) In a human λ chain constant region (the amino acid sequence of SEQ ID NO: 37) or rabbit κ chain constant region (the amino acid sequence of SEQ ID NO: 42), at least one amino acid at positions 99 to 103 is deleted.

(15) In a human λ chain constant region (the amino acid sequence of SEQ ID NO: 37) or rabbit κ chain constant region (the amino acid sequence of SEQ ID NO: 42), the amino acid at position 102 is deleted.

(16) In a human λ chain constant region (the amino acid sequence of SEQ ID NO: 37) or rabbit κ chain constant region (the amino acid sequence of SEQ ID NO: 42), the amino acid at position 103 is deleted.

(17) In a human λ chain constant region (the amino acid sequence of SEQ ID NO: 37) or rabbit κ chain constant region (the amino acid sequence of SEQ ID NO: 42), Cys is substituted for at least one amino acid at positions 99 to 103.

(18) In a human λ chain constant region (the amino acid sequence of SEQ ID NO: 37) or rabbit κ chain constant region (the amino acid sequence of SEQ ID NO: 42), Cys is substituted for at least one amino acid at positions 99 to 103, and Cys at position 104 is deleted or substituted with another amino acid.

(19) In a rabbit κ chain constant region (the amino acid sequence of SEQ ID NO: 43), amino acids are substituted or deleted so that it has at least one Cys at portions 101 to 105.

(20) In a rabbit κ chain constant region (the amino acid sequence of SEQ ID NO: 43), amino acids are substituted or deleted so that it does not have Cys at position 106.

(21) In a rabbit κ chain constant region (the amino acid sequence of SEQ ID NO: 43), amino acids are substituted or deleted so that it has at least one Cys at positions 101 to 105 but does not have Cys at position 106.

(22) In a rabbit κ chain constant region (the amino acid sequence of SEQ ID NO: 43), at least one amino acid at positions 1 to 105 is deleted.

(23) In a rabbit κ chain constant region (the amino acid sequence of SEQ ID NO: 43), at least one amino acid at positions 101 to 105 is deleted.

(24) In a rabbit κ chain constant region (the amino acid sequence of SEQ ID NO: 43), the amino acid at position 104 is deleted.

(25) In a rabbit κ chain constant region (the amino acid sequence of SEQ ID NO: 43), the amino acid at position 105 is deleted.

(26) In a rabbit κ chain constant region (the amino acid sequence of SEQ ID NO: 43), Cys is substituted for at least one amino acid at positions 101 to 105.

(27) In a rabbit κ chain constant region (the amino acid sequence of SEQ ID NO: 43), Cys is substituted for at least one amino acid at positions 101 to 105, and Cys at position 106 is deleted or substituted with another amino acid.

Furthermore, the present invention provides methods for producing antibodies, which comprise the step of culturing host cells that comprise a vector introduced with a polynucleotide encoding an antibody heavy chain comprising the heavy chain constant region with the amino acid alterations of the present invention and/or a polynucleotide encoding an antibody light chain comprising the light chain constant region with the amino acid alterations of the present invention.

More specifically, the present invention provides methods for producing antibodies that comprise a heavy chain constant region with the amino acid alterations of the present invention and/or a light chain constant region with the amino acid alterations of the present invention, which comprise the steps of:

(a) culturing host cells that comprise a vector introduced with a polynucleotide encoding an antibody heavy chain comprising the heavy chain constant region with the amino acid alterations of the present invention and/or a polynucleotide encoding an antibody light chain comprising the light chain constant region with the amino acid alterations of the present invention; and (b) collecting the antibody heavy chain and/or light chain encoded by the gene.

Such amino acid alterations of the heavy chain constant region include the amino acid substitutions or deletions described above in (1) to (4), but are not limited thereto.

Such amino acid alterations of the light chain constant region include the amino acid substitutions or deletions described above (1) to (27), but are not limited thereto.

In the methods of the present invention for producing antibodies, first, the following DNAs are expressed: a DNA encoding an antibody heavy chain in which one or more amino acid residues in the constant region have been deleted or substituted with amino acids of interest, and/or a DNA encoding an antibody light chain in which one or more amino acid residues in the constant region have been deleted or substituted with amino acids of interest. A DNA encoding a heavy chain in which one or more amino acid residues in the constant region are deleted or substituted with amino acids of interest and/or a DNA encoding a light chain in which one or more amino acid residues in the constant region are deleted or substituted with amino acids of interest can be prepared, for example, by obtaining a DNA encoding the constant region of a wild type heavy chain and/or light chain, and introducing an appropriate substitution so that a codon encoding a particular amino acid in the constant region encodes an amino acid of interest.

Alternatively, a DNA encoding a heavy chain in which one or more amino acid residues in the constant region are deleted or substituted with amino acids of interest and/or a DNA encoding a light chain in which one or more amino acid residues in the constant region are deleted or substituted with amino acids of interest can also be prepared by designing and then chemically synthesizing a DNA encoding a protein in which one or more amino acid residues in the constant region of the wild type heavy chain are deleted or substituted with amino acids of interest.

The types of amino acid substitution and deletion include the substitutions and deletions described herein, but are not limited thereto.

Alternatively, a DNA encoding a heavy chain in which one or more amino acid residues in the constant region are deleted or substituted with amino acids of interest and/or a DNA encoding a light chain in which one or more amino acid residues in the constant region are deleted or substituted with amino acids of interest can also be prepared as a combination of partial DNAs. Such combinations of partial DNAs include, for example, the combination of a DNA encoding a variable region and a DNA encoding a constant region, and the combination of a DNA encoding an Fab region and a DNA encoding an Fc region, but are not limited thereto.

Methods for expressing the above-described DNAs include the methods described below. For example, a heavy chain expression vector is constructed by inserting a DNA encoding a heavy chain variable region into an expression vector along with a DNA encoding a heavy chain constant region. Likewise, a light chain expression vector is constructed by inserting a DNA encoding a light chain variable region into an expression vector along with a DNA encoding a light chain constant region. Alternatively, these heavy and light chain genes may be inserted into a single vector. Expression vectors include, for example, SV40 virus-based vectors, EB virus-based vectors, and BPV (papilloma virus)-based vectors, but are not limited thereto.

Host cells are co-transformed with an antibody expression vector constructed by the methods described above. Such host cells include the above-described cells such as Chinese hamster ovary (CHO) cells as well as microorganisms such as *E. coli*, yeast, and *Bacillus subtilis*, and plants and animals (Nature Biotechnology (2007) 25: 563-565; Nature Biotechnology (1998) 16: 773-777; Biochemical and Biophysical Research Communications (1999) 255: 444-450; Nature Biotechnology (2005) 23: 1159-1169; Journal of Virology (2001) 75: 2803-2809; Biochemical and Biophysical Research Communications (2003) 308: 94-100). Such host cells also include human embryonic kinder cancer cell-derived HEK298H cells. The transformation can be preferably achieved by using electroporation, the lipofectin method (R. W. Malone et al., Proc. Natl. Acad. Sci. USA (1989) 86: 6077; P. L. Felgner et al., Proc. Natl. Acad. Sci. USA (1987) 84: 7413), calcium phosphate method (F. L. Graham & A. J. van der Eb, Virology (1973) 52: 456-467), DEAE-Dextran method, and the like.

In the next step of antibody production, the expression products are collected. The expression products can be collected, for example, by culturing the transformants and then separating and purifying the antibody from the transformed cells or culture media. Separation and purification of antibodies can be achieved by an appropriate combination of methods such as centrifugation, ammonium sulfate fractionation, salting out, ultrafiltration, columns of 1q, FcRn, Protein A, and Protein G, affinity chromatography, ion exchange chromatography, and gel filtration chromatography.

The present invention provides antibodies produced as described above. More specifically, the present invention relates to antibodies that can be produced by the following steps:

(a) expressing in host cells, DNAs encoding an antibody heavy chain which comprises variable and constant regions, and a light chain; and (b) collecting the antibodies expressed in (a).

A characteristic of the above-mentioned method is that the amino acid sequences of the constant regions of heavy and light chains are the above-mentioned constant regions provided by the present invention. In a preferred embodiment of the present invention, the heavy chain constant region consists of, for example, the amino acid sequence of SEQ ID NOs: 24 and 26 to 31. Linking a DNA consisting of the nucleotide sequence encoding this amino acid sequence with a DNA encoding the heavy chain variable region can produce a DNA encoding the antibody heavy chain. Meanwhile, the light chain constant region consists of, for example, the amino acid sequence of SEQ ID NOs: 32 to 34 and 37 to 39. Linking a DNA consisting of the nucleotide sequence encoding this amino acid sequence with a DNA encoding the light chain variable region can produce a DNA encoding the antibody light chain.

As described above, the variable regions that constitute the antibodies of the present invention may recognize any antigen. The variable regions that constitute the antibodies of the present invention are not particularly limited, and include, for example, those described below.

For an antibody that has IL6 receptor-neutralizing activity, the heavy-chain variable region may be, for example, variable regions having the CDR1, CDR2, and CDR3 of the humanized antibody heavy chain comprising the amino acid sequence of SEQ ID NO: 5. Meanwhile, the light-chain variable region may be variable regions having the CDR1, CDR2, and CDR3 of the humanized antibody light chain comprising the amino acid sequence of SEQ ID NO: 2.

For an antibody that has IL31 receptor-neutralizing activity, the heavy-chain variable region may be, for example, variable regions having the CDR1, CDR2, and CDR3 of the humanized antibody heavy chain comprising the amino acid sequence of SEQ ID NO: 13. Meanwhile, the light-chain variable region may be variable regions having the CDR1, CDR2, and CDR3 of the humanized antibody light chain comprising the amino acid sequence of SEQ ID NO: 12.

For an antibody that has RANKL-neutralizing activity, the heavy-chain variable region may be variable regions having the CDR1, CDR2, and CDR3 of the humanized antibody heavy chain comprising the amino acid sequence of SEQ ID NO: 17. Meanwhile, the light-chain variable region may be variable regions having the CDR1, CDR2, and CDR3 of the humanized antibody light chain comprising the amino acid sequence of SEQ ID NO: 16.

The amino acid sequences that constitute heavy chain and light chain variable regions may have one or more amino acid residue alterations and/or modifications, as long as they retain antigen-binding activity. In the present invention, when altering antibody variable regions, it is preferable to conserve the amino acid sequences of CDRs. The antigen-binding activity of the variable regions can be maintained by conserving the amino acid sequences of CDRs. The acceptable number of altered amino acid residues in a variable region is generally one to ten, for example, one to five, and preferably one or two amino acids.

For example, the modification of the N-terminal glutamine of a variable region into pyroglutamic acid by pyroglutamylation is a modification well known to those skilled in the art. Thus, when the heavy-chain N terminus is glutamine, the antibodies of the present invention comprise the variable regions in which the glutamine is modified to pyroglutamic acid.

The alterations of the present invention include substitutions, deletions, additions, and/or insertions of the above-described amino acids, and combinations thereof.

Furthermore, the present invention provides genes encoding antibody constant regions comprising the amino acid alterations of the present invention. Such genes encoding the antibody constant regions of the present invention may be any gene such as DNA or RNA.

The present invention also provides vectors carrying the genes. The type of vector can be appropriately selected by those skilled in the art depending on the host cells to be introduced with the vector. The vectors include, for example, those described above.

Furthermore, the present invention relates to host cells transformed with the vectors. Appropriate host cells can be selected by those skilled in the art. The host cells include, for example, those described above.

The present invention also relates to methods for producing the constant regions of the present invention, which comprise the steps of culturing the host cells and collecting the expressed constant regions of the present invention.

<Improvement of Antibody Function by Amino Acid Alterations of Heavy Chain Constant Region>

Furthermore, the present invention also relates to methods for improving antibody functions, which comprise the step of altering amino acids in the human IgG2 constant region of SEQ ID NO: 24. The present invention also relates to antibodies produced by methods comprising the above-described step. The improvement of antibody functions includes improvement of antibody stability, reduction of immunogenicity, and improvement of pharmacokinetics, but is not limited thereto. The methods of the present invention comprise the steps of:

(a) substituting another amino acid for Cys at position 14 (position 131 (EU numbering)) in SEQ ID NO: 24;
(b) substituting another amino acid for Arg at position 16 (position 133 (EU numbering)) in SEQ ID NO: 24;
(c) substituting another amino acid for Cys at position 103 (position 220 (EU numbering)) in SEQ ID NO: 24;
(d) substituting another amino acid for Glu at position 20 (position 137 (EU numbering)) in SEQ ID NO: 24;
(e) substituting another amino acid for Ser at position 21 (position 138 (EU numbering)) in SEQ ID NO: 24;
(f) substituting another amino acid for His at position 147 (position 268 (EU numbering)) in SEQ ID NO: 24;
(g) substituting another amino acid for Arg at position 234 (position 355 (EU numbering)) in SEQ ID NO: 24; and
(h) substituting another amino acid for Gln at position 298 (position 419 (EU numbering)) in SEQ ID NO: 24.

The amino acids after substitution are not particularly limited; however,
Cys at position 14 is preferably substituted with Ser;
Arg at position 16 is preferably substituted with Lys;
Cys at position 103 is preferably substituted with Ser;
Glu at position 20 is preferably substituted with Gly;
Ser at position 21 is preferably substituted with Gly;
His at position 147 is preferably substituted with Gln;
Arg at position 234 is preferably substituted with Gln; and
Gln at position 298 is preferably substituted with Glu.

The methods of the present invention may additionally comprise the step of altering (substituting, deleting, adding, and/or inserting) other amino acids, modifying amino acids, and such, as long as they comprise the steps described above. The methods for altering or modifying amino acids are not particularly limited, and include, for example, the above-described site-specific mutagenesis and the methods described in the Examples herein.

The methods of the present invention may also comprise, in addition to the above-described steps, the step of deleting Gly at position 325 (position 446 (EU numbering)) and Lys at position 326 (position 447 (EU numbering)) to reduce the C-terminal heterogeneity.

Furthermore, the present invention relates to methods for improving antibody functions, which comprise the step of altering amino acids of the human IgG2 constant region of SEQ ID NO: 24. The present invention also relates to antibodies produced by methods comprising the step. Such improvement of antibody functions includes, but is not limited to, improvement of antibody stability, reduction of immunogenicity, improvement of safety, and improvement of pharmacokinetics. The methods of the present invention comprise the steps of:

(a) substituting another amino acid for Cys at position 14 (position 131 (EU numbering)) in SEQ ID NO: 24;
(b) substituting another amino acid for Arg at position 16 (position 133 (EU numbering)) in SEQ ID NO: 24;
(c) substituting another amino acid for Cys at position 103 (position 220 (EU numbering)) in SEQ ID NO: 24;
(d) substituting another amino acid for Glu at position 20 (position 137 (EU numbering)) in SEQ ID NO: 24;
(e) substituting another amino acid for Ser at position 21 (position 138 (EU numbering)) in SEQ ID NO: 24;
(f) substituting another amino acid for His at position 147 (position 268 (EU numbering)) in SEQ ID NO: 24;
(g) substituting another amino acid for Arg at position 234 (position 355 (EU numbering)) in SEQ ID NO: 24;
(h) substituting another amino acid for Gln at position 298 (position 419 (EU numbering)) in SEQ ID NO: 24;
(i) substituting another amino acid for Ala at position 209 (position 330 (EU numbering)) in SEQ ID NO: 24;
(j) substituting another amino acid for Pro at position 210 (position 331 (EU numbering)) in SEQ ID NO: 24; and
(k) substituting another amino acid for Thr at position 218 (position 339 (EU numbering)) in SEQ ID NO: 24.

The amino acids after substitution are not particularly limited; however,
Cys at position 14 is preferably substituted with Ser;
Arg at position 16 is preferably substituted with Lys;
Cys at position 103 is preferably substituted with Ser;
Glu at position 20 is preferably substituted with Gly;
Ser at position 21 is preferably substituted with Gly;
His at position 147 is preferably substituted with Gln;
Arg at position 234 is preferably substituted with Gln;
Gln at position 298 is preferably substituted with Glu;
Ala at position 209 is preferably substituted with Ser;
Pro at position 210 is preferably substituted with Ser; and
Thr at position 218 is preferably substituted with Ala.

The methods of the present invention may additionally comprise the step of altering (substituting, deleting, adding, and/or inserting) other amino acids, modifying amino acids, and such, as long as they comprise the above-described steps. The methods for altering or modifying amino acids are not particularly limited, and include, for example, the above-described site-specific mutagenesis and the methods described in the Examples herein.

The methods of the present invention may also comprise, in addition to the above-described steps, the step of deleting Gly at position 325 (position 446 (EU numbering)) and Lys at position 326 (position 447 (EU numbering)) to reduce the C-terminal heterogeneity.

Furthermore, the present invention relates to methods for improving the blood kinetics (pharmacokinetics) of an antibody by controlling (or changing) the disulfide bond pattern in antibody constant regions. The antibody constant regions are not particularly limited; however, it is preferable to control the pattern of disulfide bonds between an antibody light chain constant region (κ chain constant region or λ chain constant region) and IgG2 constant region.

Specifically, the present invention relates to methods for improving pharmacokinetics of an antibody, which comprise the step of allowing specific formation of a disulfide bond between Cys in the light chain C-terminal region and Cys at position 219 (EU numbering) in the heavy-chain constant region.

In the above-described step, it is preferable to avoid formation of an additional disulfide bond between Cys in the light chain C-terminal region and Cys at position 220 (EU numbering) in the heavy-chain constant region.

In the methods of the present invention, it is not necessary that every antibody forms a disulfide bond between Cys in the light chain C-terminal region and Cys at position 219 (EU numbering) in the heavy-chain constant region. For example, it is acceptable that 80% or more, preferably 90% or more, more preferably 95% or more, and still more preferably 99% or more of the antibody forms a disulfide bond between Cys in the light chain C-terminal region and Cys at position 219 (EU numbering) in the heavy-chain constant region.

The step of allowing formation of a disulfide bond between Cys in the light chain C-terminal region and Cys at position 219 (EU numbering) in the heavy-chain constant region may be achieved by any method, for example, by substituting another amino acid for Cys at position 220 (EU numbering) in the heavy chain (position 103 in SEQ ID NO: 24). As a result of the substitution of another amino acid for Cys at position 220 (EU numbering) in the heavy chain, a disulfide bond is formed between Cys in the light chain C-terminal region and Cys at position 219 (EU numbering) in the heavy-chain constant region (position 102 in SEQ ID NO: 24), instead of between Cys in the light chain C-terminal region and Cys at position 220 (EU numbering) in the heavy-chain constant region.

In the present invention, not only Cys at position 220 (EU numbering) but also Cys at position 131 (EU numbering) may be substituted with another amino acid. The amino acids after substitution are not particularly limited, and include, for example, Ser.

Herein, for example, in the case of a human κ chain constant region, Cys in the light chain C-terminal region is typically Cys in the region of positions 102 to 106 (for example, positions 102 to 106 in the human κ chain constant region of SEQ ID NO: 32), preferably Cys in the region of positions 104 to 106. Alternatively, for example, in the case of a human λ chain constant region, the Cys is typically Cys in the region of positions 99 to 105 (for example, positions 99 to 105 in the human λ chain constant region of SEQ ID NO: 37), preferably Cys in the region of positions 102 to 104.

An IgG2 constant region used in the methods of the present invention may comprise one or more amino acid deletions, substitutions, additions, and/or insertions (for example, 20 amino acids or less, or 10 amino acids or less) in the amino acid sequence of SEQ ID NO: 24. An IgG2 constant region used in the methods of the present invention may comprise alterations specified by the description herein and combinations thereof.

Meanwhile, a human κ chain constant region used in the methods of the present invention may comprise one or more amino acid deletions, substitutions, additions, and/or insertions (for example, 20 amino acids or less, or 10 amino acids or less) in the amino acid sequence of SEQ ID NO: 32.

On the other hand, a human λ chain constant region used in the methods of the present invention may comprise one or more amino acid deletions, substitutions, additions, and/or insertions (for example, 20 amino acids or less, or 10 amino acids or less) in the amino acid sequence of SEQ ID NO: 37.

Furthermore, human κ and λ chain constant regions used in the methods of the present invention may comprise alterations specified by the description herein and combinations thereof.

Antibodies in which a disulfide bond between Cys in the light chain C-terminal region and Cys at position 219 (EU numbering) in the heavy-chain constant region has been formed are demonstrated to be superior in pharmacokinetics as compared to antibodies having a disulfide bond between Cys in the light chain C-terminal region and Cys at position 220 (EU numbering) in the heavy-chain constant region. Thus, the present invention provides antibodies with improved pharmacokinetics by allowing formation of a disulfide bond between Cys in the light chain C-terminal region and Cys at position 219 (EU numbering) in the heavy-chain constant region. The methods of the present invention are useful in producing antibodies that are superior in pharmacokinetics and excellent as pharmaceuticals.

<Functional Improvement of Antibodies by Altering Amino Acids in Light Chain Constant Regions>

Furthermore, the present invention relates to methods for reducing the heterogeneity of hinge region, which comprise the step of introducing at least one Cys at positions 102 to 106 into the human κ constant region of SEQ ID NO: 32, the mouse κ chain constant region of SEQ ID NO: 40, or the rat κ chain constant region of SEQ ID NO: 41. The present invention also relates to antibodies produced by methods comprising the above-described step.

Herein, "introducing at least one Cys at positions 102 to 106" means achieving the state where there is at least one Cys at positions 102 to 106 in a human κ chain constant region.

Furthermore, the present invention relates to methods for reducing the heterogeneity of hinge region, which comprise the step of removing (deleting) Cys at position 107 from the human κ constant region of SEQ ID NO: 32, the mouse κ chain constant region of SEQ ID NO: 40, or the rat κ chain constant region of SEQ ID NO: 41. The present invention also relates to antibodies produced by methods comprising the above-described step.

Herein, "removing Cys at position 107" means achieving the state where there is no Cys at position 107 in a human κ chain constant region.

Furthermore, the present invention relates to methods for reducing the heterogeneity of hinge region in the human κ constant region of SEQ ID NO: 32, the mouse κ chain constant region of SEQ ID NO: 40, or the rat κ chain constant region of SEQ ID NO: 41, which comprise the steps of:

(a) introducing at least one Cys at positions 102 to 106; and (b) removing (deleting) Cys at position 107.

The present invention also relates to antibodies produced by methods comprising the above-described steps.

In the present invention, the steps of introducing at least one Cys at positions 102 to 106 and the step of removing Cys at position 107 may be carried out in a single step.

The number of Cys to be introduced in the step of introducing at least one Cys at positions 102 to 106 is not particularly limited; however, the number is five or less, preferably three or less, more preferably two or one, and still more preferably one.

The position of Cys introduction is not particularly limited; however, the position is preferably 104, 105, or 106, more preferably 105 or 106, and particularly preferably 106.

Specifically, the step of introducing at least one Cys at positions 102 to 106 includes, for example, the steps described below. Such steps may be used in combination.

The step of inserting at least one Cys at positions 102 to 106.

The step of substituting Cys for at least one amino acid at positions 102 to 106.

The step of deleting one to five amino acids at positions 1 to 106.

Specifically, the step of removing Cys at position 107 includes, for example, the following steps.

The step of deleting Cys at position 107.

The step of substituting another amino acid for Cys at position 107.

The step of inserting another amino acid at position 107.

The step of relocating Cys from position 107 to another position by deleting at least one amino acid at positions 1 to 106.

In a preferred embodiment, the methods of the present invention (i.e., methods for reducing the heterogeneity of hinge region and methods for enhancing FcRn binding, which comprise the steps of:

(a) introducing at least one Cys at positions 102 to 106, and (b) deleting Cys at position 107 in the human κ constant region of SEQ ID NO: 32, mouse κ chain constant region of SEQ ID NO: 40, or rat κ chain constant region of SEQ ID NO: 41) include, for example, the step of deleting one to five amino acids at positions 1 to 106 from the human κ chain constant region. When one to five amino acids are deleted at positions 1 to 106 from the human κ chain constant region, Cys at position 107 is relocated to one of positions 102 to 106. Thus, the steps of introducing at least one Cys at positions 102 to 106 and deleting Cys at position 107 can be achieved simultaneously by this method.

The position of amino acid deletion is not particularly limited; however, the human κ chain constant region preferably comprises deletion of at least one amino acid at positions 102 to 106, more preferably deletion of the amino acid at position 105 or 106.

The number of deleted amino acids is not particularly limited; however, the number is typically one to five, preferably one to three, more preferably one or two, and still more preferably one.

Such preferred steps include, but are not limited to, for example, the following steps.

The step of deleting the amino acid at position 105.

The step of deleting the amino acid at position 106.

In another preferred embodiment, the methods of the present invention include methods comprising the steps of (a) substituting Cys for at least one amino acid at positions 102 to 106; and (b) deleting Cys at position 107 or substituting another amino acid for Cys at position 107.

The number of amino acids substituted with Cys is not particularly limited; however, the number is typically one to five, preferably one to three, more preferably one or two, and still more preferably one. The position of Cys substitution is not particularly limited; however, the position is preferably 105 or 106.

Specifically, in the case of a human κ chain constant region, such steps include, for example, the steps of (a) substituting Cys for Gly at position 105 or Glu at position 106; and (b) deleting Cys at position 107, or substituting another amino acid for Cys at position 107.

Alternatively, in the case of a mouse or rat κ chain constant region, such steps include the steps of:

(a) substituting Cys for Asn at position 105 or Glu at position 106; and (b) deleting Cys at position 107 or substituting another amino acid for Cys at position 107.

Furthermore, the present invention relates to methods for reducing the heterogeneity of hinge region, which comprise the step of introducing at least one Cys at positions 99 to 103 in the human λ constant region of SEQ ID NO: 37 or the rabbit κ chain constant region of SEQ ID NO: 42. The present invention also relates to antibodies produced by methods comprising the above-described steps.

Herein, "introducing at least one Cys at positions 99 to 103" means achieving the state where there is at least one Cys at positions 99 to 103 in the human λ chain constant region.

Furthermore, the present invention relates to methods for reducing the heterogeneity of hinge region, which comprise the step of removing (deleting) Cys at position 104 in the human λ constant region of SEQ ID NO: 37 or rabbit κ chain constant region of SEQ ID NO: 42. The present invention also relates to antibodies produced by methods comprising the above-described steps.

Herein, "removing Cys at position 104" means achieving the state where there is no Cys at position 104 in the human λ chain constant region.

Furthermore, the present invention relates to methods for reducing the heterogeneity of hinge region, which comprise the steps of (a) introducing at least one Cys at positions 99 to 103, and (b) removing Cys at position 104 in the human λ constant region of SEQ ID NO: 37 or rabbit κ chain constant region of SEQ ID NO: 42.

In the present invention, the steps of introducing at least one Cys at positions 99 to 103 and removing Cys at position 104 may be achieved in a single step.

The number of Cys introduced in the step of introducing at least one Cys at positions 99 to 103 is not particularly limited; however, the number is five or less, preferably three or less, more preferably two or one, and still more preferably one.

The position of Cys introduction is not particularly limited; however, the position is preferably 101, 102, or 103, more preferably 102 or 103, and particularly preferably 103.

Specifically, the step of introducing at least one Cys at positions 99 to 103 includes, for example, those described below. The steps described below may be used in combination.

The step of inserting at least one Cys at positions 99 to 103.

The step of substituting Cys for at least one amino acid at positions 99 to 103.

The step of deleting one to five amino acids at positions 1 to 103.

Specifically, the step of removing Cys at position 104 includes, but is not limited to, for example, those described below.

The step of deleting Cys at position 104.

The step of substituting another amino acid for Cys at position 104.

The step of inserting another amino acid at position 104.

The step of relocating Cys from position 105 to another position by deleting at least one amino acid at positions 1 to 103.

In a preferred embodiment, the methods of the present invention (i.e., methods for reducing the heterogeneity of hinge region, which comprise the steps of:

(a) introducing at least one Cys at positions 99 to 103, and (b) removing Cys at position 104 in the human λ constant region of SEQ ID NO: 37 or rabbit κ chain constant region of SEQ ID NO: 42) include, for example, methods comprising the step of deleting one to five amino acids at positions 1 to 103 in the human λ chain constant region. When one to five amino acids are deleted at positions 1 to 103 in the human κ chain constant region, Cys at position 104 is relocated to one of positions 99 to 103. Thus, the steps of introducing at least one Cys at positions 99 to 103 and deleting Cys at position 104 can be achieved simultaneously.

The position of amino acid deletion is not particularly limited; however, a human λ chain constant region preferably comprises deletion of at least one amino acid at positions 99 to 103, more preferably deletion of the amino acid at position 102 or 103.

The number of deleted amino acids is not particularly limited; however, the number is typically one to five, preferably one to three, more preferably one or two, and still more preferably one.

Such preferred steps include, but are not limited to, for example, those described below.

The step of deleting the amino acid at position 102.

The step of deleting the amino acid at position 103.

In another preferred embodiment, the methods of the present invention include methods comprising the steps of (a) substituting Cys for at least one amino acid at positions 99 to 103; and (b) deleting Cys at position 104 or substituting another amino acid for Cys at position 104.

The number of amino acids substituted with Cys is not particularly limited; however, the number is typically one to five, preferably one to three, more preferably one or two, and still more preferably one. The position of Cys substitution is not particularly limited; however, the position is preferably 102 or 103.

Specifically, in the case of a human λ chain constant region, the steps include, but are not limited to, for example, the steps of:

(a) substituting Cys for Thr at position 102 or Glu at position 103; and (b) deleting Cys at position 104, or substituting another amino acid for Cys at position 104.

Alternatively, in the rabbit κ chain constant region of SEQ ID NO: 42, the steps include, but are not limited to, the steps of:

(a) substituting Cys for Gly at position 102 or Asp at position 103; and (b) deleting Cys at position 104, or substituting another amino acid for Cys at position 104.

Furthermore, the present invention relates to methods for reducing the heterogeneity of hinge region, which comprise the step of introducing at least one Cys at positions 101 to 105 in the rabbit κ chain constant region of SEQ ID NO: 43. The present invention also relates to antibodies produced by methods comprising the above-described steps.

Herein, "introducing at least one Cys at positions 101 to 105" means achieving the state where there is at least one Cys at positions 101 to 105 in the rat κ chain constant region.

Furthermore, the present invention relates to methods for reducing the heterogeneity of hinge region, which comprise the step of removing (deleting) Cys at position 106 in the rabbit κ chain constant region of SEQ ID NO: 43. The present invention also relates to antibodies produced by methods comprising the above-described steps.

Herein, "removing Cys at position 106" means achieving the state where there is no Cys at position 106 in the rabbit κ chain constant region.

Furthermore, the present invention relates to methods for reducing the heterogeneity of hinge region, which comprise the steps of (a) introducing at least one Cys at positions 101 to 105, and (b) removing Cys at position 106 in the rabbit κ chain constant region of SEQ ID NO: 43.

In the present invention, the steps of introducing at least one Cys at positions 101 to 105 and removing Cys at position 106 may be achieved in a single step.

The number of Cys introduced in the step of introducing at least one Cys at positions 101 to 105 is not particularly limited; however, the number is five or less, preferably three or less, more preferably two or one, and still more preferably one.

The position of Cys introduction is not particularly limited; however, the position is preferably 103, 104, or 105, more preferably 104 or 105, and particularly preferably 105.

Specifically, the step of introducing at least one Cys at positions 101 to 105 includes, for example, those described below. The steps described below may be used in combination.

The step of inserting at least one Cys at positions 101 to 105.

The step of substituting Cys for at least one amino acid at positions 101 to 105.

The step of deleting one to five amino acids at positions 1 to 105.

Specifically, the step of removing Cys at position 106 includes, but is not limited to, for example, those described below.

The step of deleting Cys at position 106.

The step of substituting another amino acid for Cys at position 106.

The step of inserting another amino acid at position 106.

The step of relocating Cys from position 106 to another position by deleting at least one amino acid at positions 1 to 105.

In a preferred embodiment, the methods of the present invention (i.e., methods for reducing the heterogeneity of hinge region, which comprise the steps of:

(a) introducing at least one Cys at positions 101 to 105, and (b) removing Cys at position 106 in the rabbit κ chain constant region of SEQ ID NO: 43) include, for example, methods comprising the step of deleting one to five amino acids at positions 1 to 105 from the rabbit κ chain constant region. When one to five amino acids are deleted at positions 1 to 105, Cys at position 106 is relocated to one of positions 101 to 105. Thus, the steps of introducing at least one Cys at positions 101 to 105 and deleting Cys at position 106 can be achieved simultaneously.

The position of amino acid deletion is not particularly limited; however, a human κ chain constant region preferably comprises deletion of at least one amino acid at positions 101 to 105, more preferably deletion of the amino acid at position 104 or 105.

The number of deleted amino acids is not particularly limited; however, the number is typically one to five, preferably one to three, more preferably one or two, and still more preferably one.

Such preferred steps include, but are not limited to, for example, those described below.

The step of deleting the amino acid at position 104.

The step of deleting the amino acid at position 105.

In another preferred embodiment, the methods of the present invention include methods comprising the steps of (a) substituting Cys for at least one amino acid at positions 101 to 105; and (b) deleting Cys at position 106, or substituting another amino acid for Cys at position 106.

The number of amino acids substituted with Cys is not particularly limited; however, the number is typically one to five, preferably one to three, more preferably one or two, and still more preferably one. The position of Cys substitution is not particularly limited; however, the position is preferably 104 or 105.

Specifically, such steps include, but are not limited to, for example, the steps of.

(a) substituting Cys for Gly at position 104 or Asp at position 105; and (b) deleting Cys at position 106, or substituting another amino acid for Cys at position 106.

As long as the methods of the present invention comprise the above-described steps, they may additionally comprise other steps, for example, the step of altering (substituting, deleting, adding, and/or inserting) other amino acids or modifying amino acids.

<Pharmaceutical Compositions Comprising Antibodies>

The present invention provides pharmaceutical compositions comprising the antibodies or constant regions of the present invention.

The present invention also provides antibody pharmaceutical compositions in which the ratio of antibody having a disulfide bond between Cys in the light chain C-terminal region and Cys at position 219 (EU numbering) in the heavy chain constant region is 80% or more, preferably 90% or more, more preferably 95% or more, and still more preferably 99% or more.

The pharmaceutical compositions of the present invention can be formulated, in addition to the antibodies or constant regions, with pharmaceutically acceptable carriers by known methods. For example, the compositions can be used parenterally, when the antibodies are formulated in a sterile solution or suspension for injection using water or any other pharmaceutically acceptable liquid. For example, the compositions can be formulated by appropriately combining the antibodies with pharmaceutically acceptable carriers or media, specifically, sterile water or physiological saline, vegetable oils, emulsifiers, suspending agents, surfactants, stabilizers, flavoring agents, excipients, vehicles, preservatives, binding agents, and such, by mixing them at a unit dose and form required by generally accepted pharmaceutical implementations. The content of the active ingredient in such a formulation is adjusted so that an appropriate dose within the required range can be obtained.

Sterile compositions for injection can be formulated using vehicles such as distilled water for injection, according to standard protocols.

Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

The administration is preferably carried out parenterally, and specifically includes injection, intranasal administration, intrapulmonary administration, and percutaneous administration. For example, injections can be administered systemically or locally by intravenous injection, intramuscular injection, intraperitoneal injection, or subcutaneous injection.

Furthermore, the method of administration can be appropriately selected according to the age and symptoms of the patient. A single dose of the pharmaceutical composition containing an antibody or a polynucleotide encoding an antibody can be selected, for example, from the range of 0.0001 to 1,000 mg per kg of body weight. Alternatively, the dose may be, for example, in the range of 0.001 to 100,000 mg/patient. However, the dose is not limited to these values. The dose and method of administration vary depending on the patient's body weight, age, and symptoms, and can be appropriately selected by those skilled in the art.

As used herein, the three-letter and single-letter codes for respective amino acids are as follows:

Alanine: Ala (A)
Arginine: Arg (R)
Asparagine: Asn (N)
Aspartic acid: Asp (D)
Cysteine: Cys (C)
Glutamine: Gln (Q)
Glutamic acid: Glu (E)
Glycine: Gly (G)
Histidine: His (H)
Isoleucine: Ile (I)
Leucine: Leu (L)
Lysine: Lys (K)
Methionine: Met (M)
Phenylalanine: Phe (F)
Proline: Pro (P)
Serine: Ser (S)
Threonine: Thr (T)
Tryptophan: Trp (W)
Tyrosine: Tyr (Y)
Valine: Val (V)

All prior art documents cited herein are incorporated by reference in their entirety.

EXAMPLES

[Example 1] Improvement of C-Terminal Heterogeneities of IgG Molecules

Construction of an Expression Vector for H-Chain C-Terminal ΔGK Antibody

Heterogeneities of the C-terminal sequence of the IgG antibody H chain that have been reported are deletion of the C-terminal amino acid lysine residue, and amidation of the C-terminal carboxyl group due to deletion of both of the two C-terminal amino acids, glycine and lysine residues (Anal Biochem. 2007 Jan. 1; 360(1): 75-83). In TOCILIZUMAB which is an anti-IL-6 receptor antibody, the main component is a sequence in which the C-terminal amino acid lysine present on the nucleotide sequence is deleted by post-translational modification, but an accessory component with remnant lysine and an accessory component with an amidated C-terminal carboxyl group produced by deletion of both glycine and lysine are also present as heterogeneities. It is not easy to manufacture such an antibody as a pharmaceutical in a large scale, while maintaining differences of objective substance/related substance-related heterogeneity between productions, which will lead to increased cost. Thus, single substances are desirable as much as possible, and in developing antibodies as pharmaceuticals, such heterogeneities are desirably reduced. Therefore, in terms of development as pharmaceuticals, absence of heterogeneities of the H-chain C terminal is desirable.

Thus, the C-terminal amino acids were altered to reduce the C-terminal heterogeneity. Specifically, the present inventors altered the nucleotide sequence of wild type IgG1 to delete the C-terminal lysine and glycine from the H-chain constant region of the IgG1, and assessed whether the amidation of the C-terminal amino group due to deletion of the two C-terminal amino acids glycine and lysine could be suppressed.

According to the method of Reference Example 1, TOCILIZUMAB (hereinafter abbreviated as IL6R H0/L0-IgG1) consisting of H0-IgG1 (amino acid SEQ ID NO: 1) as an H chain and L0-k0 (amino acid SEQ ID NO: 2) as an L chain was prepared. Furthermore, the nucleotide sequence of the H chain encoding Lys at position 447 and/or Gly at position 446 (EU numbering) was converted into a stop codon. Thus, expression vectors for antibody H chain H0-IgG1AK (amino acid SEQ ID NO: 3) engineered to lack the C-terminal amino acid lysine (position 447 (EU numbering)) and antibody H chain H0-IgG1ΔGK (amino acid SEQ ID NO: 4) engineered to lack the two C-terminal amino acids glycine and lysine (positions 446 and 447 (EU numbering), respectively) were constructed.

IL6R H0-IgG1/L0-k0 consisting of H0-IgG1 (amino acid SEQ ID NO: 1) as the H chain and L0-k0 (amino acid SEQ ID NO: 2) as the L chain, IL6R H0-IgG1AK/L0-k0 consisting of H0-IgG1ΔK (amino acid SEQ ID NO: 3) as the H chain and L0-k0 (amino acid SEQ ID NO: 2) as the L chain, and IL6R H0-IgG1ΔGK/L0-k0 consisting of H0-IgG1ΔGK-k0 (amino acid SEQ ID NO: 4) as the H chain and L0-k0 (amino acid SEQ ID NO: 2) as the L chain were expressed and purified by the method described in Reference Example 1.

Cation Exchange Chromatographic Analysis of the H-Chain C-Terminal ΔGK Antibody

Heterogeneity of the purified antibodies was evaluated by performing cation exchange chromatography. ProPac™ WCX-10 high-performance liquid chromatography (HPLC) column, 4×250 mm (Dionex) was used for the column, 25 mmol/L MES/NaOH, pH 6.1 was used as mobile phase A, 25 mmol/L MES/NaOH, 250 mmol/L NaCl, pH 6.1 was used as mobile phase B, and the chromatography was performed using appropriate flow and gradient. The results of performing cation exchange chromatographic evaluations on the purified IL6R H0-IgG1/L0-k0, IL6R H0-IgG1ΔK/L0-k0, and IL6R H0-IgG1ΔGK/L0-k0 are shown in FIG. 1.

From the results, it was discovered that heterogeneity of the C-terminal amino acid can be decreased for the first time by deleting both the C-terminal lysine and glycine of the H-chain constant region, not only the C-terminal lysine of the H-chain constant region, from the nucleotide sequence. In the human antibody constant regions of IgG1, IgG2, and IgG4, the C-terminal sequence is lysine at position 447 and glycine at position 446 in the EU numbering (see Sequences of proteins of immunological interest, NIH Publication No. 91-3242) in all cases; therefore, the method of reducing C-terminal amino acid heterogeneity discovered in the present examination was considered to be applicable to the IgG2 constant region and IgG4 constant region, or their modified forms.

[Example 2] Novel Constant Regions with Reduced Heterogeneity, which Retain the Stability of Natural IgG2

Heterogeneity of Natural IgG1 and Natural IgG2

For antibody pharmaceuticals against cancer such as those that kill target cells with effector functions and such, IgG1 constant region (isotype) having effector function is preferred. However, for antibody pharmaceuticals that neutralize the functions of a target antigen or antibody pharmaceuticals that bind to target cells but do not kill them, binding to Fcγ receptors is not preferred.

As methods for decreasing the binding to Fcγ receptors, the method of changing the IgG antibody isotype from IgG1 to IgG2 or IgG4 has been considered (Ann Hematol. 1998 June; 76(6): 231-48), and from the viewpoint of binding to Fcγ receptor I and pharmacokinetics of each isotype, IgG2 was considered to be more desirable than IgG4 (Nat Biotechnol. 2007 December; 25(12): 1369-72). On the other hand, when developing antibodies into pharmaceuticals, physicochemical properties of the proteins, particularly homogeneity and stability are extremely important. The IgG2 isotype has been reported to have a very large degree of heterogeneity caused by disulfide bond linkage differences in the hinge region (J Biol Chem. 2008 Jun. 6; 283(23): 16194-205; J Biol Chem. 2008 Jun. 6; 283(23): 16206-15; Biochemistry 2008 Jul. 15; 47(28): 7496-508).

Accordingly, IL6R H0-IgG1/L0-k0 having the constant regions of natural IgG1 and IL6R H0-IgG2/L0-k0 having the constant regions of natural IgG2 were actually produced and heterogeneity evaluations were carried out for both of them. IL6R H0-IgG1/L0-k0 which was produced in Example 1 consisting of IL6R H0-IgG1 (amino acid SEQ ID NO: 1) as the H chain and IL6R L0-k0 (amino acid SEQ ID NO: 2) as the L chain and IL6R H0-IgG2/L0-k0 consisting of IL6R H0-IgG2 (amino acid SEQ ID NO: 5) as the H chain in which the H-chain constant region was converted into IgG2 and IL6R L0-k0 (amino acid SEQ ID NO: 2) as the L chain were expressed and purified by the method described in Reference Example 1.

Figure 2:
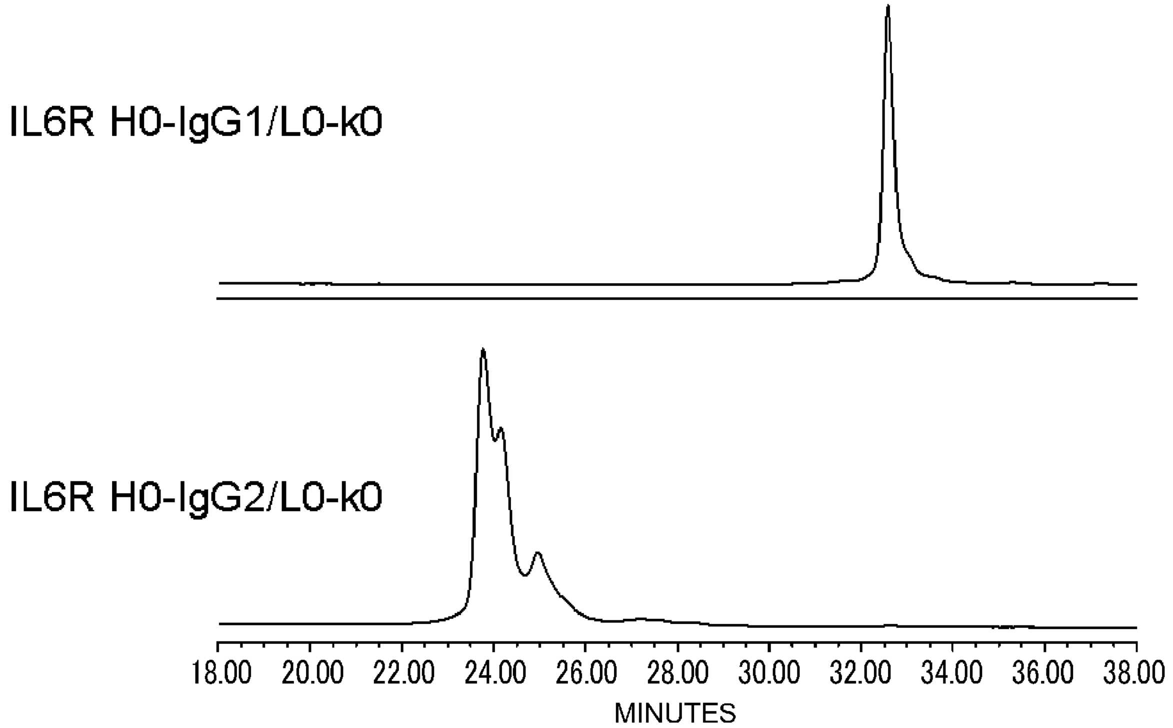
FIG. 2 shows in graphs the results of performing cation exchange chromatography on IL6R H0-IgG1/L0-k0 and IL6R H0-IgG2/L0-k0 to evaluate the heterogeneity derived from disulfide bonds. In the figure, the vertical axis shows absorbance at 280 nm and the horizontal axis shows elution time (minutes).

Evaluation by cation exchange chromatography was carried out as the method for evaluating the heterogeneity caused by disulfide bonds in IL6R H0-IgG1/L0-k0 having the constant regions of natural IgG1 and IL6R H0-IgG2/L0-k0 having the constant regions of natural IgG2. ProPac™ WCX-10 HPLC column (Dionex) was used for the column, 20 mM sodium acetate, pH 5.0 was used as mobile phase A, 20 mM sodium acetate, 1M NaCl, pH 5.0 was used as mobile phase B, and the chromatography was performed using appropriate flow and gradient. As a result, as shown in FIG. 2, IL6R H0-IgG2/L0-k0 having the constant regions of natural IgG2 showed multiple peaks and it was found to have markedly high heterogeneity compared to IL6R H0-IgG1/L0-k0 having the constant regions of natural IgG1 showing only almost single main peak.

Figure 3:
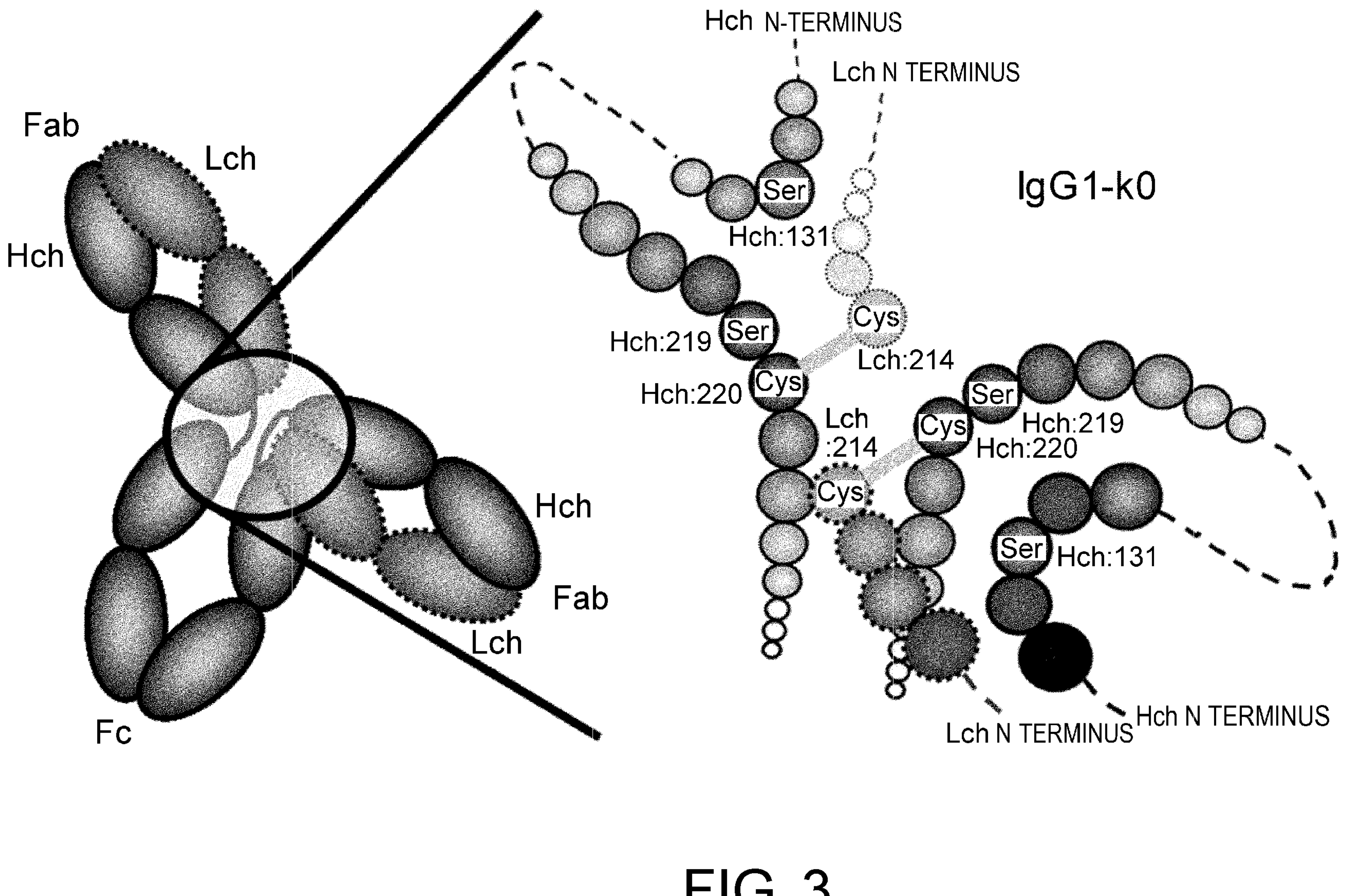
FIG. 3 shows in diagrams the IgG-type antibody and details of the structure around its hinge region (positioning of the heavy chain (H chain) and light chain (L chain) and disulfide bonds between them; detailed drawing represents IgG1-k0).
Figure 4:
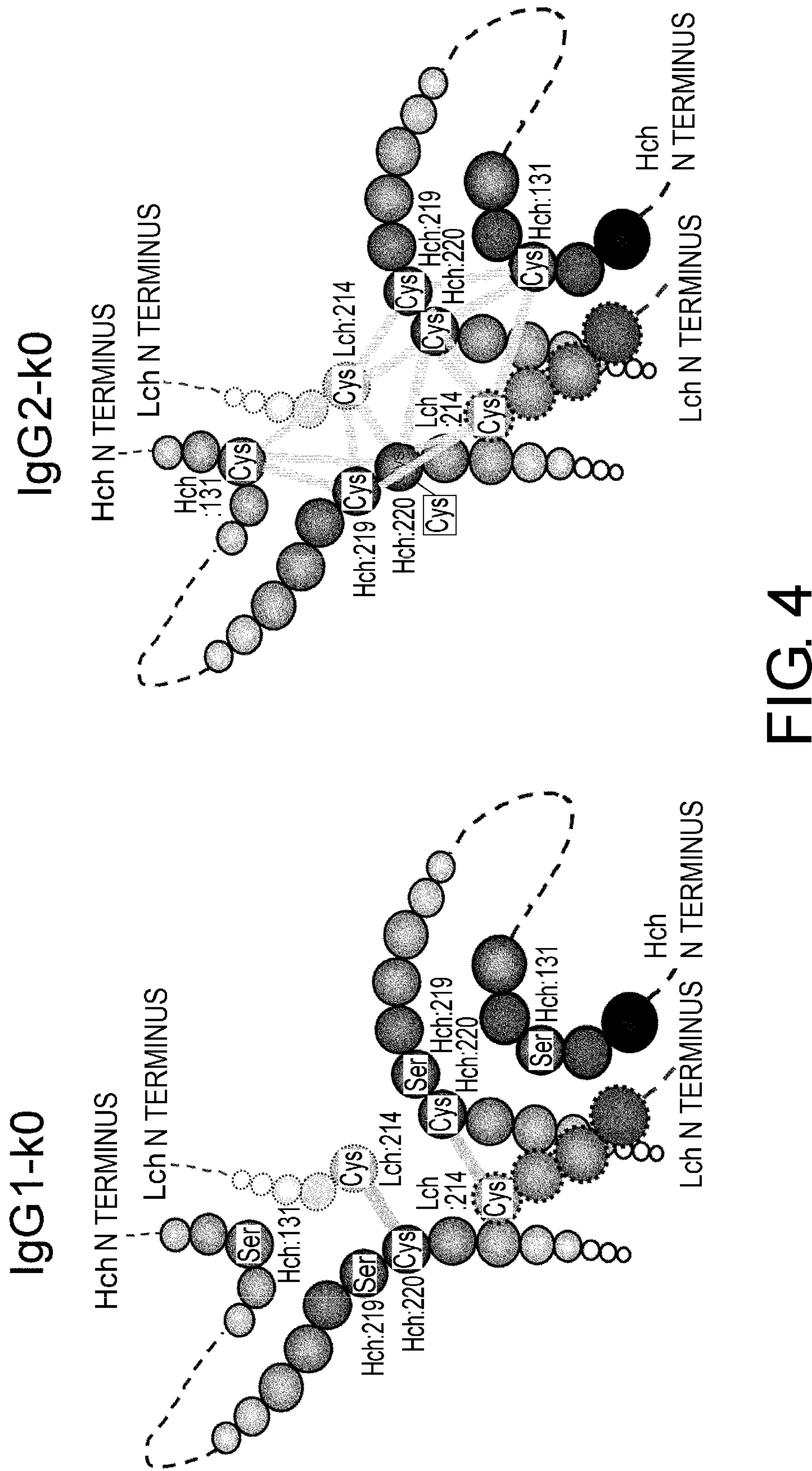
FIG. 4 shows in diagrams predicted disulfide bond patterns around the hinge region of the constant regions IgG1-k0 and IgG2-k0. Various conceivable disulfide bond patterns in IgG2-k0 are indicated by bold lines.

The details of the structure around the hinge region of an IgG-type antibody are shown in FIG. 3. In IgG antibodies, H and L chains (or two H chains) form disulfide bonds around the hinge region. This pattern of disulfide bonds differ depending on the isotypes of the IgG-type antibodies as indicated below. It is considered that since disulfide bonds in the hinge region of natural IgG1 have a single pattern such as that shown in FIG. 4, heterogeneity caused by disulfide bonds does not exist and it was eluted as a nearly single main peak in cation exchange chromatography. In contrast, as shown in FIG. 3, regarding the disulfide bonds in the hinge region of natural IgG2, natural IgG2 has two cysteines in the hinge region (positions 219 and 220 (EU numbering)), and cysteines exist adjacent to these two cysteines of the hinge region, which are cysteine at position 131 (EU numbering), present in the H-chain CH1 domain, cysteine at the L-chain C terminus, and two cysteines of the corresponding hinge region of the H chain of the dimerization partner. Therefore, around the hinge region of IgG2, there are a total of eight neighboring cysteines when an H2L2 assembly is formed. This leads to the presence of a variety of heterogeneity due to disulfide bond linkage differences in natural IgG2, and the heterogeneity is considered to be remarkably high.

It is not easy to manufacture as a pharmaceutical in large-scale while maintaining the differences of objective substance/related substance-related heterogeneity between productions (the differences originate from these disulfide bond linkage differences), and this leads to increased cost. Thus, single substances are desirable as much as possible. Therefore, in developing antibodies of the IgG2 isotype into pharmaceuticals, it is desirable to reduce heterogeneity derived from disulfide bonds without decreasing stability. In fact, it is reported in US 20060194280 (A1) that a variety of heterogeneous peaks derived from disulfide bonds were observed for natural IgG2 in ion exchange chromatographic analysis, and biological activities were also reported to be different among these peaks. As a method for unifying these heterogeneous peaks, US 20060194280 (A1) reports refolding in the purification steps, but since using these steps in the production will be costly and complicated, preferably, unifying the heterogeneous peaks by producing an IgG2 variant in which disulfide bonds will be formed in a single pattern by means of amino acid substitutions was considered desirable. However, to date, there has been no report on IgG2 variants that will form disulfide bonds in a single pattern, or IgG2 variants that have reduced heterogeneity due to disulfide bonds without having decreased stability.

Figure 5:
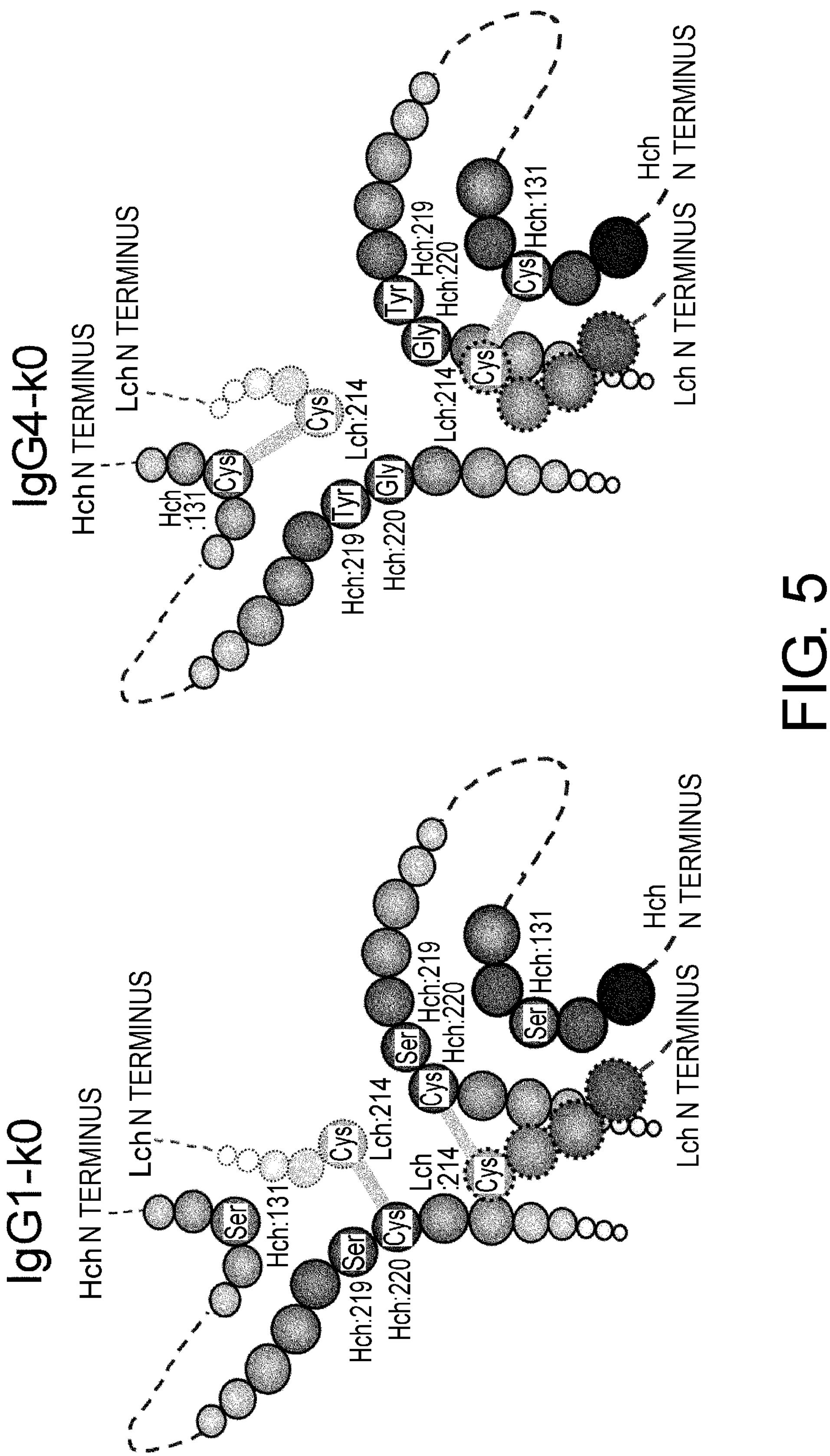
FIG. 5 shows in diagrams predicted disulfide bond patterns around the hinge region of the constant regions IgG1-k0 and IgG4-k0. Disulfide bond patterns linking H and L chains are different between IgG1-k0 and IgG4-k0.

Influence of the Disulfide Bond Patterns Between H Chain and L Chain on the Stability In natural IgG1, cysteine at position 220 (EU numbering) in the sequence of IgG1 H-chain constant region (amino acid SEQ ID NO: 23) bond to cysteine at position 214 (for the numbering system, see Sequences of proteins of immunological interest, NIH Publication No. 91-3242) in the L chain (Nat Biotechnol. 2007 December; 25(12): 1369-72; Anal Chem. 2008 Mar. 15; 80(6): 2001-9) by a disulfide bond. Meanwhile, in the natural IgG4, cysteine at position 131 (EU numbering) in the sequence of IgG4 H-chain constant region (amino acid SEQ ID NO: 25) bond to cysteine at position 214 (for the numbering system, see Sequences of proteins of immunological interest, NIH Publication No. 91-3242) by a disulfide bond in the L chain (Nat Biotechnol. 2007 December; 25(12): 1369-72; Protein Sci. 1997 February; 6(2): 407-15). It has been reported that as described above, the pattern of disulfide bonds between the H chain and L chain is different between natural IgG1 and IgG4. The disulfide bond patterns of the natural IgG1 and IgG4 are shown in FIG. 5. However, to date, there has been no report on the effect of the pattern of disulfide bonds between H chain and L chain on stability.

As prepared in Example 1, IL6R H0-IgG1/L0-k0 which consists of IL6R H0-IgG1 (amino acid SEQ ID NO: 1) as H chain and IL6R L0-k0 (amino acid SEQ ID NO: 2) as L chain, and IL6R H0-IgG4/L0-k0 which consists of IL6R H0-IgG4 (amino acid SEQ ID NO: 6) as an H-chain constant region resulting from IgG4 conversion and IL6R L0-k0 (amino acid SEQ ID NO: 2) as L chain, were expressed and purified by the method described in Reference Example 1.

To assess the stability, the midpoint of thermal denaturation (Tm value) was determined by differential scanning calorimetry (DSC) (N-DSCII, Calorimetry Science Corporation). The midpoint temperature of thermal denaturation (Tm value) is a stability indicator. Thus, higher thermal denaturation midpoints (Tm values) are preferable for producing stable preparations as pharmaceuticals (J Pharm Sci. 2008 April; 97(4): 1414-26). Purified IL6R H0-IgG1/L0-k0 and IL6R H0-IgG4/L0-k0 were dialyzed against a solution (pH 6.0) containing 20 mM sodium acetate and 150 mM NaCl using TOMY dialysis tubes. DSC measurements were carried out at a heating rate of 1° C./min in a range of 40 to 100° C., and at a protein concentration of about 0.1 mg/ml. The Tm values of the Fab domains (as listed in Table 1) are calculated based on the denaturation curves obtained by DSC. These data demonstrate that the Tm value of the IgG1 Fab domain is higher than that of the IgG4 Fab domain. The difference in the Tm value is speculated to be due to difference in the pattern of disulfide bonds between H chain and L chain. The thermal stability was demonstrated to be greatly reduced when the pattern of disulfide bonds between H chain and L chain is disulfide bond between cysteine at position 131 (EU numbering) in the H chain and cysteine at position 214 in the L chain (for the numbering system, see Sequences of proteins of immunological interest, NIH Publication No. 91-3242), as compared to disulfide bond between cysteine at position 220 (EU numbering) in the H chain and cysteine at position 214 (for the numbering system, see Sequences of proteins of immunological interest, NIH Publication No. 91-3242) in the L chain.

TABLE 1

| | Tm/° C. OF Fab |
|---|---|
| IL6R H0-IgG1/L0-k0 | 95° C. |
| IL6R H0-IgG4/L0-k0 | 88° C. |

Production of Various Types of Natural IgG2 Variants

Figure 6:
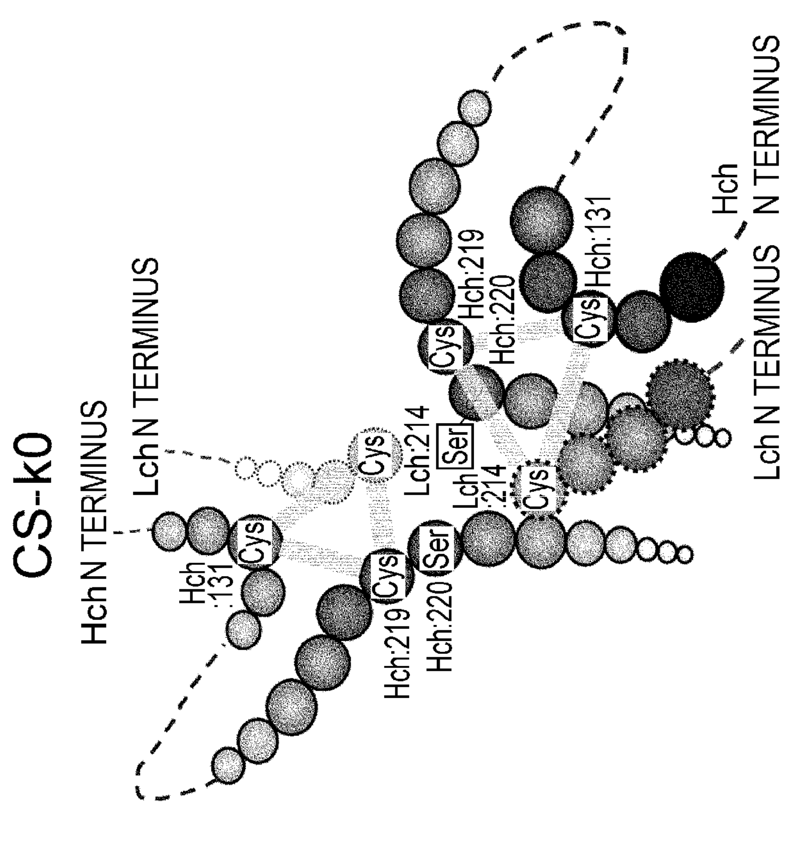
FIG. 6 shows in diagrams predicted disulfide bond patterns around the hinge region of the constant regions SC-k0 and CS-k0. Various conceivable disulfide bond patterns in SC-k0 and CS-k0 are indicated by bold lines.
Figure 6:
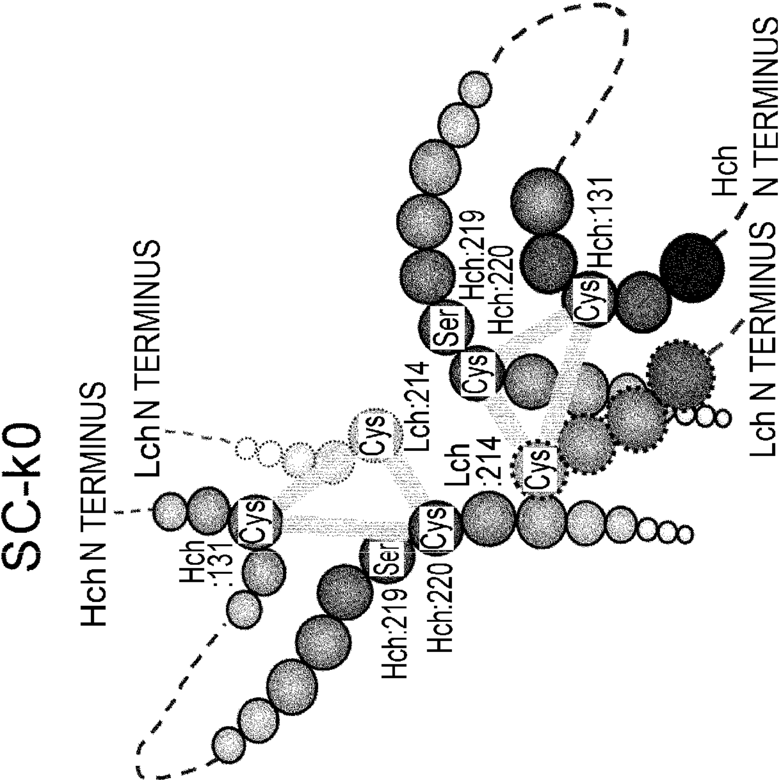

For methods for reducing the heterogeneity as a result of difference in disulfide bonds of natural IgG2, one can consider the method of substituting serine for cysteine only at position 219 (EU numbering) in the H-chain hinge region or method of substituting serine for cysteine only at position 220 (Biochemistry. 2008 Jul. 15; 47(28): 7496-508). Specifically, such H-chain constant regions include SC (SEQ ID NO: 26) and CS (SEQ ID NO: 27). SC is an H-chain constant region having substitution of serine for cysteine at position 219 (EU numbering) in the H-chain constant region sequence (amino acid SEQ ID NO: 24) of natural IgG2, while CS is an H-chain constant region having substitution of cysteine at position 220 (EU numbering). However, as shown in FIG. 6, disulfide bonds pattern of these H-chain constant regions of SC and CS are not a single but plural like natural IgG2. Such disulfide bonds also include the disulfide bond pattern where cysteine at position 131 (EU numbering) in the H chain is linked to cysteine at position 214 in the L chain (for the numbering system, see Sequences of proteins of immunological interest, NIH Publication No. 91-3242). This bond is unfavorable because it reduces stability.

Figure 7:
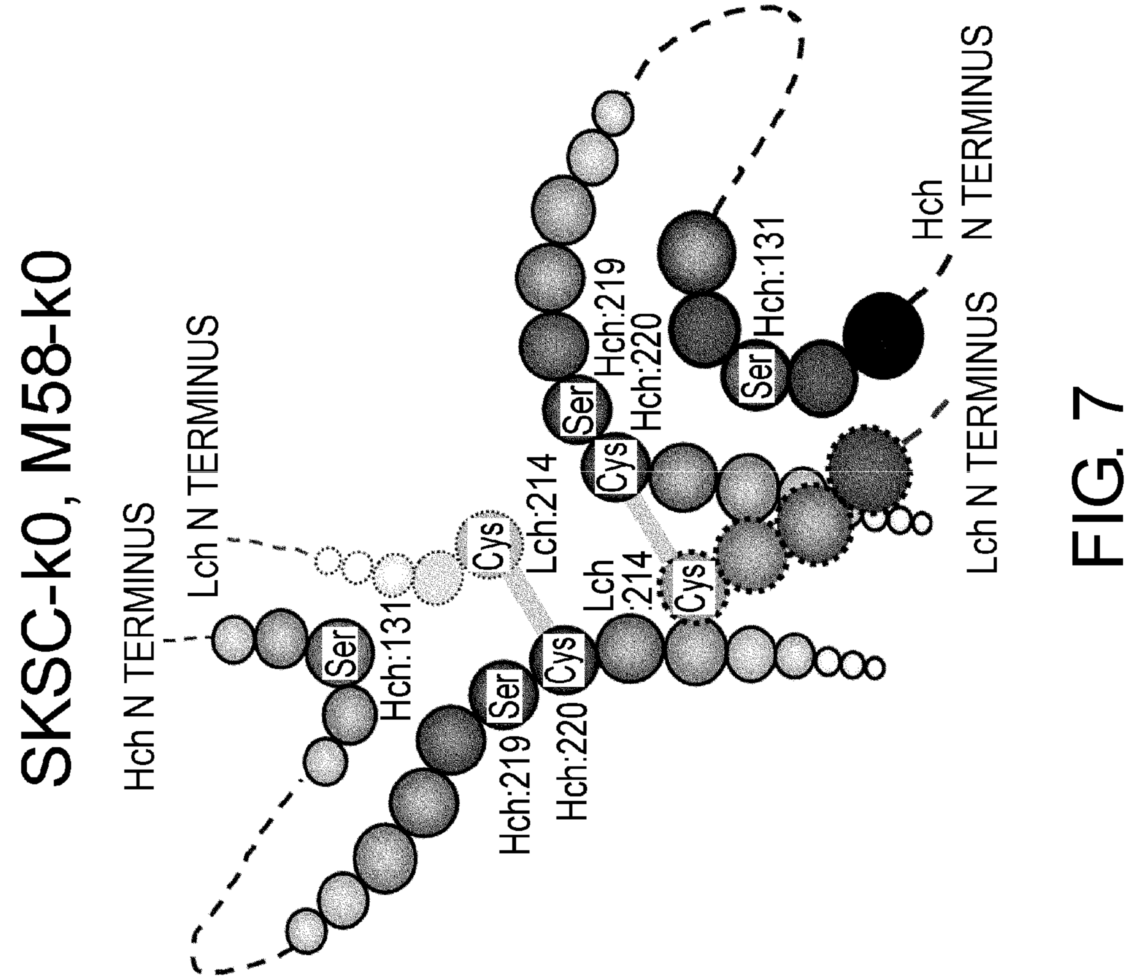
FIG. 7 shows in a diagram a predicted disulfide bond pattern around the hinge region of constant regions SKSC-k0 and M58-k0.

A possible H-chain constant region that consist of a single disulfide bond and do not reduce stability is an H-chain constant region SKSC (SEQ ID NO: 28), in which serine and lysine are substituted for cysteine at position 131 and arginine at position 133 (EU numbering) respectively, in the H chain SC (SEQ ID NO: 26). Another possible H-chain constant region is M58 (SEQ ID NO: 29) which has the following additional alterations: glycine was substituted for glutamic acid at position 137 (EU numbering) in the H chain; glycine was substituted for serine at position 138; glutamine was substituted for histidine at position 268; glutamine was substituted for arginine at position 355; and glutamic acid was substituted for glutamine at position 419 to reduce immunogenicity and improve pharmacokinetics, and the C-terminal lysine and glycine were removed in advance from the H-chain constant region by deletion from the nucleotide sequence to avoid C-terminal heterogeneity. As shown in FIG. 7, the H-chain constant regions SKSC and M58 are thought to form a single disulfide bond and do not reduce stability.

Then, expression vectors for IL6R H0-SC (amino acid SEQ ID NO: 7), IL6R H0-CS (amino acid SEQ ID NO: 8), IL6R H0-SKSC (amino acid SEQ ID NO: 9), and IL6R H0-M58 (amino acid SEQ ID NO: 10) were constructed by the method described in Reference Example 1. IL6R H0-IgG1/L0-k0 and IL6R H0-IgG2/L0-k0, each of which consists of the original H chain and IL6R L0-k0 (amino acid SEQ ID NO: 2) as L chain, and IL6R H0-SC/L0-k0, IL6R H0-CS/L0-k0, IL6R H0-SKSC/L0-k0, and IL6R H0-M58/L0-k0, which are variants derived from natural IgG2, were expressed and purified by the method described in Reference Example 1.

Analysis of Various Variants from Natural IgG2 by Cation Exchange Chromatography Various variants of natural IgG2 were assessed for their heterogeneity by the method described above using cation exchange chromatography. IL6R H0-IgG1/L0-k0 and IL6R H0-IgG2/L0-k0, and IL6R H0-SC/L0-k0, IL6R H0-CS/L0-k0, IL6R H0-SKSC/L0-k0, and IL6R H0-M58/L0-k0, which are the variants of natural IgG2, were assessed using cation exchange chromatography. The result is shown in FIG. 8.

Figure 8:
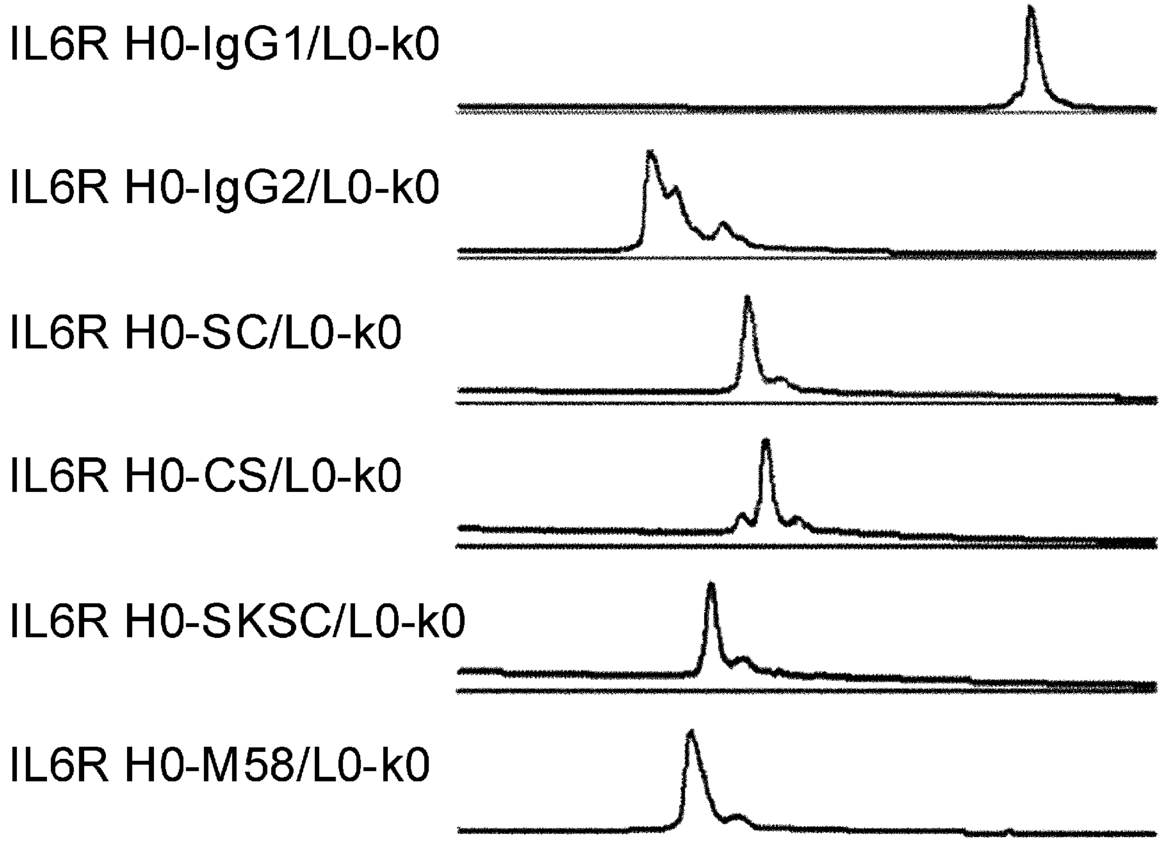
FIG. 8 shows in graphs the results of assessing the heterogeneity of IL6R H0-IgG1/L0-k0, IL6R H0-IgG2/L0-k0, IL6R H0-SC/L0-k0, IL6R H0-CS/L0-k0, IL6R H0-SKSC/L0-k0, and IL6R H0-M58/L0-k0 by cation exchange chromatography based on their disulfide bond differences. In these graphs, the vertical axis shows absorbance at 280 nm and the horizontal axis shows elution time (minutes).

As shown in FIG. 8, the result revealed that heterogeneity was increased when the H-chain constant region was converted from the IgG1 subtype into IgG2 subtype; however, heterogeneity was greatly reduced when the H-chain constant region was converted into SKSC or M58. On the other hand, when the H-chain constant region was converted into CS, the reduction of heterogeneity was insufficient. However, heterogeneity was reduced when the H-chain constant region was converted into SC and when the H-chain constant region was converted into SKSC.

DSC Analysis of Various Natural IgG2 Variants

Figure 9:
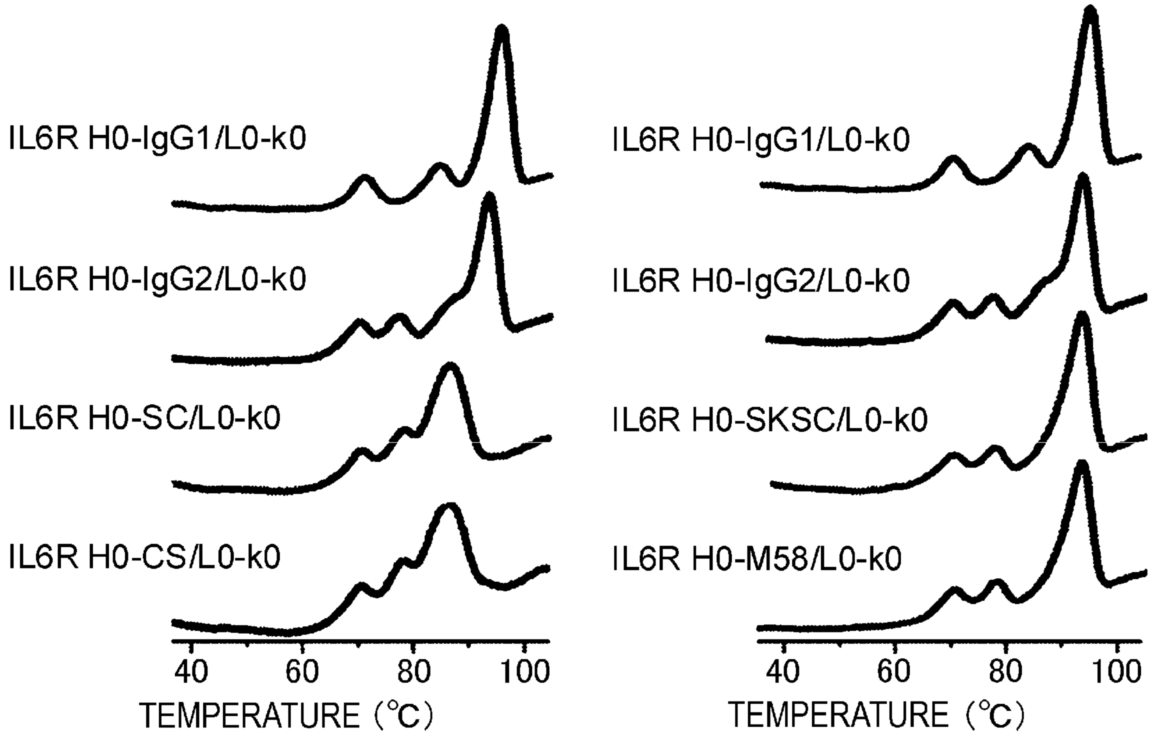
FIG. 9 shows denaturation curves determined by measuring IL6R H0-IgG1/L0-k0, IL6R H0-IgG2/L0-k0, IL6R H0-SC/L0-k0, IL6R H0-CS/L0-k0, IL6R H0-SKSC/L0-k0, and IL6R H0-M58/L0-k0 by differential scanning calorimetry (DSC).

To develop an antibody as pharmaceutical, it is generally desirable to have high stability in addition to low heterogeneity for preparing stable preparations. Thus, to assess the stability of IL6R H0-IgG1/L0-k0 and IL6R H0-IgG2/L0-k0, and IL6R H0-SC/L0-k0, IL6R H0-CS/L0-k0, IL6R H0-SKSC/L0-k0, and IL6R H0-M58/L0-k0, which are variants of natural IgG2, the midpoint of thermal denaturation (Tm value) was determined by differential scanning calorimetry (DSC) (VP-DSC, Microcal) in the same manner as described above. The purified antibodies were dialyzed against a solution (pH 6.0) containing 20 mM sodium acetate and 150 mM NaCl using TOMY dialysis tubes. DSC measurements were carried out at a heating rate of 1° C./min in a range of 40 to 100° C., and at a protein concentration of about 0.1 mg/ml. The denaturation curves obtained by DSC are shown in FIG. 9, while the Tm values for the Fab domains are listed in Table 2 below.

TABLE 2

| | Tm/° C. OF Fab |
|---|---|
| IL6R H0-IgG1/L0-k0 | 94.8° C. |
| IL6R H0-IgG2/L0-k0 | 93.9° C. |
| IL6R H0-SC/L0-k0 | 86.7° C. |
| IL6R H0-CS/L0-k0 | 86.4° C. |
| IL6R H0-SKSC/L0-k0 | 93.7° C. |
| IL6R H0-M58/L0-k0 | 93.7° C. |

IL6R H0-IgG1/L0-k0 and IL6R H0-IgG2/L0-k0WT-IgG1 exhibited almost the same Tm value for the Fab domain. The Tm values were about 94° C. (the Tm value of IgG2 was lower by about 1° C.). The Tm values of IL6R H0-SC/L0-k0 and IL6R H0-CS/L0-k0 were about 86° C. which was remarkably lower as compared to those of IL6R H0-IgG1/L0-k0 and IL6R H0-IgG2/L0-k0. Meanwhile, the Tm values of IL6R H0-SKSC/L0-k0 and IL6R H0-M58/L0-k0 were about 94° C. which was comparable to those of IL6R H0-IgG1/L0-k0 and IL6R H0-IgG2/L0-k0.

The stability of H-chain constant regions SC and CS was markedly lower as compared to IgG1 and IgG2. This suggests that SC and CS form disulfide bonds that reduce stability. As described above, the stability of the Fab domain is reduced when a disulfide bond is formed between cysteine at position 131 (EU numbering) in the H chain and cysteine at position 214 in the L chain (for the numbering system, see Sequences of proteins of immunological interest, NIH Publication No. 91-3242). The presence of molecular species having such disulfide bonds was speculated to be a cause of reduced stability of SC and CS. Thus, from the standpoint of stability, it is considered that the H-chain constant regions SKSC and M58 in which serine is substituted for cysteine at position 131 (EU numbering) in their H chains are superior as pharmaceuticals.

Furthermore, comparison of DSC denaturation curves revealed that the Fab domains of IL6R H0-IgG1/L0-k0, IL6R H0-SKSC/L0-k0, and IL6R H0-M58/L0-k0 each showed a single sharp denaturation peak. On the other hand, as compared to these, IL6R H0-SC/L0-k0 and IL6R H0-CS/L0-k0 have a broader denaturation peak for the Fab domain. IL6R H0-IgG2/L0-k0 showed a shoulder peak on the lower temperature side of the Fab domain denaturation peak. In general, the DSC denaturation peak is sharp when it contains only a single component. On the other hand, when there are a plurality of components with different Tm (i.e., heterogeneity), the denaturation peak is expected to be broader. Specifically, it is suggested that the heterogeneity detected in natural IgG2 is not sufficiently reduced in SC and CS, therefore the H-chain constant regions IgG2, SC, and CS contained a plurality of components. The finding described above suggests that not only cysteines at positions 219 and 220 (EU numbering) in the H-chain hinge region but also cysteine at position 131 (EU numbering) in the H-chain CH1 domain contributes to the heterogeneity of wild type IgG2, and it is necessary to alter not only cysteines in the hinge region but also cysteine in the CH1 domain to reduce the heterogeneity detected by DSC. Thus, from the standpoint of heterogeneity, the H-chain constant regions SKSC and M58 which have substitution of serine for cysteine at position 131 (EU numbering) in the H chain are concluded to be superior as pharmaceuticals.

As described above, SC and CS, which are H-chain constant regions having substitution of serine for cysteine only in the hinge region to reduce heterogeneity derived from the hinge region of IgG2, are assumed to be insufficient from the standpoint of both heterogeneity and stability. Thus, the present inventors demonstrated that while retaining a comparable stability to that of IgG2, the heterogeneity could be greatly reduced only when serine is substituted for cysteine in the hinge region as well as for cysteine at position 131 (EU numbering) in the H chain in the CH1 domain.

Heterogeneity-Improving Effect of Natural IgG2 Variant (M58-k0) on Various Antibodies IL31R H0-IgG1/L0-k0 (H-chain amino acid sequence/SEQ ID NO: 11; L-chain amino acid sequence/SEQ ID NO: 12), which is an anti-IL-31 receptor antibody, and RANKL H0-IgG1/L0-k0 (H-chain amino acid sequence/SEQ ID NO: 15; L-chain amino acid sequence/SEQ ID NO: 16), which is an anti-RANKL antibody, were used in addition to the anti-IL-6 receptor antibodies. The H-chain constant region of each antibody was converted from the IgG1 subtype into IgG2 subtype. The resulting antibodies were IL31R H0-IgG2/L0-k0 (H-chain amino acid sequence/SEQ ID NO: 13; L-chain amino acid sequence/SEQ ID NO: 12) and RANKL H0-IgG2/L0-k0 (H-chain amino acid sequence/SEQ ID NO: 17; L-chain amino acid sequence/SEQ ID NO: 16). The H-chain constant region was also converted from the IgG1 subtype into M58. The resulting antibodies were IL31R H0-M58/L0-k0 (H-chain amino acid sequence/SEQ ID NO: 14; L-chain amino acid sequence/SEQ ID NO: 12) and RANKL H0-M58/L0-k0 (H-chain amino acid sequence/SEQ ID NO: 18; L-chain amino acid sequence/SEQ ID NO: 16). Expression vectors were constructed to express these antibodies. The antibodies were expressed and purified by the method described in Reference Example 1.

Figure 10:
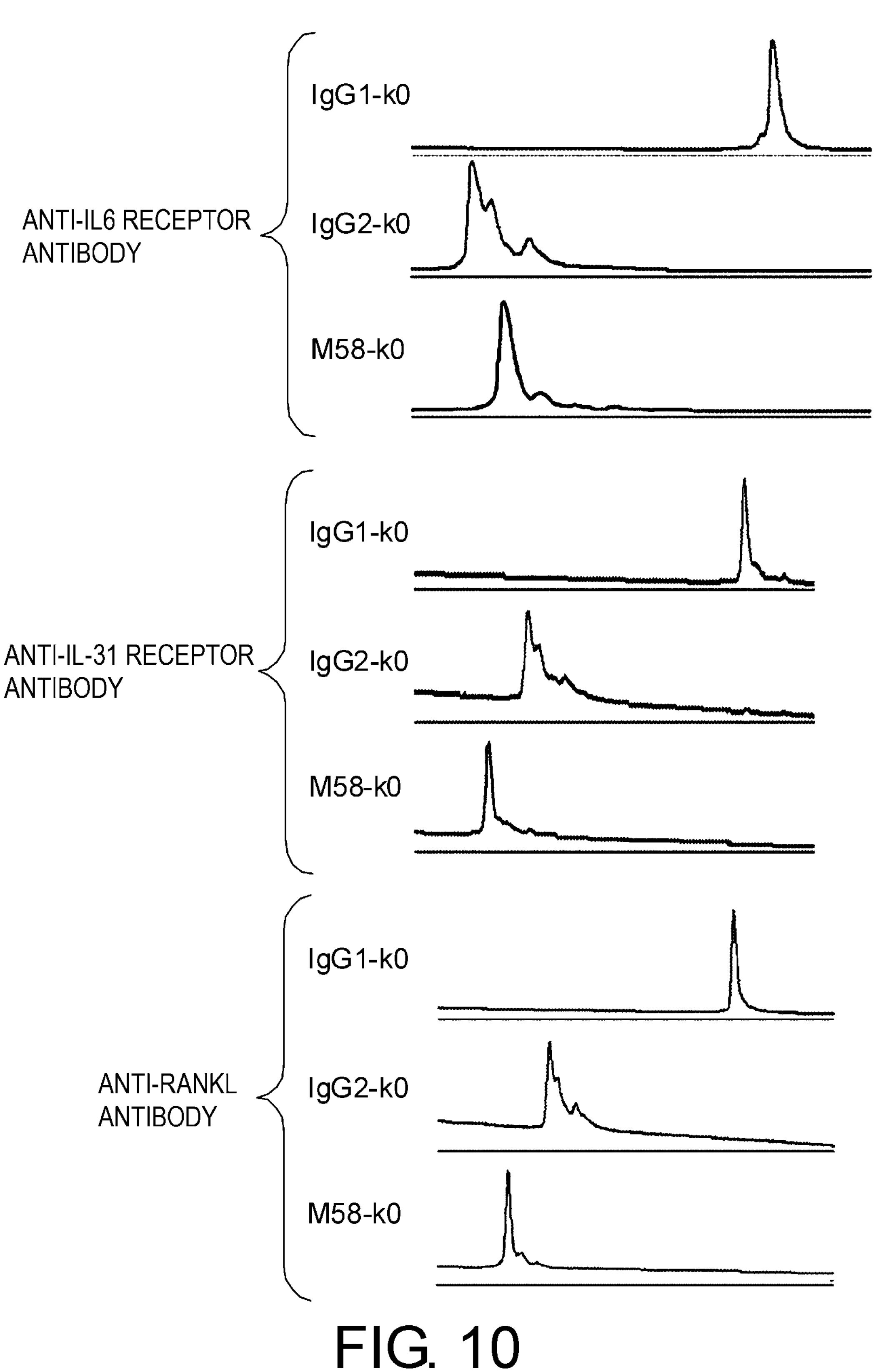
FIG. 10 shows in graphs that the heterogeneity is greatly improved in the anti-IL-6 receptor antibody, anti-IL-31 receptor antibody, and anti-RANKL antibody by converting their constant region from IgG2-k0 into M58-k0. In these graphs, the vertical axis shows absorbance at 280 nm and the horizontal axis shows elution time (minutes).

Heterogeneity was assessed by cation exchange chromatography (IEC) using the same method as described above. The results are shown in FIG. 10. As shown in FIG. 10, it was confirmed that heterogeneity was increased not only in the anti-IL-6 receptor antibodies but also in the anti-IL-31 receptor antibody and anti-RANKL antibody when the H-chain constant region was converted from the IgG1 subtype into IgG2 subtype, and that heterogeneity could be reduced in every antibody by converting the H-chain constant region from the IgG2 subtype into M58. The finding described above suggests that regardless of the sequences of antibody variable regions and antigen type, heterogeneity derived from natural IgG2 can be reduced by substituting serine for cysteine at position 131 (EU numbering) in the H-chain CH1 domain and serine for cysteine at position 219 (EU numbering) in the H-chain hinge region.

[Example 3] Pharmacokinetics-Improving Effect of Novel Constant Region M58-k0 Pharmacokinetics of IgG-Type Antibodies The prolonged retention (slow elimination) of IgG molecule in plasma is known to be due to the function of FcRn which is known as a salvage receptor of IgG molecule (Nat. Rev. Immunol. 2007 September; 7(9): 715-25). When taken up into endosomes via pinocytosis, IgG molecules bind to FcRn expressed in endosomes under the acidic conditions within the endosomes (approx. pH 6.0). While IgG molecules that do not bind to FcRn are transferred and degraded in lysosomes, those bound to FcRn are translocated to the cell surface and then released from FcRn back into plasma again under the neutral conditions in the plasma (approx. pH 7.4).

Known IgG-type antibodies include the IgG1, IgG2, IgG3, and IgG4 isotypes. The plasma half-lives of these isotypes in human are reported to be about 36 days for IgG1 and IgG2; about 29 days for IgG3; and 16 days for IgG4

(Nat. Biotechnol. 2007 December; 25(12): 1369-72). Thus, the retention of IgG1 and IgG2 in plasma is believed to be the longest. In general, the isotypes of antibodies used as pharmaceuticals are IgG1, IgG2, and IgG4. Methods reported for further improving the pharmacokinetics of these IgG antibodies include methods for improving the above-described binding to human FcRn, and this is achieved by altering the sequence of IgG constant region (J. Biol. Chem. 2007 Jan. 19; 282(3): 1709-17; J. Immunol. 2006 Jan. 1; 176(1): 346-56).

There are species-specific differences between mouse FcRn and human FcRn (Proc. Natl. Acad. Sci. USA. 2006 Dec. 5; 103(49): 18709-14). Therefore, to predict the plasma retention of IgG antibodies that have an altered constant region sequence in human, it is desirable to assess the binding to human FcRn and retention in plasma in human FcRn transgenic mice (Int. Immunol. 2006 December; 18(12): 1759-69).

Comparison of IgG1-k0 and M58-k0 for the Binding to Human FcRn

Human FcRn was prepared according to the method described in Reference Example 2. The binding to human FcRn was assessed using a Biacore™ 3000 surface plasmon resonance technology (SPR) system. An antibody was bound to Protein L or rabbit anti-human IgG Kappa chain antibody immobilized onto a sensor chip, human FcRn was added as an analyte for interaction with the antibody, and the affinity (KD) was calculated from the amount of bound human FcRn. Specifically, Protein L or rabbit anti-human IgG Kappa chain antibody was immobilized onto a Biacore™ sensor chip CM5 by the amine coupling method using 50 mM Na-phosphate buffer (pH 6.0) containing 150 mM NaCl as the running buffer. Then, IL6R H0-IgG1/L0-k0 and IL6R H0-M58/L0-k0 was each diluted with a running buffer containing 0.02% TWEEN® 20 surfactant, and injected to be bound to the chip. Human FcRn was then injected and the binding of the human FcRn to antibody was assessed.

The affinity was computed using BIAevaluation Software. The obtained sensorgram was used to calculate the amount of hFcRn bound to the antibody immediately before the end of human FcRn injection. The affinity of the antibody for human FcRn was calculated by fitting with the steady state affinity method.

As a result of evaluating the binding of IL6R H0-IgG1/L0-k0 and IL6R H0-M58/L0-k towards human FcRn by a Biacore™ SPR system, as shown in Table 3, the binding of IL6R H0-M58/L0-k0 was found to be increased approximately 1.4 times compared to that of IL6R H0-IgG1/L0-k0.

TABLE 3

| | KD/μM |
|---|---|
| IL6R H0-IgG1/L0-k0 | 1.42 |
| IL6R H0-M58/L0-k0 | 1.03 |

Comparison of IgG1-k0 and M58-k0 for Pharmacokinetics in Human FcRn Transgenic Mice The pharmacokinetics in human FcRn transgenic mice (B6.mFcRn−/−.hFcRn Tg line 276+/+ mice; Jackson Laboratories) was assessed by the following procedure. IL6R H0-IgG1/L0-k0 and IL6R H0-M58/L0-k0 was each intravenously administered once at a dose of 1 mg/kg to mice, and blood was collected at appropriate time points. The collected blood was immediately centrifuged at 15,000 rpm and 4° C. for 15 minutes to obtain blood plasma. The separated plasma was stored in a freezer at −20° C. or below until use. The plasma concentration was determined by ELISA (see Reference Example 3).

Figure 11:
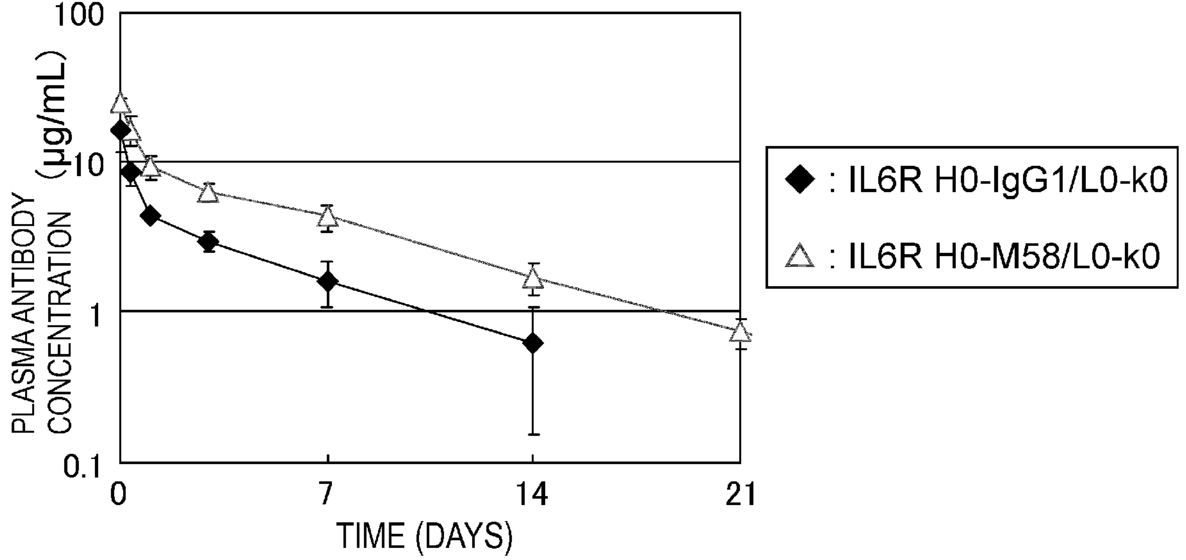
FIG. 11 shows in a graph a time course of plasma antibody concentration after administration of IL6R H0-IgG1/L0-k0 or IL6R H0-M58/L0-k0 at 1 mg/kg to human FcRn transgenic mice. In this graph, the vertical axis shows plasma antibody concentration (g/ml), and the horizontal axis shows time after administration (days). The antibodies administered were IL6R H0-IgG1/L0-k0 (filled diamond, antibody with unaltered constant region) and IL6R H0-M58/L0-k0 (open diamond, antibody with altered constant region).

As a result of evaluating the plasma retention of IL6R H0-IgG1/L0-k0 and IL6R H0-M58/L0-k0 in human FcRn transgenic mice, as shown in FIG. 11, pharmacokinetics of IL6R H0-M58/L0-k0 was confirmed to be improved compared to IL6R H0-IgG1/L0-k0. As indicated above, this was considered to be due to improvement in the binding of IL6R H0-M58/L0-k0 to human FcRn compared to IL6R H0-IgG1/L0-k0.

Comparison of IgG1-k0 or M58-k0 for the Binding to Human FcRn on Various Antibodies As described above, it was demonstrated that by converting the H-chain constant region of the anti-IL-6 receptor antibody IL6R H0-IgG1/L0-k0 from IgG1 into M58, human FcRn-binding activity and pharmacokinetics were confirmed to be improved in human FcRn transgenic mice. Then, the present inventors assessed whether the pharmacokinetics of IgG1 antibodies besides anti-IL-6 receptor antibodies could also be improved by converting the H-chain constant region into M58.

In addition to the anti-IL-6 receptor antibody, IL31R H0-IgG1/L0-k0 (H-chain amino acid sequence/SEQ ID NO: 11; L-chain amino acid sequence/SEQ ID NO: 12), which is an anti-IL-31 receptor antibody, and RANKL H0-IgG1/L0-k0 (H-chain amino acid sequence/SEQ ID NO: 15; L-chain amino acid sequence/SEQ ID NO: 16), which is an anti-RANKL antibody, were used. The H-chain constant regions of the antibodies were converted from the IgG1 subtype into M58 to prepare antibodies IL31R H0-M58/L0-k0 (H-chain amino acid sequence/SEQ ID NO: 14; L-chain amino acid sequence/SEQ ID NO: 12) and RANKL H0-M58/L0-k0 (H-chain amino acid sequence/SEQ ID NO: 18; L-chain amino acid sequence/SEQ ID NO: 16). The resulting antibodies were assessed for their human FcRn-binding activity by the method described above. The results are shown in Table 4.

TABLE 4

| | KD/μM | | |
|---|---|---|---|
| | ANTI-IL-6 RECEPTOR ANTIBODY | ANTI-IL-31 RECEPTOR ANTIBODY | ANTI-RANKL ANTIBODY |
| IgG1-k0 | 1.42 | 1.07 | 1.36 |
| M58-k0 | 1.03 | 0.91 | 1.03 |

As shown in Table 4, like the anti-IL-6 receptor antibody, the anti-IL-31 receptor antibody and anti-RANKL antibody were also demonstrated to be improved in terms of human FcRn-binding activity by converting the H-chain constant region from the IgG type into M58. This finding suggests the possibility that regardless of the sequences of antibody variable regions and antigen type, the pharmacokinetics in human was improved by converting the H-chain constant region from the IgG1 subtype into M58.

[Example 4] Novel Constant Region M66-k0 Generated by Further Improving the Pharmacokinetics of M58-k0

Preparation of Novel Constant Region M66-k0

As described in Example 2, the disulfide bond pattern in the hinge region of an IgG molecule was revealed to greatly influence heterogeneity and stability. Meanwhile, Example 3 demonstrates that the H-chain constant region M58 is superior to IgG1 in pharmacokinetics. Then, the present inventors thought that a novel constant region superior to M58 in pharmacokinetics could be produced by optimizing the disulfide bond pattern in the hinge region, and assessed this possibility.

Figure 12:
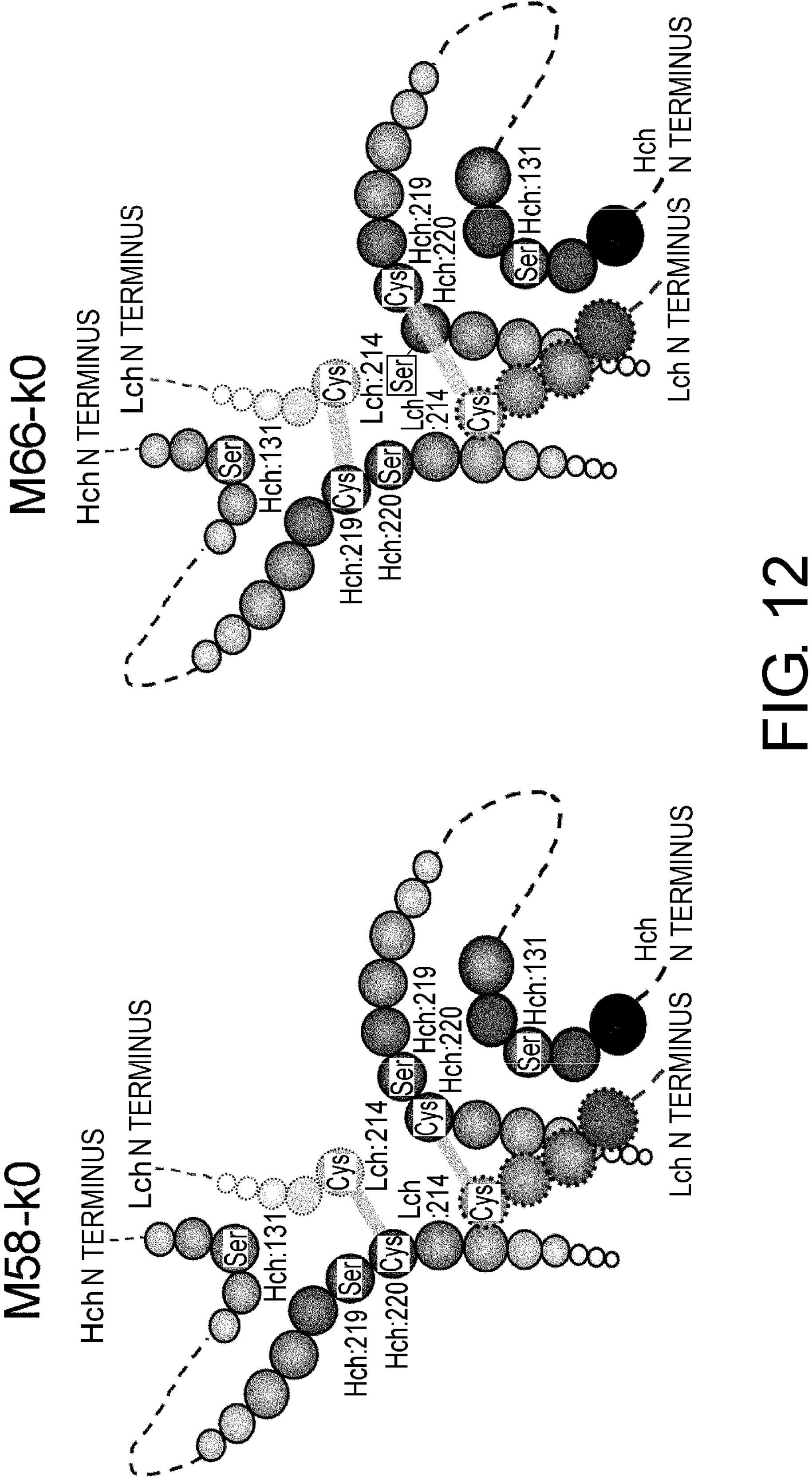
FIG. 12 shows in diagrams predicted disulfide bond patterns around the hinge regions of constant regions M58-k0 and M66-k0.

As shown in FIG. 12, since the constant region M58 has substitutions of serine for cysteine at positions 131 and 219 (EU numbering) in the H chain, cysteine at position 220 (EU numbering) in the H chain is assumed to form a disulfide bond with cysteine at position 214 in the L chain (for the numbering system, see Sequences of proteins of immunological interest, NIH Publication No. 91-3242). On the other hand, as described in Example 2, stability is greatly reduced when cysteine at position 131 (EU numbering) in the H chain is linked via a disulfide bond to cysteine at position 214 in the L chain (for the numbering system, see Sequences of proteins of immunological interest, NIH Publication No. 91-3242).

Then, as shown in FIG. 12, an expression vector for IL6R H0-M66 (amino acid SEQ ID NO: 19) was constructed by the method described in Reference Example 1 to assess the novel H-chain constant region M66 (amino acid SEQ ID NO: 30), which has substitutions of serine for cysteine at positions 131 and 220 (EU numbering) in the H chain, so that cysteine at position 219 (EU numbering) in the H chain forms a disulfide bond with cysteine at position 214 in the L chain (for the numbering, see Sequences of proteins of immunological interest, NIH Publication No. 91-3242). IL6R H0-M66/L0-k0 which consists of IL6R H0-M66 (amino acid SEQ ID NO: 19) as H chain and IL6R L0-k0 (amino acid SEQ ID NO: 2) as L chain was expressed and purified by the method described in Reference Example 1.

Comparison of IgG1-k0, M58-k0, and M66-k0 for Pharmacokinetics in Human FcRn Transgenic Mice IL6R H0-IgG1/L0-k0, IL6R H0-M58/L0-k0, and IL6R H0-M66/L0-k0 were assessed for pharmacokinetics using human FcRn transgenic mice (B6.mFcRn−/−.hFcRn Tg line 276+/+ mice; Jackson Laboratories) by the method described in Example 3.

Figure 13:
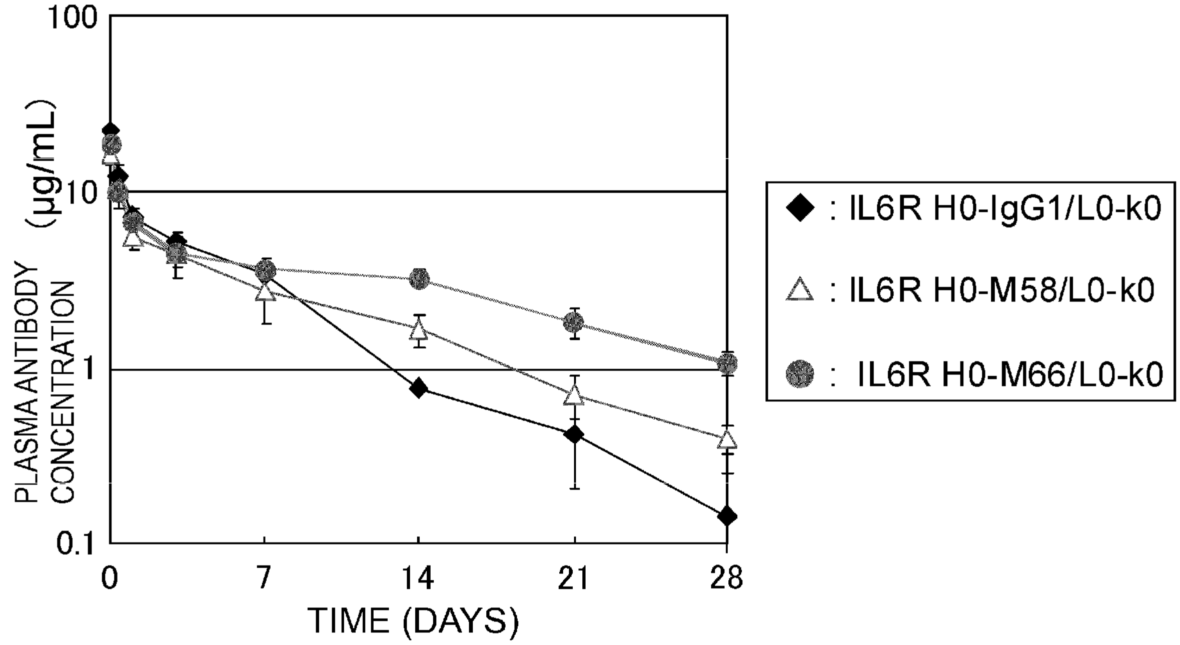
FIG. 13 shows in a graph a time course of plasma antibody concentration after administration of IL6R H0-IgG1/L0-k0, IL6R H0-M58/L0-k0, or IL6R H0-M66/L0-k0 at 1 mg/kg to human FcRn transgenic mice. In this graph, the vertical axis shows plasma antibody concentration (g/ml), and the horizontal axis shows time after administration (days). The antibodies administered were IL6R H0-IgG1/L0-k0 (filled diamond, antibody with unaltered constant region), IL6R H0-M58/L0-k0 (open diamond, antibody with altered constant region), and IL6R H0-M66/L0-k0 (filled circle, antibody with altered constant region).

IL6R H0-IgG1/L0-k0, IL6R H0-M58/L0-k0, and IL6R H0-M66/L0-k0 were assessed for plasma retention in human FcRn transgenic mice. As shown in FIG. 13, the result demonstrated that the pharmacokinetics of IL6R H0-M66/L0-k0 was improved as compared to that of IL6R H0-M58/L0-k0.

The amino acid sequences of IL6R H0-M58/L0-k0 and IL6R H0-M66/L0-k0 are different in that at positions 219 and 220 (EU numbering) in the H chain, IL6R H0-M58/L0-k0 has serine and cysteine, respectively, while IL6R H0-M66/L0-k0 has cysteine and serine, respectively. Specifically, cysteine at position 214 in the L chain (for the numbering, see Sequences of proteins of immunological interest, NIH Publication No. 91-3242) forms a disulfide bond with cysteine at position 220 (EU numbering) in the H chain of IL6R H0-M58/L0-k0 while cysteine at position 214 forms a disulfide bond with cysteine at position 219 (EU numbering) in the H chain of IL6R H0-M66/L0-k0. Thus, the two are different in the position of their disulfide bond.

There is no previous report demonstrating whether the pharmacokinetics of IgG varies depending on the position of disulfide bond. As described in "J Biol. Chem., 2008 Jun. 6; 283(23): 16194-205; J Biol. Chem., 2008 Jun. 6; 283(23): 16206-15; Biochemistry, 2008 Jul. 15; 47(28): 7496-508", there are many different disulfide bond patterns (isoforms) in natural IgG2, such as form A and form B. According to the report of "J Biol. Chem., 2008 Oct. 24; 283(43): 29266-72", the pharmacokinetics does not change across isoforms having disulfide bonds at different positions.

By the assessment described above, it was found for the first time that the pharmacokinetics differed greatly between IL6R H0-M58/L0-k0 and IL6R H0-M66/L0-k0 due to difference in the position of disulfide bond. Specifically, it was demonstrated that the pharmacokinetics could be greatly improved by changing the position of disulfide bond from between position 220 (EU numbering) in the H chain and position 214 in the L chain (for the numbering system, see Sequences of proteins of immunological interest, NIH Publication No. 91-3242) to between position 219 (EU numbering) in the H chain and position 214 in the L chain (for the numbering system, see Sequences of proteins of immunological interest, NIH Publication No. 91-3242).

Analysis of Novel Constant Region M66-k0 by DSC

To assess stability, the midpoint of thermal denaturation (Tm value) was determined by differential scanning calorimetry (DSC) (N-DSCII, Calorimetry Science Corporation) in a similar manner as described in Example 2. The purified IL6R H0-IgG1/L0-k0, IL6R H0-M58/L0-k0, and IL6R H0-M66/L0-k0 were dialyzed against a solution (pH 6.0) containing 20 mM sodium acetate and 150 mM NaCl using TOMY dialysis tubes. DSC measurements were carried out at a heating rate of 1° C./min in a range of 40 to 100° C., and at a protein concentration of about 0.1 mg/ml. The Tm values for the Fab domains (as listed in Table 5) are calculated based on the denaturation curves obtained by DSC.

TABLE 5

| | Tm/° C. OF Fab |
|---|---|
| IL6R H0-IgG1/L0-k0 | 95° C. |
| IL6R H0-M58/L0-k0 | 94° C. |
| IL6R H0-M66/L0-k0 | 93° C. |

As shown in Table 5, the Tm value of IL6R H0-M66/L0-k0 was found to be comparable to that of H0-M58/L0-k0. This demonstrates that when M66 (amino acid SEQ ID NO: 30) is used as an H-chain constant region, the pharmacokinetics can be improved as compared to M58 (SEQ ID NO: 29) without decreasing the stability.

Cation Exchange Chromatography Analysis of Novel Constant Region M66-k0

IL6R H0-IgG1/L0-k0, IL6R H0-IgG2/L0-k0, IL6R H0-M58/L0-k0, and IL6R H0-M66/L0-k0 were assessed by cation exchange chromatography using the method described in Example 2. The result is shown in FIG. 14.

Figure 14:
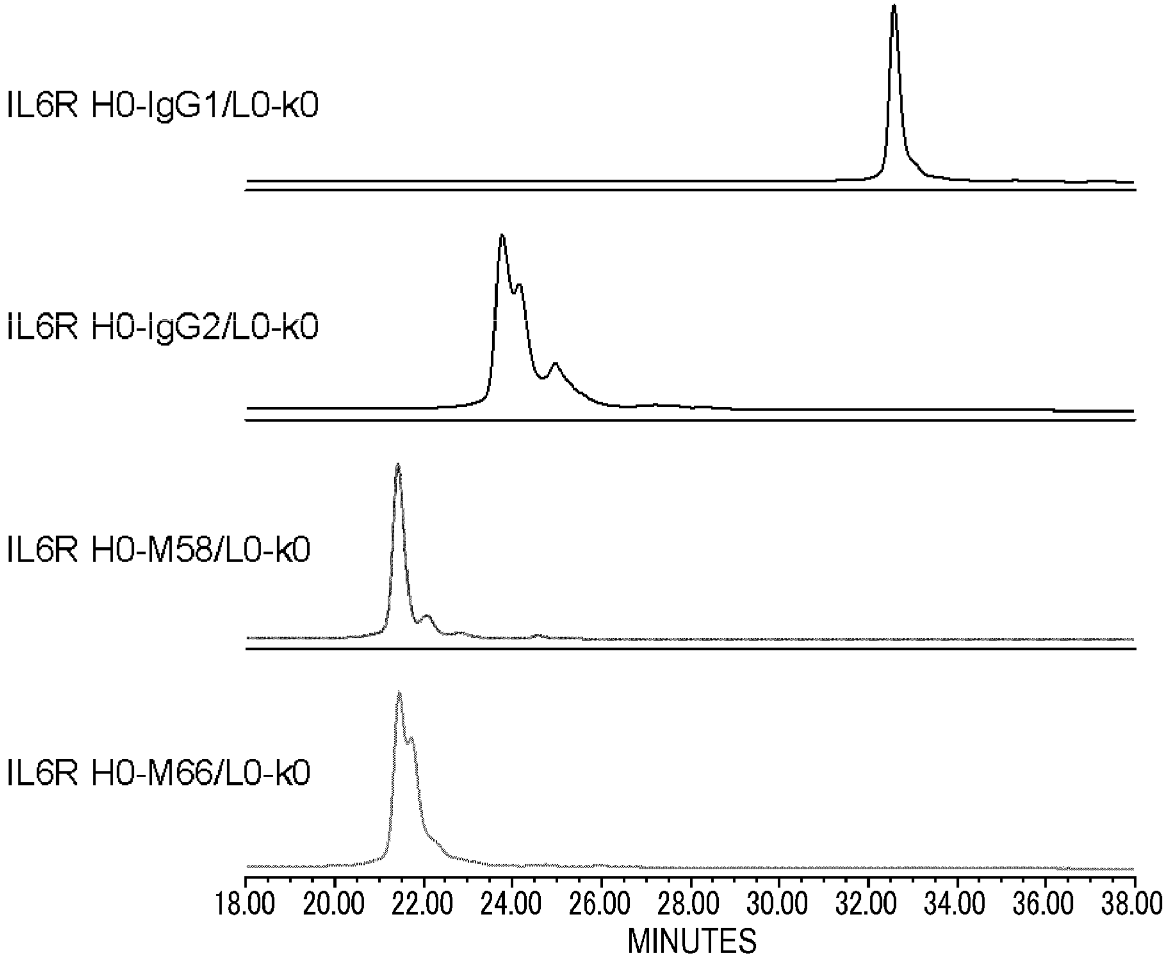
FIG. 14 shows in graphs the results of assessing the heterogeneity of IL6R H0-IgG1/L0-k0, IL6R H0-IgG2/L0-k0, IL6R H0-M58/L0-k0, and IL6R H0-M66/L0-k0 by cation exchange chromatography based on their disulfide bond differences. In these graphs, the vertical axis shows absorbance at 280 nm and the horizontal axis shows elution time (minutes).

As described in FIG. 14, the result showed that the H-chain constant region M58 showed a single peak while the H-chain constant region M66 exhibited two major peaks. Likewise, for the anti-IL-31 receptor antibody, M58 showed a single peak while M66 showed two major peaks.

M58 has serine and cysteine at positions 219 and 220 (EU numbering) in the H chain, respectively, while M66 has cysteine and serine at positions 219 and 220, respectively. This minor difference remarkably improved the pharmacokinetics of M66 compared to M58. However, the new peak in M66, which was not observed with M58, indicated heterogeneity. Thus, M66 was demonstrated to show heterogeneity (isoforms) because of the presence of two types of components.

[Example 5] Novel Constant Regions M66-k3 and M66-k4 Generated by Improvement of M66-k0 in Terms of Heterogeneity by the L-Chain Constant Region Modification Preparation of Novel Constant Regions M66-k3 and M66-k4

Figure 16:
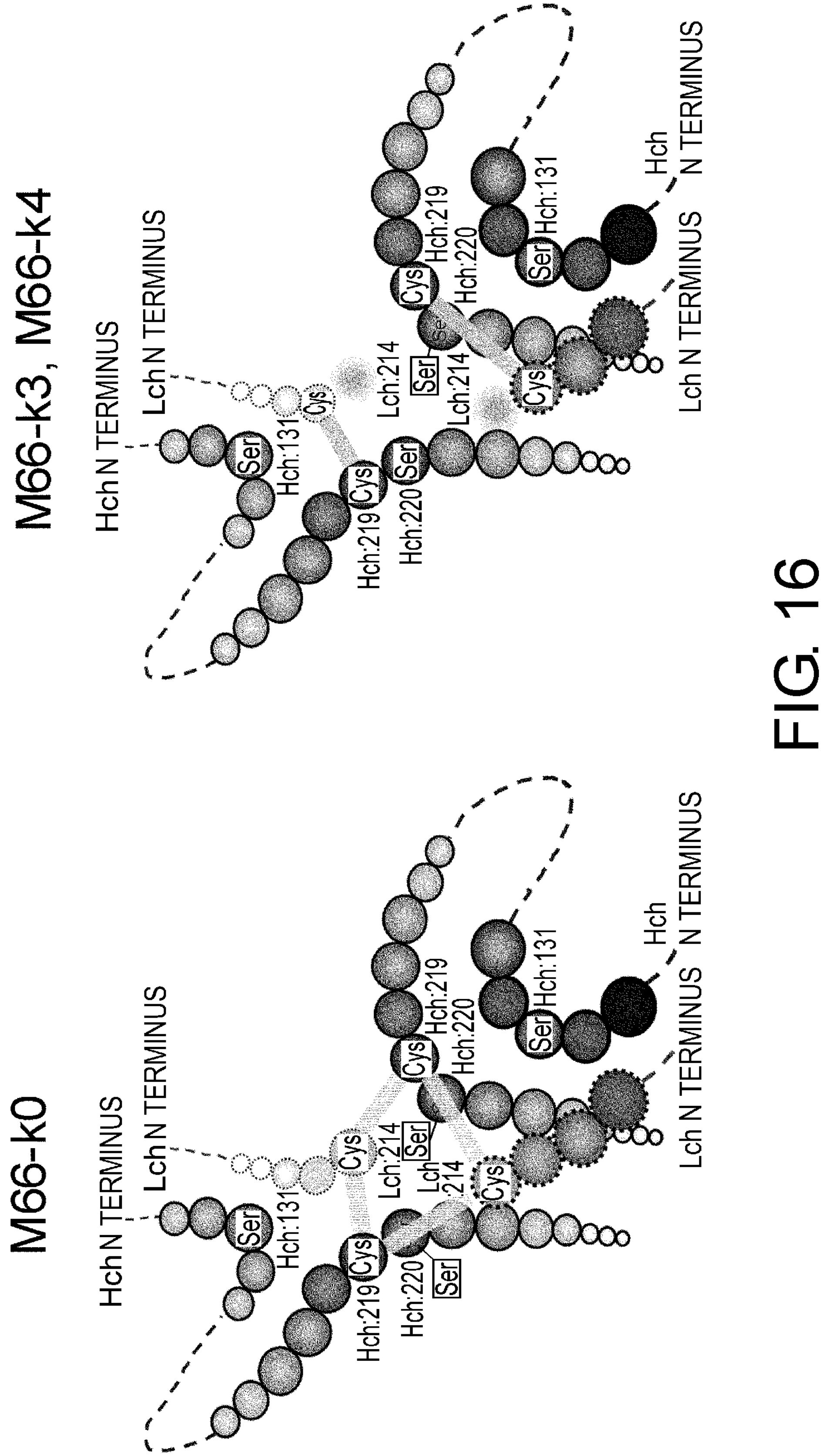
FIG. 16 shows in diagrams predicted disulfide bond patterns around the hinge region of constant region M66-k0, M66-k3, or M66-k4. The disulfide bonds which correspond to the two peaks of M66 are indicated by bold lines.

The heterogeneity (two types of components) of IL6R H0-M66/L0 confirmed as described in Example 4 was speculated to be due to difference in the pattern of disulfide bonds between H chain and L chain. Specifically, it is thought that two types of components corresponding to the two types of disulfide bond patterns shown in FIG. 15 were detected. It is thought that the C-terminal cysteine at position 214 (for the numbering system, see Sequences of proteins of immunological interest, NIH Publication No. 91-3242) in the L chain (k0 amino acid SEQ ID NO: 32) (cysteine at position 107 in k0 of amino acid SEQ ID NO: 32) can form a disulfide bond with both cysteines at position 219 (EU numbering) in the two H chains. Thus, the present inventors predicted that as shown in FIG. 16, heterogeneity (to generate a single component) could be reduced when cysteine in the L chain was capable of forming a disulfide bond with cysteine at position 219 (EU numbering) in only one of the two H chains. Then, the present inventors conceived that the above-described C-terminal cysteine was moved towards the N-terminal side in the L chain to reduce heterogeneity. This could increase the distance between the C-terminal cysteine in the L chain and cysteine at position 219 (EU numbering) in one of the H chains, and as a result the L-chain C-terminal cysteine could form a disulfide bond with cysteine only at position 219 (EU numbering) in the other H chain. A possible method for relocating the L-chain C-terminal cysteine to a position on the N-terminal side was to shorten the peptide length of L chain at the C terminus. Specifically, the hypothesis was assessed using a novel antibody L-chain constant region k3 (amino acid SEQ ID NO: 33) resulting from deletion of glutamic acid at position 106 from the natural L-chain constant region k0 (amino acid SEQ ID NO: 32) and a novel antibody L-chain constant region k4 (amino acid SEQ ID NO: 34) resulting from deletion of glycine at position 105 from the natural L-chain constant region k0 (amino acid SEQ ID NO: 32). Thus, expression vectors for IL6R L0-k3 (amino acid SEQ ID NO: 21) having k3 as an L-chain constant region and IL6R L0-k4 (amino acid SEQ ID NO: 22) having k4 as an L-chain constant region were constructed by the method described in Reference Example 1.

IL6R H0-M66/L0-k3, which consists of IL6R H0-M66 (amino acid SEQ ID NO: 19) as H chain and IL6R L0-k3 (amino acid SEQ ID NO: 21) as L chain, and IL6R H0-M66/L0-k4, which consists of IL6R H0-M66 (amino acid SEQ ID NO: 19) as H chain and IL6R L0-k4 (amino acid SEQ ID NO: 22) as L chain were expressed and purified by the method described in Reference Example 1.

Cation Exchange Chromatography Analysis of Novel Constant Region M66-k3 and M66-k4

IL6R H0-IgG1/L0-k0, IL6R H0-IgG2/L0-k0, IL6R H0-M58/L0-k0, IL6R H0-M66/L0-k0, IL6R H0-M66/L0-k3, and IL6R H0-M66/L0-k4 were assessed by cation exchange chromatography using the method described in Example 2. The assessment result is shown in FIG. 17.

Figure 17:
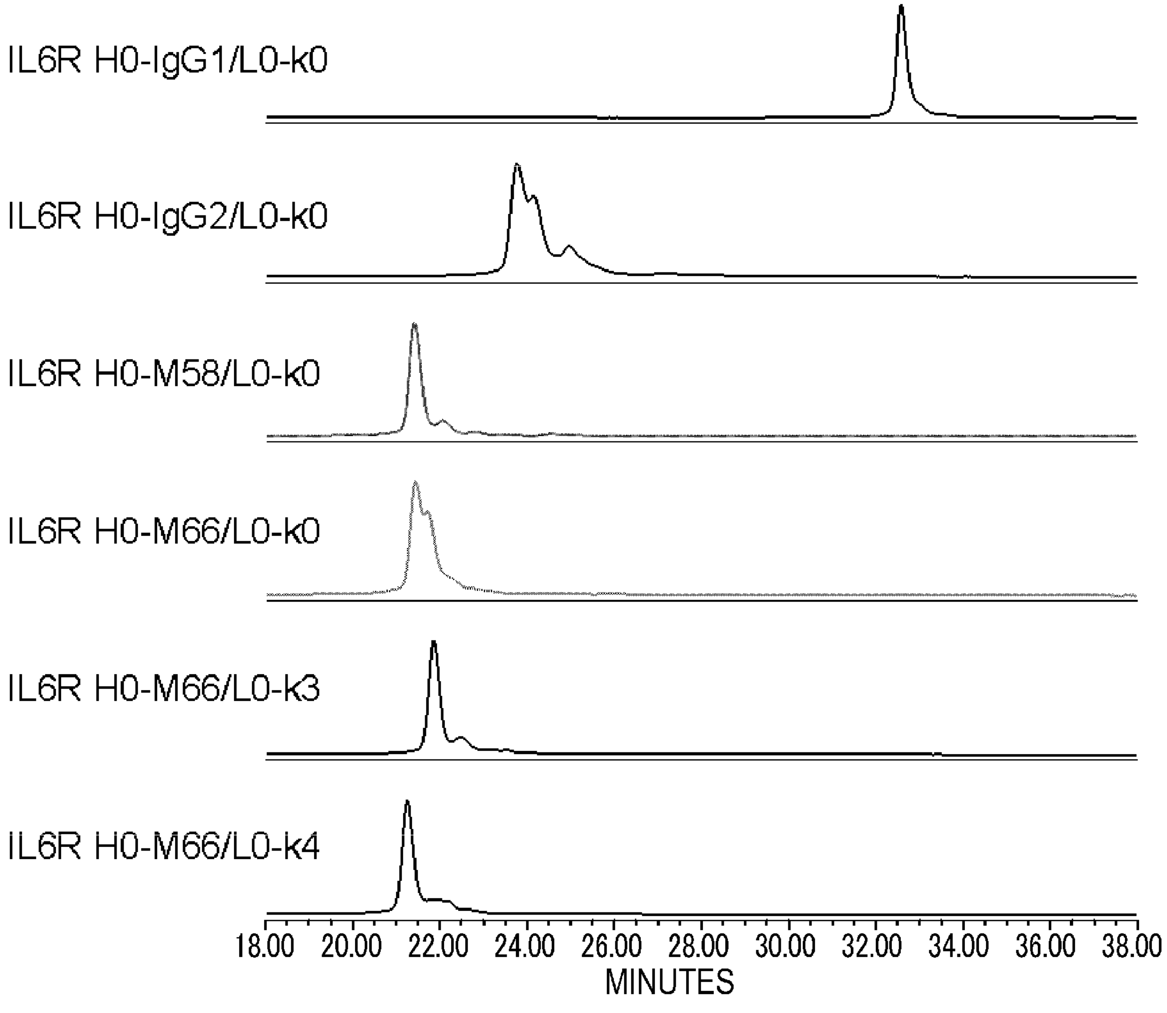
FIG. 17 shows in graphs the results of assessing the heterogeneity of IL6R H0-IgG1/L0-k0, IL6R H0-IgG2/L0-k0, IL6R H0-M58/L0-k0, IL6R H0-M66/L0-k0, IL6R H0-M66/L0-k3, and IL6R H0-M66/L0-k4 by cation exchange chromatography based on their disulfide bond differences. In these graphs, the vertical axis shows absorbance at 280 nm and the horizontal axis shows elution time (minutes).

As shown in FIG. 17, the result demonstrated that H0-M66/L0-k0 showed two single peaks, while H0-M66/L0-k3 and H0-M66/L0-k4 each showed a single peak like H0-M58/L0-k0. This finding suggests that heterogeneity can be reduced by relocating the L-chain C-terminal cysteine position toward the N-terminal side by shortening the peptide length of the L chain at the C terminus, so that the L chain cysteine can form a disulfide bond with cysteine only at position 219 (EU numbering) in one of the two H chains.

A previously assessed method for reducing the heterogeneity (isoforms) of the disulfide bond pattern in the natural IgG2 (J Biol Chem. 2008 Jun. 6, 283(23): 16194-205; J Biol Chem. 2008 Jun. 6, 283(23): 16206-15) is to substitute serine for cysteine in the H-chain constant region. The Examples herein demonstrated for the first time that heterogeneity could be reduced by relocating the C-terminal cysteine in the L-chain constant region. There is no previous report on L-chain constant regions that result from relocation of the L-chain C-terminal cysteine.

In addition to the method described above, methods for relocating the L-chain C-terminal cysteine toward a position on the N-terminal side include, for example, deletion of arginine at position 104 from the natural L-chain constant region k0 (amino acid SEQ ID NO: 32), deletion of asparagine at position 103 from the natural L-chain constant region k0 (amino acid SEQ ID NO: 32), and substitution of cysteine for glutamic acid at position 106 in the natural L-chain constant region k0 (amino acid SEQ ID NO: 32), in combination with substitution of an amino acid other than cysteine for cysteine at position 107.

The human L-chain constant region used in this Example is a κ chain (k0, amino acid SEQ ID NO: 32). The same method is expected to be applicable to the λ chain constant region (amino acid SEQ ID NO: 37). The λ chain constant region has cysteine at position 104 in amino acid SEQ ID NO: 37 (at position 214 in the numbering system described in "Sequences of proteins of immunological interest, NIH Publication No. 91-3242"). Thus, the method includes deletion of glutamic acid at position 103, deletion of threonine at position 102, deletion of proline at position 101, deletion of alanine at position 100, and substitution of cysteine for glutamic acid at position 103, in combination with substitution of an amino acid other than cysteine for cysteine at position 104 in the natural λ chain constant region (amino acid SEQ ID NO: 37).

Assessment of Novel Constant Regions M66-k0 and M66-k3 for the Binding to Human FcRn IgG is known to bind to FcRn with divalent avidity (Traffic. 2006 September; 7(9): 1127-42). In the method described in Example 3, IgG is immobilized onto a sensor chip and then FcRn is injected as an analyte. IgG binds to FcRn with monovalent affinity. Then, the present inventors assessed in this Example the binding of IgG to FcRn with divalent avidity by immobilizing human FcRn onto a sensor chip and injecting IgG as an analyte to more closely mimic the in vivo case. In a Biacore™ T100 SPR system (GE Healthcare), H0-IgG1/L0-k0, H0-M58/L0-k0, H0-M66/L0-k0, and H0-M66/L0-k3 were each injected as an analyte into the sensor chip immobilized with the FcRn to analyze the affinity of the antibody variants for human FcRn at pH 6.0.

The methods of immobilization and analysis of the interaction are described below. First, about 2,000 RU of human FcRn was immobilized onto sensor chip CM4 (GE Healthcare) by the amino coupling method. Reagents used in the amino coupling were: ethanol amine (GE Healthcare), 50 mM NaOH solution (GE Healthcare), NHS (GE Healthcare), EDC (GE Healthcare). HBS-EP+ solution (10×HBS-EP+ solution (GE Healthcare) was used after dilution) was used as the mobile phase. Then, antibodies were each injected as an analyte into the sensor chip immobilized with human FcRn for three minutes to observe the binding of FcRn to the antibodies. After this observation, the mobile phase was injected for five minutes to assess the dissociation of each antibody variants from FcRn. All measurements were carried out at 25° C. The mobile phase used was 10 mM Cit (pH 6.0)/150 mM NaCl/0.05% 20 TWEEN® surfactant.

From the obtained sensorgrams, the association rate constant ka (1/Ms) and dissociation rate constant kd (1/s) were calculated for the three minutes of binding phase using Biacore™ T100 Evaluation Software (GE Healthcare). The dissociation constant KD (M) was determined based on these values. KDs are listed in Table 6.

TABLE 6

| | KD/nM |
|---|---|
| IL6R H0-IgG1/L0-k0 | 4.00 |
| IL6R H0-M58/L0-k0 | 3.85 |
| IL6R H0-M66/L0-k0 | 3.54 |
| IL6R H0-M66/L0-k3 | 3.26 |

As described in Examples 3 and 4, the pharmacokinetics of H0-IgG1/L0-k0, H0-M58/L0-k0, and H0-M66/L0-k0 in human FcRn transgenic mice was correlated with binding of the antibodies with human FcRn in this assay system. The human FcRn binding activity of H0-M66/L0-k3 was comparable to or greater than that of H0-M66/L0-k0. This suggests that the pharmacokinetics of H0-M66/L0-k3 in human FcRn transgenic mice is comparable or superior to that of H0-M66/L0-k0.

Analysis of Novel Constant Region M66-k3 and M66-k4 by DSC

To assess the stability, the midpoint of thermal denaturation (Tm value) was determined by differential scanning calorimetry (DSC) (N-DSCII, Calorimetry Science Corporation) in a similar manner as described in Example 2. The purified IL6R H0-IgG1/L0-k0, IL6R H0-M66/L0-k0, IL6R H0-M66/L0-k3, and IL6R H0-M66/L0-k4 were dialyzed against a solution (pH 6.0) containing 20 mM sodium acetate and 150 mM NaCl using TOMY dialysis tubes. DSC measurements were carried out at a heating rate of 1° C./min in a range of 40 to 100° C., and at a protein concentration of about 0.1 mg/ml. The Tm values for the Fab portions are calculated based on the denaturation curves obtained by DSC, which are listed in Table 7.

TABLE 7

| | Tm/° C. OF Fab |
|---|---|
| IL6R H0-IgG1/L0-k0 | 95° C. |
| IL6R H0-M66/L0-k0 | 93° C. |
| IL6R H0-M66/L0-k3 | 94° C. |
| IL6R H0-M66/L0-k4 | 94° C. |

As shown in Table 7, the Tm values of IL6R H0-M66/L0-k3 and IL6R H0-M66/L0-k4 were found to be comparable to that of H0-M66/L0-k0. This demonstrates that when k3 (amino acid SEQ ID NO: 33) or k4 (amino acid SEQ ID NO: 34) is used as an L-chain constant region, the pharmacokinetics can be improved without decreasing the stability as compared to natural L-chain constant region k0 (SEQ ID NO: 32).

As shown in FIG. 14, H0-M66/L0-k0 which was designed to form a disulfide bond between position 219 (EU numbering) in the H chain and position 214 in the L chain (for the numbering system, see Sequences of proteins of immunological interest, NIH Publication No. 91-3242) was demonstrated to have two types of isoforms. These two components can be ascribed to the two disulfide bond patterns shown in FIG. 15. Thus, it was found that the heterogeneity derived from natural IgG2 could not be completely eliminated by substitution of serine for only cysteine at positions 137 and 220 (EU numbering) in the H chain. Then, the present inventors demonstrated that the heterogeneity derived from disulfide bonds of natural IgG2 could be eliminated only when using H0-M66/L0-k3 or H0-M66/L0-k4 generating from relocation of the C-terminal cysteine in the L-chain constant region. H0-M66/L0-k3 retains the original stability and human FcRn-binding activity as compared to H0-M66/L0-k0. Furthermore, in H0-M66/L0-k3, the C-terminal heterogeneity of the H chain has been eliminated by alteration of the C-terminal ΔGK in the H chain described in Example 1. Thus, M66/k3 and M66/k4 were concluded to be very useful as antibody H chain/L chain constant regions.

[Example 6]M106-k3 with Reduced Fcγ Receptor-Binding of M66-k3 Preparation of Novel Constant Region M106-k3

In antibody pharmaceuticals aimed at neutralizing an antigen, effector functions such as the ADCC of Fc domain are unnecessary and therefore the binding to Fcγ receptor is unnecessary. The binding to Fcγ receptor is assumed to be unfavorable from the perspectives of antigenicity and side effect (Nat Rev Drug Discov. 2007 January; 6(1): 75-92; Ann Hematol. 1998 June; 76(6): 231-48). For example, the humanized anti-IL-6 receptor IgG1 antibody TOCILIZUMAB does not need to bind to Fcγ receptor, because it only needs to specifically bind to IL-6 receptor and neutralize its biological activity in order to be used as a therapeutic agent for diseases associated with IL-6, such as rheumatoid arthritis.

A possible method for reducing the Fcγ receptor binding is to convert the IgG antibody isotype from IgG1 into IgG2 or IgG4 (Ann. Hematol. 1998 June; 76(6): 231-48). As a method for completely eliminating the binding to Fcγ receptor, a method of introducing an artificial modification into Fc domain has been reported. For example, since the effector functions of anti-CD3 antibody and anti-CD4 antibody cause side effects, amino acid mutations that are not present in the wild type sequence have been introduced into the Fcγ receptor-binding region of Fc domain (J Immunol. 2000 Feb. 15; 164(4): 1925-33; J Immunol. 1997 Oct. 1; 159(7): 3613-21.), and the resulting Fcγ receptor-nonbinding anti-CD3 and anti-CD4 antibodies are currently under clinical trials (Nat Rev Drug Discov. 2007 January; 6(1): 75-92, Transplantation. 2001 Apr. 15; 71(7): 941-50). According to another report (US 20050261229A1), Fcγ receptor-nonbinding antibodies can be prepared by converting the FcγR-binding domain of IgG1 (at positions 233, 234, 235, 236, 327, 330, and 331 in the EU numbering) into the sequence of IgG2 (at positions 233, 234, 235, and 236 in the EU numbering) or IgG4 (at positions 327, 330, and 331 in the EU numbering). However, if all of the above mutations are introduced into IgG1, novel peptide sequences of nine amino acids, which potentially serve as non-natural T-cell epitope peptides, will be generated, and this increases the immunogenicity risk. The immunogenicity risk should be minimized in developing antibody pharmaceuticals.

Alterations in the IgG2 constant region were considered to overcome the above-described problem. In the FcγR-binding domain of the IgG2 constant region, the amino acids at positions 233, 234, 235 and 236 (EU numbering) are amino acids of nonbinding type; however, the amino acids at positions 330 and 331 (EU numbering) in the FcγR-binding domain are different from the nonbinding sequence of IgG4. Therefore, it is necessary to change the amino acids at positions 330 and 331 (EU numbering) to the sequence of IgG4 (G2Δa described in Eur J Immunol. 1999 August; 29(8): 2613-24). However, since the amino acid at position 339 (EU numbering) in IgG4 is alanine while the corresponding residue in IgG2 is threonine, a simple alteration of the amino acids at positions 330 and 331 (EU numbering) to the sequence of IgG4 unfavorably generates a new peptide sequence of nine amino acids, potentially serving as a non-natural T-cell epitope peptide, and thus increases the immunogenicity risk. Then, the present inventors found that generation of the new peptide sequence could be prevented by introducing the substitution of Ala for Thr at position 339 (EU numbering) in IgG2, in addition to the alteration described above. Thus, the above-described mutations were introduced into the constant region M66 (amino acid SEQ ID NO: 30), and the resulting constant region M106 (amino acid SEQ ID NO: 31) was assessed. Then, an expression vector for IL6R H0-M106 (amino acid SEQ ID NO: 20) containing the H-chain constant region M106 was constructed by the method described in Reference Example 1.

IL6R H0-M106/L0-k0 which consists of IL6R H0-M106 (amino acid SEQ ID NO: 20) as H chain and IL6R L0-k0 (amino acid SEQ ID NO: 2) as L chain, IL6R H0-M106/L0-k3 which consists of IL6R H0-M106 (amino acid SEQ ID NO: 20) as H chain and IL6R L0-k3 (amino acid SEQ ID NO: 21) as L chain, and IL6R H0-M106/L0-k4 which consists of IL6R H0-M106 (amino acid SEQ ID NO: 20) as H chain and IL6RL0-k4 (amino acid SEQ ID NO: 22) as L chain were expressed and purified by the method described in Reference Example 1.

Cation Chromatography Analysis of Novel Constant Region M106-k3

IL6R H0-IgG1/L0-k0, IL6R H0-IgG2/L0-k0, IL6R H0-M106/L0-k0, IL6R H0-M106/L0-k3, and IL6R H0-M106/L0-k4 were assessed by cation exchange chromatography using the method described in Example 2. The result is shown in FIG. 18.

Figure 18:
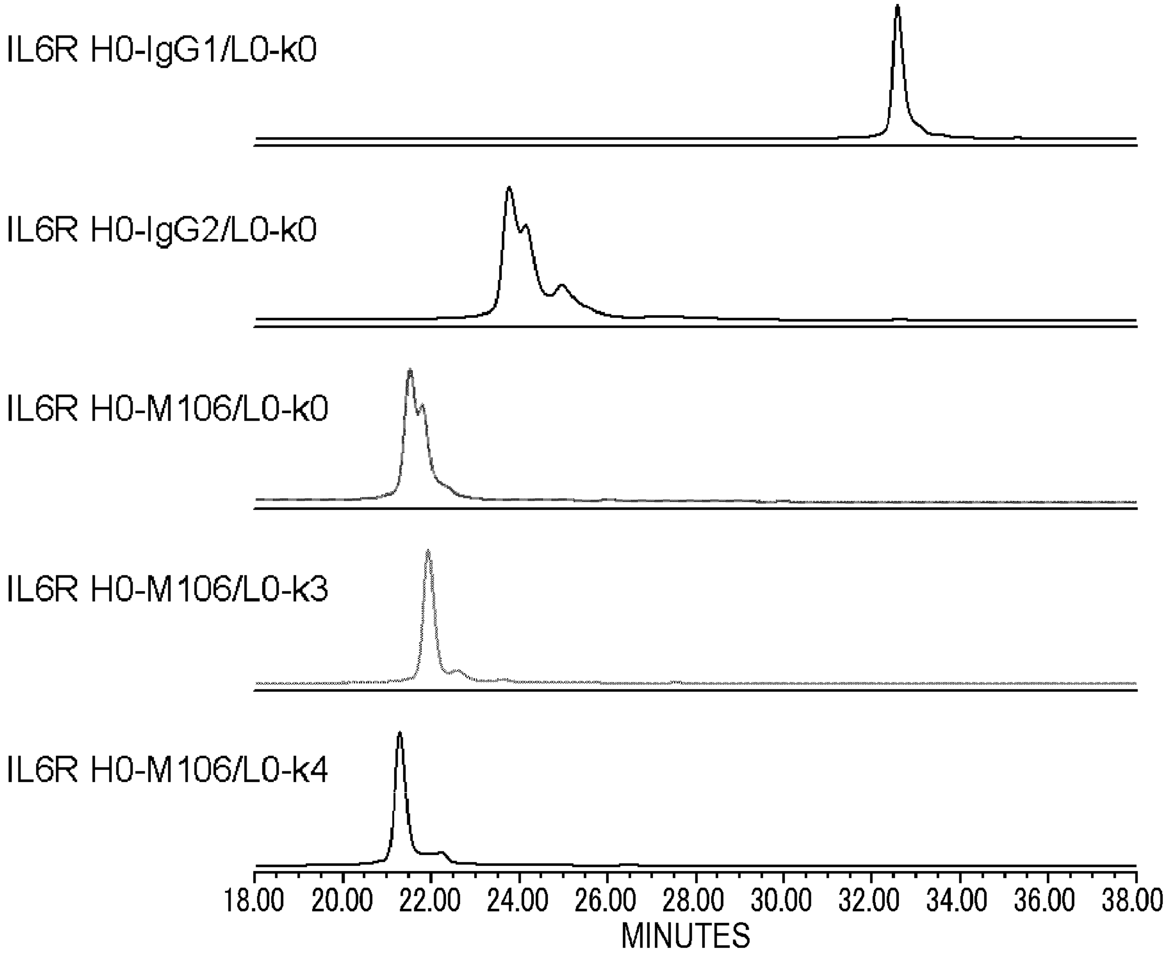
FIG. 18 shows in graphs the results of assessing the heterogeneity of IL6R H0-IgG1/L0-k0, IL6R H0-IgG2/L0-k0, IL6R H0-M106/L0-k0, IL6R H0-M106/L0-k3, and IL6R H0-M106/L0-k4 by cation exchange chromatography based on their disulfide bond differences. In these graphs, the vertical axis shows absorbance at 280 nm and the horizontal axis shows elution time (minutes).

As shown in FIG. 18, the result demonstrated that H0-M106/L0-k0 showed two single peaks, while H0-M106/L0-k3 and H0-M106/L0-k4 each showed a single peak like H0-M66/L0-k3 and H0-M66/L0-k4. This finding suggests that heterogeneity can be reduced by relocating the L-chain C-terminal cysteine toward the N-terminal side by shortening the peptide length of the L chain at the C-terminus, so that the L chain cysteine can form a disulfide bond with cysteine only at position 219 (EU numbering) in one of the two H chains. Thus, heterogeneity has been reduced in the H-chain constant region variant M106 as well as in the H-chain constant region variant M66.

Assessment of Novel Constant Region M106-k3 for the Binding to Various Fcγ Receptors H0-IgG1/L0-k0, H0-IgG2/L0-k0, and H0-M106/L0-k3 were assessed for the binding to Fcγ receptor using the active Fcγ receptors, FcγRI, FcγRIIa, and FcγRIIIa.

The binding to Fcγ receptor was assessed using Biacore™ T100 SPR system (GE Healthcare). The human Fcγ receptors were allowed to interact with the antibodies captured by Protein L immobilized onto a sensor chip. The binding was assessed by comparing the amount of binding. Specifically, Protein L (ACTIgen) was immobilized onto a Biacore™ SPR sensor chip CM5 by the amino coupling method using HBS-EP+ (GE Healthcare) as a running buffer. Then, H0-IgG1/L0-k0, H0-IgG2/L0-k0, and H0-M106/L0-k3 were captured by Protein L immobilized onto the sensor chip, and allowed to interact with the following analytes: running buffer, and FcγRI, FcγRIIa, and FcγRIIIa (R&D systems) diluted to 10 g/ml with running buffer. Since it was difficult to keep the amounts of the respective antibodies captured by Protein L constant in this assay, the amounts were corrected to be constant. Specifically, the binding amount when running buffer alone was used in the interaction was subtracted from the binding amount of each human Fcγ receptor, and the resulting value was divided by the amount of each antibody captured. The obtained value was multiplied by 100, and the resulting value was used as "Normalized response".

Figure 19:
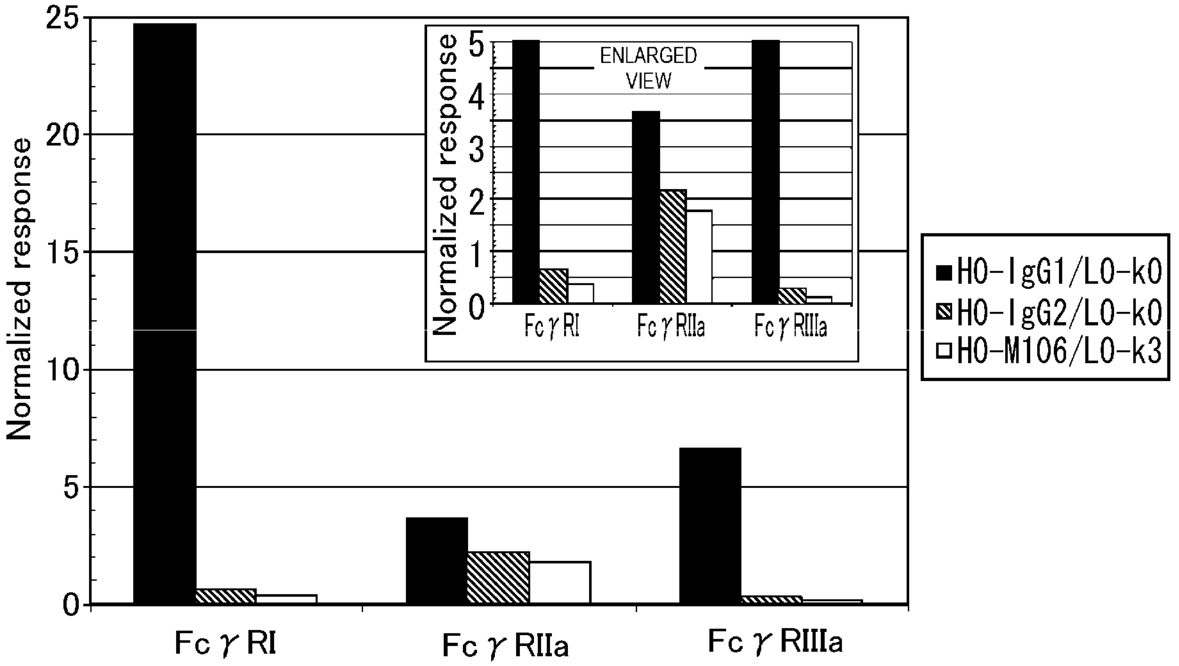
FIG. 19 shows in a diagram the binding of H0-IgG1/L0-k0, H0-IgG2/L0-k0, or H0-M106/L0-k3 to various types of Fcγ receptors.

The result of comparison of binding intensities between various antibodies and human Fcγ receptor using "Normalized response" is shown in FIG. 19. The result revealed that the binding activity of H0-M106/L0-k3 to various active Fcγ receptors was significantly lower than that of natural IgG1 and also lower than that of H0-IgG2/L0-k0. Thus, the Fcγ receptor-binding activity of the novel constant region M106-k3 was demonstrated to be lower than that of natural IgG2. This finding suggests that the immunogenicity risk due to Fcγ receptor-mediated internalization into APC and side effects caused by the effector function such as ADCC can be reduced to less than those of natural IgG2 by using H0-M106/L0-k3.

[Example 7] Cation Exchange Chromatography Analysis of IgG2-k3

IL6R H0-IgG2/L0-k3 which consists of IL6R H0-IgG2 (amino acid SEQ ID NO: 5) as H chain and IL6R L0-k3 (amino acid SEQ ID NO: 21) as L chain was expressed and purified by the method described in Reference Example 1. IL6R H0-IgG1/L0-k0, IL6R H0-IgG2/L0-k0, and IL6R H0-IgG2/L0-k3 were assessed by cation exchange chromatography using the method described in Example 2. The result is shown in FIG. 20.

Figure 20:
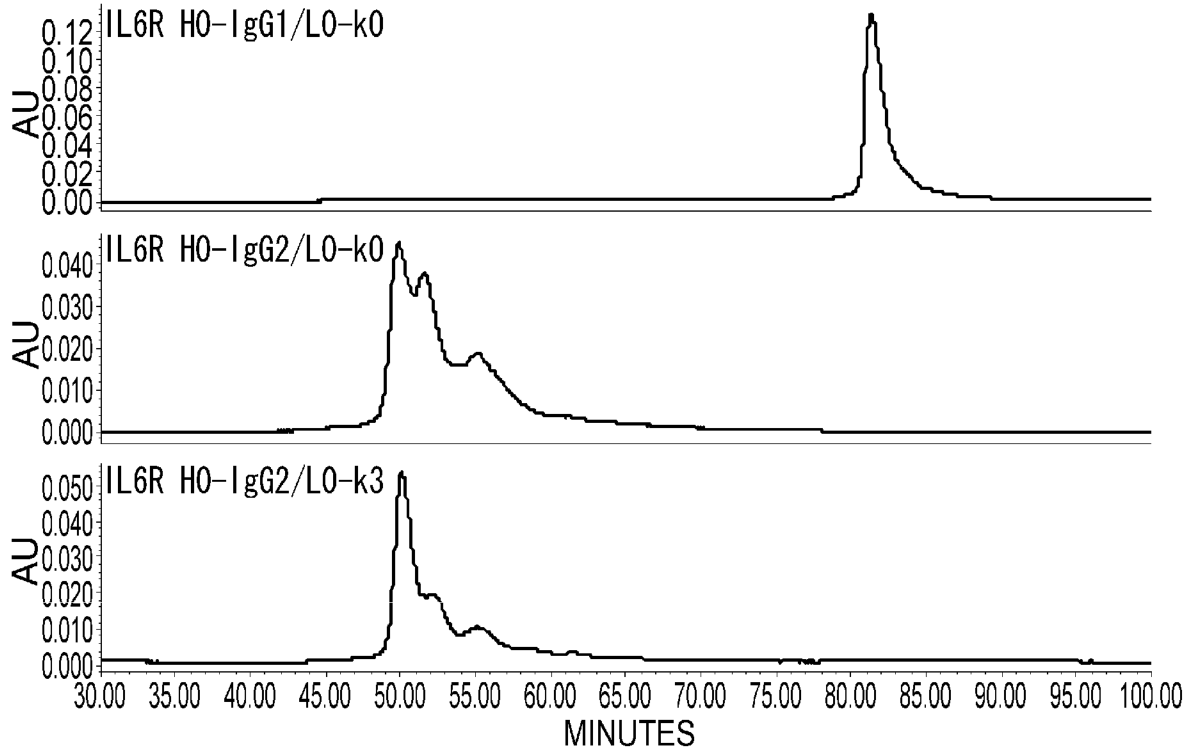
FIG. 20 shows in graphs the results of assessing the heterogeneity of IL6R H0-IgG1/L0-k0, IL6R H0-IgG2/L0-k0, and IL6R H0-IgG2/L0-k3 by cation exchange chromatography based on their disulfide bond differences. In these graphs, the vertical axis indicates absorbance at 280 nm and the horizontal axis indicates elution time (minutes).

As shown in FIG. 20, the result confirmed heterogeneity in IgG2-k0 and showed reduction of heterogeneity in IgG2-k3. IgG2-k0, which is a natural IgG2, exhibits heterogeneity as a result of different disulfide bond patterns. It was demonstrated that heterogeneity could be reduced by merely relocating the L-chain C-terminal cysteine toward a position on the N-terminal side by shortening the peptide length of the L chain at the C terminus (IgG2-k3).

[Example 8] Comparison of IgG1-k0, M66-k0, M66-k3, M106-k3, and IgG2-k3 on Pharmacokinetics in Human FcRn Transgenic Mice IL6R H0-IgG1/L0-k0, IL6R H0-M66/L0-k0, IL6R H0-M66/L0-k3, IL6R H0-M106/L0-k3, and IL6R H0-IgG2/L0-k3 were assessed for the pharmacokinetics using human FcRn transgenic mice (B6.mFcRn−/−.hFcRn Tg line 276+/+ mice; Jackson Laboratories) by the method described in Example 3.

Figure 21:
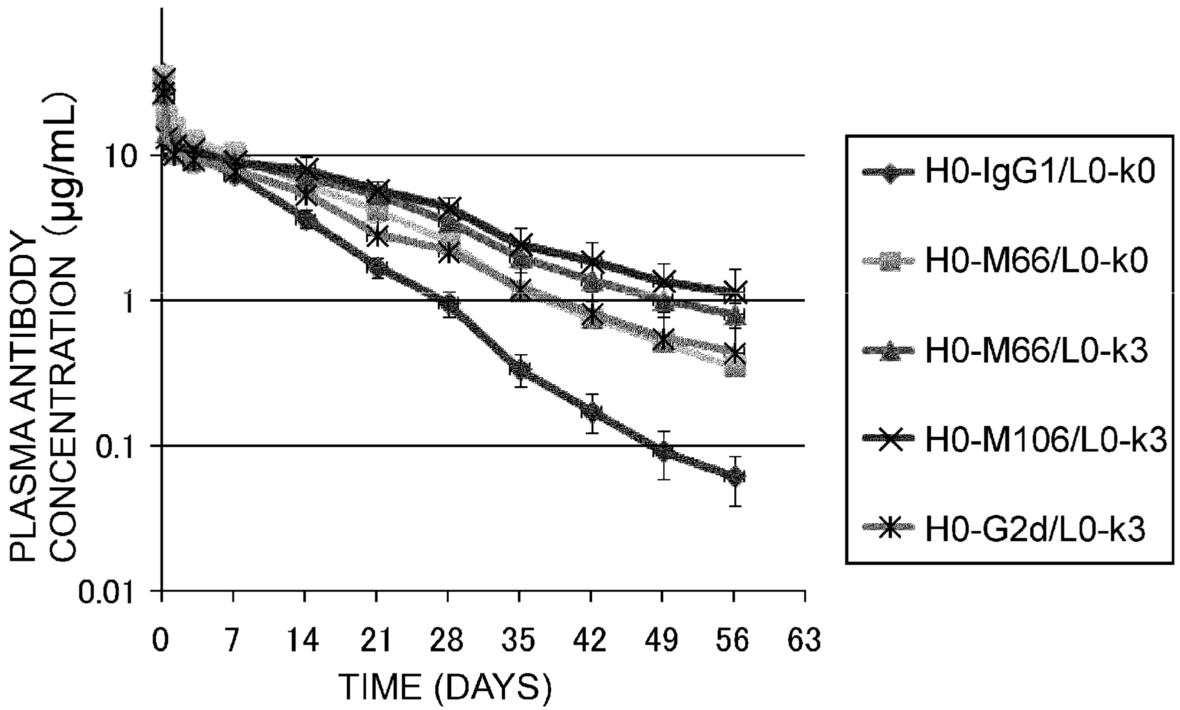
FIG. 21 shows in a graph a time course of plasma antibody concentration after administration of IL6R H0-M66/L0-k0, IL6R H0-M66/L0-k3, IL6R H0-M106/L0-k3, or IL6R H0-IgG2/L0-k3 at 1 mg/kg to human FcRn transgenic mice. In this graph, the vertical axis shows plasma antibody concentration (g/ml), and the horizontal axis shows time after administration (days).

IL6R H0-M66/L0-k0, IL6R H0-M66/L0-k3, IL6R H0-M106/L0-k3, and IL6R H0-IgG2/L0-k3 were assessed for the plasma retention in human FcRn transgenic mice. As shown in FIG. 21, the result demonstrated that IL6R H0-M66/L0-k3 was improved in terms of the pharmacokinetics as compared to IL6R H0-M66/L0-k0. It is thought that this reflects the evaluation results of FcRn binding described in Example 5. L-chain constant region k3 (amino acid SEQ ID NO: 33) generated from deleting glutamic acid at position 106 from the natural L-chain constant region k0 (amino acid SEQ ID NO: 32). Thus, it is thought that the improved plasma retention was due to the substitution of L0-k3 for L0-k0 in the L chain. Since FcRn binds to the Fc domain of the H-chain constant region, the L-chain constant region is in general believed not to affect antibody pharmacokinetics. Indeed, there is no previous report describing that the pharmacokinetics in human FcRn transgenic mice was improved by amino acid substitution in the L-chain constant region. The present inventors for the first time revealed that the pharmacokinetics was improved by amino acid substitution in the L-chain constant region. Furthermore, IL6R H0-M106/L0-k3 exhibited improved plasma retention as compared to IL6R H0-M66/L0-k3.

The constant regions M66-k3, M106-k3, and IgG2-k3 were each eluted as a single peak in the assay using cation exchange chromatography. The assay demonstrated that the binding of M66-k3, M106-k3, and IgG2-k3 to Fcγ receptor were significantly reduced relative to natural IgG1 and that the pharmacokinetics of constant regions M66-k3, M106-k3, and IgG2-k3 were greatly improved in human FcRn transgenic mice as compared to that of natural IgG1.

[Reference Example 1] Production of Antibody Expression Vectors and Expression and Purification of Antibodies Genes encoding the nucleotide sequences of the H chain and L chain of the antibody of interest were amplified using PCR and such by methods known to those skilled in the art. Introduction of amino acid substitutions were carried out by methods known to those skilled in the art using QuikChange™ Site-Directed Mutagenesis Kit (Stratagene), PCR, or such. The obtained plasmid fragment was inserted into an animal cell expression vector, and the H-chain expression vector and L-chain expression vector of interest were produced. The nucleotide sequence of the obtained expression vector was determined by a method known to those skilled in the art. The antibodies were expressed by the following method. Human embryonic kidney cancer-derived HEK293H cells (Invitrogen) were suspended in DMEM (Invitrogen) supplemented with 10% Fetal Bovine Serum (Invitrogen). The cells (10-ml/plate; cell density of 5 to $6\times10^5$ cells/ml) were plated on dishes for adherent cells (10 cm in diameter; CORNING) and cultured in a $CO_2$ incubator (37° C., 5% $CO_2$) for one whole day and night. Then, the medium was removed by aspiration, and 6.9 ml of CHO-S-SFM-II medium (Invitrogen) was added. The prepared plasmids were introduced into cells by lipofection method. The obtained culture supernatants were collected and centrifuged (approx. 2000 g, 5 min, room temperature) to remove the cells, and sterilized through 0.22-μm filter MILLEX®-GV (Millipore) to prepare culture supernatant. Antibodies were purified from the obtained culture supernatant by a method known to those skilled in the art using rProtein A Sepharose™ Fast Flow medium (Amersham Biosciences). Absorbance at 280 nm was measured using a spectrophotometer to know the purified antibody concentrations. Extinction coefficient calculated from the obtained value by the PACE method was used to calculate the antibody concentration (Protein Science (1995) 4: 2411-2423).

[Reference Example 2] Preparation of Human FcRn

FcRn is a complex of FcRn and β2-microglobulin. Oligo-DNA primers were prepared based on the human FcRn gene sequence disclosed (J. Exp. Med. (1994) 180(6): 2377-2381). A DNA fragment encoding the whole gene was prepared by PCR using human cDNA (Human Placenta Marathon®-Ready cDNA, Clontech) as a template and the prepared primers. Using the obtained DNA fragment as a template, a DNA fragment encoding the extracellular domain containing the signal region (Met1-Leu290) was amplified by PCR, and inserted into an animal cell expression vector (the amino acid sequence of human FcRn as set forth in SEQ ID NO: 35). Likewise, oligo-DNA primers were prepared based on the human β2-microglobulin gene sequence disclosed (Proc. Natl. Acad. Sci. USA. (2002) 99(26): 16899-16903). A DNA fragment encoding the whole gene was prepared by PCR using human cDNA (Hu-Placenta Marathon®-Ready cDNA, CLONTECH) as a template and the prepared primers. Using the obtained DNA fragment as a template, a DNA fragment encoding the whole β2-microglobulin containing the signal region (Met1-Met119) was amplified by PCR and inserted into an animal cell expression vector (the amino acid sequence of human β2-microglobulin as set forth in SEQ ID NO: 36).

Soluble human FcRn was expressed by the following procedure. The plasmids constructed for human FcRn and β2-microglobulin were introduced into cells of the human embryonic kidney cancer-derived cell line HEK293H (Invitrogen) using 10% Fetal Bovine Serum (Invitrogen) by lipofection. The resulting culture supernatant was collected, and FcRn was purified using IgG Sepharose™ 6 Fast Flow medium (Amersham Biosciences) by the method described in J. Immunol. 2002 Nov. 1; 169(9): 5171-80, followed by further purification using HiTrap® Q HP protein purification columns (GE Healthcare).

[Reference Example 3] Measurement of Plasma Antibody Concentration in Mice

Measurement of the mouse plasma antibody concentration was carried out by the ELISA method using anti-human IgG antibodies and using each of the antibodies as standards according to a method known to those skilled in the art.

INDUSTRIAL APPLICABILITY

The present invention is useful in the production of antibodies which will be administered to living organisms as pharmaceuticals. More specifically, antibodies comprising the constant regions of the present invention are advantageous in maintaining the quality of the pharmaceuticals since heterogeneity is low. In other words, by using an antibody comprising a constant region of the present invention as a pharmaceutical, a steady supply of homogeneous antibodies will be possible. For example, TOCILIZUMAB (common name) which is an antibody against the IL-6 receptor is a humanized antibody used for treatment of autoimmune diseases and such. Therefore, for example, quality can be kept stable by substituting a constant region provided by the present invention for the constant region of this antibody.

Furthermore, the present invention provided antibodies with improved pharmacokinetics by altering the amino acid sequence of the constant regions. Antibodies subjected to improvement of pharmacokinetics by the present invention maintain activity for a longer time in a living body. Therefore, for example, by substituting a constant region provided by the present invention for the constant region of TOCILIZUMAB (common name) which is an antibody against the IL-6 receptor, its pharmacokinetics is improved, and it can be an antibody that may maintain the active concentration in a living body for a long time.

The invention claimed is:

1. An antibody constant region comprising the amino acid sequence of SEQ ID NO: 24 with at least the following substitutions and optional deletions:

Ser is substituted for Cys at position 14, which corresponds to EU numbering position 131;

Lys is substituted for Arg at position 16, which corresponds to EU numbering position 133;

Ser is substituted for Cys at position 103, which corresponds to EU numbering position 220;

Gly is substituted for Glu at position 20, which corresponds to EU numbering position 137;

Gly is substituted for Ser at position 21, which corresponds to EU numbering position 138;

Gln is substituted for His at position 147, which corresponds to EU numbering position 268;

Gln is substituted for Arg at position 234, which corresponds to EU numbering position 355; and Glu is substituted for Gln at position 298, which corresponds to EU numbering position 419, wherein Gly at position 325 and Lys at position 326 of SEQ ID NO: 24, corresponding to EU numbering positions 446 and 447, respectively, are optionally deleted.

2. An antibody constant region comprising the amino acid sequence of SEQ ID NO: 24 with at least the following substitutions and optional deletions:

Ser is substituted for Cys at position 14, which corresponds to EU numbering position 131;

Lys is substituted for Arg at position 16, which corresponds to EU numbering position 133;

Ser is substituted for Cys at position 103, which corresponds to EU numbering position 220;

Gly is substituted for Glu at position 20, which corresponds to EU numbering position 137;

Gly is substituted for Ser at position 21, which corresponds to EU numbering position 138;

Gln is substituted for His at position 147, which corresponds to EU numbering position 268;

Gln is substituted for Arg at position 234, which corresponds to EU numbering position 355;

Glu is substituted for Gln at position 298, which corresponds to EU numbering position 419;

Ser is substituted for Ala at position 209, which corresponds to EU numbering position 330;

Ser is substituted for Pro at position 210, which corresponds to EU numbering position 331; and Ala is substituted for Thr at position 218, which corresponds to EU numbering position 339, wherein Gly at position 325 and Lys at position 326 of SEQ ID NO: 24, corresponding to EU numbering positions 446 and 447, respectively, are optionally deleted.

3. The antibody constant region of claim 1, wherein Gly at position 325 and Lys at position 326 of SEQ ID NO: 24 are deleted.

4. The antibody constant region of claim 2, wherein Gly at position 325 and Lys at position 326 of SEQ ID NO: 24 are deleted.

5. An antibody comprising the constant region of any one of claims 1, 2, 3, and 4.

6. A pharmaceutical composition comprising the antibody of claim 5.

* * * * *